(12) United States Patent
Nguyen et al.

(10) Patent No.: US 10,238,482 B2
(45) Date of Patent: Mar. 26, 2019

(54) AXIAL LENGTHENING THROMBUS CAPTURE SYSTEM

(71) Applicant: KP Medcure, Inc., Anaheim, CA (US)

(72) Inventors: Thanh Van Nguyen, Anaheim, CA (US); Duy Nguyen, Anaheim, CA (US); Tung Hoang Ngo, Anaheim, CA (US)

(73) Assignee: KP Medcure, Inc., Anaheim, CA (US)

( * ) Notice: Subject to any disclaimer, the term of this patent is extended or adjusted under 35 U.S.C. 154(b) by 0 days.

(21) Appl. No.: 16/011,251

(22) Filed: Jun. 18, 2018

(65) Prior Publication Data

US 2018/0296315 A1   Oct. 18, 2018

Related U.S. Application Data

(63) Continuation of application No. 15/604,531, filed on May 24, 2017, now Pat. No. 9,999,493, which is a
(Continued)

(51) Int. Cl.
*A61F 2/01* (2006.01)
*A61B 17/221* (2006.01)
(Continued)

(52) U.S. Cl.
CPC ............ *A61F 2/013* (2013.01); *A61B 17/221* (2013.01); *A61B 17/22032* (2013.01); *A61B 17/320758* (2013.01); *A61M 25/1006* (2013.01); *A61B 2017/00867* (2013.01); *A61B 2017/00871* (2013.01); *A61B 2017/00938* (2013.01); *A61B 2017/00942* (2013.01); *A61B 2017/2212* (2013.01); *A61B 2017/2215* (2013.01); *A61B 2017/2217* (2013.01); *A61B 2017/22034* (2013.01); *A61B 2017/22038* (2013.01); *A61B 2017/22069* (2013.01);
(Continued)

(58) Field of Classification Search
CPC .......... A61B 17/221; A61B 17/320758; A61B 2017/320064; A61B 2017/320775; A61B 2017/2212; A61B 2017/00867; A61B 2017/00893; A61B 2017/320716
USPC ...................................................... 623/1.53
See application file for complete search history.

(56) References Cited

U.S. PATENT DOCUMENTS

| 3,506,011 A | 4/1970 | Silverman |
| 5,011,488 A | 4/1991 | Ginsburg |

(Continued)

FOREIGN PATENT DOCUMENTS

| WO | WO 2008/070996 A1 | 6/2008 |
| WO | WO 2015079401 A2 | 6/2015 |
| WO | WO 2017/024258 | 2/2017 |

OTHER PUBLICATIONS

US 8,668,714 B2, 03/2014, Cully et al. (withdrawn)
(Continued)

*Primary Examiner* — Julian W Woo
(74) *Attorney, Agent, or Firm* — Knobbe, Martens, Olson & Bear, LLP

(57) ABSTRACT

Systems and methods can remove material of interest, including blood clots, from a body region, including but not limited to the circulatory system for the treatment of pulmonary embolism (PE), deep vein thrombosis (DVT), cerebrovascular embolism, and other vascular occlusions.

20 Claims, 103 Drawing Sheets

Related U.S. Application Data continuation of application No. 15/428,076, filed on Feb. 8, 2017, now Pat. No. 9,744,024, which is a continuation of application No. 15/230,109, filed on Aug. 5, 2016, now Pat. No. 9,579,116.

(60) Provisional application No. 62/202,074, filed on Aug. 6, 2015, provisional application No. 62/273,418, filed on Dec. 30, 2015, provisional application No. 62/345,863, filed on Jun. 6, 2016.

(51) Int. Cl.
*A61B 17/3207* (2006.01)
*A61M 25/10* (2013.01)
*A61B 17/22* (2006.01)
*A61B 17/32* (2006.01)
*A61B 17/00* (2006.01)

(52) U.S. Cl.
CPC ........... *A61B 2017/22079* (2013.01); *A61B 2017/22081* (2013.01); *A61B 2017/22084* (2013.01); *A61B 2017/320024* (2013.01); *A61B 2017/320052* (2013.01); *A61B 2017/320716* (2013.01); *A61B 2017/320775* (2013.01); *A61B 2217/005* (2013.01); *A61F 2002/011* (2013.01); *A61F 2002/016* (2013.01); *A61F 2002/018* (2013.01); *A61F 2230/0091* (2013.01); *A61F 2250/0003* (2013.01); *A61F 2250/0039* (2013.01)

(56) References Cited

U.S. PATENT DOCUMENTS

| | | | |
|---|---|---|---|
| 5,102,415 A | 4/1992 | Guenther et al. |
| 5,135,484 A | 8/1992 | Wright |
| 5,846,251 A | 12/1998 | Hart |
| 5,868,708 A | 2/1999 | Hart |
| 5,895,398 A | 4/1999 | Wensel et al. |
| 5,935,139 A | 8/1999 | Bates |
| 5,947,985 A | 9/1999 | Imran |
| 6,066,149 A | 5/2000 | Samson et al. |
| 6,126,635 A | 10/2000 | Simpson et al. |
| 6,165,196 A | 12/2000 | Stack et al. |
| 6,179,859 B1 | 1/2001 | Bates et al. |
| 6,210,370 B1 | 4/2001 | Chi-Sing et al. |
| 6,221,006 B1 | 4/2001 | Dubrul et al. |
| 6,264,663 B1 | 7/2001 | Cano |
| 6,270,477 B1 | 8/2001 | Bagaoisan et al. |
| 6,391,044 B1 | 5/2002 | Yadav et al. |
| 6,432,122 B1 | 8/2002 | Gilson et al. |
| 6,569,181 B1 | 5/2003 | Burns |
| 6,605,102 B1 | 8/2003 | Mazzocchi et al. |
| 6,620,182 B1 | 9/2003 | Khosravi et al. |
| 6,635,070 B2 | 10/2003 | Leeflang et al. |
| 6,645,224 B2 | 11/2003 | Gilson et al. |
| 6,663,650 B2 | 12/2003 | Sepetka et al. |
| 6,824,545 B2 | 11/2004 | Sepetka et al. |
| 6,840,950 B2 | 1/2005 | Stanford et al. |
| 6,945,977 B2 | 9/2005 | Demarais et al. |
| 7,094,249 B1 | 8/2006 | Broome et al. |
| 7,220,271 B2 | 5/2007 | Clubb et al. |
| 7,491,210 B2 | 2/2009 | Dubrul et al. |
| 7,621,870 B2 | 11/2009 | Berrada et al. |
| 7,662,165 B2 | 2/2010 | Gilson et al. |
| 7,766,921 B2 | 8/2010 | Sepetka et al. |
| 7,780,696 B2 | 8/2010 | Daniel et al. |
| 7,785,342 B2 | 8/2010 | Gilson et al. |
| 7,901,426 B2 | 3/2011 | Gilson et al. |
| 8,070,769 B2 | 12/2011 | Broome |
| 8,092,486 B2 | 1/2012 | Berrada et al. |
| 8,236,024 B2 | 8/2012 | Stanford et al. |
| 8,252,017 B2 | 8/2012 | Paul, Jr. et al. |
| 8,255,193 B2 | 8/2012 | Humphrey et al. |
| 8,298,252 B2 | 10/2012 | Krolik et al. |
| 8,313,503 B2 | 11/2012 | Cully et al. |
| 8,337,520 B2 | 12/2012 | Cully et al. |
| 8,388,644 B2 | 3/2013 | Parker |
| 8,460,335 B2 | 6/2013 | Carpenter |
| 8,475,487 B2 | 7/2013 | Bonnette et al. |
| 8,491,623 B2 | 7/2013 | Vogel et al. |
| 8,545,526 B2 | 10/2013 | Martin et al. |
| 8,613,717 B2 | 12/2013 | Aklog et al. |
| 8,657,849 B2 | 2/2014 | Parker |
| 8,734,374 B2 | 5/2014 | Aklog et al. |
| 8,771,289 B2 | 7/2014 | Mohiuddin et al. |
| 8,777,976 B2 | 7/2014 | Brady et al. |
| 8,795,305 B2 | 8/2014 | Martin et al. |
| 8,795,322 B2 | 8/2014 | Cully et al. |
| 8,801,748 B2 | 8/2014 | Martin |
| 8,919,389 B2 | 12/2014 | Gries |
| 8,926,642 B2 | 1/2015 | Nelson |
| 8,932,319 B2 | 1/2015 | Martin et al. |
| 8,948,848 B2 | 2/2015 | Merhi |
| 8,956,384 B2 | 2/2015 | Berrada et al. |
| 8,968,330 B2 * | 3/2015 | Rosenbluth ..... A61B 17/320725 606/127 |
| 8,998,944 B2 | 4/2015 | Thornton |
| 9,254,371 B2 | 2/2016 | Martin et al. |
| 9,283,066 B2 | 3/2016 | Hopkins et al. |
| 9,301,769 B2 | 4/2016 | Brady et al. |
| 9,308,007 B2 | 4/2016 | Cully et al. |
| 9,408,620 B2 | 8/2016 | Rosenbluth et al. |
| 9,427,244 B2 | 8/2016 | Lund-Clausen et al. |
| 9,526,864 B2 | 12/2016 | Quick |
| 9,579,116 B1 | 2/2017 | Nguyen et al. |
| 9,636,206 B2 | 5/2017 | Nguyen et al. |
| 9,744,024 B2 | 8/2017 | Nguyen et al. |
| 9,844,386 B2 | 12/2017 | Nguyen et al. |
| 9,999,493 B2 | 6/2018 | Nguyen et al. |
| 10,070,879 B2 | 9/2018 | Nguyen et al. |
| 2002/0169474 A1 | 11/2002 | Kusleika et al. |
| 2003/0176884 A1 | 9/2003 | Berrada et al. |
| 2003/0216770 A1 | 11/2003 | Persidsky et al. |
| 2004/0039411 A1 | 2/2004 | Gilson et al. |
| 2004/0073198 A1 | 4/2004 | Gilson et al. |
| 2004/0098025 A1 | 5/2004 | Sepetka et al. |
| 2004/0098033 A1 | 5/2004 | Leeflang et al. |
| 2006/0025804 A1 | 2/2006 | Krolik et al. |
| 2006/0155305 A1 | 7/2006 | Freudenthal et al. |
| 2006/0212062 A1 | 9/2006 | Farascioni |
| 2007/0010702 A1 | 1/2007 | Wang et al. |
| 2007/0088382 A1 | 4/2007 | Bei et al. |
| 2007/0112374 A1 | 5/2007 | Paul, Jr. et al. |
| 2007/0282303 A1 | 12/2007 | Nash et al. |
| 2008/0167678 A1 | 7/2008 | Morsi |
| 2009/0292307 A1 | 11/2009 | Razack |
| 2010/0211095 A1 | 8/2010 | Carpenter |
| 2010/0249815 A1 | 9/2010 | Jantzen et al. |
| 2010/0268264 A1 | 10/2010 | Bonnette et al. |
| 2011/0125181 A1 | 5/2011 | Brady et al. |
| 2011/0166586 A1 | 7/2011 | Sepetka et al. |
| 2012/0197285 A1 | 8/2012 | Martin et al. |
| 2012/0310251 A1 | 12/2012 | Sepetka et al. |
| 2012/0330346 A1 | 12/2012 | Frimerman |
| 2012/0330350 A1 | 12/2012 | Jones et al. |
| 2013/0102996 A1 | 4/2013 | Strauss |
| 2013/0178891 A1 | 7/2013 | Russell et al. |
| 2013/0184738 A1 | 7/2013 | Laroya et al. |
| 2013/0184741 A1 | 7/2013 | Laroya et al. |
| 2013/0197567 A1 | 8/2013 | Brady et al. |
| 2013/0238009 A9 | 9/2013 | Hopkins et al. |
| 2013/0267993 A1 | 10/2013 | Carpenter |
| 2013/0338703 A1 | 12/2013 | Hansen et al. |
| 2014/0005712 A1 | 1/2014 | Martin |
| 2014/0005717 A1 | 1/2014 | Martin et al. |
| 2014/0046358 A1 | 2/2014 | Cully et al. |
| 2014/0052103 A1 | 2/2014 | Cully et al. |
| 2014/0128894 A1 | 5/2014 | Sepetka et al. |
| 2014/0249568 A1 | 9/2014 | Adams et al. |
| 2014/0276403 A1 | 9/2014 | Follmer et al. |
| 2014/0276922 A1 | 9/2014 | McLain et al. |
| 2014/0277013 A1 | 9/2014 | Sepetka et al. |

(56) References Cited

U.S. PATENT DOCUMENTS

| | | |
|---|---|---|
| 2014/0350593 A1 | 11/2014 | Laroya et al. |
| 2014/0371781 A1 | 12/2014 | Morgan |
| 2015/0005781 A1 | 1/2015 | Lund-Clausen et al. |
| 2015/0018929 A1 | 1/2015 | Martin et al. |
| 2015/0088190 A1 | 3/2015 | Jensen |
| 2015/0196380 A1 | 7/2015 | Berrada et al. |
| 2015/0265299 A1 | 9/2015 | Cooper et al. |
| 2015/0306311 A1 | 10/2015 | Pinchuk et al. |
| 2016/0022290 A1 | 1/2016 | Johnson et al. |
| 2016/0022291 A1 | 1/2016 | Johnson et al. |
| 2016/0038271 A1 | 2/2016 | Johnsen et al. |
| 2016/0192953 A1 | 7/2016 | Brady |
| 2017/0035445 A1 | 2/2017 | Nguyen et al. |
| 2017/0086960 A1 | 3/2017 | Nguyen et al. |
| 2017/0143359 A1 | 5/2017 | Nguyen et al. |
| 2017/0224366 A1 | 8/2017 | Nguyen et al. |
| 2017/0259042 A1 | 9/2017 | Nguyen et al. |
| 2018/0055619 A1 | 3/2018 | Nguyen et al. |
| 2018/0125512 A1 | 5/2018 | Nguyen et al. |

OTHER PUBLICATIONS

PCT Search Report and Written Opinion dated Dec. 1, 2016 in PCT Application No. PCT/US2016/045862 in 8 pages.

Notice of Allowance in U.S. Appl. No. 15,230,109 dated Oct. 17, 2016 in 7 pages.

Notice of Allowance in U.S. Appl. No. 15/376,448 dated Mar. 8, 2017 in 9 pages.

Notice of Allowance in U.S. Appl. No. 15/428,076 dated Apr. 10, 2017 in 16 pages.

Notice of Allowance in U.S. Appl. No. 15/376,448 dated Sep. 18, 2017 in 9 pages.

Notice of Allowance in U.S. Appl. No. 15/604531 dated Feb. 7, 2018 in 8 pages.

Notice of Allowance in U.S. Appl. No. 15/687,789 dated Apr. 20, 2018 in 9 pages.

PCT Search Report and Written Opinion dated May 24, 2018 in PCT Application No. PCT/US2018/016976 in 10 pages.

Notice of Allowance in U.S. Appl. No. 15/845,086 dated Jul. 23, 2018 in 9 pages.

\* cited by examiner

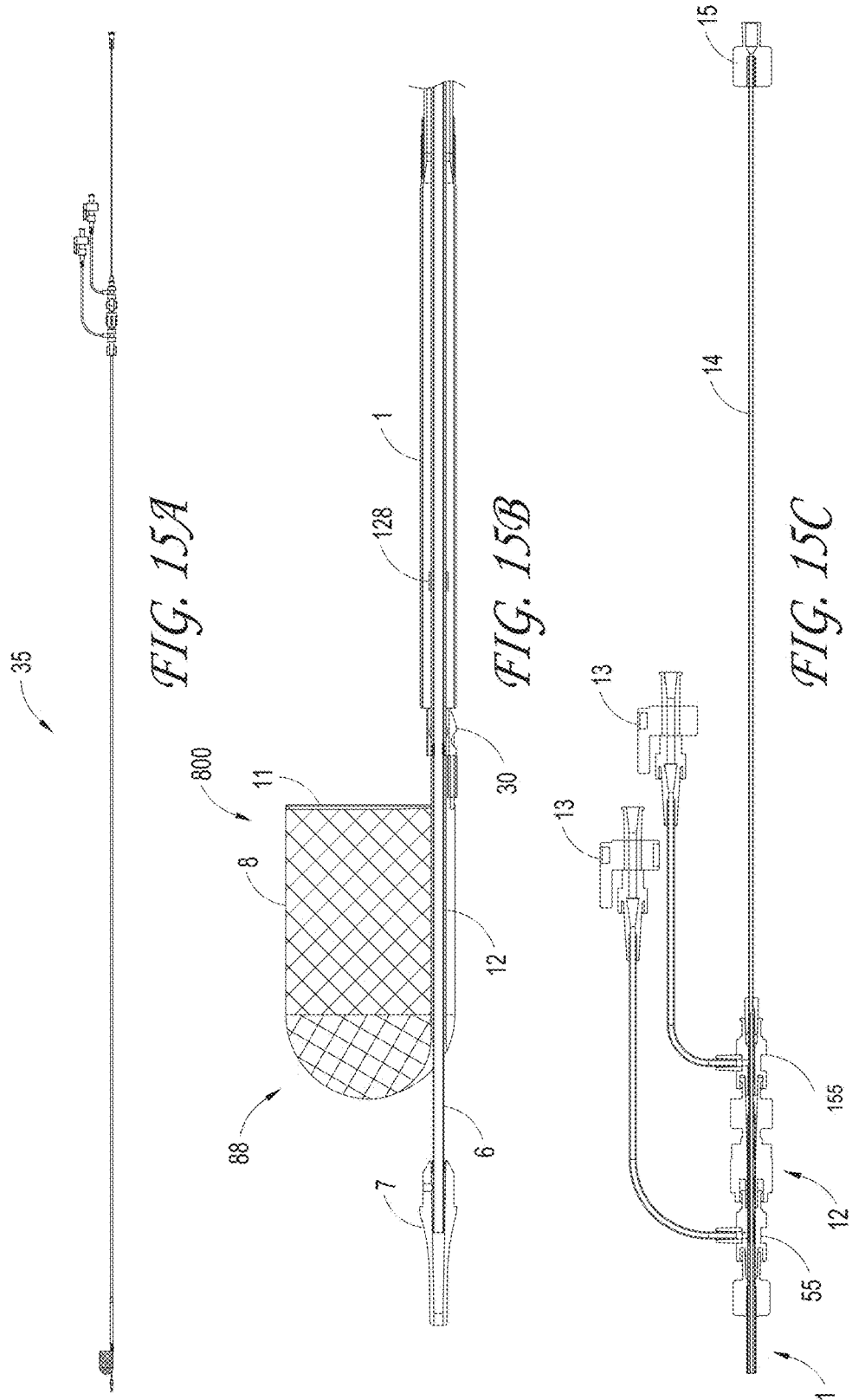

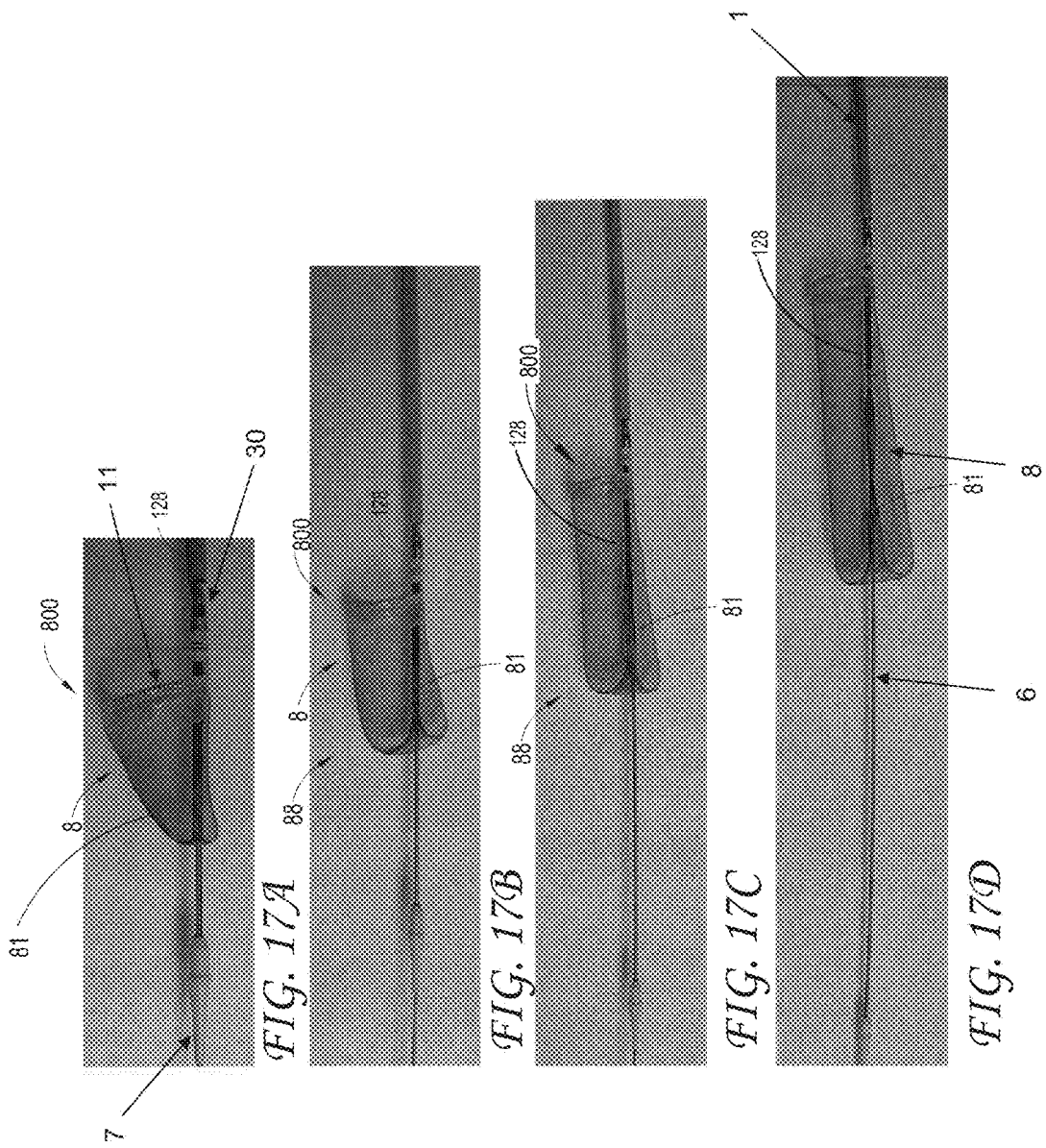

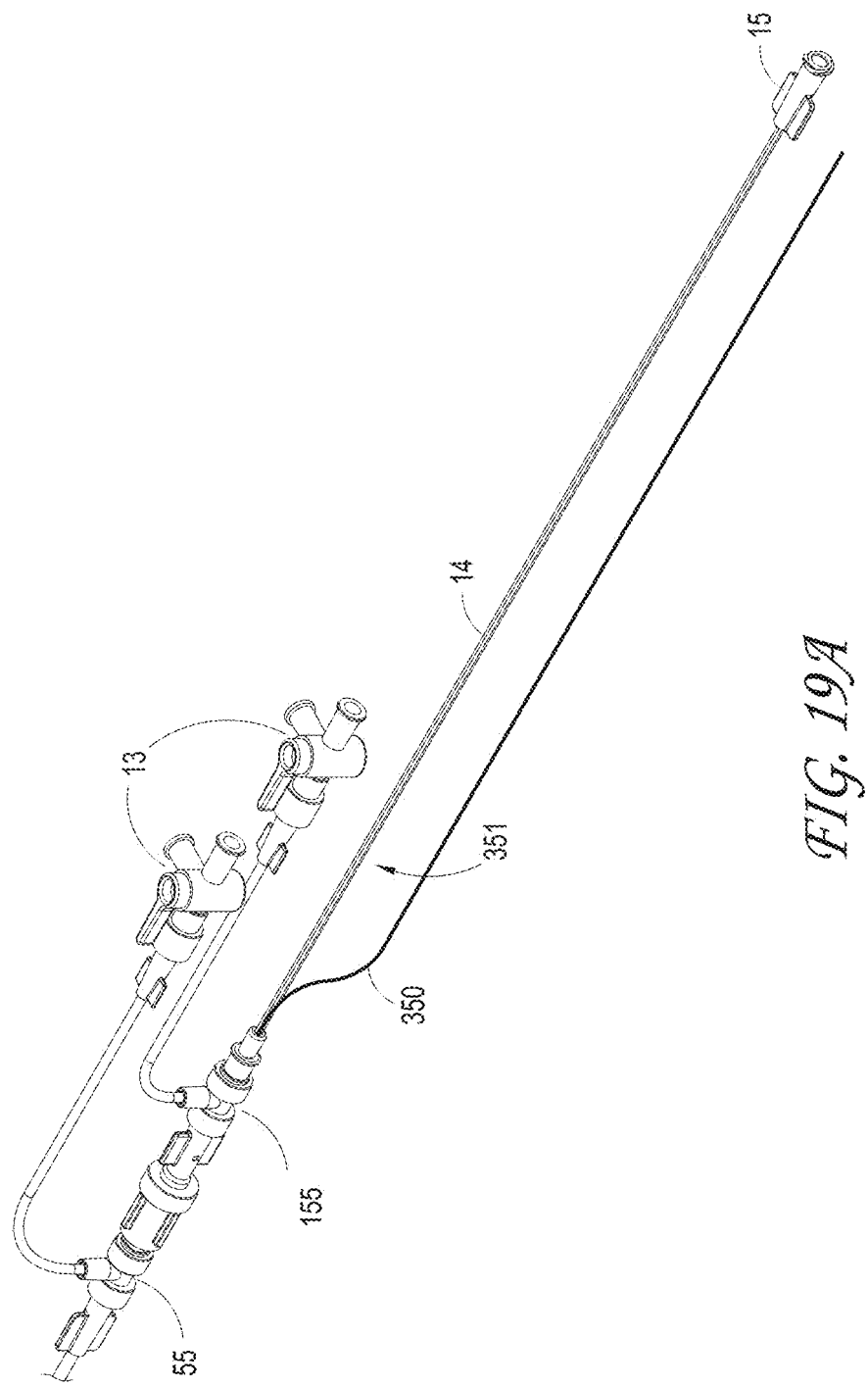

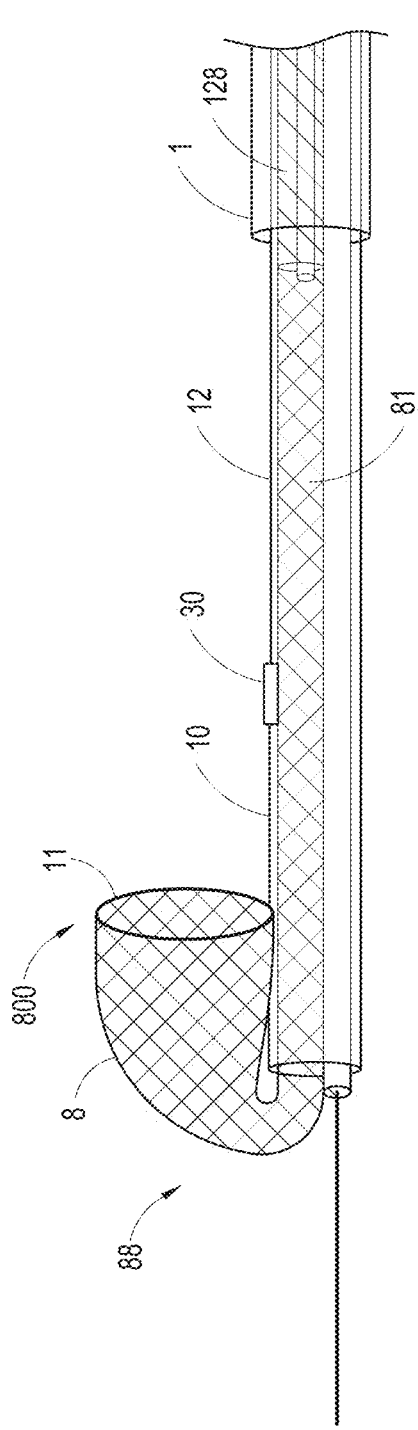
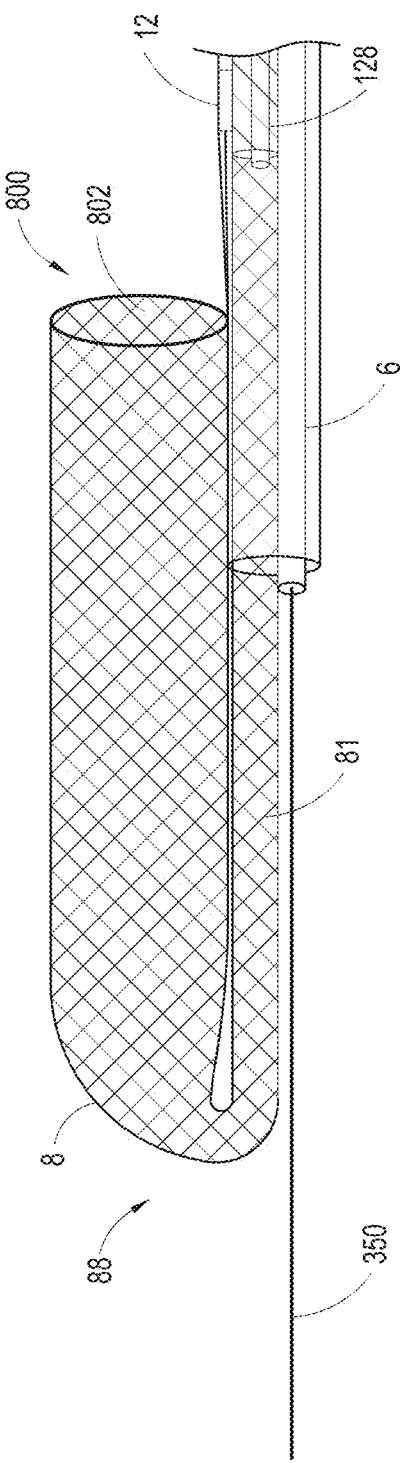
FIG. 49A
FIG. 49B

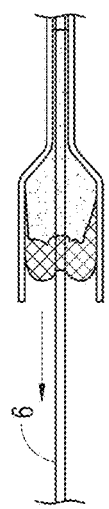
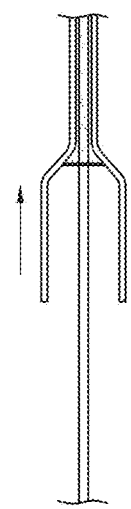
FIG. 50E    FIG. 50F    FIG. 50G
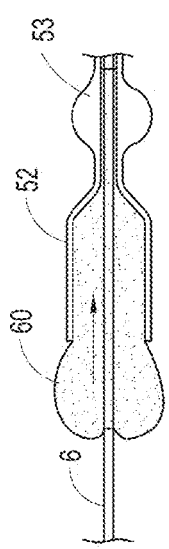
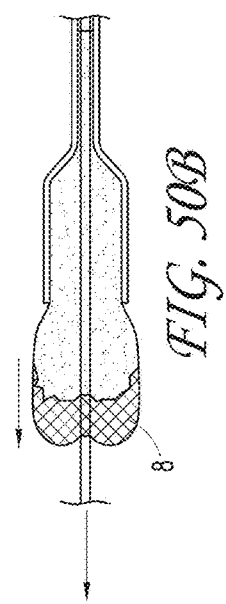
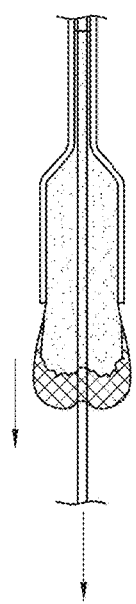
FIG. 50A    FIG. 50B    FIG. 50C    FIG. 50D

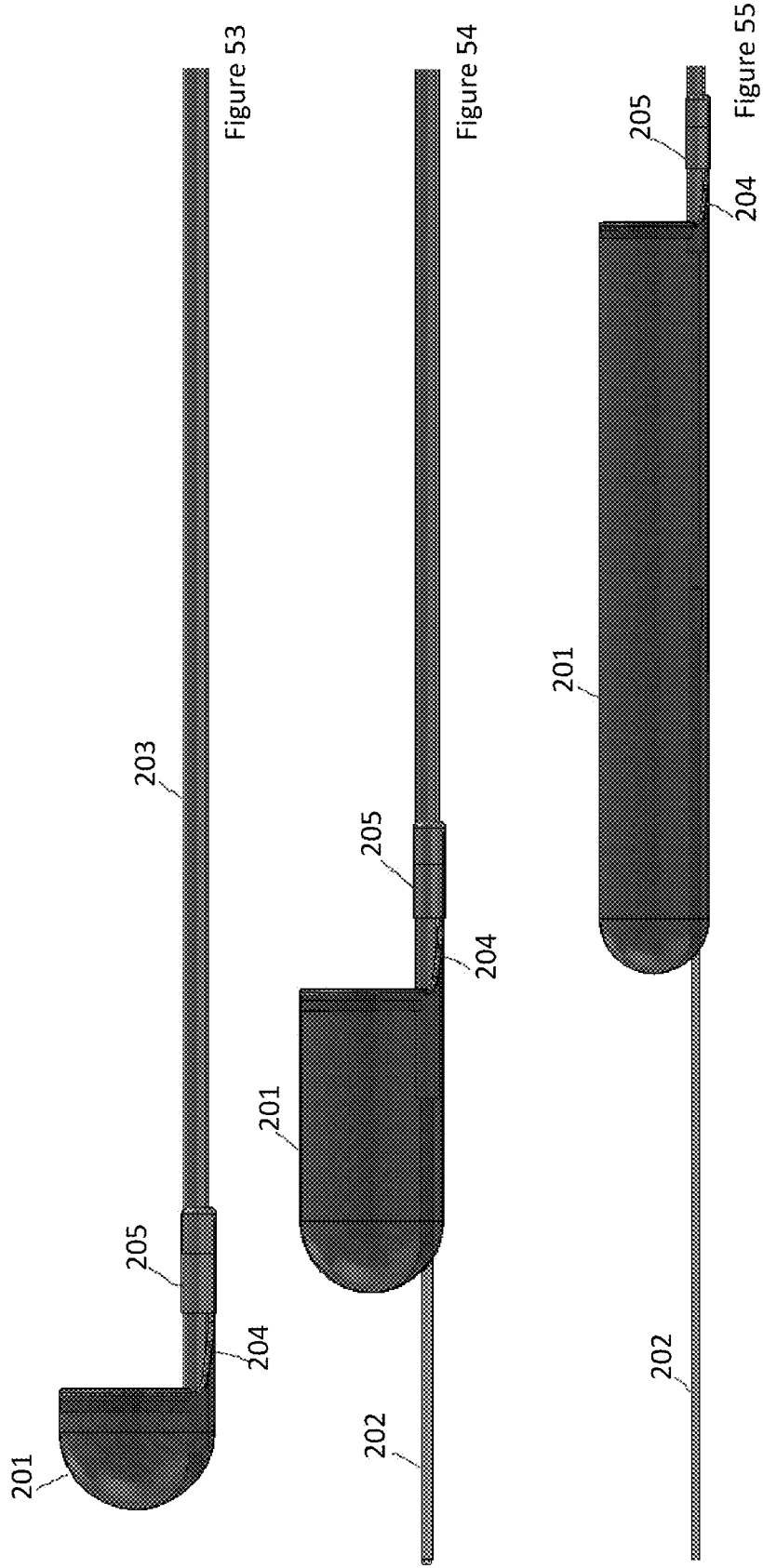

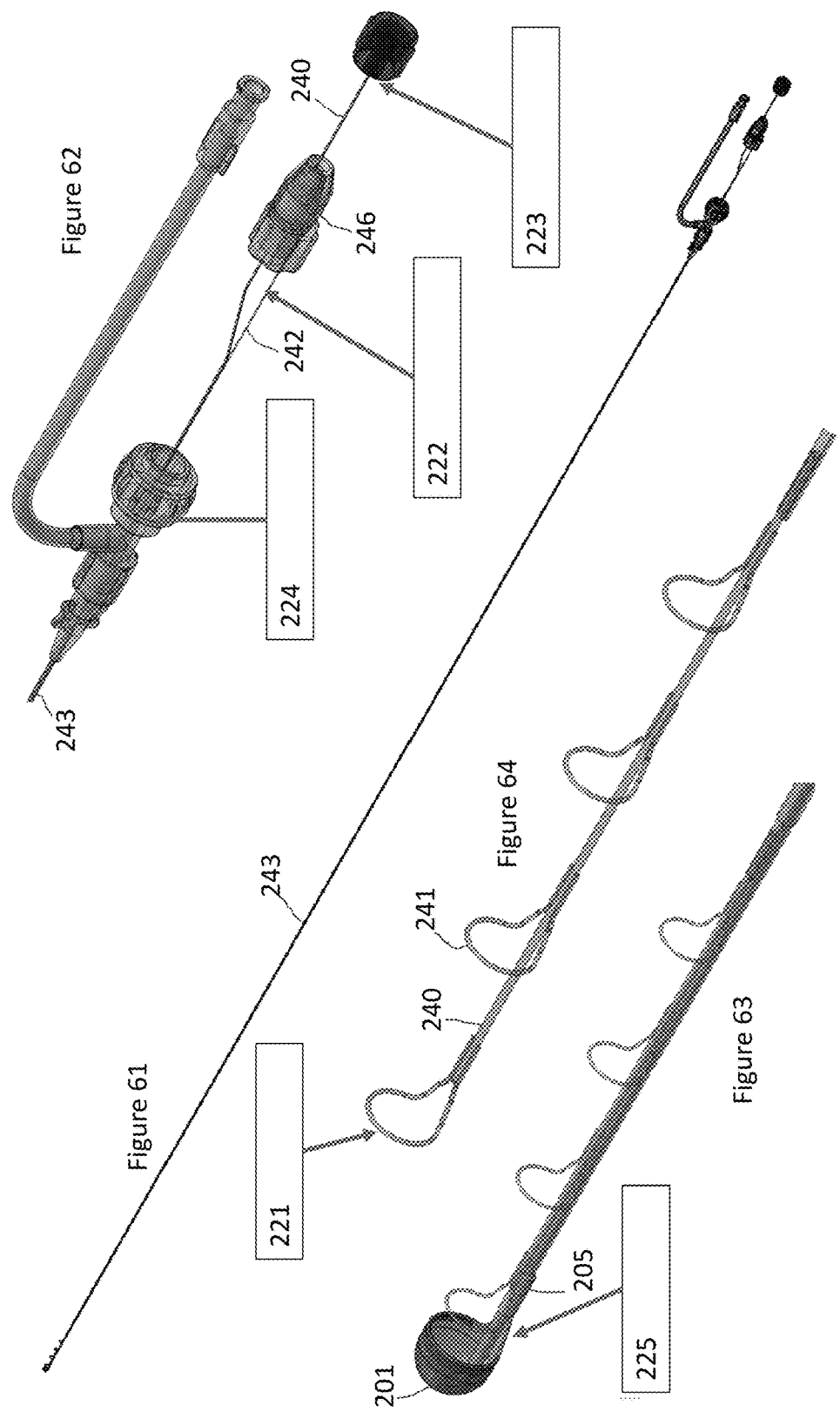

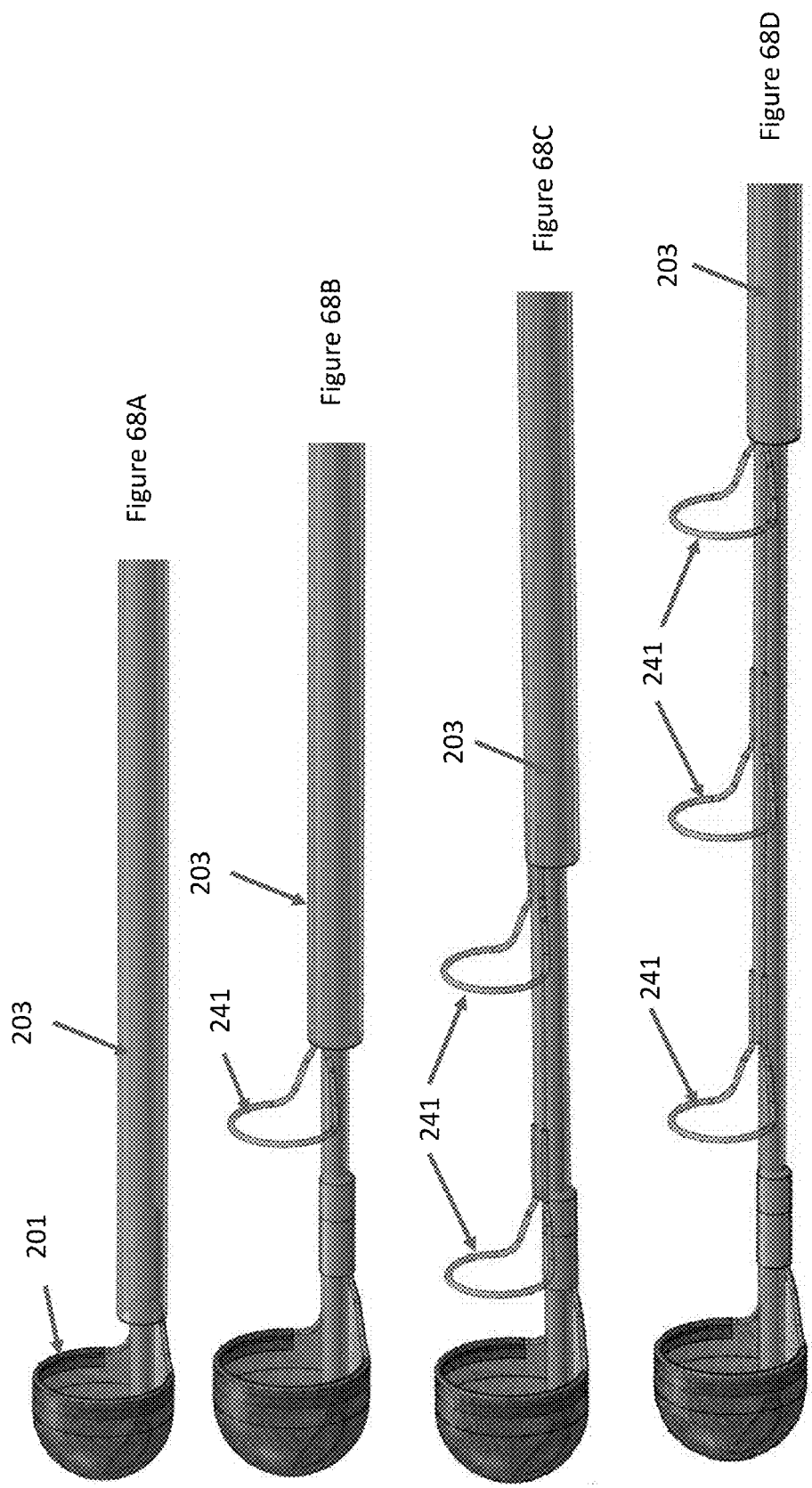

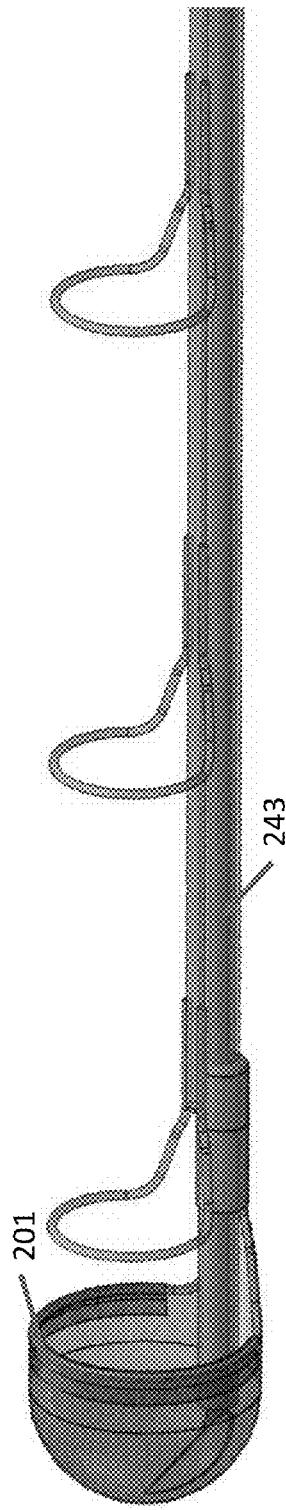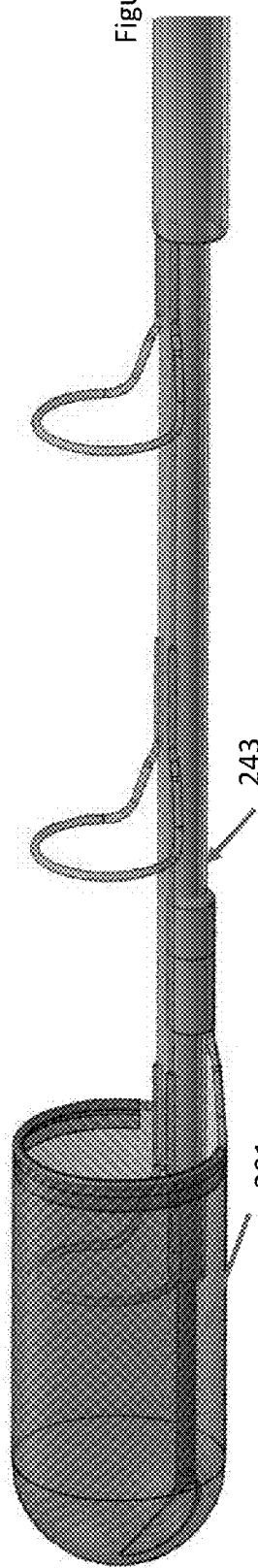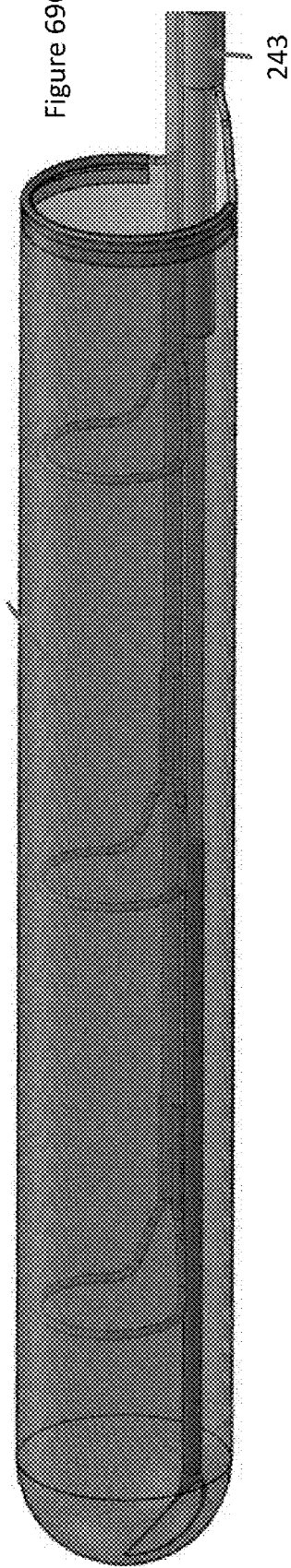

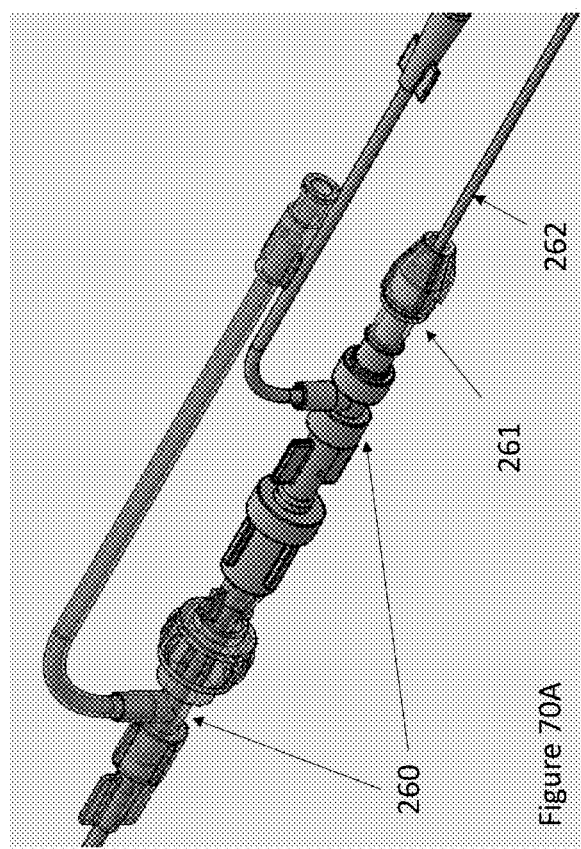
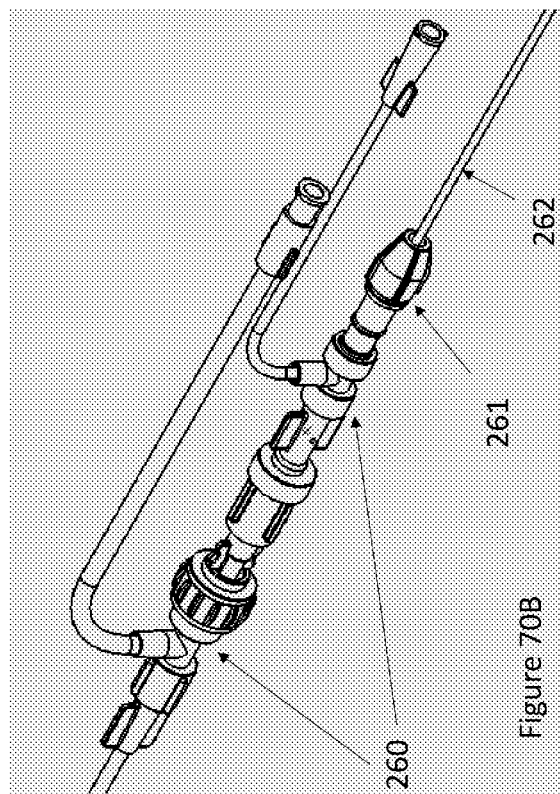

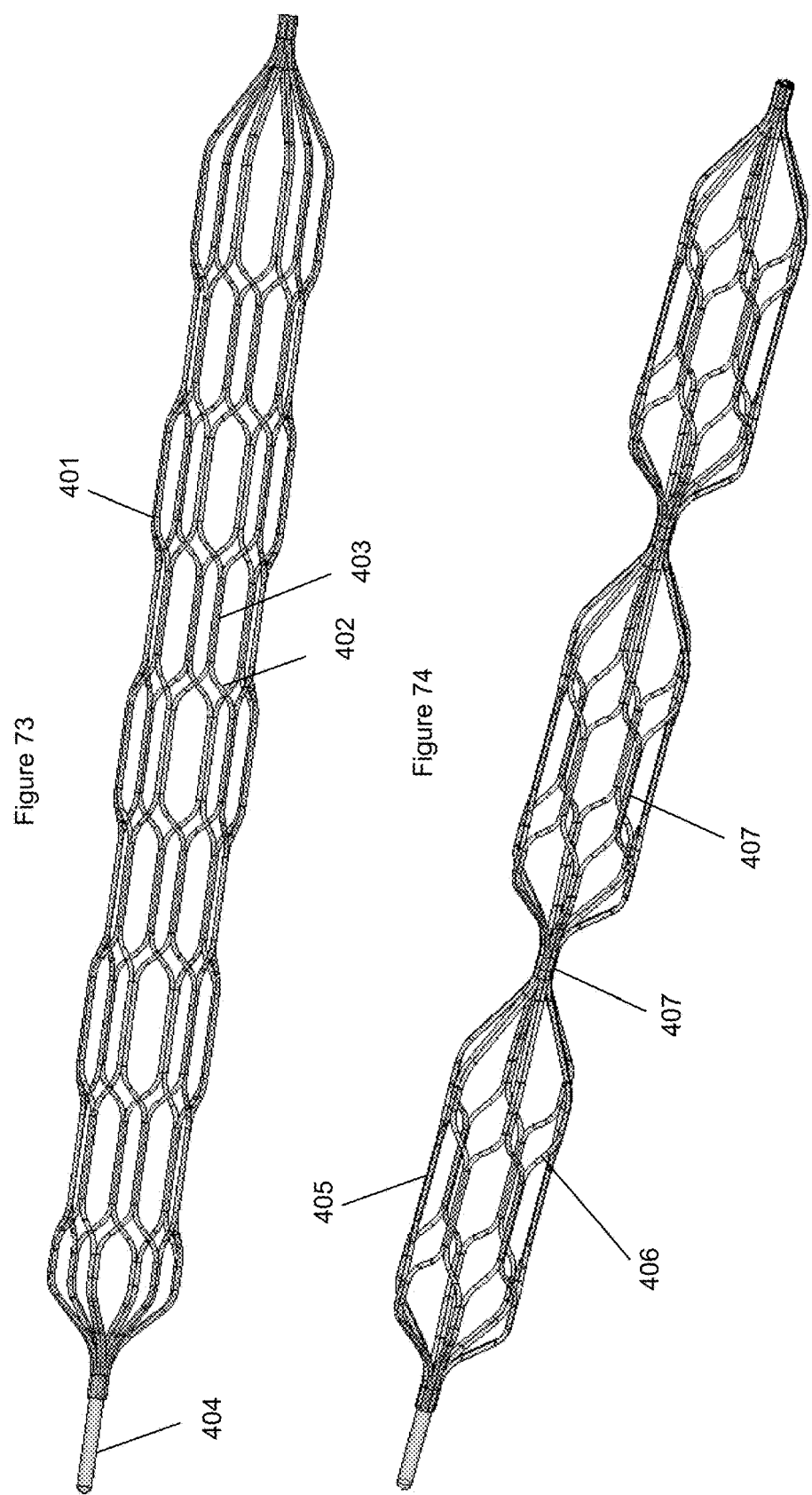

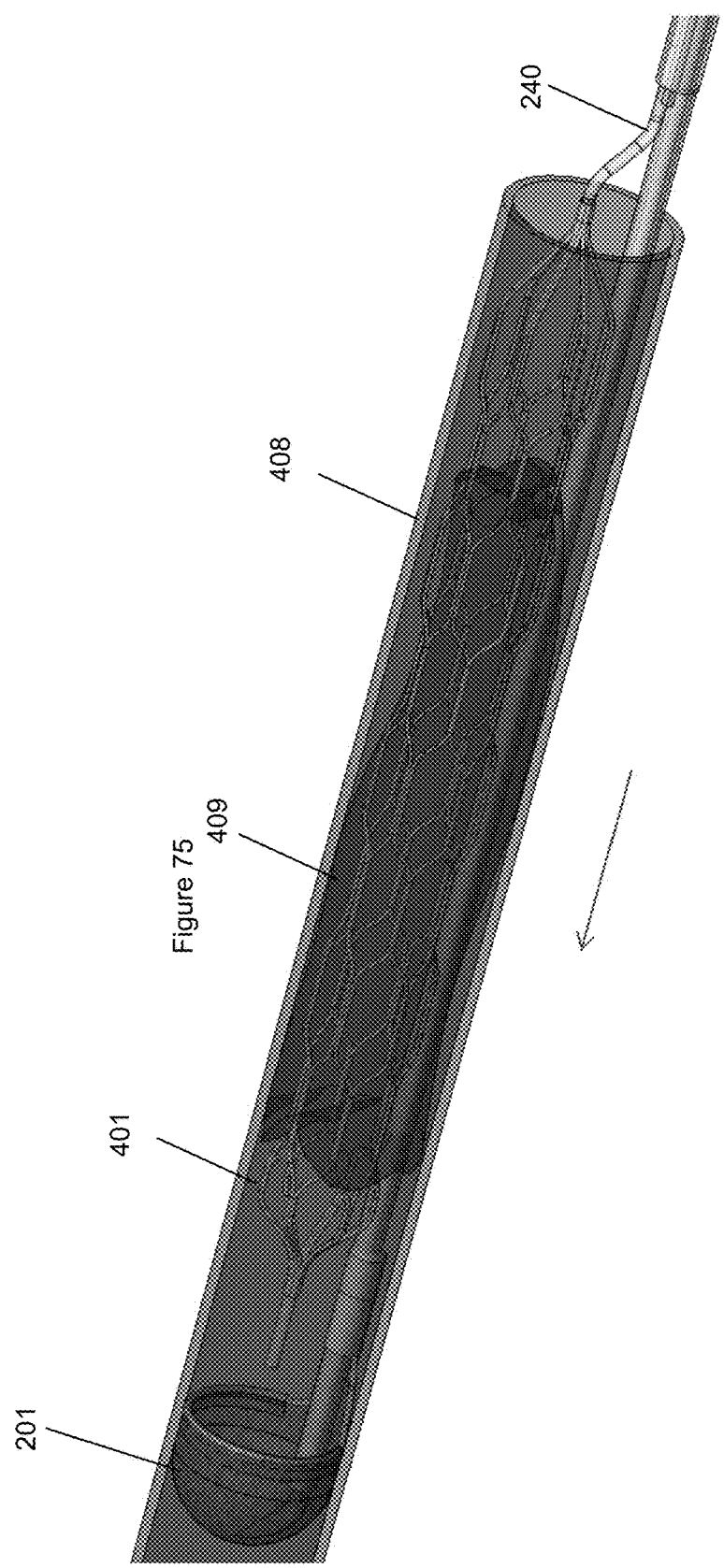

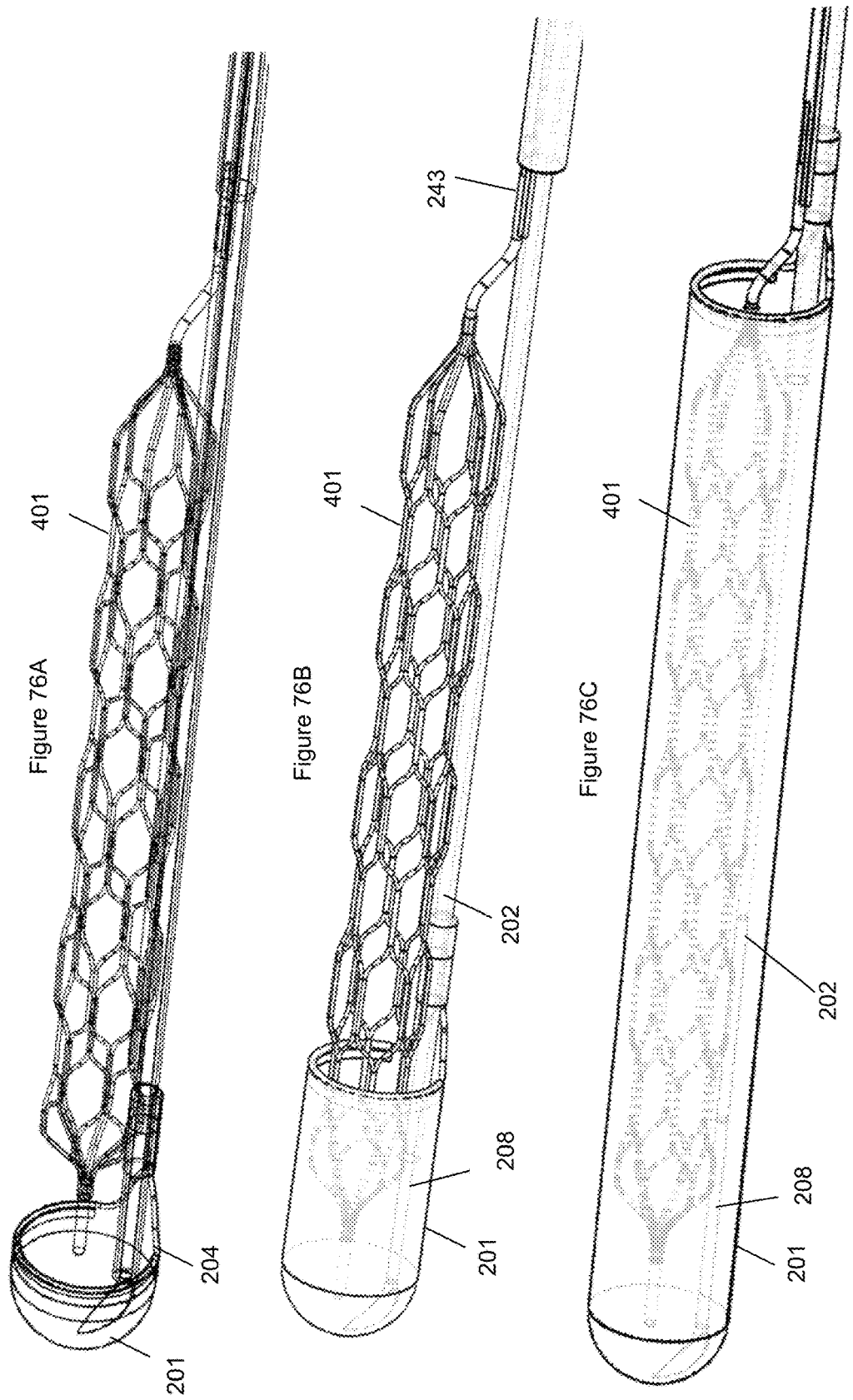

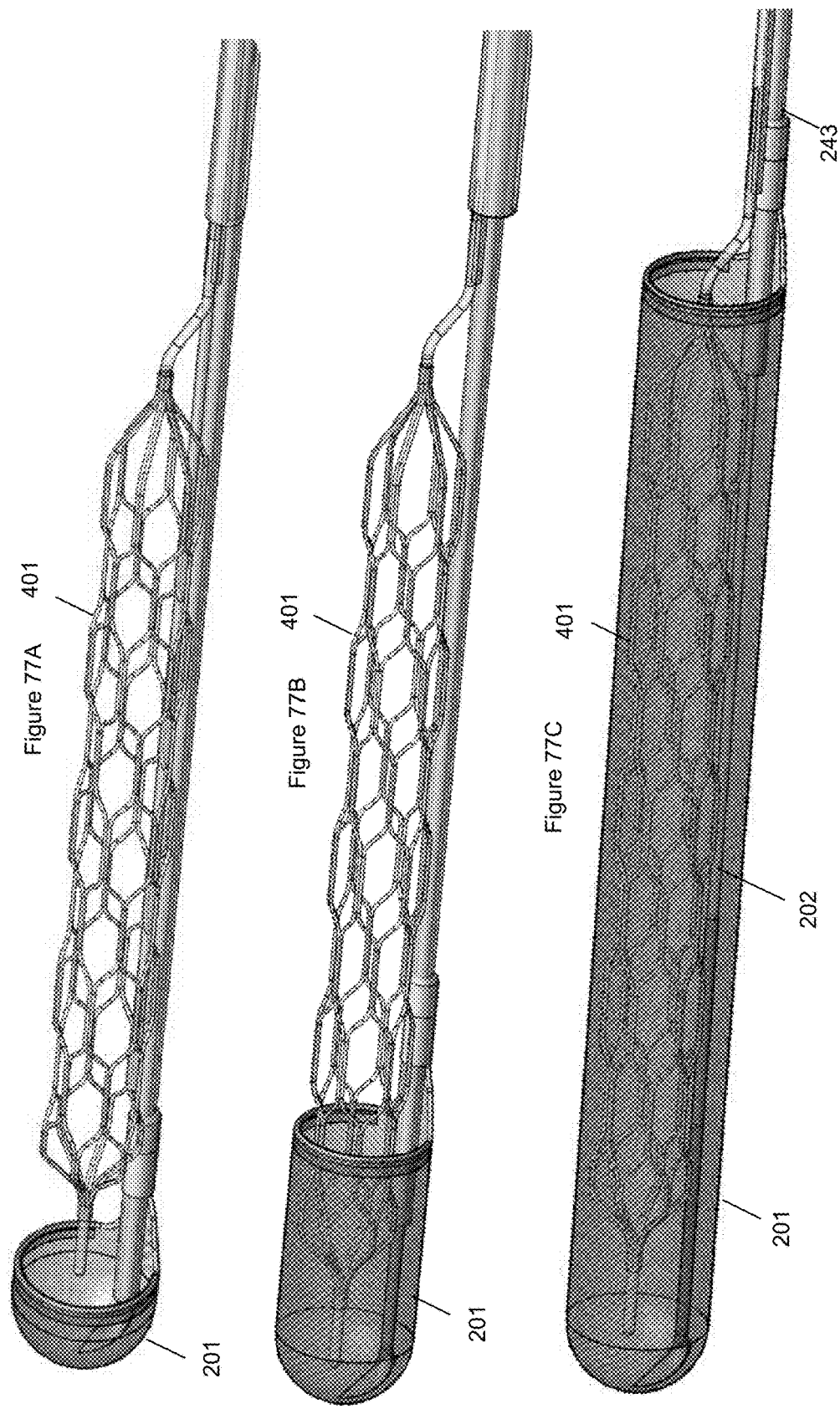

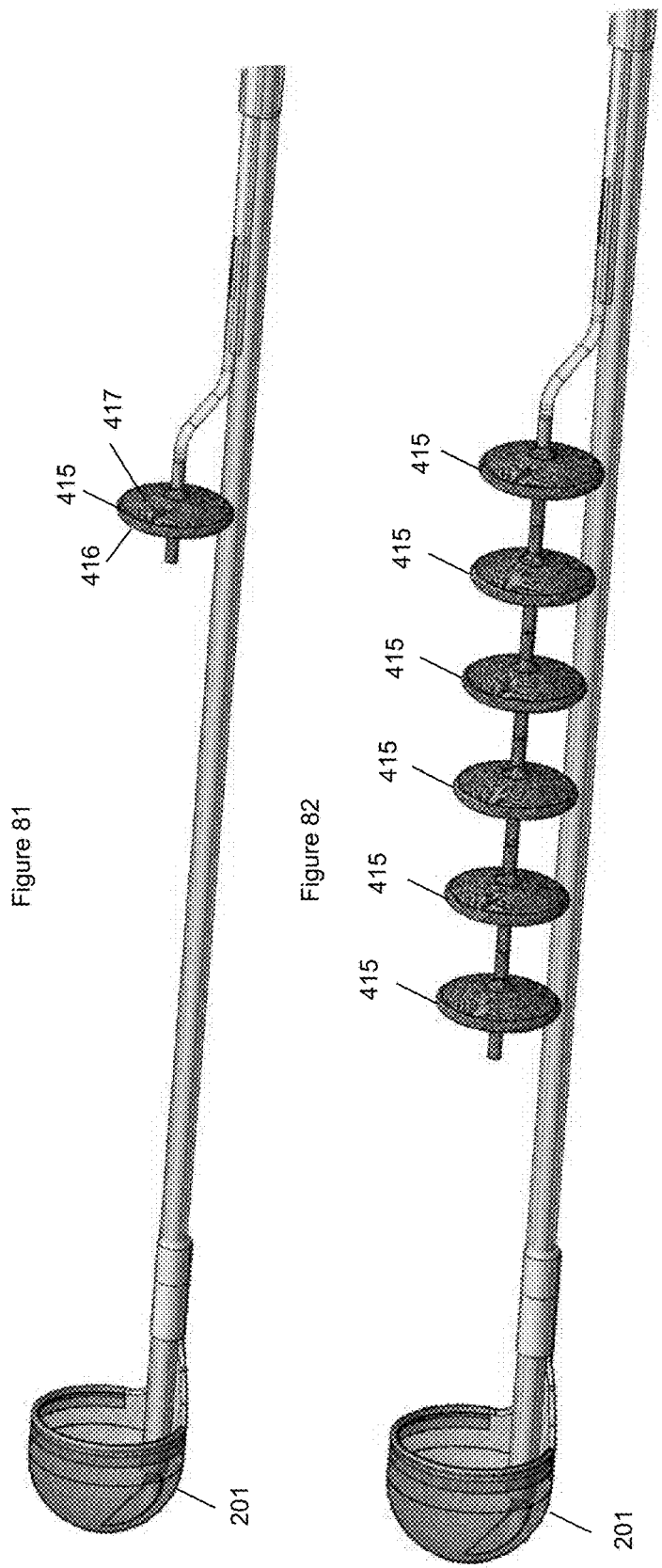

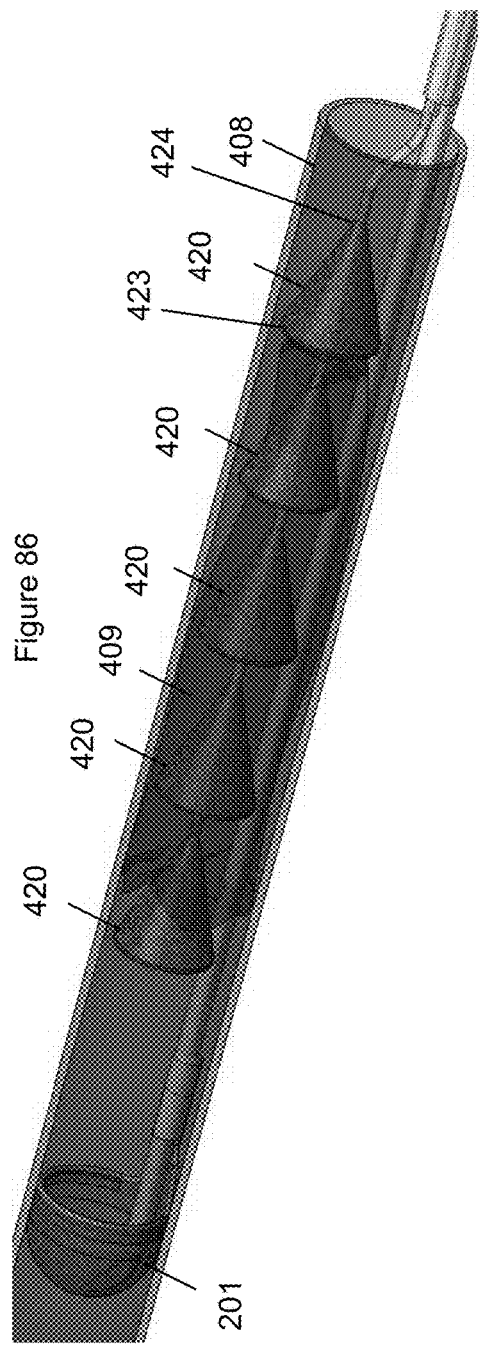
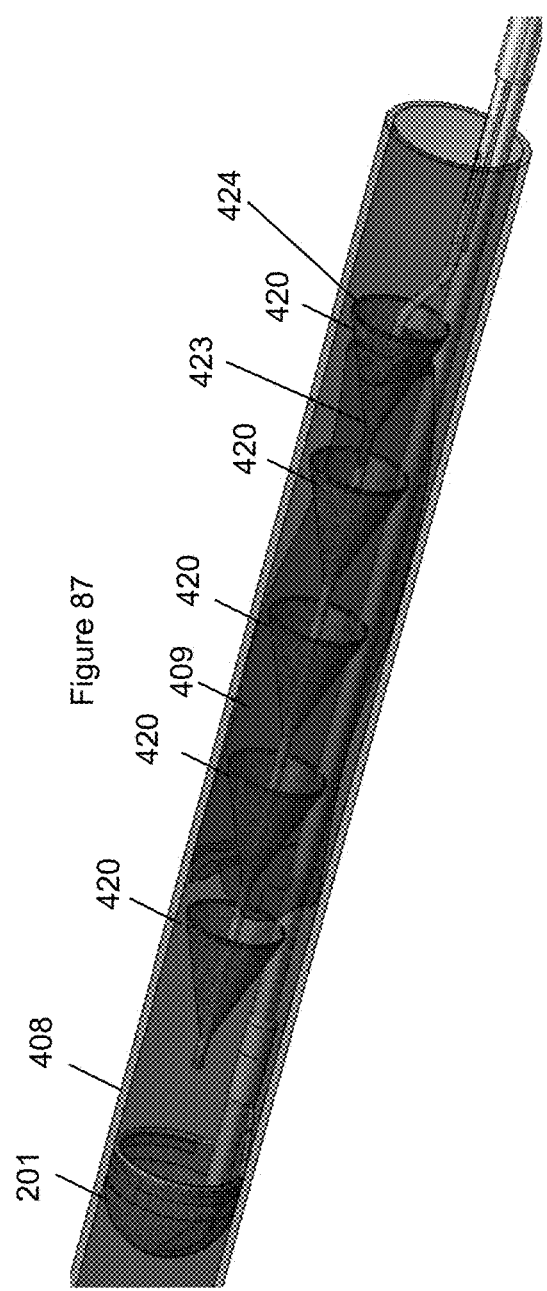

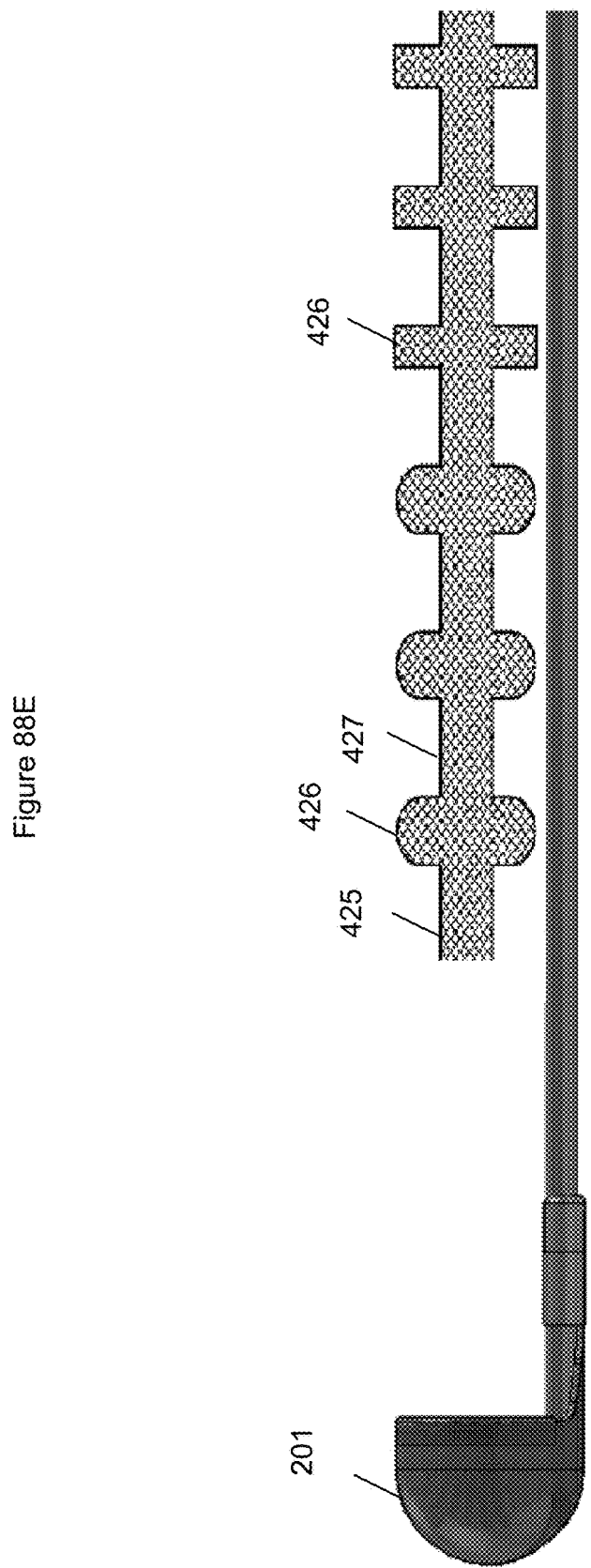

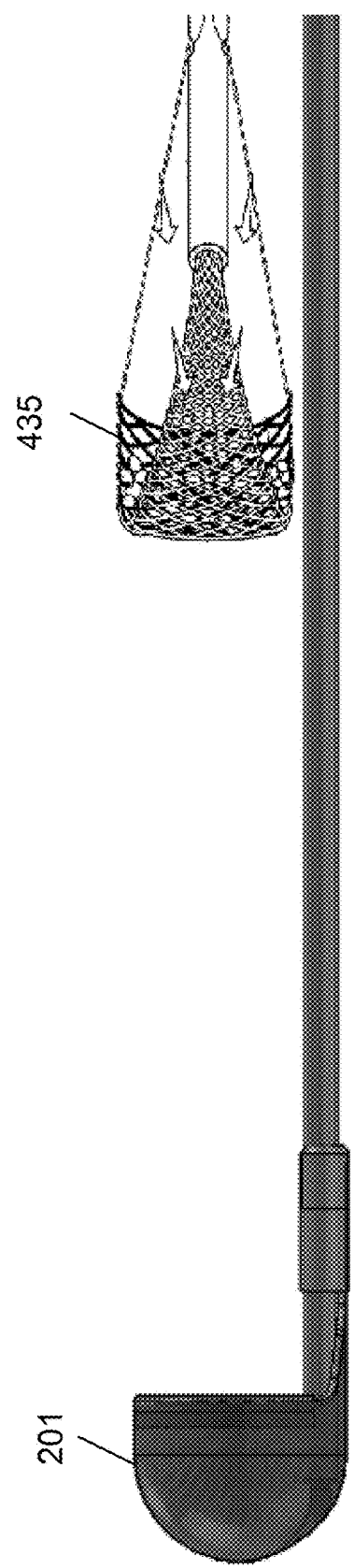

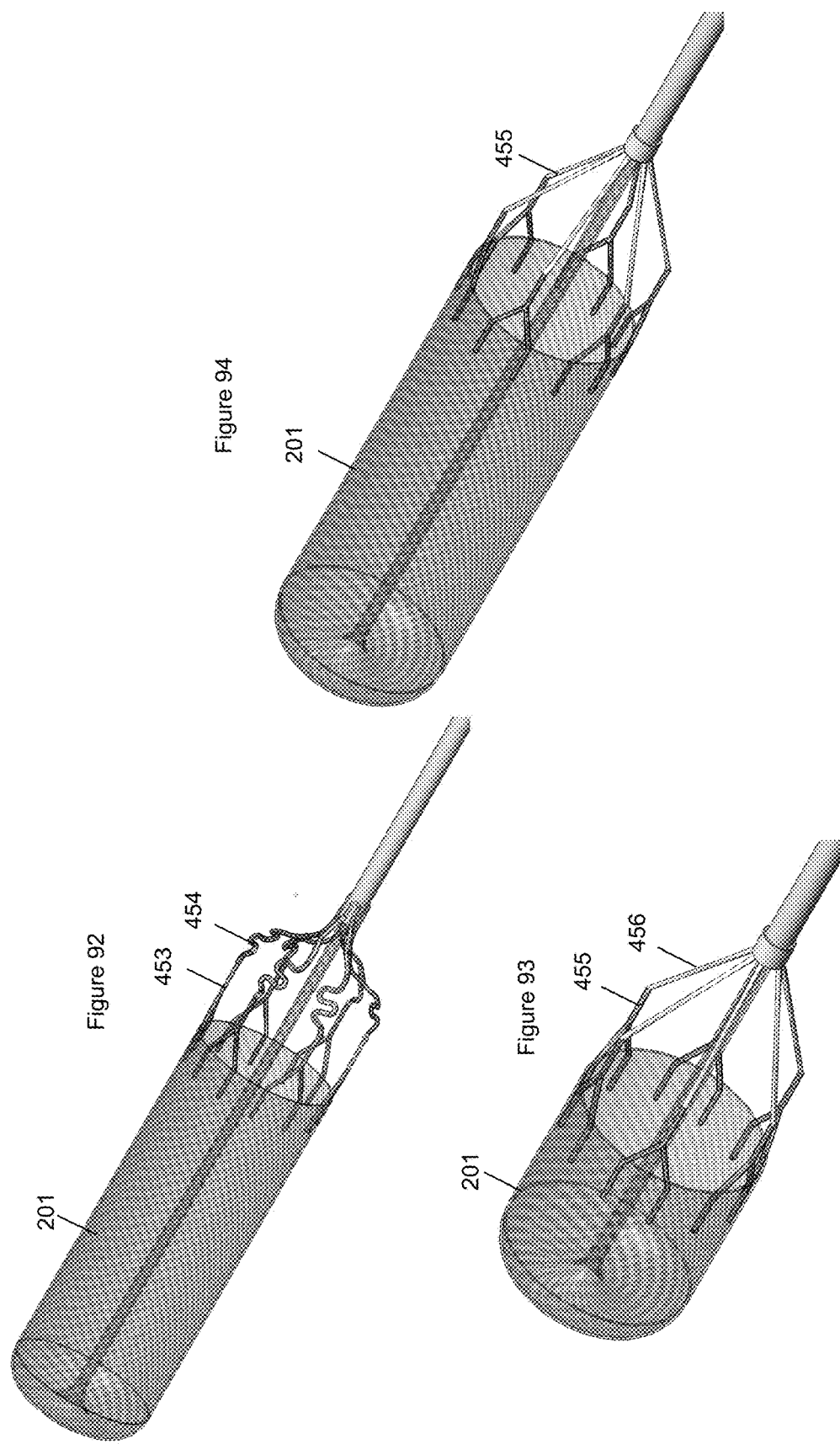

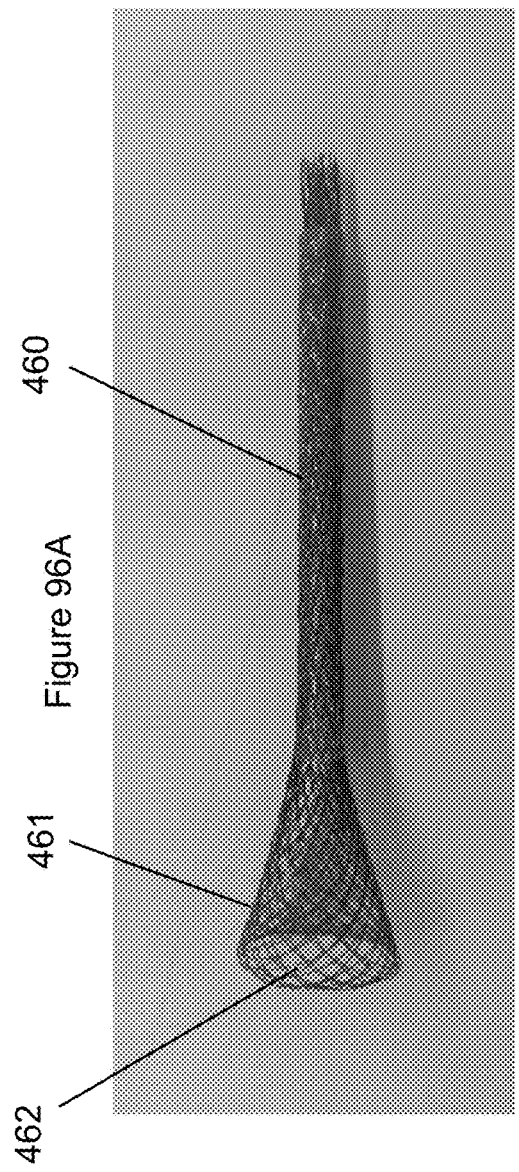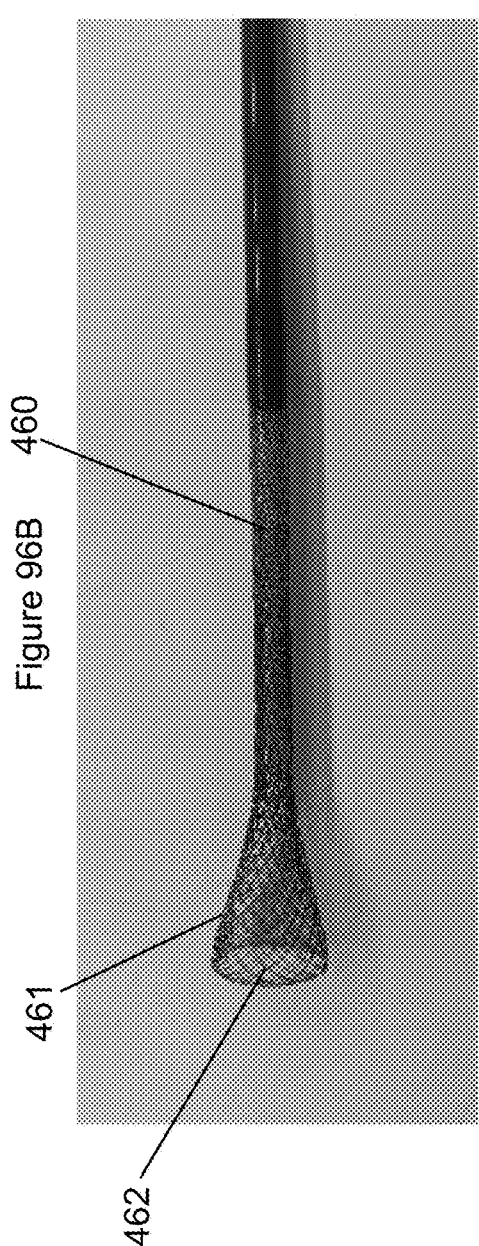

AXIAL LENGTHENING THROMBUS CAPTURE SYSTEM

PRIORITY CLAIM

This application claims the benefit under 35 U.S.C. § 120 as a continuation application of U.S. patent application Ser. No. 15/604,531 filed on May 24, 2017, now U.S. Pat. No. 9,999,493, which is continuation-in-part application of U.S. patent application Ser. No. 15/428,076 filed on Feb. 8, 2017, now U.S. Pat. No. 9,744,024, which is a continuation-in-part application of U.S. patent application Ser. No. 15/230,109 filed on Aug. 5, 2016, now U.S. Pat. No. 9,579,116, which claims the benefit under 35 U.S.C. § 119(e) as a nonprovisional application of each of U.S. Provisional App. Nos. 62/202,074 filed on Aug. 6, 2015, 62/273,418 filed on Dec. 30, 2015, and 62/345,863 filed on Jun. 6, 2016. Each of the aforementioned priority applications is hereby incorporated by reference in their entireties.

BACKGROUND

Field of the Invention

The invention relates to, in some aspects, systems and methods to remove materials of interest, including blood clots, from a body region, including but not limited to the circulatory system for the treatment of pulmonary embolism (PE), deep vein thrombosis (DVT), cerebrovascular embolism, and other vascular occlusions.

Description of the Related Art

It is understood that undesirable materials such as blood clots (which could be referred to as thrombi, thromboemboli, or emboli herein) in the blood vessels may partially or completely occlude blood vessels in areas of the coronary, cerebrovascular, pulmonary, peripheral venous, and peripheral arterial circulation resulting in myocardial infarction, stroke, pulmonary embolism, deep vein thrombosis, and infarction of an extremity respectively.

Various therapies and devices are known to either dissolve, debulk and/or aspirate the thromboemboli. For instance, anticoagulant agents such as heparin and warfarin help stabilize blood clots and prevent further forming of clots while thrombolytic agents such as urokinase, streptokinase, and tPA assist in dissolving blood clots. These agents can be delivered via systemic infusion or catheter-based infusion to the intended location. While thrombolytic agents can be effective in dissolving blood clots, they require a long time duration in order for the agents to dissolve the blood clots; thus patients may need to remain in the hospital intensive care unit (ICU) during thrombolytic infusion. Relatively long lengths of stay can increase healthcare costs significantly. A major limitation for these thrombolytic agents is that they can potentially cause intracranial, gastrointestinal, retroperitoneal, and pericardial bleeding, among other sites, which can be often life-threatening and cause significant morbidity and mortality risks.

Mechanical debulking and/or aspiration devices can be used to remove the obstruction. These mechanical techniques can either macerate, aspirate, or a combination thereof in order to remove the blood clots. An advantage of mechanical therapy is that it can remove thrombus directly from the blockage area and immediately eliminates the obstruction and may be superior to thrombolytic agents in some cases. However, current mechanical therapies have some major limitations. There is minimal to no flow during the procedure thus there is little time before patients may become hemodynamically instable. The debris removed from mechanical treatment can travel distally creating additional embolization. The small size devices are unable to remove large amount of blood clots in short time periods thus patients may become hemodynamically instable.

Catheter-based removal of blood clots from larger blood vessels (e.g., pulmonary arteries) have had limited success compared to smaller blood vessels (e.g., coronary arteries). Catheter pulmonary embolectomy is where pulmonary emboli are removed percutaneously using several techniques. Fragmentation thrombectomy breaks blood clots into smaller pieces, most of which travel further downstream, resulting in distal embolization. It is sometimes used in combination with thrombolytics. With the rheolytic thrombectomy, high velocity saline jets create a Venturi effect and draw the fragments of the clot into the catheter. This method poses risk of hemolysis. Finally the aspiration techniques draw the clot into a catheter via suction. All of these techniques rely on the catheter used to remove the clots from blood vessels. The users use small catheters to remove or break up large amounts of blood clot. This procedure is therefore time-consuming and inefficient. Once the blood clots are broken into small pieces, the debris can migrate distally and create unwanted emboli. Rheolytic therapy poses the risk of hemolysis. Additionally, the ability to suction is limited due the small catheter size suctioning large emboli. These limitations cause in some cases unnecessary duress to the user and risk to the patient.

Catheter-based removal of blood clots in general also has a major limitation when distal working space within a body lumen is limited. Conventional devices may require full axial and/or radial deployment and expansion to be functional, and as such flexibility to use such devices for a variety of clinical situations involving differing clot or other material sizes to be removed can be very limited. Therefore, conditions where there is limited distal space of blood vessels can render these conventional devices ineffective.

It is evident that all of the therapeutic options available to patients with blood clots or other undesirable material in blood vessels and other body lumens have limitations. Anticoagulation only limits propagation of clots but does not actively remove it. Thrombolytic therapy poses a risk of major bleeding. Catheter embolectomy is not effective to manage removal of material in large vessels. Additionally, these devices require distal space to fully deploy to be functional thus ineffective in tight distal spaces. Surgical embolectomy can be highly effective but highly invasive, and has a high rate of morbidity and mortality. There is a need for a direct mechanical treatment that is as or more effective as surgical embolectomy removing large blood clots but can be performed using endovascular techniques and restore immediate blood flow, and cause a lower incidence of complications.

SUMMARY

In some embodiments, disclosed herein is a capture system for selected materials within a body. The capture system can include a capture assembly configured to isolate unwanted material, e.g., a blood clot that can include a shape memory body such as made of, for example, a mesh material and having a distal end connected to a capture guide having a distal opening. The shape memory body can further include a proximal end connected to a first shaft, and a tubular sidewall between the proximal end and the distal end. The capture assembly can be configured to expand the capture guide and the distal opening end when the shape memory body proximal end is compressed in the delivery system. The shape memory body can be movable from a first configuration having a first axial length and a second configuration having a second axial length. The shape memory body can be configured to roll out, invert, evert, and/or variably lengthen proximally or distally from the first configuration to the second configuration. The second axial length can be different from the first axial length. The width of the capture assembly can, in some cases not substantially change from the first configuration to the second configuration. The capture system can also include a control line configured to independently move the capture assembly from the first configuration to the second configuration. The first shaft can extend within the longitudinal axis of the capture assembly.

In some embodiments, disclosed herein is a material, e.g., a clot capture system. The system can include a first, outer tubular shaft comprising a central lumen, the first outer tubular shaft comprising a proximal portion and a distal portion, the distal portion more radially expandable than the proximal portion. The system can also include a second tubular shaft configured to be positioned within the central lumen of the first shaft. The system can also include a third tubular shaft configured to be positioned within a central lumen of the second shaft. The shape memory tubular body can include a first end, a second end, and an axial length therebetween, the first end having a proximal-facing opening and a ring-shaped capture guide attached to a circumference of the proximal-facing opening, the capture guide operably attached to the second tubular shaft, the second end attached to an outer wall of the third tubular shaft. The shape memory tubular body can be compressed within the central lumen of the second tubular shaft in a first delivery configuration. The shape memory tubular body can be transformable to a second configuration in which the first end and the capture guide is radially expanded up to a dynamic fold point, but the second end and a segment of the shape memory tubular body extends in a different direction, such as proximally past the dynamic fold point, and remains radially compressed within the central lumen of the second tubular shaft and the second end is positioned proximal to the first end and the shape memory tubular body has a first expanded axial length. The shape memory tubular body can be transformable to a third configuration in which the shape memory tubular body has a second expanded axial length greater than the first expanded axial length, and a width of the shape memory tubular shaft along its second expanded axial length is the same or substantially the same as a width of the shape memory tubular shaft along its first expanded axial length. The first tubular shaft can be configured to be reversibly coupled with respect to the second tubular shaft in the delivery configuration and axially movable with respect to the third tubular shaft in the second configuration. In some embodiments, the second expanded axial length is about or at least about, for example, 105%, 110%, 115%, 120%, 125%, 130%, 150%, 200%, 250%, 300%, 350%, 400%, 450%, 500%, or more of the first axial length. The capture system of claim 1, wherein the shape memory body can be porous, semi-permeable, and non-porous, and include nitinol braided, woven, or non-woven mesh, or nitinol wire. In some embodiments, the tubular body is coated with a hydrophilic or hydrophobic agent, or noncoated, and may not include a shape memory metal or material. In some embodiments, the tubular mesh body is configured to invert, evert, or roll out with respect to the first, second, and/or third shaft. The system can also include a control line extending proximally from the capture guide, either terminating on a sleeve on one of the shafts or extending proximally to the proximal end of the system. In some embodiments, the system includes a suction element configured to operably connect with the proximal opening of the shape memory tubular body. The system can also include a mechanical thrombectomy element, such as a macerator. The system can also include a filter collection chamber configured to collect and filter blood obtained from the suction element.

The system can further include an expanding guide catheter configured to receive the capture assembly in the form of a kit. The expanding guide element can include an open funnel distal tip, that can be porous in some embodiments to allow flow around the funnel distal tip.

In some embodiments, disclosed herein is a material, such as a clot capture system that can include a first, outer tubular shaft comprising a central lumen; a second tubular shaft configured to be positioned within the central lumen of the first shaft, the second tubular shaft comprising a proximal portion and a distal portion, the distal portion more radially expandable than the proximal portion; a third tubular shaft configured to be positioned within a central lumen of the second shaft; a tubular mesh comprising a first end, a second end, and an axial length therebetween, the first end having a proximal-facing opening and a ring-shaped capture guide attached to a circumference of the proximal-facing opening, the capture guide operably attached to the second tubular shaft, the second end attached to an outer wall of the third tubular shaft. The tubular mesh can be compressed within the central lumen of the second tubular shaft in a delivery configuration. The tubular mesh can also be transformable to a second configuration in which the first end and the capture guide is radially expanded but the second end and a portion, such as a minority, half, or a majority of the tubular mesh remains radially compressed within the central lumen of the second tubular shaft and the second end is positioned proximal to the first end and the tubular mesh has a first expanded axial length. The tubular mesh can be transformable to a third configuration in which the tubular mesh has a second expanded axial length greater than the first expanded axial length, wherein a width of the tubular mesh along its second expanded axial length is substantially the same as a width of the tubular mesh along its first expanded axial length, wherein the third tubular shaft extends distally through the proximal end opening as well as the second axial expanded length of the shape memory tubular body. In some embodiments, the tubular mesh is not under tension or substantially under tension in the second configuration or the third configuration defining an axial working range of the tubular mesh.

In some embodiments, a material, such as a clot capture system includes a first, outer tubular shaft comprising a central lumen; a second tubular shaft configured to be positioned within the central lumen of the first shaft, the second tubular shaft comprising a proximal portion and a distal portion, the distal portion more radially expandable than the proximal portion; a third tubular shaft configured to be positioned within a central lumen of the second shaft; a tubular body that may include shape memory materials that includes a first end, a second end, and an axial length therebetween, the first end having a proximal-facing opening and a ring-shaped capture guide attached to a circumference of the proximal-facing opening, the capture guide operably attached to the second tubular shaft via a sleeve circumscribing a portion of the second tubular shaft, the second end attached to an outer wall of the third tubular shaft. The shape memory tubular body can be compressed within the central lumen of the second tubular shaft in a delivery configuration. The shape memory tubular body can be transformable to a second configuration by axial movement of the second tubular shaft with respect to the first tubular shaft, in which the first end and the capture guide is radially expanded but the second end and a segment of the shape memory tubular body remains radially compressed within the central lumen of the second tubular shaft and the second end is positioned proximal to the first end and the shape memory tubular mesh body has a first expanded axial length. The shape memory tubular body can be transformable to a third configuration by movement of the second tubular shaft with respect to the third tubular shaft, in which the shape memory tubular body has a second expanded axial length greater than the first expanded axial length, wherein a width of the shape memory tubular shaft along its second expanded axial length is substantially the same as a width of the shape memory tubular shaft along its first expanded axial length, wherein the third tubular shaft extends distally through the proximal end opening as well as the second axial expanded length of the shape memory tubular body. The shape memory tubular body can, in some cases, be transformable to a fourth configuration by movement of the second tubular shaft with respect to the third tubular shaft. The shape memory tubular body can have a third expanded axial length greater than the second expanded axial length, wherein a width of the shape memory tubular shaft along its third expanded axial length is less than the width of the shape memory tubular shaft along its second expanded axial length. The clot capture system can also include a sleeve that includes a metal or polymer, and the sleeve can be partially or fully radiopaque or radiolucent under fluoroscopy or other imaging.

Also disclosed herein is a method of performing a thrombectomy. The method can include, for example, accessing the interior of a blood vessel; advancing a thrombus capture device comprising a capture assembly through the blood vessel; positioning the thrombus capture device such that a distal end of the device is distal to the thrombus; actuating the capture assembly to isolate the thrombus within the capture device, wherein the capture assembly is movable from a first configuration having a first axial length and a second configuration having a second axial length, the second axial length being different from the first axial length, wherein the width of the capture assembly does not substantially change from the first configuration to the second configuration; and suctioning, macerating, and/or mechanically removing the thrombus.

In some embodiments, a method of performing a thrombectomy can include, for example, accessing the interior of a blood vessel; advancing an expanding guiding catheter through the blood vessel; positioning the expanding guiding catheter such that a distal end of the device is proximal to a thrombus; retracting the expanding guide catheter outer member to expand a funnel tip and exposing an expandable inner member; advancing a thrombus capture device comprising a capture assembly through the expanding guide catheter; positioning the thrombus capture device such that a distal end of the device is distal to or within the thrombus; and actuating the capture assembly to isolate the thrombus within the capture device. The capture assembly can be movable from a first configuration having a first axial length and a second configuration having a second axial length, the second axial length being different from the first axial length. The width of the capture assembly may not substantially change from the first configuration to the second configuration. The method can also include retracting the capture assembly with the thrombus into an expanding guide catheter funnel tip and expandable inner body. The method can also include axially lengthening the thrombus capture device distally and retracting the thrombus into the funnel tip of the expanding guide catheter. The method can further include radially shortening the thrombus capture device to compress the thrombus and promote removal of the thrombus.

In some embodiments, disclosed herein is a clot capture system that can include a capture assembly configured to isolate a blood clot. The system can include a shape memory body that has a distal end connected to a capture guide comprising a distal or proximal opening. The shape memory body can also include a proximal end connected to a first shaft, and a sidewall between the proximal end and the distal end. The capture guide and the distal zone of the shape memory body opening end can also be fully or partially recaptured inside the outer sheath. The capture assembly can be configured to radially expand the capture guide and a distal zone of the shape memory body opening end while the shape memory body proximal end remains compressed in the delivery configuration. The capture assembly can be movable from a first configuration having a first axial length to a second configuration having a second axial length. The shape memory body can be configured to roll out, invert, evert, and/or variably lengthen proximally from the first configuration to the second configuration. The second axial length can be different from the first axial length. The width of the capture assembly can in some cases not substantially change from the first configuration to the second configuration.

Also disclosed herein is a capture assembly configured to isolate a blood clot including a shape memory body including a proximal end and a distal end connected to a capture guide including a distal opening, a proximal end connected to a shaft, and a sidewall between the proximal end and the distal end. The capture assembly can be configured to expand the capture guide and the distal shape memory body opening end while the shape memory body proximal end is compressed in the delivery configuration between a first shaft and a second shaft, and movable from a first configuration having a first axial length and a second configuration having a second axial length. The shape memory body can be configured to roll out/unroll, invert, evert, and/or variably lengthen proximally from the first configuration to the second configuration. The second axial length can be different from the first axial length. In some cases, the width of the capture assembly does not substantially change from the first configuration to the second configuration. Furthermore, the shape memory body can be fully or partially recaptured inside the outer sheath once deployed. The system can also include a sleeve coupled a control line connected to the second shaft configured to move the capture assembly from the first configuration to the second configuration. The first shaft and the second shaft can be off-axis with respect to the capture assembly.

Also disclosed herein is a method of performing a thrombectomy. The method can include any number of the following: accessing the interior of a blood vessel; advancing a thrombus capture device comprising a capture assembly through the blood vessel; positioning the thrombus capture device such that a distal end of the device is distal to the thrombus; actuating the capture assembly to isolate the thrombus within the capture device, wherein the capture assembly is movable from a first configuration having a first axial length and a second configuration having a second axial length, the second axial length being different from the first axial length, wherein the width of the capture assembly does not substantially change from the first configuration to the second configuration; and suctioning the thrombus.

In some embodiments, the methods can include any number of the following: accessing the interior of a blood vessel; advancing an expanding guiding catheter through the blood vessel; positioning the expanding guiding catheter such that a distal end of the device is proximal to a thrombus; retracting the expanding guide catheter outer member to expand a funnel tip and exposing an expandable inner member; advancing a thrombus capture device comprising a capture assembly through the expanding guide catheter; positioning the thrombus capture device such that a distal end of the device is distal to or within the thrombus; actuating the capture assembly to isolate the thrombus within the capture device, wherein the capture assembly is movable from a first configuration having a first axial length and a second configuration having a second axial length, the second axial length being different from the first axial length wherein the width of the capture assembly does not substantially change from the first configuration to the second configuration; and retracting the thrombus into an expanding guide catheter funnel tip and expandable inner body. In some embodiments, the capture guide is first recaptured into the outer sheath of the delivery catheter and then retract into the expanding guide catheter funnel tip and expandable inner body.

In some embodiments, disclosed herein is a clot capture system. The system can include a first tubular member comprising a central lumen. The system can include a second tubular member. The system can include a shape memory tubular body comprising a first end, a second end, and an axial length therebetween, the first end having an end opening, the second end attached to the second tubular member. In some embodiments, at least part of the shape memory tubular body is compressed within the central lumen of the first tubular shaft in a first delivery configuration. In some embodiments, the shape memory tubular body is transformable to a second configuration in which the first end is radially expanded while the second end and a majority of the shape memory tubular body remains radially compressed within the central lumen of the first tubular shaft and the second end is positioned proximal to the first end and the shape memory tubular body has a first expanded axial length. In some embodiments, the shape memory tubular body is transformable to a third configuration via movement of the first tubular shaft with respect to the second tubular shaft in which the shape memory tubular body has a second expanded axial length greater than the first expanded axial length, wherein a width of the shape memory tubular body along its second expanded axial length is substantially the same as a width of the shape memory tubular body along its first expanded axial length.

The system can include a capture guide attached to the first end opening. In some embodiments, the capture guide at least partially circumscribes the first end opening. In some embodiments, the capture guide fully partially circumscribes the first end opening. The system can include an expandable cover element circumscribing the capture guide. In some embodiments, the expandable cover element is inflatable. The system can include a control line extending proximally from the capture guide. The system can include a sleeve attached to the first tubular shaft and the first end opening of the shape memory tubular body. In some embodiments, the shape memory tubular body is configured to invert, evert, or roll out with respect to the first tubular shaft or the second tubular shaft. In some embodiments, the end opening of the shape memory tubular body is proximal-facing. In some embodiments, the shape memory tubular body comprises a mesh. In some embodiments, the shape memory tubular body is configured to allow fluid flow therethrough. In some embodiments, the second tubular member comprises a central lumen. The system can include an expanding guide element configured to receive the capture assembly. In some embodiments, the expanding guide element comprises an open funnel distal tip. In some embodiments, the open funnel distal tip is porous to allow flow. In some embodiments, the shape memory tubular body has a maximal length of between about 0.5 cm and about 125 cm. In some embodiments, the shape memory tubular body is transformable to a fourth configuration wherein the shape memory tubular body has a third axial expanded length greater than the second axial expanded length, wherein a width of the shape memory tubular body along its third expanded axial length is less than the width of the shape memory tubular body along its second expanded axial length.

In some embodiments, disclosed herein is a system for capturing material of interest within a body lumen. The system can include a first tubular member comprising a central lumen. The system can include a second tubular member. The system can include a shape memory tubular body comprising a first end, a second end, and an axial length therebetween, the first end having an end opening, the second end attached to an outer wall of the second tubular member. In some embodiments, the shape memory tubular body is compressed within the central lumen of the first tubular shaft in a first delivery configuration. In some embodiments, the shape memory tubular body is transformable to a second configuration in which the first end opening and a first segment of the shape memory tubular body extending axially in a first direction from the first end opening is radially expanded to a fold point, while a second segment of the shape memory tubular body extends axially from the fold point to the second end of the shape memory tubular body in a second direction opposite the first direction, the second segment relatively radially compressed with respect to the first segment, the second end positioned proximal to the first end. In some embodiments, the shape memory tubular body is transformable to a third configuration via movement of the first tubular shaft with respect to the second tubular shaft in which the axial length of the first segment increases by a first amount, the shape memory tubular body has a second expanded axial length greater than the first expanded axial length, wherein a width of the shape memory tubular body along its second expanded axial length is substantially the same as a width of the shape memory tubular body along its first expanded axial length.

In some embodiments, disclosed herein is a clot capture system. The system can include a first tubular member comprising a central lumen. The system can include a second tubular member. The system can include a shape memory tubular body comprising a first end, a second end, and an axial length therebetween, the first end having an end opening, the second end attached to an outer wall of the second tubular member. In some embodiments, the shape memory tubular body is compressed within the central lumen of the first tubular shaft in a first delivery configuration. In some embodiments, the shape memory tubular body is transformable to a second configuration in which the first end opening and a first segment of the shape memory tubular body extending axially in a first direction from the first end opening is radially expanded to a fold point, while a second segment of the shape memory tubular body extends axially from the fold point in a second direction opposite the first direction to the second end, the second segment radially compressed with respect to the first segment, the second end positioned proximal to the first end. In some embodiments, the shape memory tubular body is transformable to a third configuration via movement of the first tubular shaft with respect to the second tubular shaft in which the axial length of the first segment increases by a first amount, the shape memory tubular body has a second expanded axial length greater than the first expanded axial length, wherein a width of the shape memory tubular body along its second expanded axial length is substantially the same as a width of the shape memory tubular body along its first expanded axial length.

In some embodiments, disclosed herein is a clot capture system. The system can include an outer sheath comprising a central lumen. The system can include a dual lumen shaft configured to be positioned within the central lumen of the outer sheath. The system can include an inner pusher configured to be positioned within a first lumen of the dual lumen shaft. The system can include an anchor pusher configured to be positioned within a second lumen of the dual lumen shaft. The system can include an anchor coupled to the anchor pusher. The system can include a shape memory tubular body comprising a first end, a second end, and an axial length therebetween, the first end having an opening and a capture guide attached to a portion of the opening. In some embodiments, the shape memory tubular body and the anchor are compressed in a first configuration. In some embodiments, the shape memory tubular body is transformable to a second configuration in which the first end and the capture guide are radially expanded but the second end and a majority of the shape memory tubular body remains radially compressed within the lumen of the dual lumen shaft and the shape memory tubular body has a first expanded axial length with a first cross-section, wherein the first cross-section is substantially similar to the cross-section of the capture guide. In some embodiments, the shape memory tubular body is transformable to a third configuration in which the shape memory tubular body has a second expanded axial length greater than the first expanded axial length, wherein the shape memory tubular body encapsulates the anchor in the third configuration.

The system can include, for example, one, two, or more anchors. The anchors can have any desired configuration to stabilize or associate with a clot to facilitate removal, including a J-hook shape in some cases. The anchors can penetrate a clot or other material to be captured in some embodiments, or do not penetrate but rather circumscribe or otherwise stabilize or reversibly secure at least a portion of the clot or other material to be captured. In some embodiments, the anchors have a central longitudinal axis that is coaxial. The system can include three anchors, or more. In some embodiments, the cross-section of the anchor is round, ovoid, square, rectangular, or another cross section. In some embodiments, the anchor comprises nitinol. In some embodiments, the anchor forms an angle with the anchor pusher, wherein the angle is approximately 90 degrees. In some embodiments, the anchor forms an angle with the anchor pusher, wherein the angle is approximately 45 degrees. In some embodiments, the anchor forms an angle with the anchor pusher, wherein the angle is between 5 degrees and 135 degrees. In some embodiments, the diameter of the anchor is less than the diameter of the shape memory tubular body when radially expanded. In some embodiments, a portion of the anchor pusher is crescent shaped. In some embodiments, the capture guide comprises nitinol. In some embodiments, the capture guide comprises a central longitudinal axis and wherein the dual lumen shaft is offset from the central longitudinal axis. In some embodiments, the second end of the shape memory tubular body is coupled to the inner pusher. In some embodiments, the capture guide forms a continuous loop. In some embodiments, the capture guide forms a non-continuous loop.

In some embodiments, disclosed herein is a clot capture system. The system can include an inner pusher. The system can include a shape memory tubular body comprising a first end, a second end, and an axial length therebetween, the first end having an opening and a capture guide attached to at least a portion of the opening, the second end coupled to the inner pusher. In some embodiments, the shape memory tubular body and the capture guide are compressed in a first configuration. In some embodiments, the shape memory tubular body is transformable to a second configuration in which the first end and the capture guide are radially expanded but the second end and a majority of the shape memory tubular body remains radially compressed and the shape memory tubular body has a first expanded axial length with a first cross-section, wherein the first cross-section is substantially similar to the cross-section of the capture guide. In some embodiments, the shape memory tubular body is transformable to a third configuration in which the shape memory tubular body has a second expanded axial length greater than the first expanded axial length. In some embodiments, the capture guide forms a continuous loop. In some embodiments, the capture guide forms a non-continuous loop.

Also disclosed herein is a method of using a clot capture system. The method can include any number of the following: positioning a system near a blood clot in the first configuration; transforming the shape memory tubular body to the second configuration; and transforming the shape memory tubular body to the third configuration to encapsulate the clot. The system can include an inner pusher. The system can include a shape memory tubular body comprising a first end, a second end, and an axial length therebetween, the first end having an opening and a capture guide attached to at least a portion of the opening, the second end coupled to the inner pusher. In some embodiments, the shape memory tubular body and the capture guide are compressed in a first configuration. In some embodiments, the shape memory tubular body is transformable to a second configuration in which the first end and the capture guide are radially expanded but the second end and a majority of the shape memory tubular body remains radially compressed and the shape memory tubular body has a first expanded axial length with a first cross-section, wherein the first cross-section is substantially similar to the cross-section of the capture guide. In some embodiments, the shape memory tubular body is transformable to a third configuration in which the shape memory tubular body has a second expanded axial length greater than the first expanded axial length. In some embodiments, the blood clot is within the CNS.

Also disclosed herein is a method of using a clot capture system. The method can include any number of the following: positioning a system near a blood clot; transforming the shape memory tubular body to the second configuration; expanding the anchor; and transforming the shape memory tubular body to the third configuration to encapsulate the anchor. The system can include an outer sheath comprising a central lumen. The system can include a dual lumen shaft configured to be positioned within the central lumen of the outer sheath. The system can include an inner pusher configured to be positioned within a first lumen of the dual lumen shaft. The system can include an anchor pusher configured to be positioned within a second lumen of the dual lumen shaft. The system can include an anchor coupled to the anchor pusher. The system can include a shape memory tubular body comprising a first end, a second end, and an axial length therebetween, the first end having an opening and a capture guide attached to a portion of the opening. In some embodiments, the shape memory tubular body and the anchor are compressed in a first configuration. In some embodiments, the shape memory tubular body is transformable to a second configuration in which the first end and the capture guide are radially expanded but the second end and a majority of the shape memory tubular body remains radially compressed within the lumen of the dual lumen shaft and the shape memory tubular body has a first expanded axial length with a first cross-section, wherein the first cross-section is substantially similar to the cross-section of the capture guide. In some embodiments, the shape memory tubular body is transformable to a third configuration in which the shape memory tubular body has a second expanded axial length greater than the first expanded axial length, wherein the shape memory tubular body encapsulates the anchor in the third configuration. In some embodiments, deploying the anchor comprises securing the anchor within the clot. In some embodiments, transforming the shape memory tubular body to the third configuration to encapsulate the anchor further comprises encapsulating the clot. In some embodiments, the blood clot is a neurological blood clot.

In some embodiments, disclosed herein is a clot capture system. The system can include a first tubular member comprising a central lumen. The system can include a second tubular member. The system can include a plurality of axially spaced-apart anchors extending radially outwardly from the first tubular member or the second tubular member. The system can include a shape memory tubular body comprising a first end, a second end, and an axial length therebetween, the first end having an end opening, the second end attached to the second tubular member. In some embodiments, at least part of the shape memory tubular body is compressed within the central lumen of the first tubular shaft in a first delivery configuration. In some embodiments, the shape memory tubular body is transformable to a second configuration in which the first end is radially expanded while the second end and a majority of the shape memory tubular body remains radially compressed within the central lumen of the first tubular shaft and the second end is positioned proximal to the first end and the shape memory tubular body has a first expanded axial length. In some embodiments, the shape memory tubular body is transformable to a third configuration via movement of the first tubular shaft with respect to the second tubular shaft in which the shape memory tubular body has a second expanded axial length greater than the first expanded axial length, wherein a width of the shape memory tubular body along its second expanded axial length is substantially the same as a width of the shape memory tubular body along its first expanded axial length.

BRIEF DESCRIPTION OF THE FIGURES

FIGS. 15A-C illustrate an embodiment of the ALTC system, a distal portion of the ALTC System and a proximal portion of the ALTC System respectively.

FIGS. 17A-D illustrate different configurations of the ALTC device, according to some embodiments of the invention.

FIGS. 19A-C illustrates an embodiment of an axially-lengthening thrombus capture system, configured to allow the guidewire to distally exit the system prior to exiting the luer port at the proximal end of the system.

FIGS. 49A and 49B illustrate another embodiment of the axial lengthening thrombus capture device wherein the guidewire lumen and capture catheter is offset to the longitudinal axis of the axial lengthening thrombus capture device, according to some embodiments of the invention.

FIGS. 50A-50G illustrate an embodiment of the retrieval of thrombus into the expanding guide catheter wherein the ALTC device lengthens distally and creates additional space and the thrombus is redistributed and enable better retrieval into the expanding guide catheter. The funnel tip and expanding section of the expanding guide catheter also facilitate the ease of thrombus retrieval.

FIG. 53 illustrates the distal end of the capture device of the system of FIG. 51 in an initial deployed configuration.

FIG. 54 illustrates the distal end of the capture device of the system of FIG. 51 in a second configuration.

FIG. 55 illustrates the distal end of the capture device of the system of FIG. 51 in a third configuration.

FIG. 61 illustrates an embodiment of a system.

FIG. 62 illustrates a distal end of the capture device system of the system of FIG. 61.

FIG. 63 illustrates a proximal end of the system of FIG. 61.

FIG. 64 illustrates an anchor assembly of the system of FIG. 61.

FIG. 68A illustrates the capture device of the system of FIG. 61 in an initial deployed configuration.

FIG. 68B illustrates the capture device and first anchor release of the system of FIG. 61 when the outer sheath retracts proximally.

FIG. 68C illustrates the capture device, first anchor, and second anchor release of the system of FIG. 61 when the outer sheath is retracted.

FIG. 68D illustrates the capture device, first anchor, second anchor, and third anchor release of the system of FIG. 61 when the outer sheath is retracted.

FIG. 69A illustrates the capture device of the system of FIG. 61 in an initial deployed configuration and the anchors are fully released.

FIG. 69B illustrates the capture device of the system of FIG. 61 lengthened proximally to encapsulate the first anchor.

FIG. 69C illustrates the capture device of the system of FIG. 61 lengthened proximally to encapsulate the anchors.

FIGS. 70A and 70B illustrate views of an embodiment of a pusher lock system.

FIG. 73 illustrates an embodiment of an anchor.

FIG. 74 illustrates an embodiment of an anchor.

FIG. 75 illustrates a distal end of a capture device system including the anchor in a vessel of FIG. 73.

FIG. 76A illustrates the capture device of the system of FIG. 75 in an initial deployed configuration and the anchor is fully expanded.

FIG. 76B illustrates the capture device of the system of FIG. 75 lengthened proximally to encapsulate a portion of the anchor.

FIG. 76C illustrates the capture device of the system of FIG. 75 lengthened proximally to encapsulate the anchor.

FIG. 77A illustrates the capture device of the system of FIG. 75 in an initial deployed configuration and the anchor is fully expanded.

FIG. 77B illustrates the capture device of the system of FIG. 75 lengthened proximally to encapsulate a portion of the anchor.

FIG. 77C illustrates the capture device of the system of FIG. 75 lengthened proximally to encapsulate the anchor.

FIG. 81 illustrates a distal end of a capture device system including an embodiment of an anchor.

FIG. 82 illustrates a distal end of a capture device system including an embodiment of an anchor.

FIG. 86 illustrates the capture device system in a vessel of FIG. 85.

FIG. 87 illustrates a capture device system in a vessel.

FIG. 92 illustrates a distal end of a system including an embodiment of an anchor.

FIG. 93 illustrates a distal end of a system including an embodiment of an anchor.

FIG. 94 illustrates the capture device of the system of FIG. 93 lengthened proximally to encapsulate the anchor.

FIGS. 96A-96B illustrate an embodiment of an expandable guide catheter.

DETAILED DESCRIPTION

The present invention provides, in some embodiments, systems and methods that can be delivered percutaneously in a body to retrieve and removal materials including blood clots, stones/calculi, and/or foreign materials in a body lumen, including a blood vessel, such as an arterial vessel or a venous vessel within the circulatory system. The present invention can, in some embodiments, also apply to nonvascular areas to treat, for example, gallstones, kidney stones, common bile duct stones, and the like.

Figure 1:
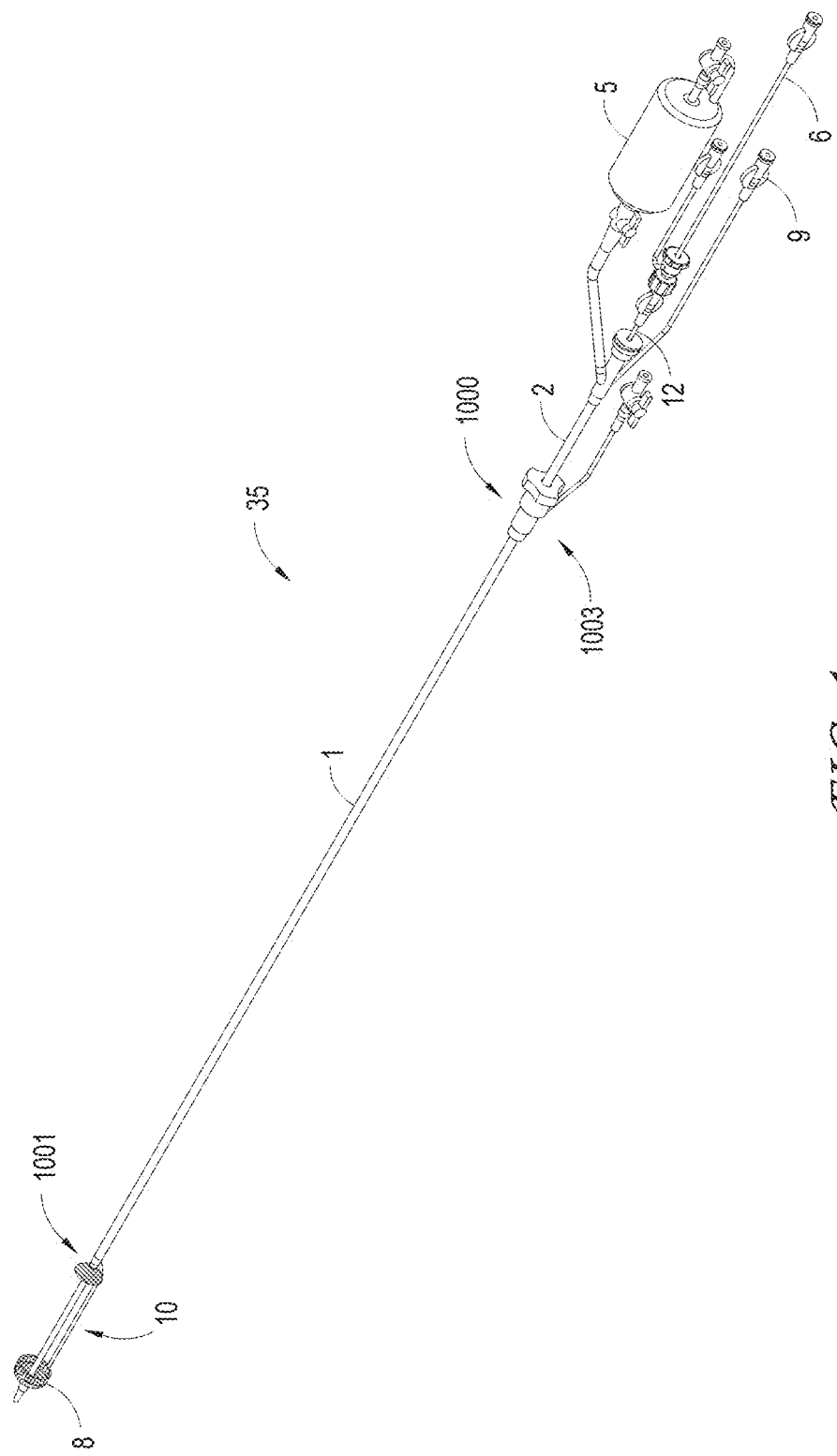
FIG. 1 illustrates examples of a catheter system, and various possible elements that can be included in a material capture system, according to some embodiments of the invention.

Systems can be delivered percutaneously, via a cut-down approach, a thoracoscopic approach, or via other approaches, for example, using a catheter system 35, of which a perspective view of an embodiment is shown in FIG. 1. FIG. 1 also illustrates examples of various possible elements that can be included in a material capture system, according to some embodiments of the invention. As illustrated in FIG. 1, included in some embodiments are any number of, such as one, two, or more of the following components: a first tubular member, such as an outer sheath 1, a second tubular member, such as a capture catheter 12, a third tubular member, such as a guidewire tube 6 an axial lengthening thrombus capture device 8, a suction catheter 2, and a filter collection chamber 5. The outer sheath 1 can, in some embodiments, be an elongate tubular member with a central lumen therethrough, and have a proximal end 1000 and a distal end 1001. The distal end 1001 of the outer sheath 1 can be operably connected to a capture device (e.g., tubular mesh 8), which can be movably axially with respect to the outer sheath 1. In some embodiments, the outer sheath 1 has a relatively rigid proximal portion and a distal portion that is more flexible than the relatively rigid proximal portion, which can be advantageous to flexibly expand if necessary to accommodate the passage of large clots and/or other materials. The proximal end 1000 of the outer sheath 1 can connect to a proximal hub 1003 that may include any number of: the suction catheter 2, capture catheter 12, guidewire tube 6, and filter collection chamber 5. Non-limiting examples of other optional elements that can be included in the system (not shown in FIG. 1) include a macerator tool (described elsewhere herein) and a discrete expanding guide catheter (described elsewhere herein. In some embodiments, the outer sheath 1 has a lumen configured to house the suction catheter 2, which in turn has a lumen configured to house the capture catheter 4, which in turn has a lumen configured to house the guidewire tube/guidewire lumen assembly 6 and the axial lengthening thrombus capture device (ALTC device) 8, which in turn has a lumen configured to house a guidewire (not shown) therethrough. An ALTC device as defined herein can include any structure, such as a net-like structure for example, configured to capture materials within a body location and axially lengthen and shorten through a working range, with or without radially shortening in width or diameter throughout that working range depending on the desired clinical result. In some embodiments, the outer sheath 1 has an inner diameter configured to house the capture catheter 12 coaxially therein, and the capture catheter 12, which in turn has a lumen configured to house the guidewire tube 6 and the body of the ALTC device 8. The ALTC device 8 can in some embodiments including a mesh net-like structure with a proximal-facing opening at one end that can be made of a shape memory metal or polymer, a non-shape memory metal such as stainless steel, or another non-shape memory fabric, embodiments of which are described in detail elsewhere herein. In some embodiments, conventional net-like structures such as used in IVC and other embolic filters can be utilized with systems and methods herein. In some embodiments, a thrombus capture device can be configured in some embodiments to axially lengthen throughout a working range, with or without radially shortening the device throughout the working range.

Figure 2:
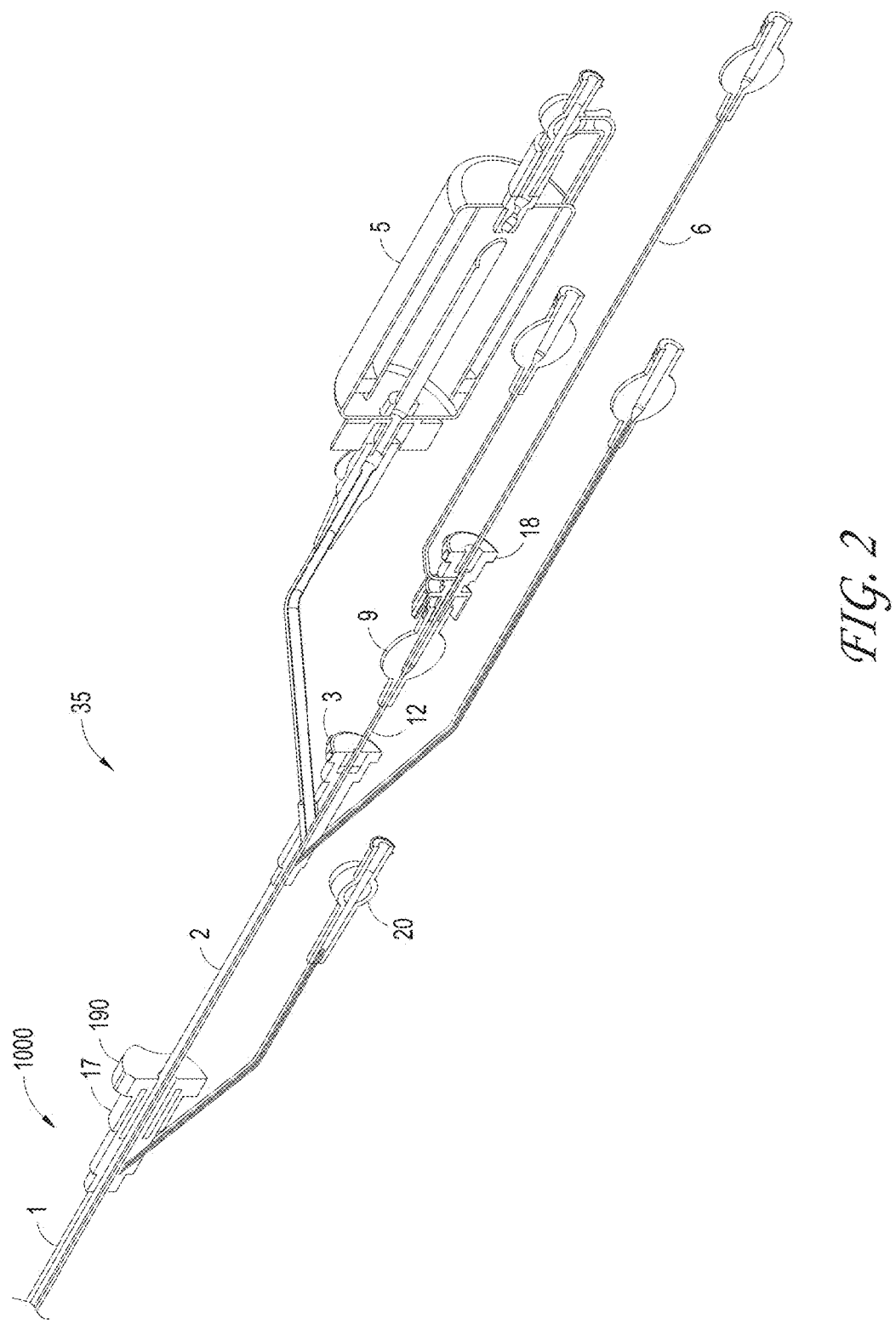
FIG. 2 illustrates a close-up view of the thrombus capture systems of FIGS. 1 and 2.

FIG. 2 illustrates a close-up view of the proximal end 1000 of the thrombus capture systems of FIG. 1. Illustrated is outer sheath 1 configured to, in some embodiments, house suction catheter 2 therethrough. Also illustrated is the proximal end of the outer sheath 1 which can terminate in a connector 17 and hemostasis seal 190, of which another tube, such as the suction catheter 2 (and/or capture catheter 4) can be inserted coaxially into. The proximal end of the suction catheter 2 can also include a connector 3 having a seal, and a lumen of which the capture catheter 12 can be inserted into. The capture catheter 4 can also include a connector with a seal 18 at its proximal end. The guidewire tube 6 with a lumen to house a guidewire therethrough can be configured to fit coaxially within the capture catheter shaft 12. Also illustrated is an optional filter collection chamber 5 with a lumen fluidly connected to a lumen of the suction catheter 2. A proximal hub 17 is also illustrated, as well as a flush port 20. In some embodiments, suction is not required (and as such a suction catheter 2 is not included in the system), and the clot or other materials can be captured either mechanically, hydraulically and/or maceration via the ALTC device 8.

Figure 3:
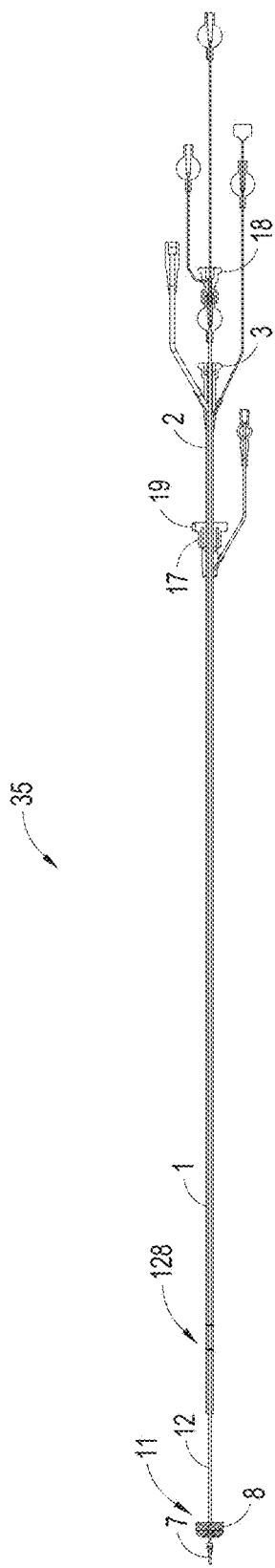
FIG. 3 illustrates an axially-lengthening thrombus capture (ALTC) system in the initial deployment configuration with the ALTC device expanded, according to some embodiments of the invention.

FIG. 3 illustrates an axially-lengthening thrombus capture system 35 in the initial deployment configuration with the ALTC device 8 radially expanded, according to some embodiments of the invention. Also illustrated is nose tip 7 distal to the ALTC device 8. Relative axial movement of the outer tube 1 with respect to capture catheter 4 can allow for transformation of a first end (e.g., an expanded proximal end with a proximal-facing opening, or distal or laterally facing opening in other embodiments) of the ALTC device 8 from a radially compressed to a radially expanded configuration. In some embodiments, the proximal end opening of the ALTC device 8 includes a capture guide 11 that takes the form of, in some embodiments, a radially expandable shape memory partial or full ring-like annular structure that expands once free of the sidewall of the outer tube 1 along with a portion of the ALTC device mesh 8 attached to the capture guide 11. In the illustrated configuration, however, a significant portion of the surface area and/or the axial length of the mesh of the ALTC device remains in a compressed configuration within the lumen of the capture catheter 4, as the other end of the ALTC device mesh 8 is still operably attached, such as fixed to the outer diameter sidewall of the guidewire catheter 6.

Figure 4:
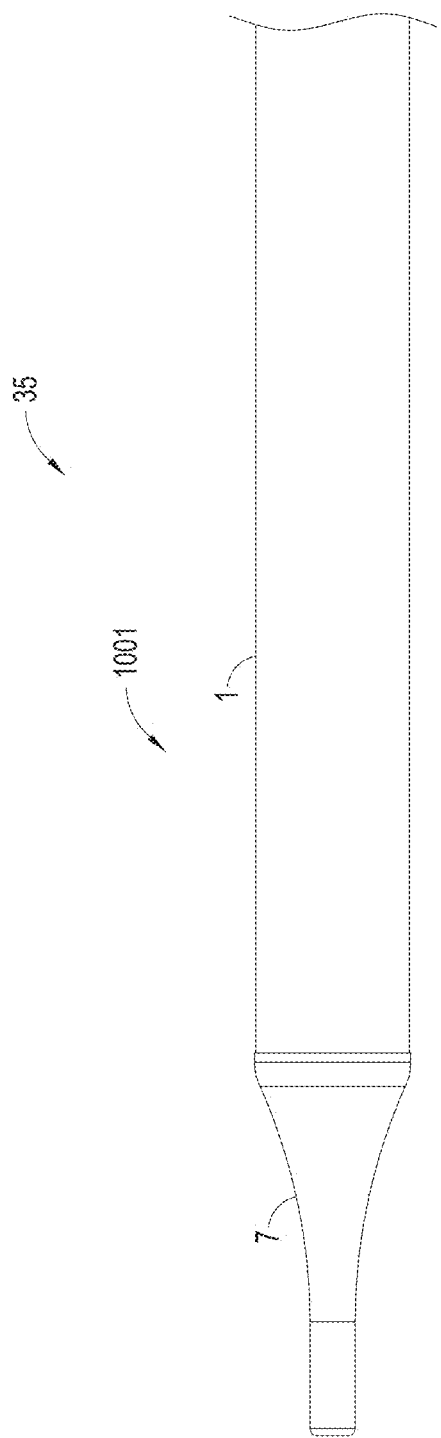
FIG. 4 illustrates a close up view of the ALTC system distal segment position in the delivery configuration indicating the outer sheath and nose tip, according to some embodiments of the invention.

FIG. 4 illustrates a close up view of the distal end of the ALTC catheter system 35 in the delivery configuration including the distal end 1001 of the outer sheath 1 and nose tip 7, which can be atraumatic and tapered as shown, according to some embodiments of the invention.

The ALTC Device 8 can function to retrieve and capture materials such as thromboemboli. The capture catheter 4 is shown, along with the ALTC Device 8, capture catheter shaft body 12, pull wire 10, and thrombus capture guide 11.

As illustrated in FIGS. 5-9 for example, a thrombus capture guide 11 can attach to a portion, such as an open end of the ALTC Device 8 and one, two, or more capture pull wires 10 where the capture pull wires are positioned inside the side lumen of the suction catheter 2 or outside of the lumen in other embodiments, and extends proximally. The distal end of the capture pullwire 10 can be connected to the proximal end of the ALTC device 8 at the capture guide 11 as illustrated. The capture pullwire 10 can extend proximally through the length of the outer sheath 1, and the proximal end of the pullwire 10 can be pushed or pulled allow a user to control, such as adjust the axial length of the ALTC device 8, for example when axially elongating the ALTC device in a proximal direction. In some embodiments, the capture pullwire 10 and the capture guide 11 are the only elements attached to the proximal end of the ALTC device 8. In some embodiments, the capture pullwire 10 and the capture guide 11 can be made into a single component such as a Loop. In some other embodiments, the capture guide and the proximal end of the ALTC device is sutured in place using silk or polymeric filaments such as Ultra-High Molecular Weight polyethylene, Nylon, PET, PTFE. In some embodiments, the open end of the ALTC device is covered with a low durometer film or coating and is then folded over the capture guide 11 and suture to secure the assembly. In another embodiment, the open end of the ALTC device 8, capture guide 11 and sutured assembly is coated with a low durometer polymeric materials. Another method to secure the wire ends is to apply polymeric fabric either on the outer or inner surface of the tubular structure and secure via suturing in place with suture filaments. The fabric can be at least one piece initially wrapped either on the inner or outer surface of the tubular structure and then folded over to the opposite side to secure and protect with wire ends. The two sides of the fabric can secured to the tubular structure using suture filament. Other means of securing the fabric to the tubular structure such as thermal bonding, press, lamination, chemicals, mechanical securement, and lasers can be used in some embodiments. The closed end of the ALTC device can be attached to an outer surface of the guidewire tube 6, which in turn can be positioned within a lumen of the capture catheter shaft 12. As such, axial elongation of the ALTC device in a distal direction can be achieved by, for example, movement of the guidewire tube 6 and pullwire 10 distally with respect to the capture catheter shaft 12. The axial elongation of the ALTC device in a proximal direction can be achieved by, for example, movement of the capture pullwire and capture catheter shaft proximally. The Thrombus Capture Guide 11 can be formed, for example, from metallic, shape memory, or other appropriate materials. In some embodiment, the thrombus capture guide 11 can include a loop configuration and be formed from nitinol shape memory wire of various geometries such as round, oval, elliptical, flat, and the like. The thrombus capture guide 11 can be formed of different shapes such as a circular loop, oval loop, z-shape, etc. In some embodiment, the loop 11 can be shaped set either into coils, multiple full circles, full circle or partial circles where the ends of the wire formed into two legs. The partial circle can be from, for example, 180 degrees to 359 degrees or 220 degrees to 359 degrees. The legs can be configured to be off-axis to the loop such that it can be right angle, acute or obtuse angle relative to the loop. It can be arcuate and form a partial or full ring as illustrated, and can circumscribe or otherwise form an outer diameter, and define the proximal-most end of the ALTC Device 8. The thrombus capture guide 11 can in some embodiments include a single loop or multiple loops positioned along the length of the ALTC Device 8 and not necessarily be present or have the entire guide 11 at the proximal-facing end opening end of the ALTC device 8. In some embodiments, the thrombus capture guide 11 does not include a loop. The ALTC Device tubular structure can be configured to be compressed and positioned within the Capture Catheter Shaft 12 lumen during introduction into the vascular system where the Capture Catheter Shaft 12 is configured to be positioned coaxially within and extend through the tubular structure and thrombus capture guide 11.

Figure 5:
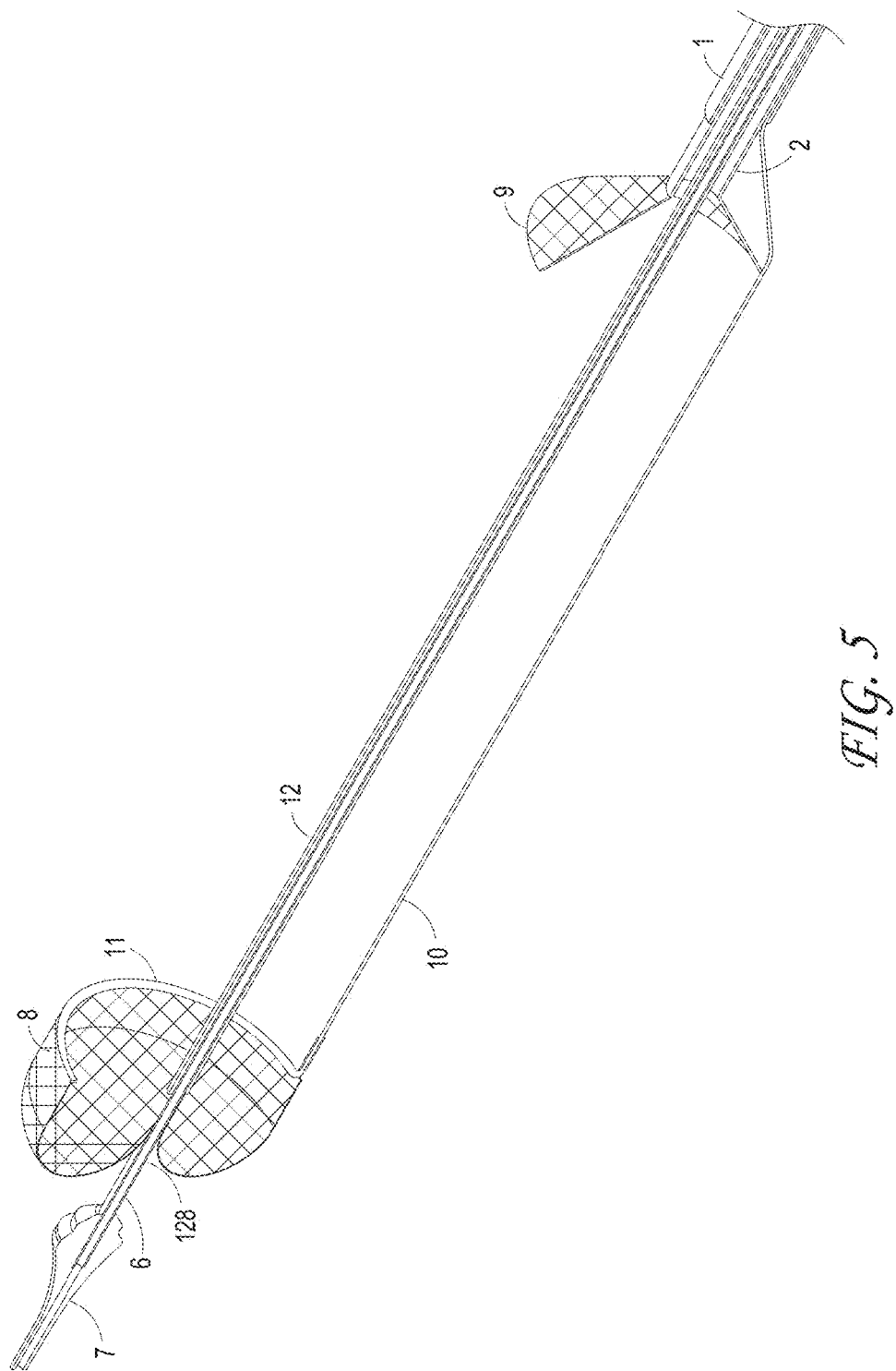
FIG. 5 illustrates the distal end of an axial lengthening thrombus capture device at the initial deployment position, according to some embodiments of the invention.

As illustrated in FIG. 5, the Axial Lengthening Thrombus Capture Device (ALTC Device) 8 can be in some embodiments a generally tubular net-like mesh structure that is collapsible, expandable and configured to axially lengthen or shorten, such as within a working range, while maintaining or substantially maintaining its diameter within the working range to retrieve and capture foreign or otherwise unwanted materials within the body, including the vascular system such as blood clots, thrombus and/or foreign materials.

Figure 6:
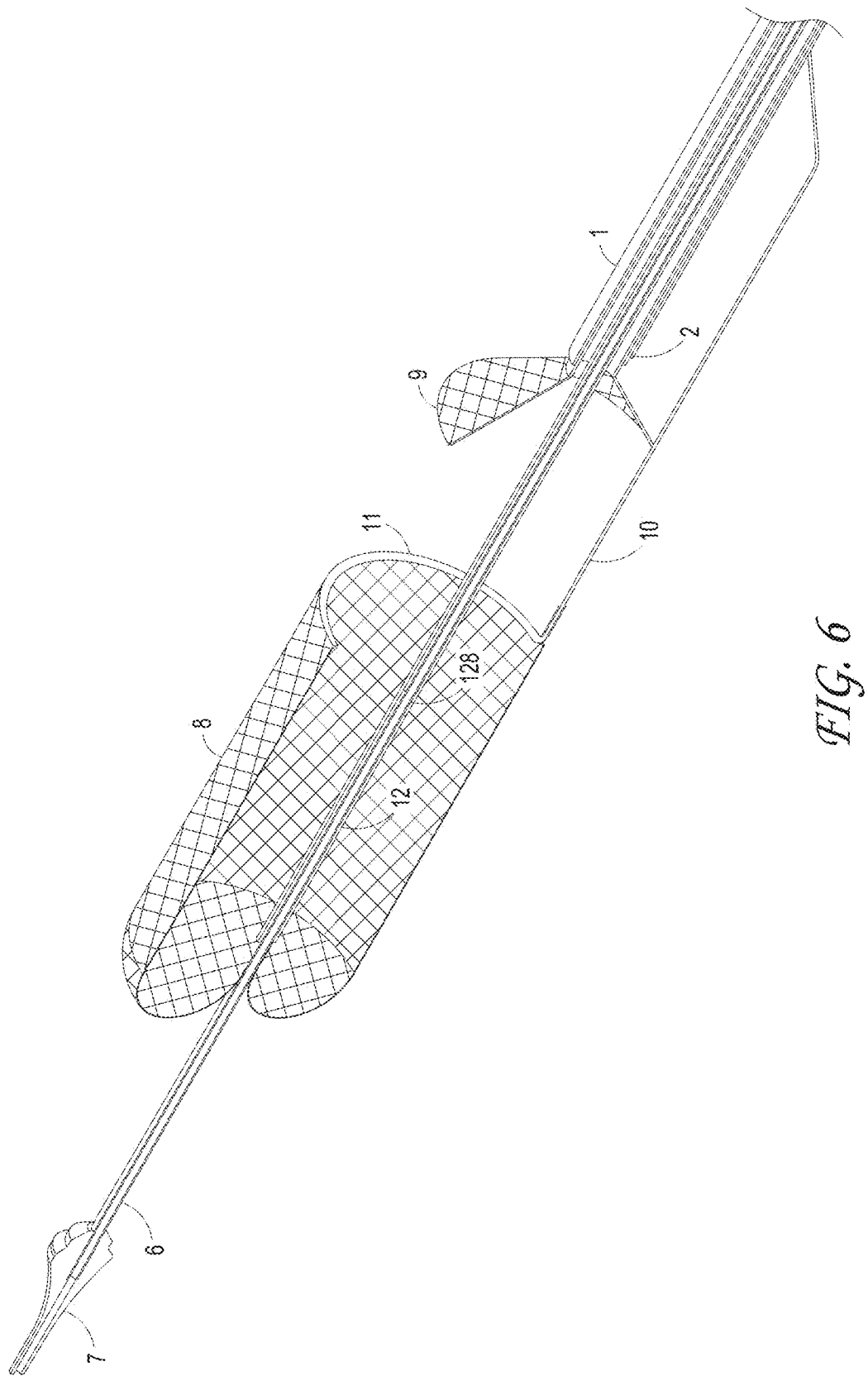
FIG. 6 illustrates the axial lengthen thrombus capture device retracting proximally to deploy and lengthen, according to some embodiments of the invention.

As shown, for example, in FIG. 6, it can also be possible to lengthen the ALTC Device 8 in an appropriate direction, such as distally, by pushing the capture catheter 12 relative to the guidewire shaft 6, thereby allowing additional reserve radially compressed length of the tubular mesh 8 to radially expand out of the confines of the lumen of the capture catheter 12 to axially lengthen the Thrombus Capture Device 8 and maintain its constant or substantially constant diameter through a working range. The other end of the ALTC device 8 at its radially compressed end can be fixed to the outer sidewall of the guidewire tube 6. A combination technique of, for example, manipulating the Capture Pull wire 10 attached to the Capture Catheter shaft 12 movement (FIG. 6) can position the ALTC device at a desired location within the body lumen, and movement of the guidewire catheter 6 axially with respect to the capture catheter shaft 12 will also axially lengthen or shorten the ALTC Device 8 while maintaining its diameter through a working range. When the ALTC Device 8 is in the deployed (expanded) configuration, the ALTC Device 8 can also be stretched beyond the working range to an extended axial length to reduce its diameter.

Figure 7:
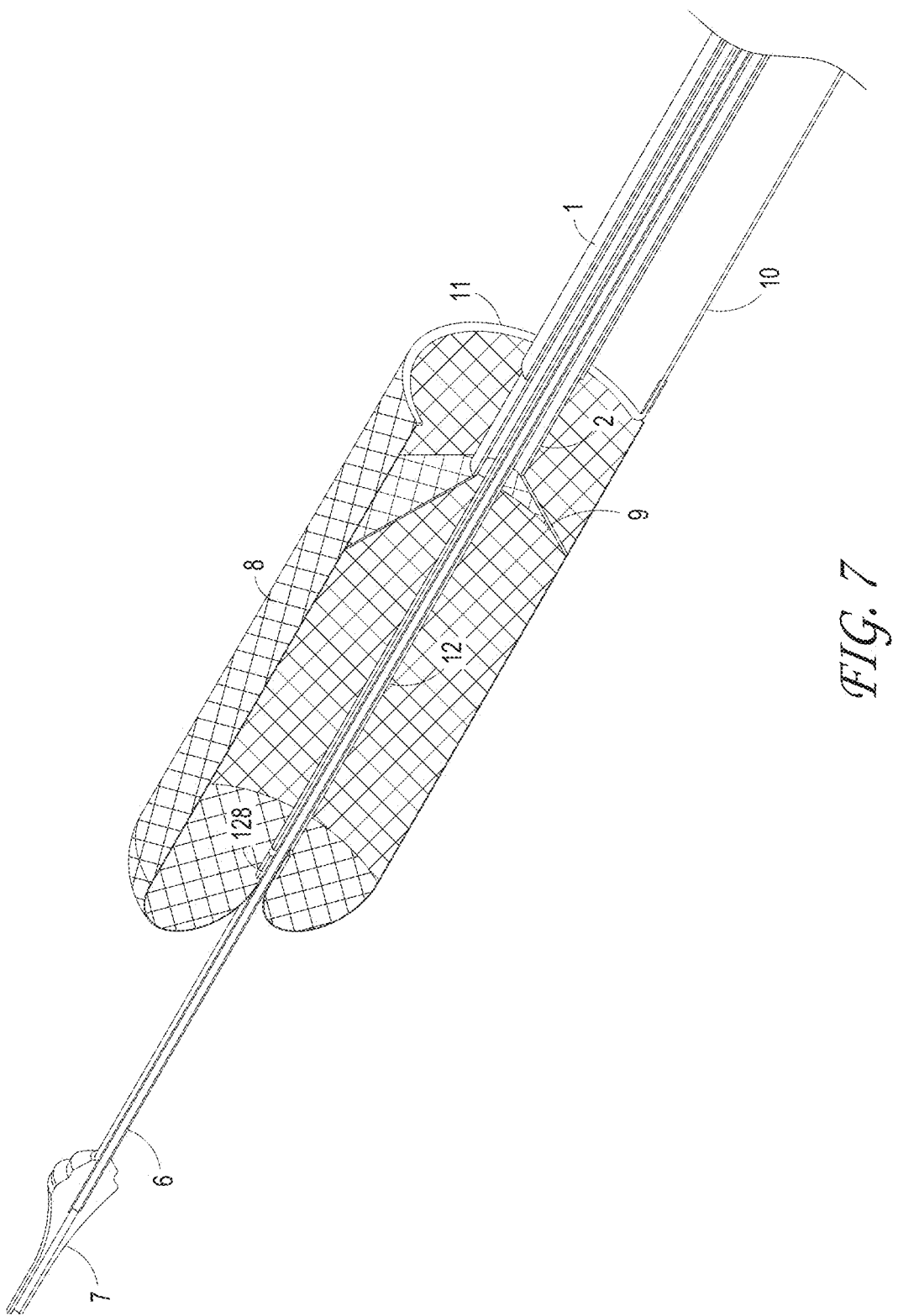
FIG. 7 illustrates the axial lengthen thrombus capture device is fully deployed and the funnel tip of the guide catheter is positioned within the ALTC device, according to some embodiments of the invention.

FIG. 7 illustrates the axial lengthening thrombus capture device 8 is fully deployed such that the attachment site 128 of the ALTC device 8 on the guidewire lumen 6 outer diameter is distal to the distal end of the capture catheter shaft 12 and the funnel tip 9 of the suction catheter is positioned within the ALTC, according to some embodiments of the invention.

Figure 8:
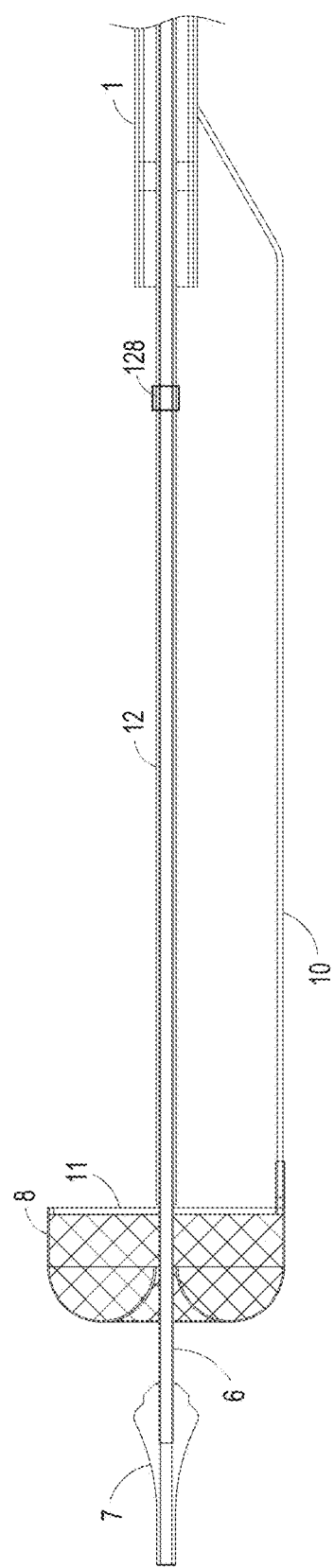
FIGS. 8 and 9 illustrate different views of the initial deployment position of the ALTC Device and the funnel tip of the suction catheter, according to some embodiments of the invention.
Figure 9:
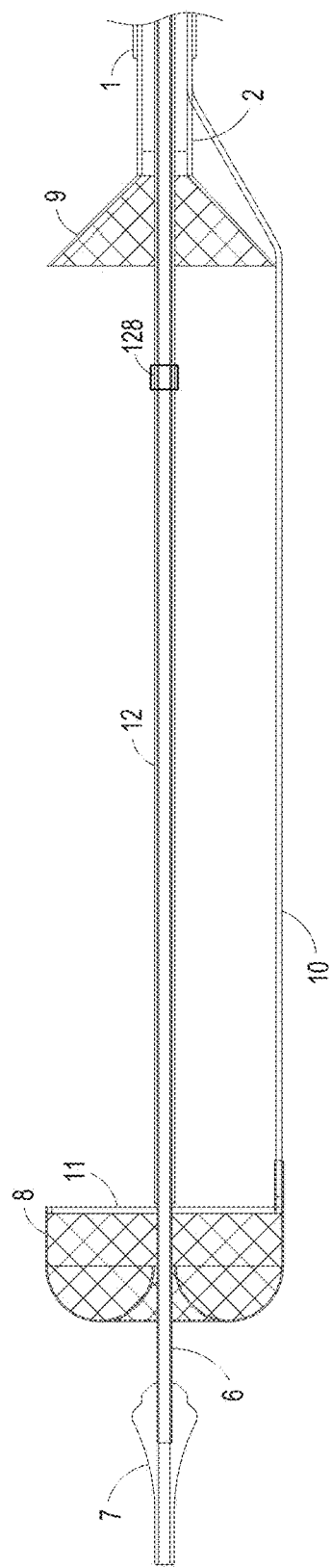

FIGS. 8 and 9 illustrate different views of the initial deployment position of the ALTC Device 8 and the funnel tip of the optional suction catheter 2, according to some embodiments of the invention.

Figure 10:
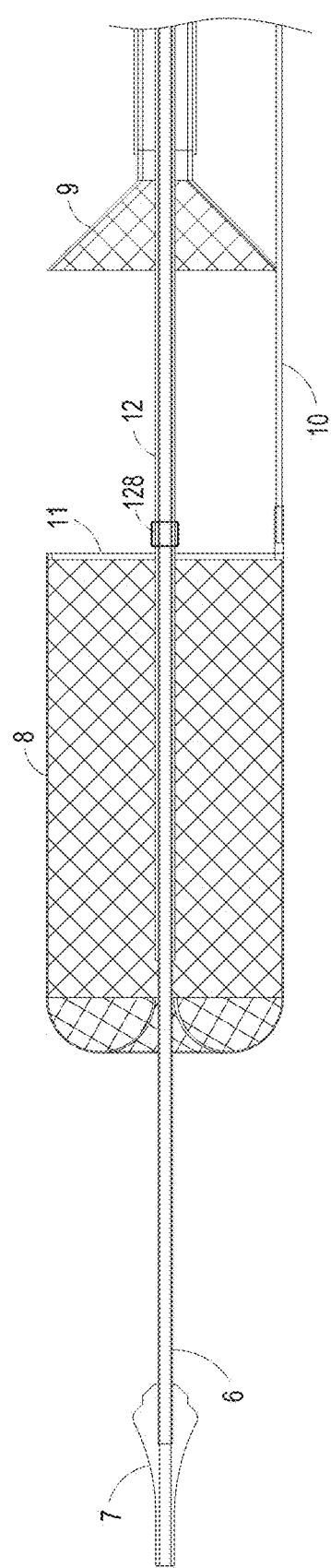
FIG. 10 illustrates the partially deployed ALTC Device, according to some embodiments of the invention.

FIG. 10 illustrates the partially deployed ALTC Device, according to some embodiments of the invention, where the ALTC device 8 is axially lengthened while maintaining its width normal to the axial direction.

Figure 11:
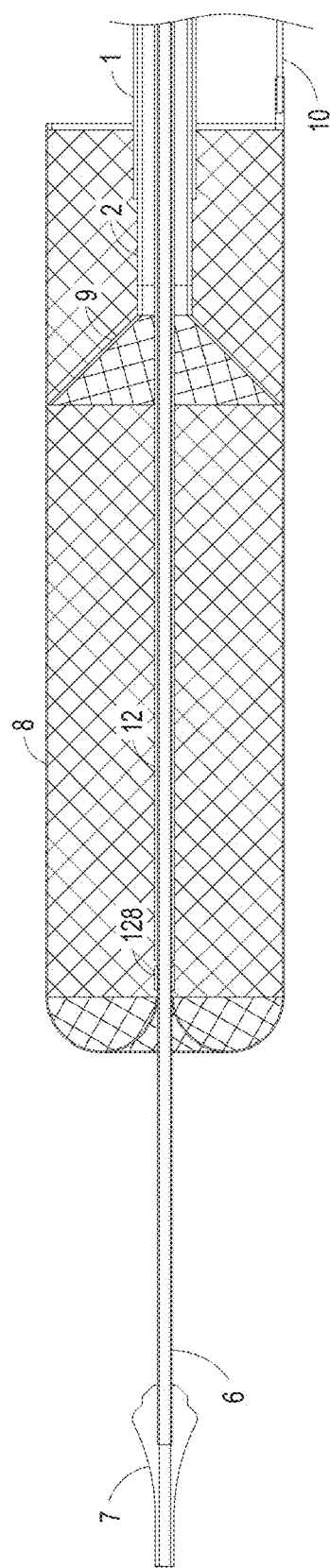
FIG. 11 illustrates an ALTC device deployed configuration where the funnel tip of the suction catheter is positioned inside the ALTC device, according to some embodiments of the invention.

FIG. 11 illustrates an ALTC device deployed configuration where the funnel tip of the suction catheter is positioned inside the ALTC device, according to some embodiments of the invention.

As illustrated, a Guidewire Lumen Assembly 6 can include a nose tip 7, shaft, lumen, and a proximal connector and port where a guidewire can be inserted therethrough. The central lumen can have a distal opening in some embodiments The guidewire tube 6 can be used to navigate and track over the guidewire in the vascular system. The guidewire tube 6 can extend coaxially within the lumen of the catheter shaft 12. A nose tip 7 can form or otherwise connect to the distal end of the guidewire tube 6 6 shaft to aid tracking the system through the vascular system, and can be atraumatic in some embodiments. The guidewire tube 6 can be made of polymeric materials such as, and not limited to Polyimide, Nylon, Polyurethane, Pebax, Polyethylene, PET, PTFE or ePTFE. The guidewire tube 6 can have, in some embodiments, radiopaque markers along its length for use to indicate the location of the ALTC Device, initial deployment, partial deployment, final deployment, the percent of length deployed and/or any combination thereof.

Figure 12:
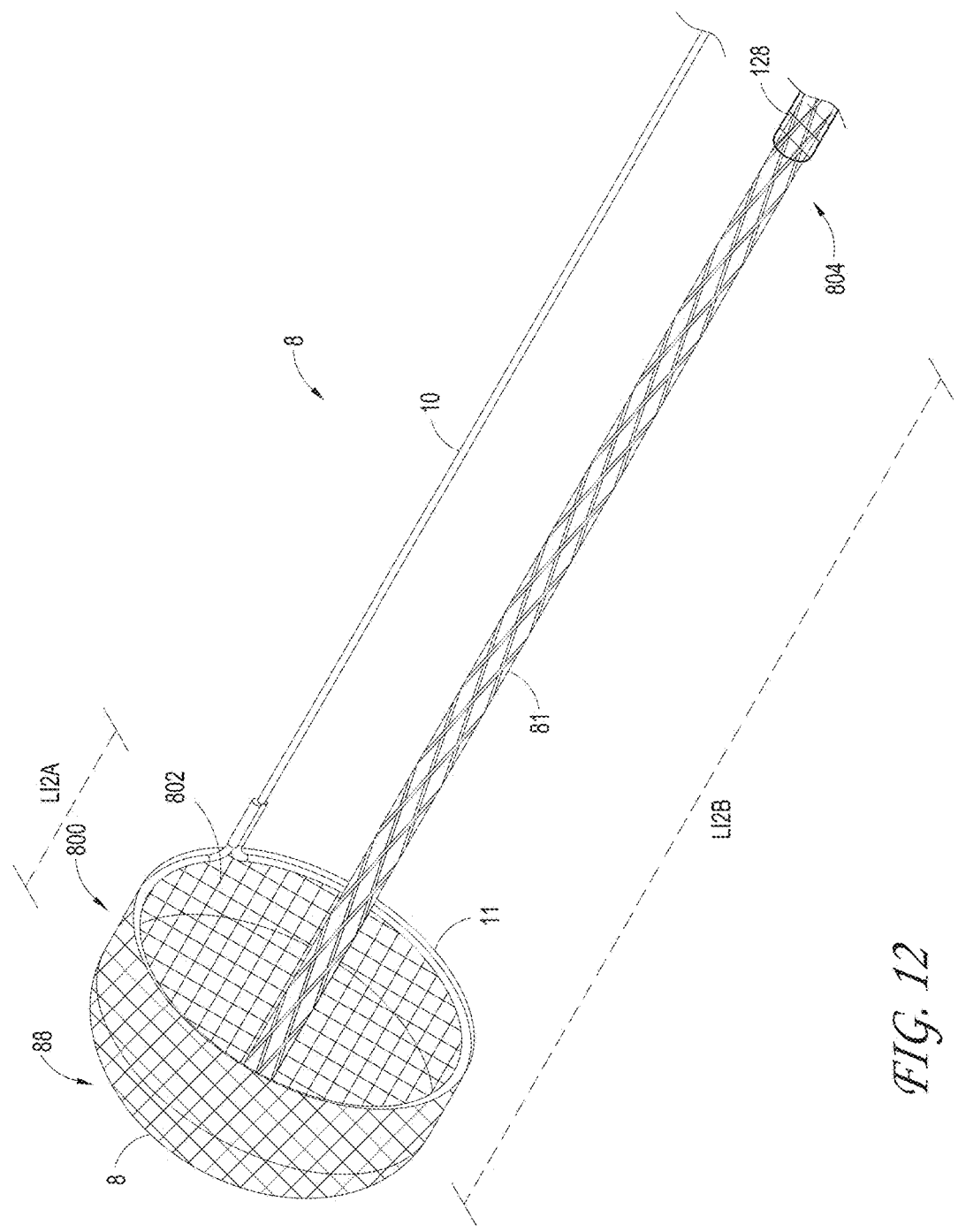
FIG. 12 illustrates the Axial Lengthening Thrombus Capture (ALTC) assembly wherein the distal end of the ALTC device is in the expanded (deployed) configuration and is fixed to the thrombus capture guide and capture pullwire, according to some embodiments of the invention. For purpose of illustration, the proximal end is in a collapsed configuration and extends proximally.

FIG. 12 illustrates the Axial Lengthening Thrombus Capture (ALTC) assembly 8 without the outer sheath, capture catheter 4, or guidewire catheter 6 present for clarity. As illustrated, end 800 with proximal-facing opening 802 of the ALTC device 8 is in the expanded (deployed) configuration and is fixed to the thrombus capture guide 11 and capture pullwire 10, according to some embodiments of the invention. For purpose of illustration, a reserve portion of unexpanded mesh 81 including end 804 is in a collapsed configuration and extends proximally toward attachment site 128.

In some embodiments, the tubular mesh structure 8 can axially lengthen or shorten without reducing or substantially reducing its diameter through a working length/axial range because the radially expanded portion of the tubular mesh structure is subject to none or minimal tension as it elongates or shortens axially through that axial working range. Not to be limited by theory, this can be accomplished at least in part because the tubular mesh structure can elongate axially throughout the working range by unrolling, everting, or otherwise expanding or transforming a radially compressed reserve segment of tubular mesh, such as unexpanded mesh 81. As such, an expanded "end" opposite the end of the radially expanded device with the capture guide and proximal end opening, such as dynamic fold point 88 of the radially expanded portion of the tubular mesh 8 may not be the absolute end of the tubular mesh fixed to a tubular shaft at zone 128, but rather an intermediate dynamic fold point 88 that is not fixed at that point to a tubular shaft, and as such not under any, or not substantially under any tension. The radially compressed reserve segment of tubular mesh 81 thus extends back in a different or the opposite direction (e.g., proximally in some cases) and ends at the terminal fixation point to the tubular shaft (e.g., at location 128). If it has not exceeded the working length of the expanded tubular shaft, the distance between the dynamic fold point 88 and the distal end of the entire catheter system (e.g., the nose tip) can increase as the radially expanded portion of the tubular mesh 8 lengthens, and the radially compressed reserve segment is used up.

Once the compressed reserve segment 81 of tubular mesh 8 is nearly or completely expanded to, or almost to its actual end at 128 and the tubular mesh 8 is axially elongated beyond its working length range, further axial elongation can start to exert significantly increased tension on the fully axially expanded tubular mesh structure 8, causing it to assume a configuration in which it radially contracts as it further axially lengthens.

A tubular net-like structure with one open end as disclosed above and elsewhere herein can be highly advantageous as a relatively small axial segment of the tubular mesh can be radially expanded and be fully functional to capture emboli and/or other materials in tight working environments, such as in obstructed body lumens with limited space to maneuver distal to the treatment location of interest. If it is desired that a greater axial length of radially expanded tubular mesh is required, such as to capture a relatively long length thromboemboli, the compressed reserve segment of tubular mesh can be unrolled, everted or otherwise expanded or transformed to a specific axial length as desired. Having a compressed reserve segment that can be stored along the length of the catheter system in a compact manner can be very advantageous in providing a long effective capture length tubular mesh without requiring the entire capture system to have a long fixed length as would be required in conventional filters/nets, which can be fixed at both ends and thus are functional and fully radially expanded when the first end is spaced apart from the second end at a single specific axial distance.

As illustrated in FIG. 12, some or most of the axial length of the ALTC device, e.g., the tubular mesh structure 8 remains radially compressed as part of the reserve segment between the outer diameter of the guidewire catheter 6 and the inner diameter of the shaft 12 of the capture catheter (distance between of which is length L12B), with the radially expanded portion of the tubular mesh structure 8 being defined along the axial length between proximal end 800 with proximal-facing opening 802 and the dynamic fold point 88 (distance between of which is length L12A), the sum of L12A and L12B amounting to the absolute length of the tubular mesh 8. In this initial configuration, the length L12B of the radially compressed reserve segment 81 can be about, or at least about 10%, 20%, 30%, 40%, 50%, 60%, 70%, 80%, 90%, or more of the absolute length of the tubular mesh 8.

Figure 13:
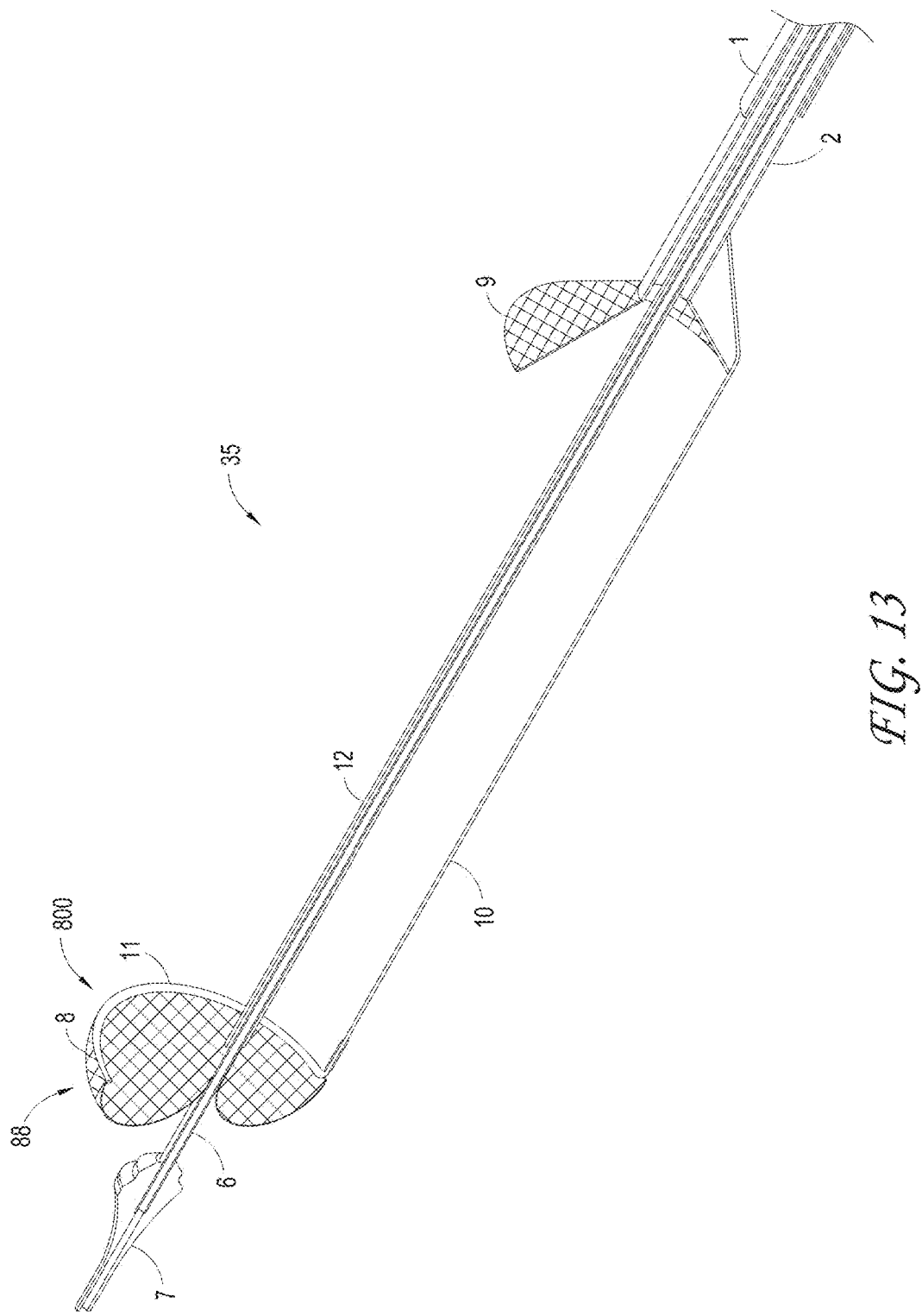
FIG. 13 illustrates the axial lengthening thrombus capture device in the initial deployed configuration, according to some embodiments of the invention.
Figure 14:
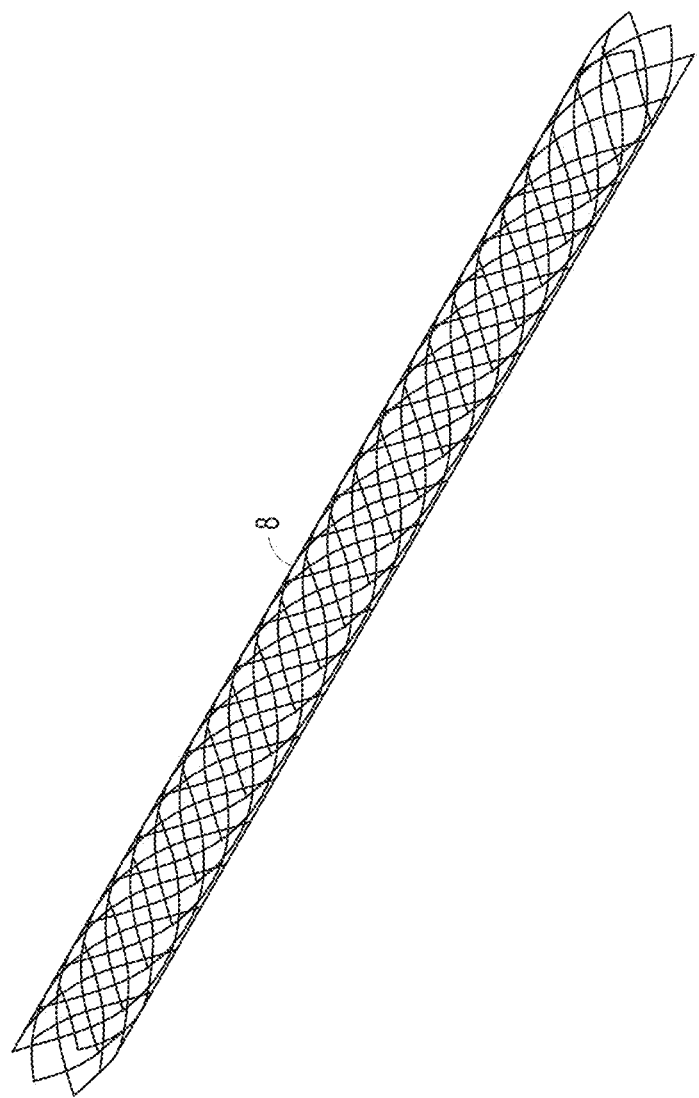
FIG. 14 illustrates the thrombus capture element of the ALTC device that can include a stent or braided mesh, according to some embodiments of the invention.

FIG. 13 illustrates the axial lengthening thrombus capture device 35 in the initial deployed configuration, according to some embodiments of the invention, with the radially expanded segment of the mesh 8 between end 800 and dynamic fold point 88 and the reserve compressed segment (not shown) extending axially proximally past end 800 to fixation point 128 on the outer surface of the guidewire shaft (not shown). FIG. 14 illustrates the thrombus capture element 15 of the ALTC device that can include a stent, braided, woven, laser cut, or other mesh such as a net-like structure, according to some embodiments of the invention. The tubular mesh structure need not necessarily be porous, and can be covered by nonporous or other layers. The ALTC Device tubular mesh structure 8 can be made of any suitable polymeric materials such as but not limited to polyethylene terephthalate (PET), polyethylene (PE) polypropylene (PP), nylon, silk, UHMWPE, PTFE, Kevlar, cotton, and/or metallic materials including superelastic material, nitinol, stainless steel, cobalt-chromium-nickel-molybdenum-iron alloy, or cobalt-chrome alloy, Chronichrome, or Elgiloy. The tubular structure can be braided, extruded, woven, knitted, laser cut, dip, film cast from a polymeric and/or metallic flat sheet, metallic filaments, polymeric filament or fabric in some embodiments. The tubular structure can be film cast with laser cut holes in some embodiments. The tubular structure can also be braided from polymeric and/or metallic filaments or any combination thereof. In some cases, the tubular structure can be made of nitinol wire mesh having multiple wire strands. Furthermore, the tubular structure can include at least one wire strand made of high radiopaque material such as tantalum, platinum, gold or nitinol drawn filler tube with a platinum core to enable viewing the tubular structure under fluoroscopy. In some embodiments, the tubular structure can include one, two, or more radiopaque markers. Depending of the diameter of the ALTC device, the number of wire strands can range from, for example, 1 to 576 wire strands. The ALTC Device can have 2, 4, 144, 288, or another number of wire strands in some embodiments. In some embodiment, the ALTC device is configured to have one wire strand. The wire strand diameter can range from, for example, 0.0002" up to 0.015". In some embodiments, the wire strand diameter is about 0.001". The tubular structure can be impermeable in some sections, permeable in other sections and/or a combination thereof. The tubular structure can be non-coated, or coated with one, two, or more anti-thrombogenic agents such as heparin to prevent clotting, or other therapeutic agents. The tubular structure can also be coated with a hydrophilic or hydrophobic agent. The tubular structure can have different pore sizes to assist with capturing small emboli or larger pore sizes to allow perfusion or blood flow. The tubular structure can have uniform pore sizes through the entire length or a combination of different pore sizes along its entire length. For example, when utilized as a cerebral protection filter, the ALTC device pore size can be sufficiently large to capture clinical relevant emboli size as small as, for example, about 200, 175, 150, 125, 100, 75, 50 microns or less while maintaining perfusion or blood flow. During retrieval, the ALTC device 8 can be repositioned to a particular section of the tubular structure that has smaller pore size and retrieve the blood clots/thrombus. In some embodiments, the ALTC device can deploy and enmesh within the blood clot to capture the blood clot in, for example, the neurovascular system. During retrieval, the ALTC device can lengthen sufficiently beyond the captured thrombus to create a protection filter distal to the captured thrombus. This can be clinically beneficial to prevent thrombus from dislodging during retrieval and thereby prevent secondary stroke. The ALTC Device tubular structure 8 proximal end can, in some embodiments, attach to the guidewire tube 6 outer surface, such as near attachment site 128. In some embodiments the proximal end of the ALTC Device tubular structure can be wrapped and sutured with polymeric filaments and encapsulated with low durometer polymeric material to fixably secure the wire ends to the shaft, such as the guidewire lumen assembly. Other means of attachment to secure the wire ends such as mechanically, thermally or chemically bonding the polymer to secure the wire ends can be used. In another embodiment, the ALTC Device proximal end can be fixed to the outer surface of the guidewire shaft using adhesive and is sandwiched between the outer surface of the guidewire shaft and cover tubes.

FIGS. 15A-C illustrate another embodiment of a clot capture system, a distal portion of the ALTC System and a proximal portion of the ALTC System respectively. FIG. 15A schematically illustrates the catheter system 35, while FIG. 15B shows the distal nose tip 7 operably connected to the distal end of the guidewire shaft 6 that includes a lumen for a guidewire to pass therethrough. One end of the ALTC device 8 can be fixably attached to the guidewire shaft 6 at one or more locations 128 and the other end 800 that includes proximal or distal-facing opening 802 is attached to capture guide 11, such as in the form of a loop 11, and it is movable axially distally and proximally via capture guide 11

Loop can include, for example, one, two, or more linear segments that extend proximally from the loop 11 onto the capture catheter shaft 12, which are in turn secured proximally to the capture catheter shaft 12 by a the sleeve 30. The sleeve 30 in some embodiments can be present instead of the pullwire(s) extending proximally all the way through the device. This can in some cases be advantageous ergonomically and allow for more streamlined control at the proximal end for a user. The axially expanded length of the tubular mesh 8 is shown extending from end 800 to dynamic fold point 88, with the reserve length of compressed tubular mesh (not shown) running proximally along the outer sidewall of the guidewire shaft 6 to its end at fixation point 128. FIG. 15C illustrates an embodiment of the proximal end of the system, including one or more flush ports 13, hub 55 of the outer sheath 1, hub 155 of the capture catheter 12, and hypotube pusher 14, and proximal-most hub 15 with a lumen configured to slide a guidewire therethrough. The hypotube pusher 14 can in some embodiments be coextensive with, such as welded or otherwise attached to the third tubular member (e.g., the guidewire tube 6), and when manipulated by an operator effect axial movement of the guidewire tube 6 in a proximal or distal direction. In some embodiments, there can be an integral guidewire tube 6 from the proximal most hub 15 to the distal nose tip 7. The third tubular member 14 can be configured to be placed within a lumen of a second tubular member (e.g., capture catheter shaft 12), such as at its proximal end at hub 155. The second tubular member can be configured to be placed within a lumen of a first tubular member (e.g., outer sheath 1), such as its proximal end at hub 55. In some embodiments, hub 55 and hub 155 can include complementary threads or other reversible locking features to allow for the outer sheath 1 to be reversibly coupled to the capture catheter 12 to allow for axial movement of the two tubular members in concert with each other. Uncoupling the hubs 55, 155 can allow for axial movement of the capture catheter 12 with respect to the outer sheath 1 and vice versa.

Still referring to FIGS. 15A-C, in some embodiments as illustrated, if a sleeve 30 is present, no separate pullwire extends from the capture guide 11 proximally to the proximal end of the system. In some such embodiments, axial movement of the capture catheter shaft 12 proximally with respect to the guidewire tube shaft 6 facilitates radial expansion of at least a portion of the ALTC device 8 and positioning of the ALTC device 8 within a body lumen. Axial lengthening and/or shortening of the ALTC device 8 in some embodiments can be effectuated by movement of the guidewire tube 6 (of which the other end of the ALTC device not attached to the capture catheter 12 via sleeve 30 is attached to, such as at attachment site 128) with respect to the capture catheter 12 and/or movement of the capture catheter 12 with respect to the guidewire tube 6.

Figure 16A:
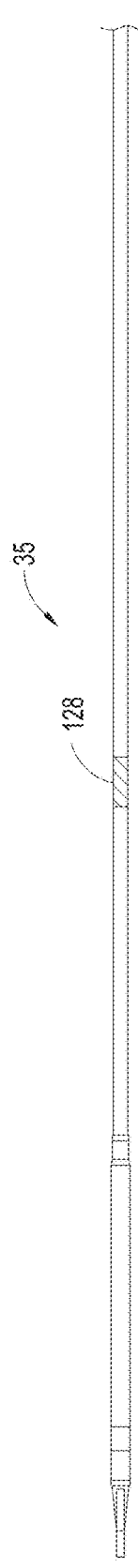
FIG. 16A illustrates another embodiment of the axial lengthening thrombus capture device in the delivery configuration, according to some embodiments of the invention.

FIG. 16A illustrates another embodiment of a distal portion of the axial lengthening thrombus capture device 35 in the delivery configuration, according to some embodiments of the invention.

Figure 16B:
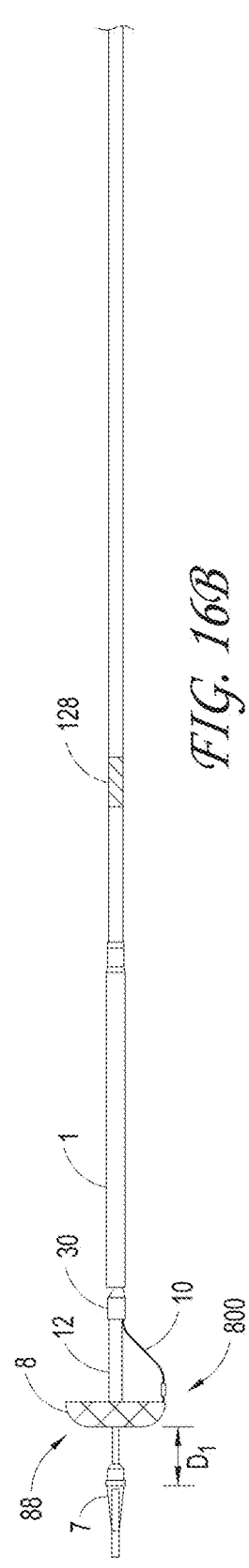
FIG. 16B illustrates the axial lengthening thrombus capture device in the initial deployed configuration wherein the outer sheath is retracted to expanded the axial lengthen thrombus capture device. The loop is coupled to the sleeve wherein it is coupled to the capture catheter shaft, according to some embodiments of the invention.

FIG. 16B illustrates the axial lengthening thrombus capture device in the initial deployed configuration wherein the outer sheath 1 is retracted, e.g., proximally to radially expand an end that includes the proximal-facing opening 802 of the axial lengthen thrombus capture device (e.g., tubular mesh 8) to dynamic fold point 88 which serves as the effective expanded distal end of the tubular mesh 8. The capture guide 11 and associated terminal wires 10 are operably coupled to the sleeve 30, and the sleeve 30 is coupled to the outer wall of the capture catheter shaft 12, according to some embodiments of the invention. The compressed reserve length segment (not shown) of the tubular mesh, such as about or at least about 10%, 20%, 30%, 40%, 50%, 60%, 70%, 80%, 90% or more of the absolute axial length of the ALTC device 8 (e.g., tubular mesh) taking into account folds remains inverted, rolled up, and/or otherwise radially compressed and circumscribed by the inner sidewall of the capture catheter shaft 12, up to the point where the other end of the ALTC device 8 is attached on an outer diameter of the guidewire tube 6 at attachment site 128. As illustrated, the dynamic fold point 88 varies along the length of the tubular mesh 8 depending on the length of the compressed reserve length segment that is expanded. The dynamic fold point 88 "floats" and is not directly attached to the guidewire shaft 6 nor the capture catheter shaft 12, and as such moves axially proximally when the expanded segment of the tubular mesh 8 axially lengthens.

Figure 16C:
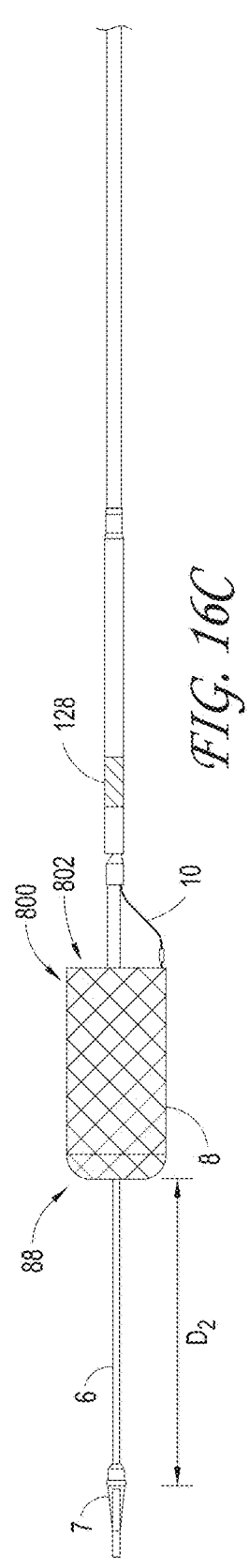
FIG. 16C illustrates the axial lengthening thrombus capture device retracting proximally and lengthening, according to some embodiments of the invention.
Figure 16D:
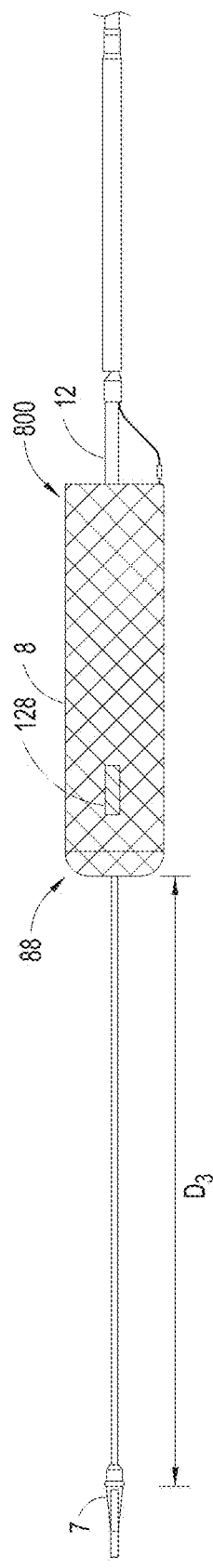
FIG. 16D illustrates the lengthening of the axial lengthening thrombus capture device and in some cases at full deployment, according to some embodiments of the invention.

As such, when the guidewire shaft 6 with distal nose tip 7 is maintained in a constant position, axial elongation of the expanded tubular mesh 8 results in an increase in the axial distance D between the distal nose tip 7 and the dynamic fold point 88, so distance D3 is greater than D2, which is in turn greater than D1. Furthermore, as shown in FIG. 16B the first end 800 of the tubular mesh is distal to the unexpanded end of the tubular mesh (at location 128) fixed to the outer sidewall of the guidewire tube 6, but moves closer proximally in FIG. 16C and becomes proximal to the unexpanded end of the tubular mesh at FIG. 16D while the dynamic fold point 88 moves proximally but is still slightly distal to the unexpanded distal end of the tubular mesh 8 in FIG. 16D, where the expanded axial length is even greater, or in some cases at its maximum working length. As noted, the diameter/width of the expanded tubular mesh remains constant or relatively constant between FIGS. 16A-D. Upon exhaustion of the compressed reserve segment which has transformed into expanded tubular mesh, continued axial expansion can result in increased tensile forces on the tubular mesh, resulting in a configuration in which radial contraction begins to occur.

FIGS. 17A-D illustrate different configurations of the ALTC device, according to some embodiments of the invention. During delivery, the capture guide 11 (e.g., ring-shaped in some embodiments) connected to the expanded end 800 of the tubular mesh 8 can be configured to collapse within the outer sheath 1 lumen during introduction into the vascular system and is configured to radially expand first when the outer sheath 1 retracts proximally while the length of reserve tubular mesh structure 81 of the ALTC device 8 extending proximally from the dynamic fold point 88 to fixation point 128 on the guidewire shaft 6 remains compressed in the capture catheter shaft 12 lumen. The dynamic fold point 88 serves as the effective expanded distal end of the tubular mesh 8. Upon further retracting the thrombus capture guide 11 via pulling the Capture Pull Wire 10 (or sleeve 30 as shown) and capture catheter shaft 12 proximally, the portion of the ALTC Device 8 tubular structure that is compressed within the Capture Catheter Shaft 12 lumen expands and can transform via, e.g., roll out proximally, inversion, and/or eversion, and axially lengthening the ALTC Device 8. Advance of the Capture Catheter Shaft 12 distally can collapse at least a portion of the ALTC Device 8 tubular structure into the Capture Catheter Shaft 12 lumen, as previously shown in FIGS. 7-9. The ALTC Device's ability to expand, roll out, axially lengthen and maintaining a substantially constant diameter through a working range creates a cavity (or pocket) within the sidewall of the radially expanded segment of the ALTC Device 8 to retrieve and capture foreign materials such as, for example, blood clots/thrombus. In another embodiment a sleeve 30 (FIGS. 16A-D and 17A-D) can be used to couple, such as permanently, the Capture Pull Wire 10 to a portion of the Capture Catheter shaft 12 to enable both components to operate together. Coupling the Capture Pull Wire 10 and the Capture Catheter shaft 12 can allow the user to manage the capture device more efficiently and easily. In another embodiment, the capture guide 11 takes the form of a loop and can attach to the Sleeve 30, which is coupled to the Capture Catheter Shaft 12.

Figure 18A:
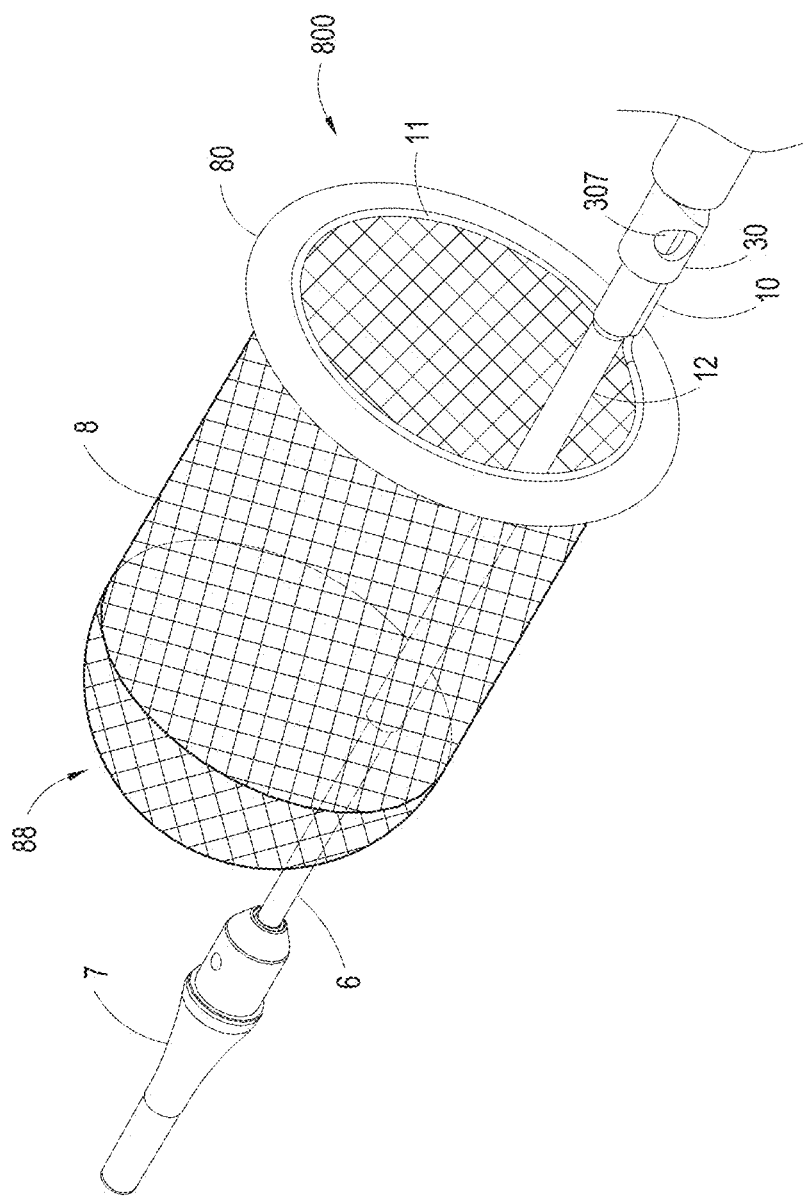
FIGS. 18A-B illustrate an embodiment of a distal portion of the axially-lengthening thrombus capture system with a cover element radially outward of, and partially or completely circumscribing the capture guide of the ALTC device, which can be in the shape of a ring as illustrated.
Figure 18B:
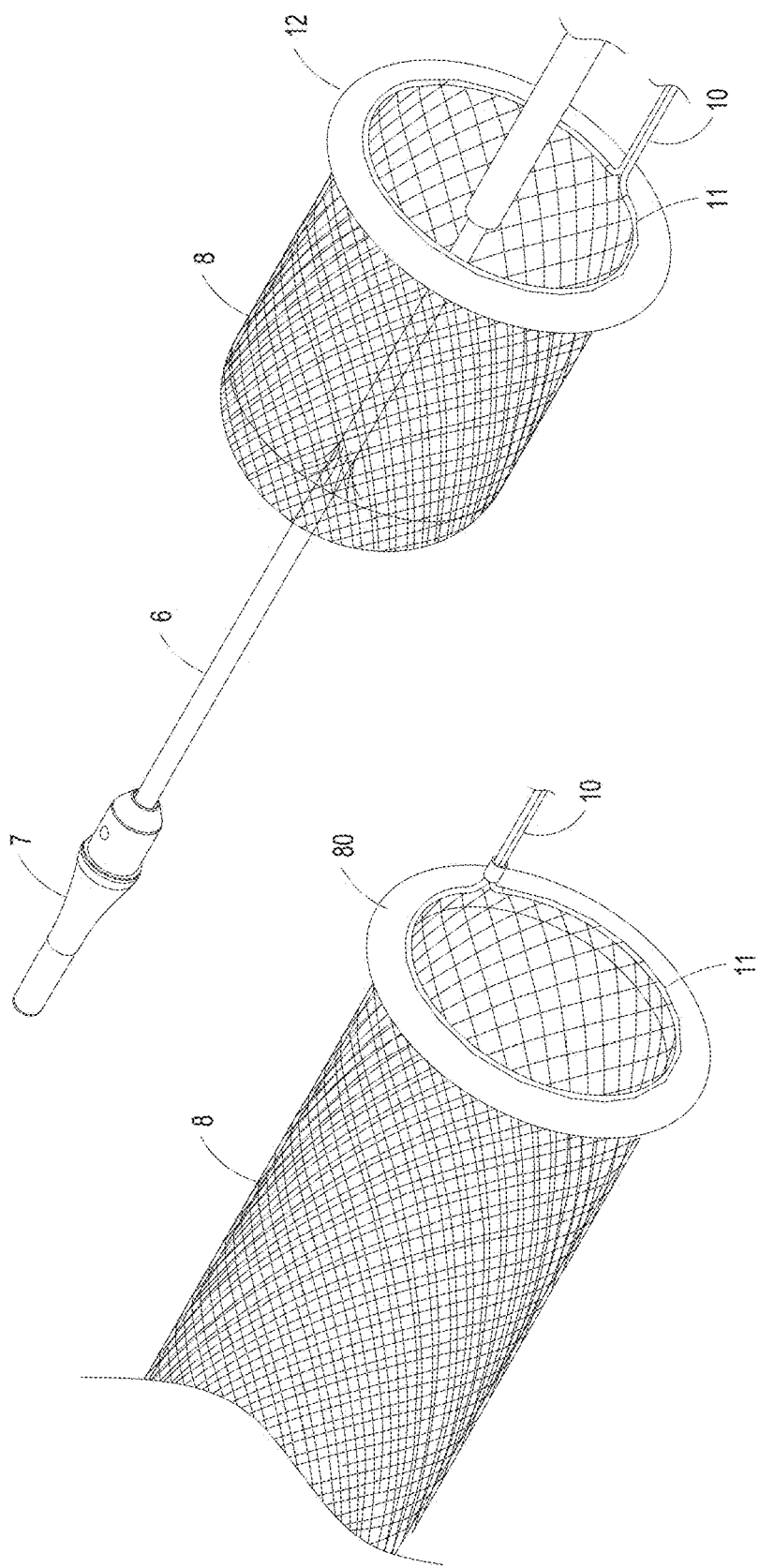

FIGS. 18A-B illustrate an embodiment of a distal portion of the axially-lengthening thrombus capture system with a cover element 80 radially outward of, and partially or completely circumscribing the capture catheter shaft 12 or loop 11 of the ALTC device, which can be in the shape of a ring as illustrated. In some embodiments, the cover element 80 can function to protect one or more of the capture guide, ALTC device, and the luminal wall of the lumen being treated. The ring 80 can also be configured to provide a seal against the luminal wall, e.g., of the vessel, to prevent leakage or migration or embolization of unwanted material around the tubular mesh 8. In some embodiments, the cover 80 can also include a skirt portion. The cover 80 can be axially and/or radially expandable, such as an inflatable balloon, a soft polymer, a gel, a foam, a textile fabric, shape memory, and/or include other materials. If the cover 80 is expandable, it can be configured to reversibly contract to allow for fluid flow around the cover 80 once the procedure is completed. Also as illustrated is sleeve 30 serving to attach the capture guide 11 connected to one or more wires 10. Sleeve 30 can include one or more apertures 307 that serve as relatively radiolucent markers, and/or the sleeve 30 could be made of a radiopaque material in some embodiments. Also as illustrated, the capture catheter 12 as well as guidewire tube 6 can extend through the tubular mesh 6 from first end 800 through dynamic fold point 88. The reserve segment of compressed tubular mesh is not shown for clarity.

Figure 19B:
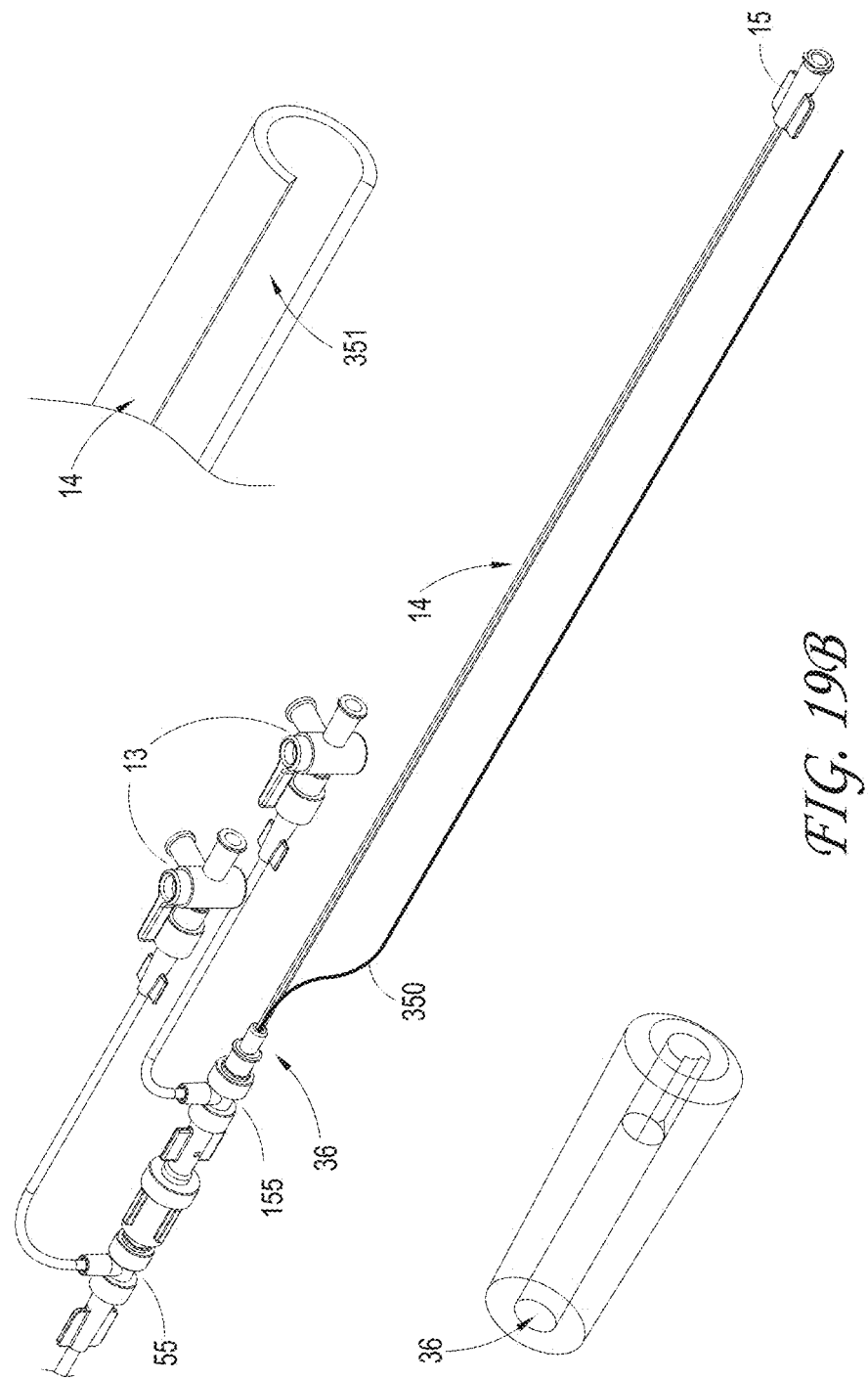
Figure 19C:
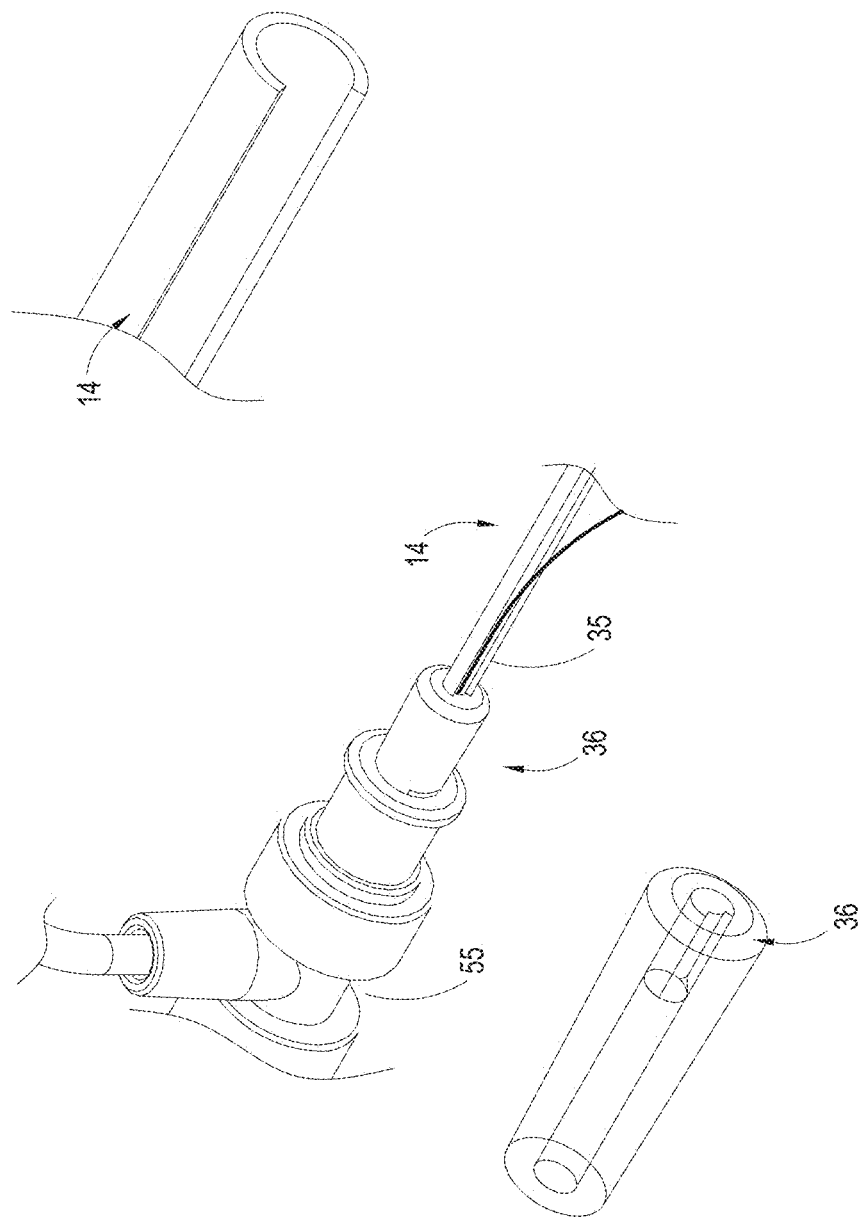

FIGS. 19A-C illustrate an embodiment of an axially-lengthening thrombus capture system, configured to allow the guidewire 350 to distally exit the system prior to exiting the luer/proximal-most port 15 at the proximal end of the system. The guidewire's proximal end can exit the system through an aperture or slot 351 in the sidewall once it passes the reversibly couplable hemostasis seals 55, 155 of the outer sheath 1 assembly and the capture catheter 12 respectively. In some embodiments, the guidewire 350 is configured to exit sideways, that is laterally. In some embodiments, a keyed cap 36 is positioned distal to the hemostasis seals 55, 155, which is in turn proximal to a shaft 14, which can serve as a hypotube pusher connected to or coextensive with the guidewire tube and be made of metal in some embodiments. The shaft 34 can include a sidewall groove 351 fully or partially axially from the port 15 to the hub 155 and/or one, two, or more discrete slots as illustrated.

Such embodiments can be advantageous, for example, to utilize a shorter length guidewire needed when the delivery system overall length increases. In some embodiments, when the ALTC capture device increase in length, the hypotube is also lengthened to accommodate thus increase the distance for user to manage the guidewire and system. The side guidewire feature can minimize the distance resulting in better handling, and the proximal end of the guidewire 350 need not necessarily extend past the proximal end of the entire system, such as at port 15. As such, the guidewire as part of the system can advantageously have a total length in some embodiments that is the same as, or even less than the axial length of the entire material capture system from proximal port 15 to distal nose tip 7, which may otherwise not be possible.

The guidewire 350 can be located near the hemostasis seals 55, 155 area during the procedure, and as such the entire procedure/operation can be done with the user not needing to look down to see where the components are located. As such, the user can hold the hemostasis seals 55, 155 housing in one hand while at the same time manipulating the guidewire 350 and hypotube pusher 14 with the other hand in the general area without substantially moving away from the area. The users can hold and maneuver the hypotube pusher 14 or hold and maneuver the guidewire 350 or hold both the hypotube pusher 14 and guidewire 350 at the same time. In some embodiments, the inner diameter of the shaft 14 with groove can be generally larger than the guidewire 350 that allows the guidewire 350 to exit laterally. The keyed cap 36 with a boss profile can mate to the groove of the metal shaft 14 to prevent the metal shaft 14 from rotating and still allow the shaft 34 to slide back and forth axially.

Figure 20A:
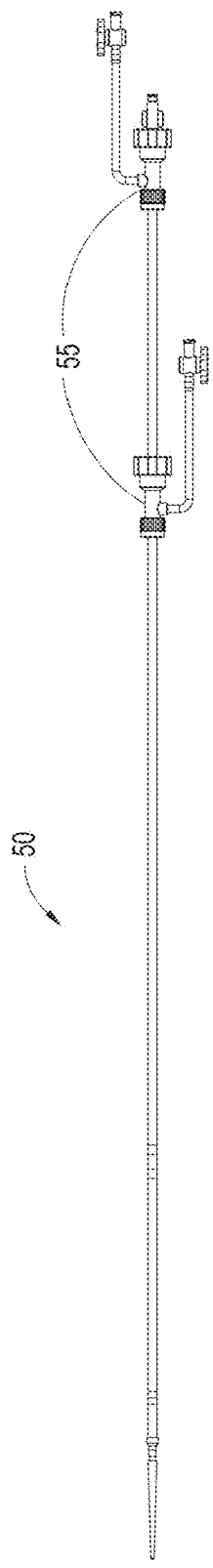
FIG. 20A illustrates the expanding guide catheter system in the delivery configuration, according to some embodiments of the invention.
Figure 20B:
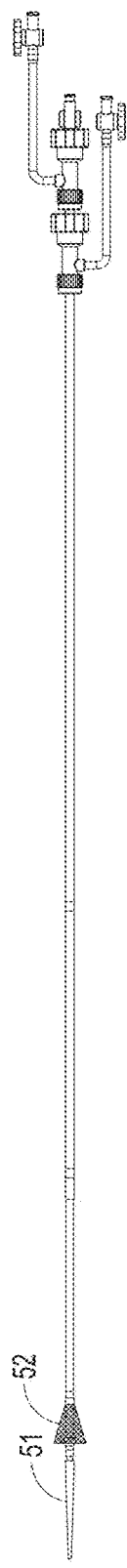
FIG. 20B illustrates the expanding guide catheter system wherein the funnel tip is in deployed position and the obturator is positioned in the expanding guide catheter lumen, according to some embodiments of the invention.
Figure 20C:
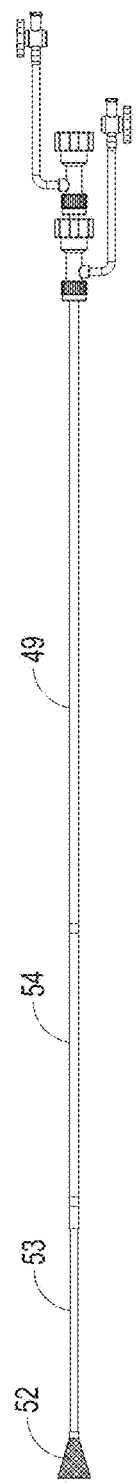
FIG. 20C illustrates the expanding guide catheter having a funnel tip, expanding distal segment and non-expanding proximal segment, according to some embodiments of the invention.
Figure 20D:
FIG. 20D illustrates an obturator, according to some embodiments of the invention.

In some embodiments, an Expanding Guide Catheter 50 (shown in FIGS. 20-21 for example) is a discrete catheter that can be utilized together with the clot capture system, and functions to assist in retrieving the ALTC Device 8 (and associated catheter system 35) and capture blood clots and other undesired materials. In some embodiments, the Expanding Guide Catheter 50 can include a first tubular member, such as an outer sheath 49 with a proximal end, a distal end, a lumen extending from the proximal end and the distal end, and a port on the proximal end, which can be coaxial as illustrated or offset from the longitudinal axis of the outer sheath 49. A second tubular member, such as inner catheter 54 can have a proximal end, a distal end, and a lumen extending from the proximal end to the distal end and can be configured to be placed within the lumen of the outer sheath 49. The inner catheter 54 can also have a proximal port, a removable obturator 51 positionable in the inner catheter lumen, distal expandable funnel tip 52, expandable shaft section 53 proximal to the funnel tip 52, an inner shaft 54, and connectors with seal 55. The obturator 51 can be used to aid in inserting and navigating the Expanding Guide Catheter 50 in the vascular system. The obturator 51 can be made of polymeric materials such as Polyethylene, Nylon, Pebax, Polyurethane, PET or PTFE for example. The obturator 51 can have a tapered distal end in some embodiments to aid in introducing the Expanding Guide Catheter 50 in the vasculature or other body lumen. Alternatively, other embodiments of the obturator 51 includes an expandable member such as a balloon operably connected to the distal end. Expansion of the expandable member, such as inflating the balloon can create a smooth tip transition. The balloon can be made of polymeric materials such Nylon, Polyurethane, PET, etc. Inflating the balloon can also secure the balloon obturator to the guide catheter such that when applying axial load proximally to the obturator shaft will articulate the tip of guiding catheter. The funnel tip 52, illustrated for example in FIGS. 20B-C, can include a distal funnel-like segment, and be adjacent to an expandable proximal segment 53 wherein it is connected to a more proximal portion of the inner shaft 54. The funnel tip 52 can be, in some embodiments, made of either polymeric and/or metallic materials. It can be either tubular in shape, woven or braided. The braid configurations can be, in some cases, 1×1 or 1×2 or 2×1 or 2×2 or any combination thereof. The picks per inch (PPI) can range from, in some embodiments, 5 to 60. The number can be, in some embodiments, from one wire filament up to 288 wire filaments. The wire shape can be, e.g., round, flat, oval, rectangular or square. The wire diameter can be, e.g., from 0.0005" up to 0.015". The flat wire thickness can be, e.g., from 0.0005" up to 0.010" and the wire width can be, e.g., from 0.001" up to 0.030". The funnel tip 52 distal segment can have various shapes or configurations to allow better retrieving the blood clots or thrombus. In some embodiments, the funnel tip 52 distal segment has a large open end where it contacts the vessel wall when expanded and transitions to smaller opening proximal segment 53. The distal segment open end can range from, in some embodiments, about 5 mm to about 80 mm in diameter. The funnel tip distal segment 52 also has, in some embodiments, openings or holes (perforations) along the side to allow blood flow. The funnel distal segment 52 can have either one layer of braid or multiple layers. In some embodiments, the funnel distal segment has two layers. In some one layer embodiments, the most distal open end of the funnel does not have the wire end terminate or exposed such that the wire ends are located at the proximal end of the funnel assembly. The funnel tip proximal segment 53 can be configured such that it is capable of expanding and receive the ALTC device and captured blood clots or thrombus. The proximal segment 53 can be configured to expand to receive object that is larger than its inner diameter and recovery after passage. The proximal segment 53 can include a PTFE inner layer and compliance and/or low durometer polymeric materials such as Polyurethane, Silicone, Tecoflex, Pebax 25D and/or 35D or braid and/or non-braided such as Pebax/Propel/BaSO4 outer layer. The proximal segment 53 can also include other lower durometer polymeric materials. The composite funnel tip and proximal segment can be laminated via dipped coat, spray or reflow process or any combination thereof. The braid materials can be either metallic and/or polymer and/or combination thereof. The braid configurations can be, e.g., 1×1 or 1×2 or 2×1 or 2×2 or any combination thereof. The picks per inch (PPI) can range from, for example, 5 to 60. The number can be, e.g., from one wire filament up to 288 wire filaments. The wire cross-sectional shape can be, for example, round, flat, oval, rectangular or square. The wire diameter can be, e.g., from 0.0005" up to 0.015". The flat wire thickness can be, e.g., from 0.0005" up to 0.010" and the wire width can be, e.g., from 0.001" up to 0.030". In some embodiments, an advantageous feature is the ability to expand and contract without buckling under compression. The inner diameter can range from, e.g., 2 F to 30 F. In some embodiments, the inner diameter can range from, e.g., 6 F to 18 F. The expanded length section can be up to the entire catheter length. In some embodiments, the length is about 20 cm. The funnel distal 52 and proximal segment 53 can also be made as one component wherein the braid configuration is continuous. Coupled to or continuous with the funnel tip proximal segment 53, the inner shaft 54 can be made from materials such as and not limited to Nylon, Polyurethane, Pebax, Polyethylene, PET, PTFE, or ePTFE. The inner shaft 54 can be braided or non-braided. The outer shaft 49 can function to slide over and collapses the funnel tip and provide support during introduction into the vasculature. The outer shaft 49 retracts to deploy the funnel tip. The outer shaft 49 can be made of polymeric materials such as Nylon, Polyurethane, Pebax, Polyethylene, PET, PTFE, ePTFE, FEP or combination thereof. The outer shaft 49 diameter can range from, e.g., 4 F to 34 F. The outer shaft 49 inner diameter can range from, for example, 3 F to 32 F. In some embodiments, the inner diameter has substantially the same throughout the lumen shaft. In some embodiments, the inner diameter at the distal end is larger than the proximal end inner diameter. The change in inner diameter can be in one location, two or more locations. The outer diameter is substantially the same throughout the entire length of the outer sheath shaft. In some embodiments, the outer shaft 49 is about 22 F or smaller in diameter. The outer shaft 49 can include a radiopaque marker at the distal end or radiopaque filler along its shaft length for visibility under fluoroscopy. In some embodiment, the outer shaft can be deflectable (via, for example, one, two, or more pullwires on the distal end) at various locations and multiple deflectable directions along the shaft length to accommodate various tortuous paths such as entry into the right atrium, right ventricle, main pulmonary artery, and left and right pulmonary artery for pulmonary embolism applications.

Still referring to FIGS. 20A-20D, in some embodiments the expanding guide catheter 50 can be utilized to retrieve blood clots or thrombus. The expanding guide catheter 50 and obturator 51 can be introduced over a wire into the vasculature and advanced near the treatment area. The obturator 51 is removed. The outer member 49 of the expanding guide catheter is retracted proximally to expand the funnel tip 52 and the expandable section 53 of the guide catheter 50. In some embodiments, the guide outer shaft 49 is inserted into the vessel together with the obturator 51 and the obturator 51 is removed once the outer shaft 49 is in a desired position. The inner guide member can include the funnel tip 52, proximal segment 53 and the inner shaft 54 is then inserted into the outer shaft 49 up to the distal tip of the outer shaft 49. The outer shaft 49 can then be retracted (or the inner shaft 54 advanced) to expand and deploy the distal funnel 52 and the proximal segment 53. The capture catheter system 35 is inserted over the wire and through the lumen of the expanding inner guide member 54. Once the ALTC Device 8 is deployed and captures the blood clots, the ALTC Device 8 is retracted along with the captured blood clots into the funnel tip 52 and expanding guide inner member 53, (shown later in FIG. 50). When high resistance is encountered at the funnel tip due to the large blood clot position at the tip, the guidewire lumen can advances distally to lengthen the ALTC Device. Lengthening the ALTC device can create additional space within the ALTC device such that the blood clot volume is redistributed thereby reduces the large blood clots pooled at the tip of expanding guide catheter. The expanding guide catheter distal section also allows larger clots to be captured due to its expandability increasing the lumen size. Continuing to retract the ALTC device will retrieve additional captured blood clots inside the expanding guide catheter. Repeated lengthening of the ALTC during the procedure will continue to redistribute the clot and retrieve inside the Expanding Guide Catheter, advantageously allowing for improved thrombus processing and redistribution. In some embodiments, a kit can include a capture catheter system 35 as described herein and configured to be reversibly placed within, and move axially with respect to an inner lumen of a discrete expanding guide catheter system 50 as described herein.

Figure 21A:
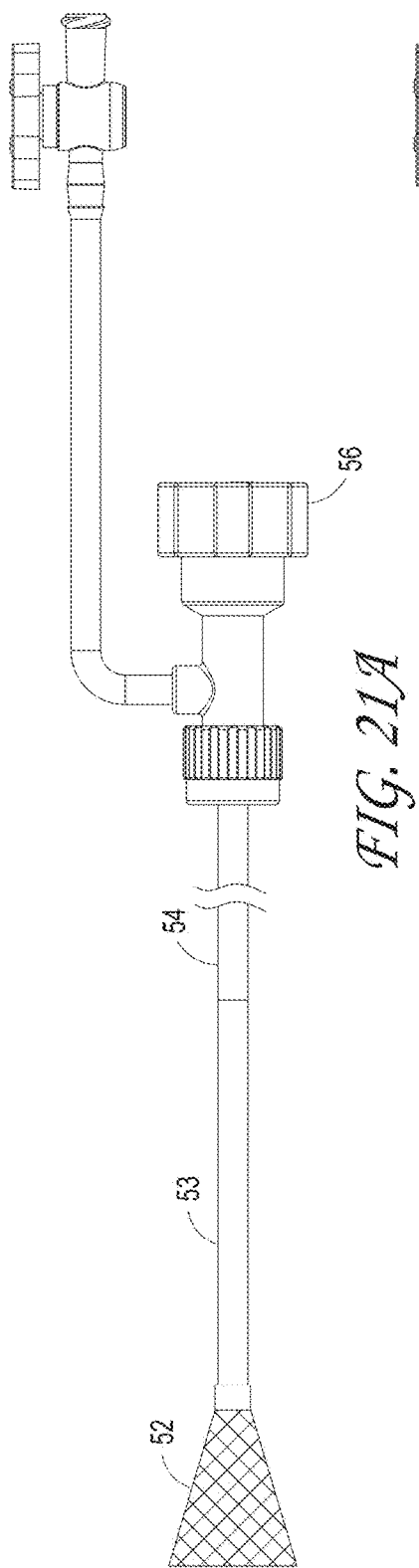
FIGS. 21A-C illustrate the expanding guide catheter system including the expanding guide catheter, outer cover and obturator, according to some embodiments of the invention.
Figure 21B:
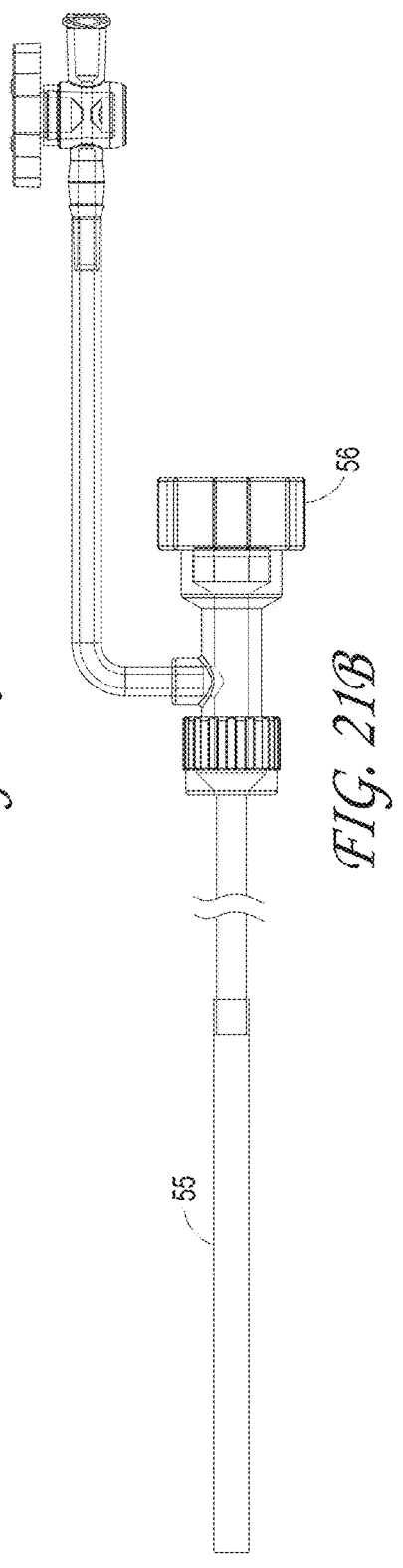
Figure 21C:
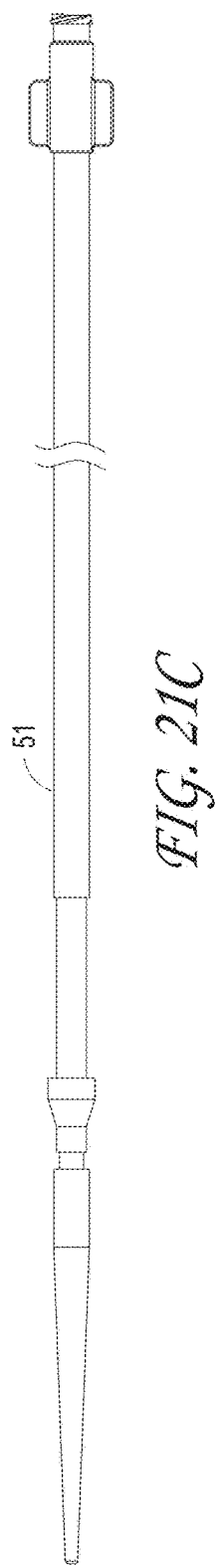
Figure 21D:
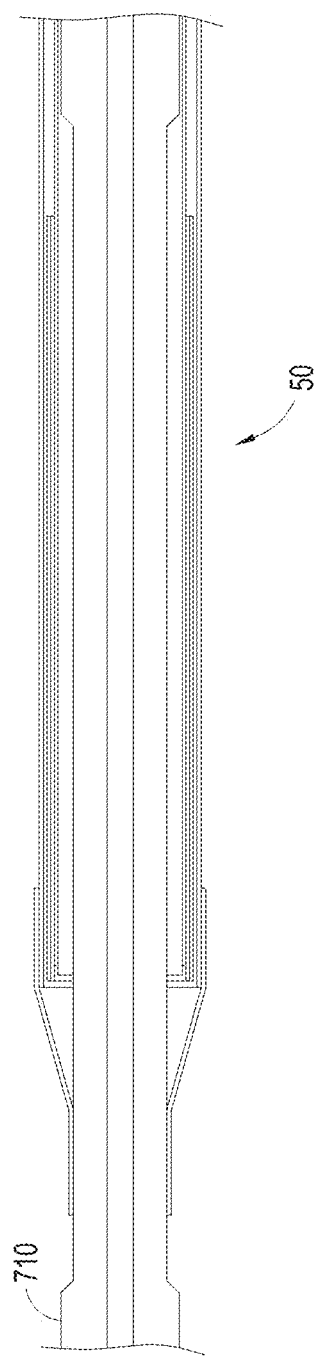
FIG. 21D illustrates an embodiment wherein a cover tip encapsulates the distal end of the outer cover of the expanding guide catheter system, according to some embodiments of the invention.
Figure 21E:
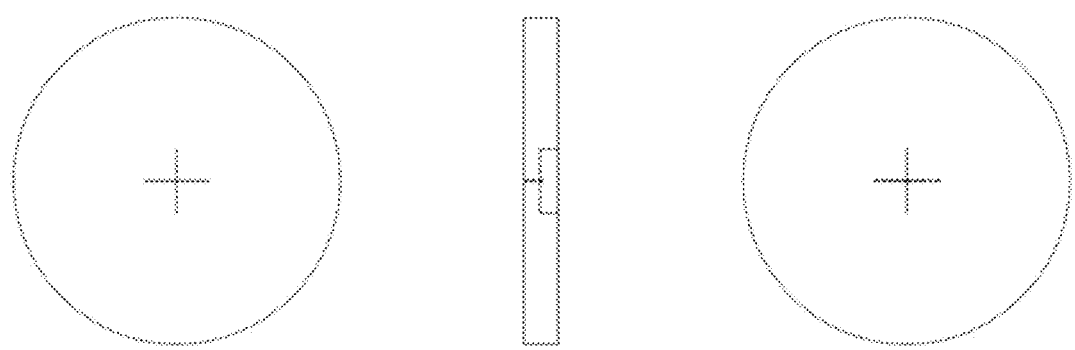
FIGS. 21E-F illustrate an embodiment of a hemostasis valve for use within a hemostasis guide catheter system.
Figure 21F:
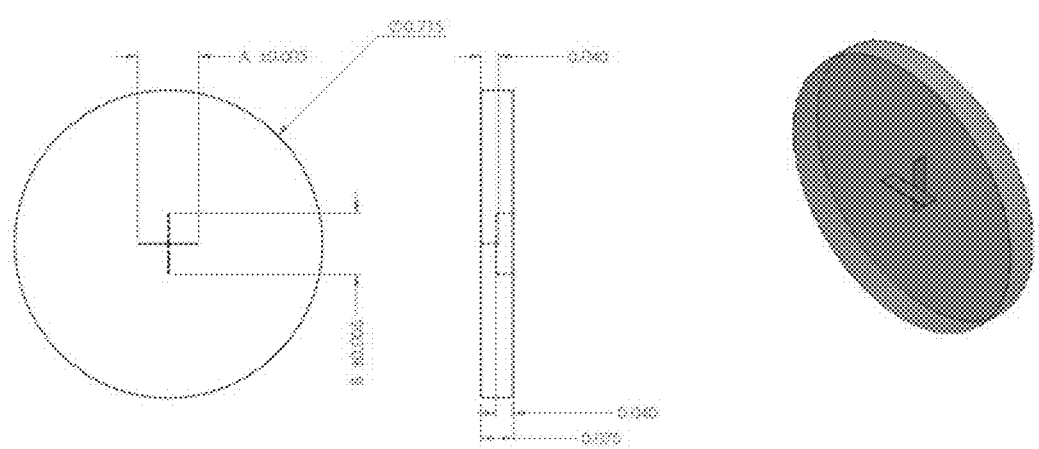

FIG. 21D illustrates an embodiment wherein a cover tip 710 encapsulates the distal end of the outer cover of the expanding guide catheter system, according to some embodiments of the invention. In some embodiments, a guide catheter is part of a hemostasis guide system that can includes one or more obturators, an inner shaft member, an outer shaft member, and a hemostasis valve disposed within a housing of the system. The inner shaft member can include a non-expandable braided proximal segment, a distal expandable segment and a braided funnel distal end which can be as described elsewhere herein. The inner shaft member can be positioned within the lumen of the outer shaft member. The outer shaft member can have, for example, a braided polymeric configuration with a flexible kink resistance distal segment. The inner shaft and outer shaft member can be attached to the housing body. The housing body can be, for example, at a proximal end of the guide catheter system. The hemostasis valve can be disposed within the housing body. The hemostasis valve can be in some embodiments a flexible disc-like valve. The hemostasis valve can be configured to provide hemostasis and prevent leakage, such as with nothing inside. In some embodiments, the system can be configured for use with a 0.035" guidewire, 5 Fr catheter, and include sizes between about 12 F and about 17 F, such as about 12 F, 16 F, or 17 F. The hemostasis valve can include two surfaces, an upper surface and a lower surface. The upper surface and lower surface can be opposing surfaces in some embodiments. The upper surface can include a slit extending partially across the upper surface and a depth into the valve without protruding all the way through the thickness of the lower surface. The lower surface can include a slit extending across the lower surface and a depth into the valve without protruding all the way through the thickness of the upper surface. In some embodiments, the valve has a diameter of between about 0.50" and about 1.00", such as about 0.5", 0.6", 0.7", 0.8", 0.9", or 1.0". In some embodiments, the valve has a thickness of between about 0.050" and about 0.0100", such as about 0.075". In some embodiments, the slits can have a depth/thickness of between about 0.020" and about 0.060", such as about 0.040". The midpoint of a slit can be in some cases at or proximate the center of the surface of the disc. The upper slit and the lower slits can intersect at, for example, a point location within the valve. The slits can extend beyond the intersection point by a desired distance, such as between about 0.001" and about 0.010" or approximately 0.005" beyond the intersection point. In some embodiments, the arrangement of the slits along the valve permits insertion and removal of shafts therethrough while preventing leakage of blood or air back across the valve. The upper and lower slits can have long axes that intersect at an angle. The angle could be in some embodiments between about 45 degrees and about 135 degrees, or about 45, 60, 75, or 90 degrees in some cases.

Figure 22:
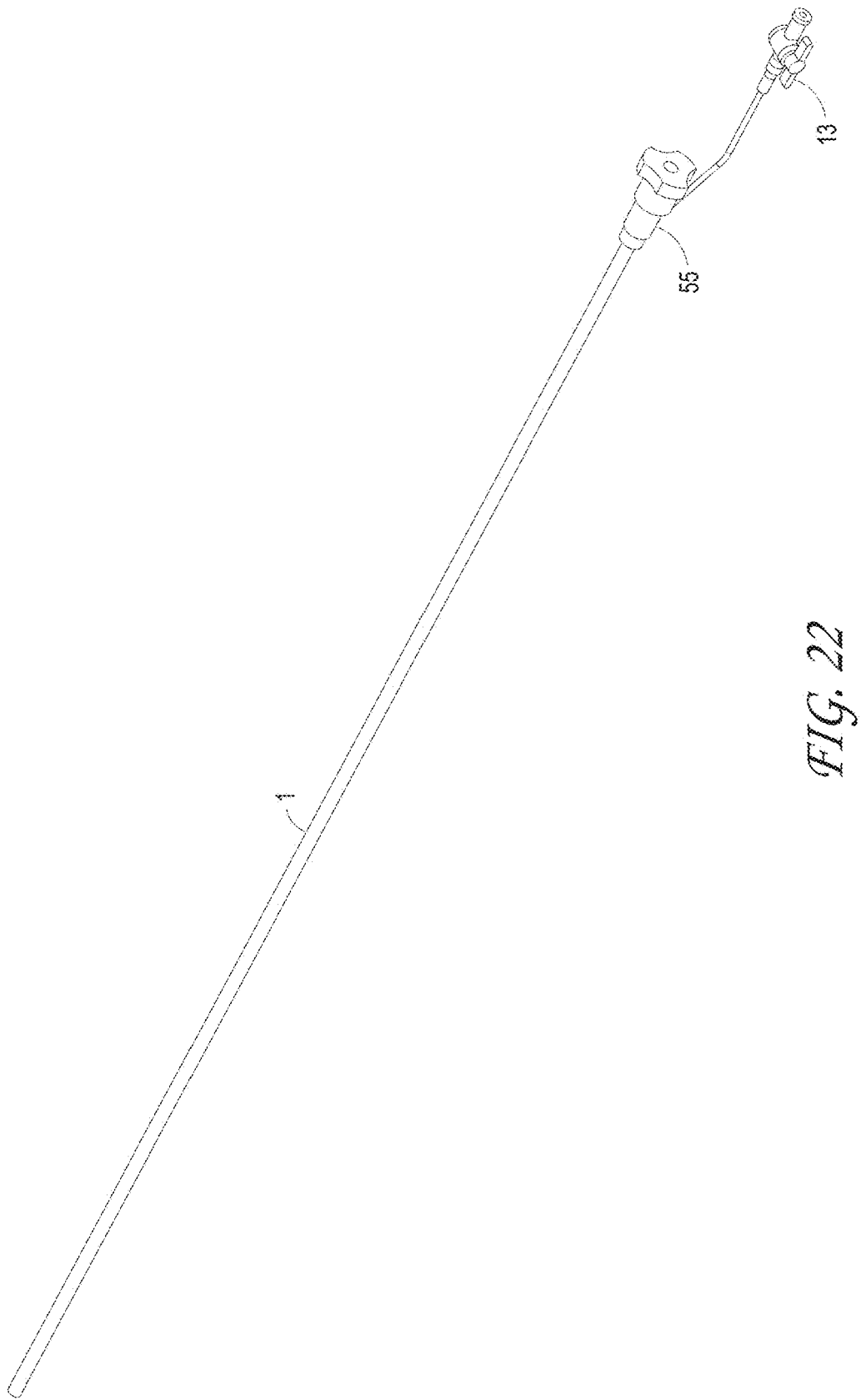
FIG. 22 illustrates the outer sheath assembly of the capture device, according to some embodiments of the invention.
Figure 23:
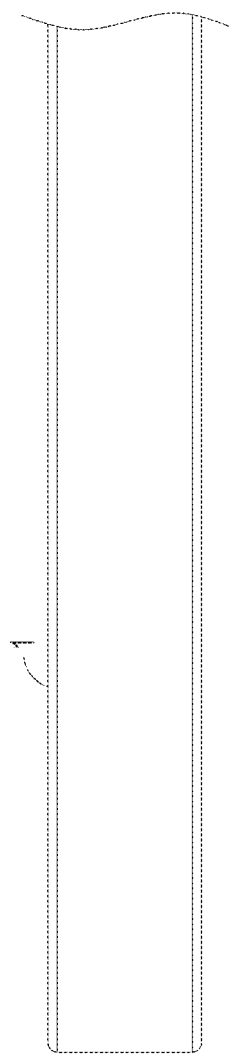
FIGS. 23 and 24 illustrate the distal end and proximal end of the outer sheath assembly respectively.
Figure 24:
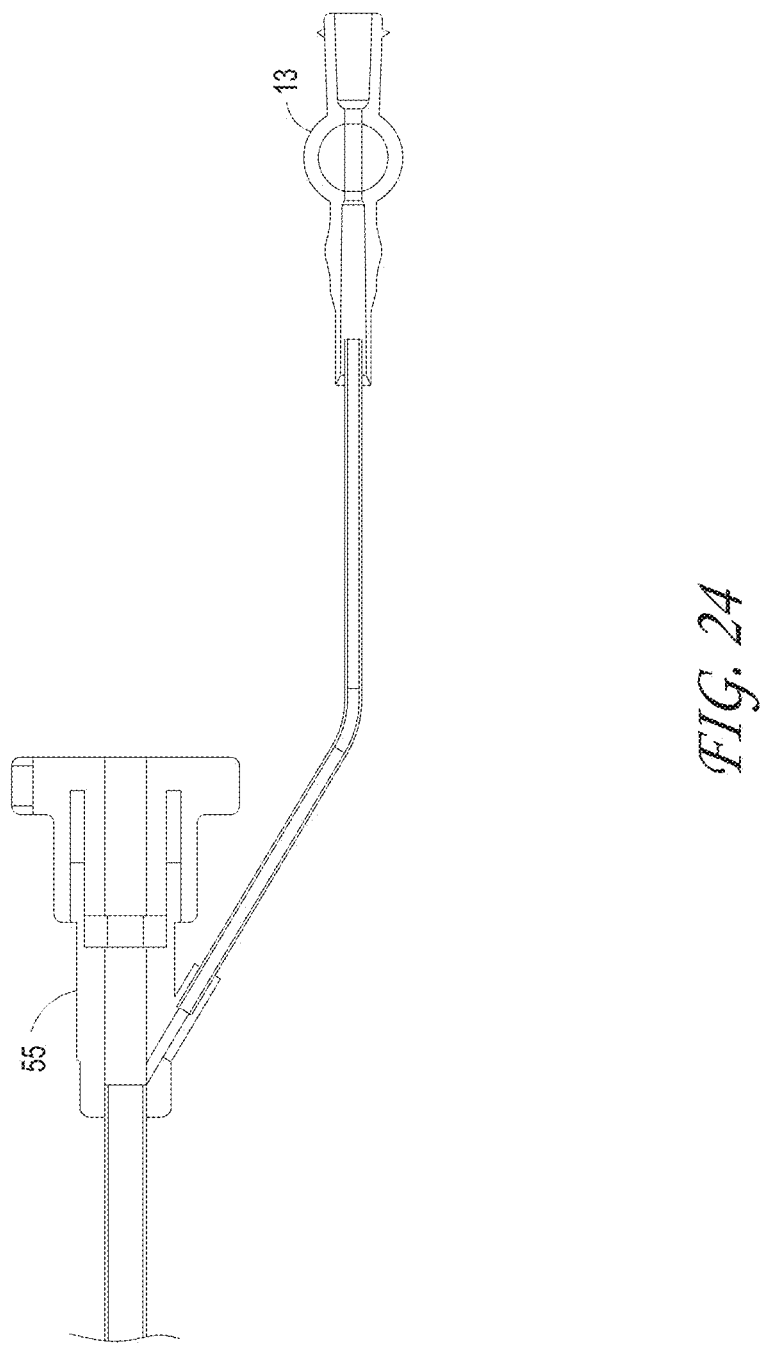
Figure 26:
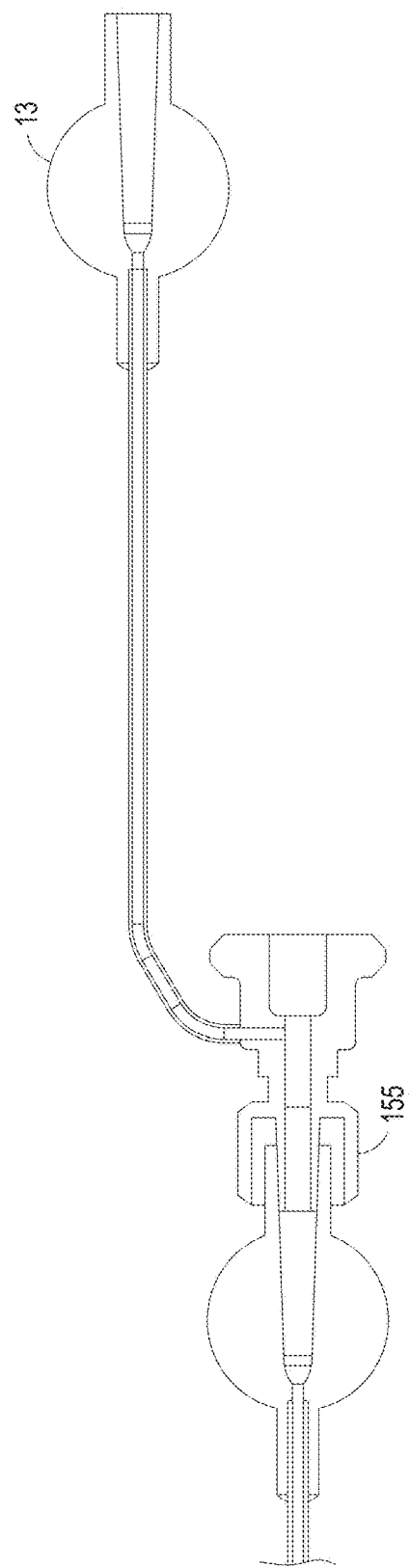
FIG. 26 illustrates the proximal end of the capture catheter, according to some embodiments of the invention.

FIGS. 22-24 illustrate the outer sheath assembly 1 of the capture device, according to some embodiments of the invention. The outer sheath 1 can function to contain, protect, and deliver the Axial Lengthening Thrombus Capture Device (tubular mesh 8 (not shown)) to the desired anatomical location, such as in a radially compressed configuration. As shown in FIG. 22, the Outer Sheath 1 can include a soft atraumatic distal tip, a shaft body that can be tubular in some embodiments, an interior channel/lumen configured to house and reversibly couple at its proximal end a second tubular member, such as a capture catheter as described elsewhere herein, and a proximal connector with a seal 55 and flush tube/port 13. The Outer Sheath 1 can be made from suitable medical grade materials, including but not limited to Nylon, Polyurethane, Pebax, Polyethylene, PET, PTFE, ePTFE, PEEK, PEBAX/Propell and polypropylene. The polymeric materials can include radiopaque materials such as, for example, barium sulfate, bismuth subcarbonate or bismuth trioxide to enable viewing under fluoroscopy. The radiopaque materials can form one, two, or more discrete marker elements in some embodiments, such as at the distal tip, and/or spaced apart at regular or irregular intervals along the length of the outer sheath 1. The outer diameter of the outer sheath 1 can range from, for example, 3 F to 30 F. The inner diameter of the outer sheath 1 can range from, for example, 2 F to 28 F. In some embodiments, the inner diameter is substantially constant throughout the interior channel, e.g., the lumen shaft. In some embodiments, the inner diameter at the distal end is about or at least about 10%, 20%, 30%, 40%, 50%, or more than the proximal end. The change in inner diameter can be, for example, stepwise or gradual in one location or two or more locations. The outer diameter can be substantially the same the entire length of the catheter, in some embodiments. The outer sheath 1 working length can be, in some cases, from about 10 cm to about 150 cm. In some embodiment, the Outer Sheath 1 working length is about 135 cm in some embodiments. The Outer Sheath 1 shaft can be braided or non-braided. In some embodiments, the Outer Sheath 1 shaft can be deflectable (via, for example, one, two, or more pullwires on the distal end) at various locations and multiple deflectable directions along the shaft length to accommodate various tortuous paths such as entry into a left or right heart atrium, heart ventricle, main pulmonary artery, and left and right pulmonary artery for pulmonary embolism applications, or a vein such as the great saphenous vein, superficial femoral, common femoral, SVC, IVC, or other upper or lower extremity, visceral, or other superficial or deep veins for deep venous thrombosis removal applications. The distal end of the shaft of the outer sheath 1 can be configured to deflect up to 360 degrees in some cases. Additionally, the distal tip of the Outer Sheath 1 can be configured to deflect or bias toward or away from the vessel wall. The distal tip of the outer sheath 1 can include one, two, or more radiopaque markers to indicate tip location. Alternatively, the distal tip can include radiopaque materials such as, for example, Barium Sulfate, Bismuth Subcarbonate or Bismuth Trioxide. FIGS. 23 and 24 illustrate the distal end and proximal end of the outer sheath assembly respectively. As shown in FIG. 26, the proximal end of the outer sheath 1 connects to the outer sheath connector 55 with seal and coupler to a capture catheter connector, and flush port 13.

Figure 25:
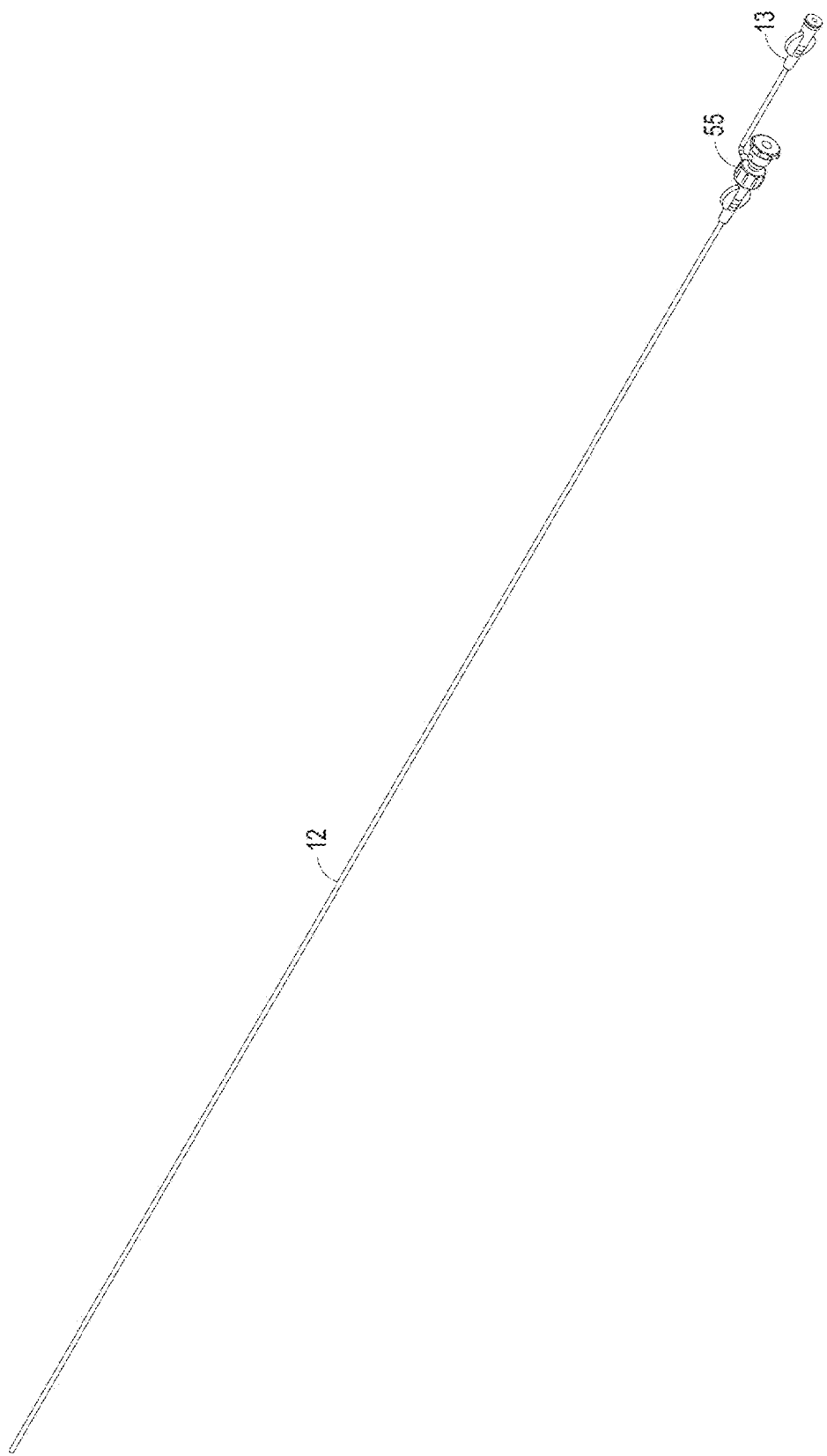
FIG. 25 illustrates the capture catheter assembly, according to some embodiments of the invention.

FIG. 25 illustrates the capture catheter assembly 12, according to some embodiments of the invention, showing catheter shaft 12 and outer sheath 1. FIG. 26 illustrates the proximal end of the capture catheter, according to some embodiments of the invention, showing a connector with seal 155 operably connected to a flush port 13.

Figure 27:
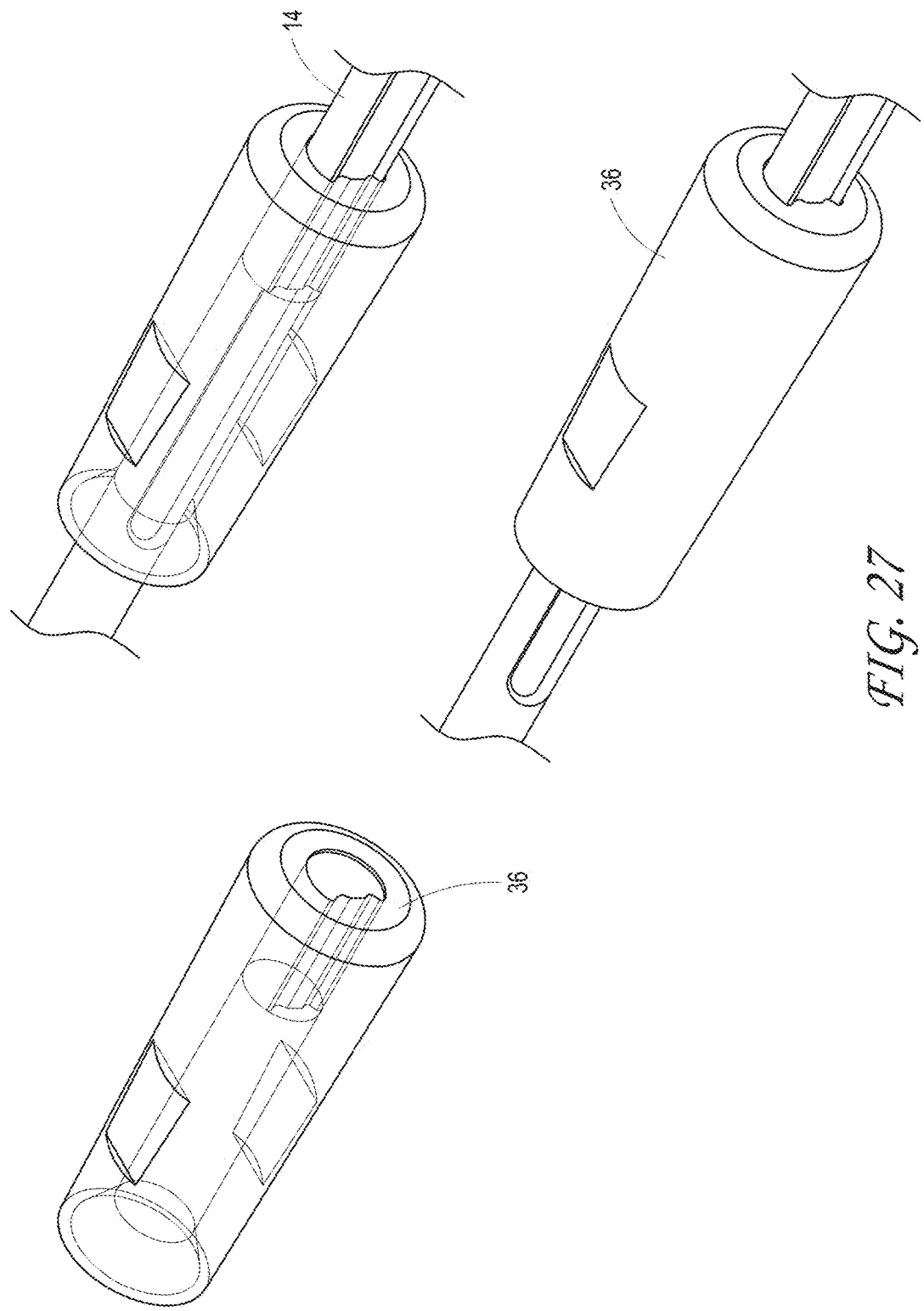
FIG. 27 illustrates an embodiment of a key cap feature to enable an anti-rotation of the hypotube pusher.

FIG. 27 illustrates an embodiment of a key cap 36 feature to prevent or inhibit rotation of the hypotube pusher 14. As illustrated, the key cap 36 can be a tubular member with a lumen to fit the hypotube pusher 14 therethrough. The lumen is non-circular in some embodiments, and/or have a non-circular zone, or otherwise configured to prevent or limit rotation. In some embodiments, the lumen includes teeth or other projections into the lumen as shown to prevent undesired rotation of the hypotube pusher. In some embodiments, the lumen or a portion thereof has a square, rectangular, triangular, oval, pentagonal, hexagonal, or other non-circular geometry, and configured to limit rotation.

Figure 28:
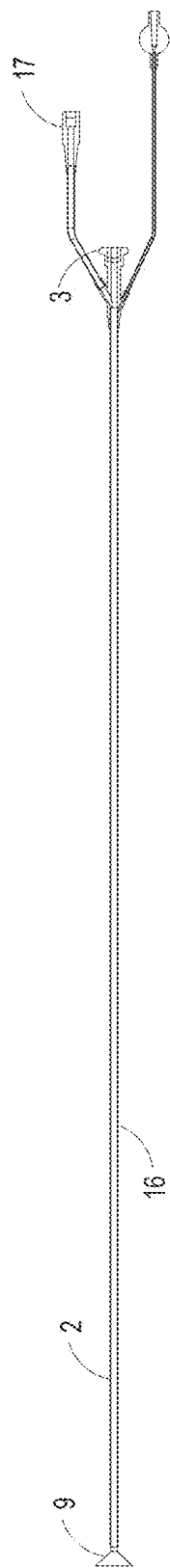
FIGS. 28 and 29 illustrates the suction catheter that can include a funnel tip, catheter shaft, and connector with seal, according to some embodiments of the invention.
Figure 29:
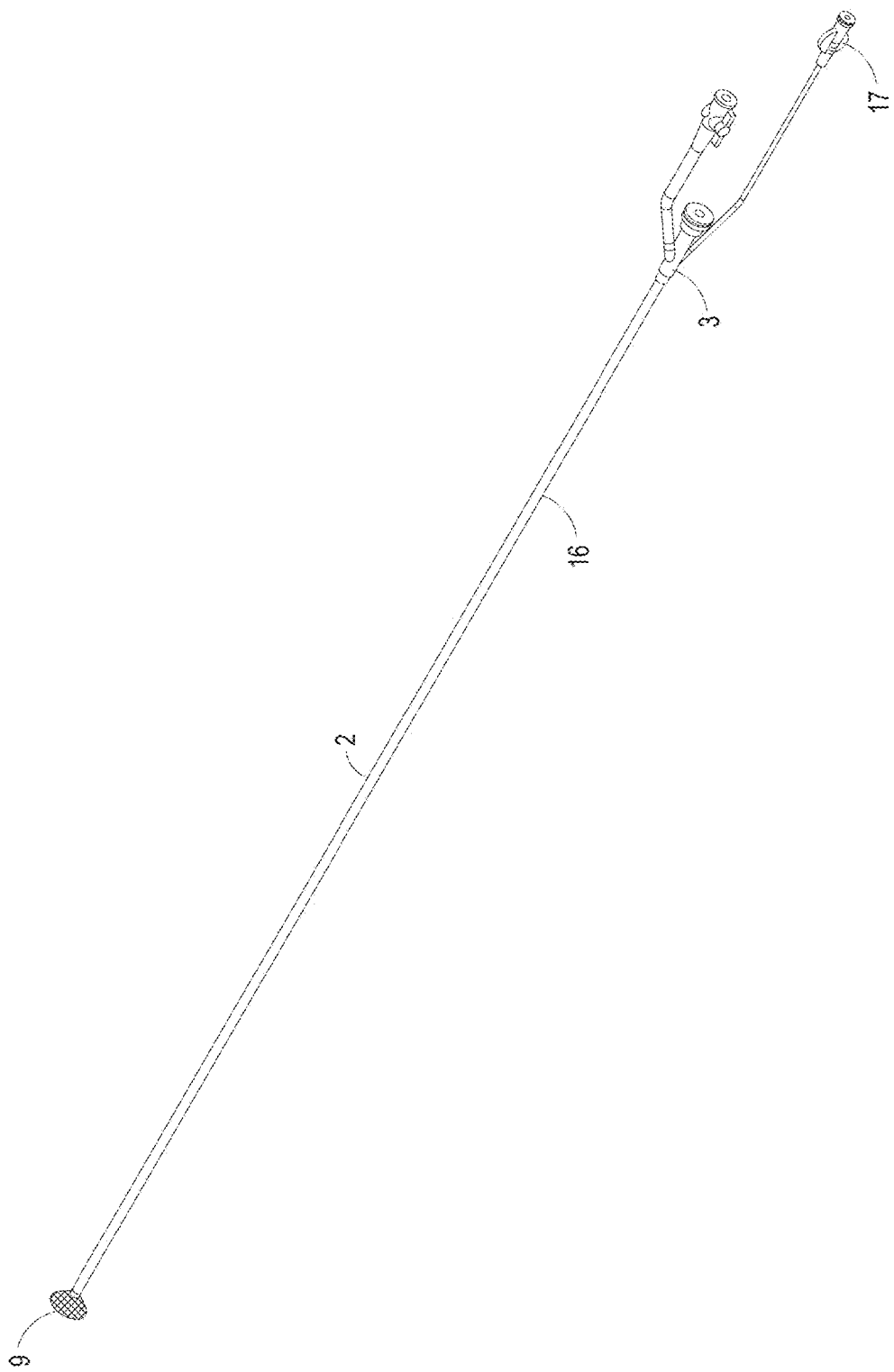
Figure 30:
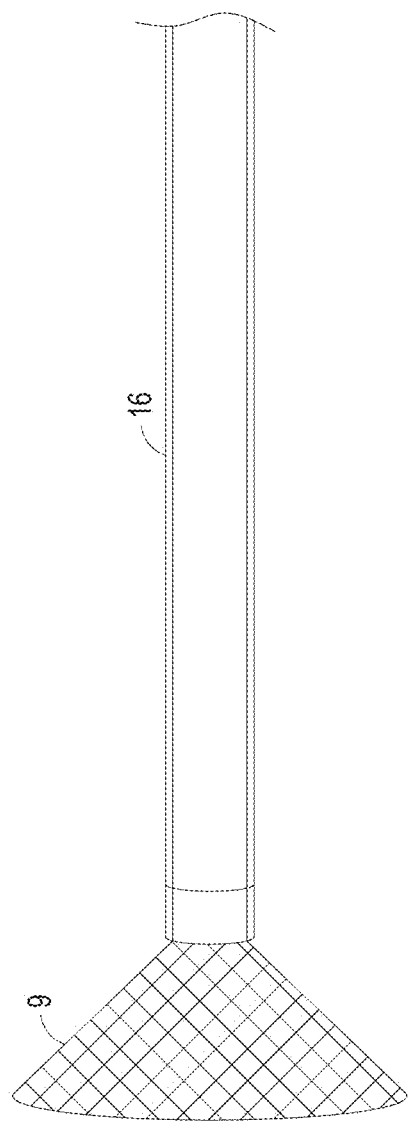
FIG. 30 illustrates the distal end of the suction catheter indicating the funnel tip and catheter shaft, according to some embodiments of the invention.
Figure 31:
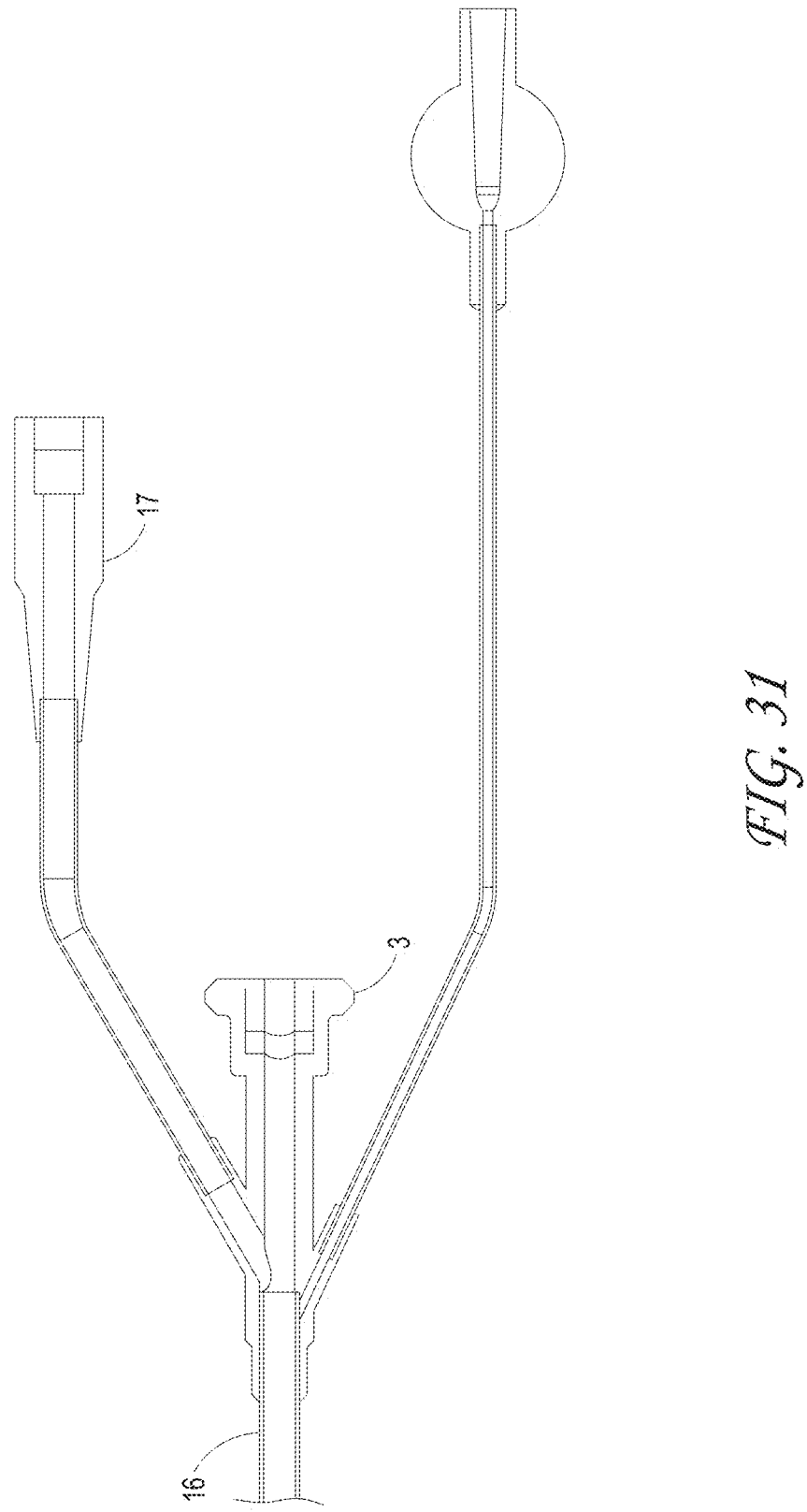
FIG. 31 illustrates the proximal end of the suction catheter indicating the connector with seal and ports for use with filter chamber and access to flush catheter lumen, according to some embodiments of the invention.
Figure 32:
FIGS. 32-41 illustrate different macerator designs and shapes, according to some embodiments of the invention.
Figure 33:
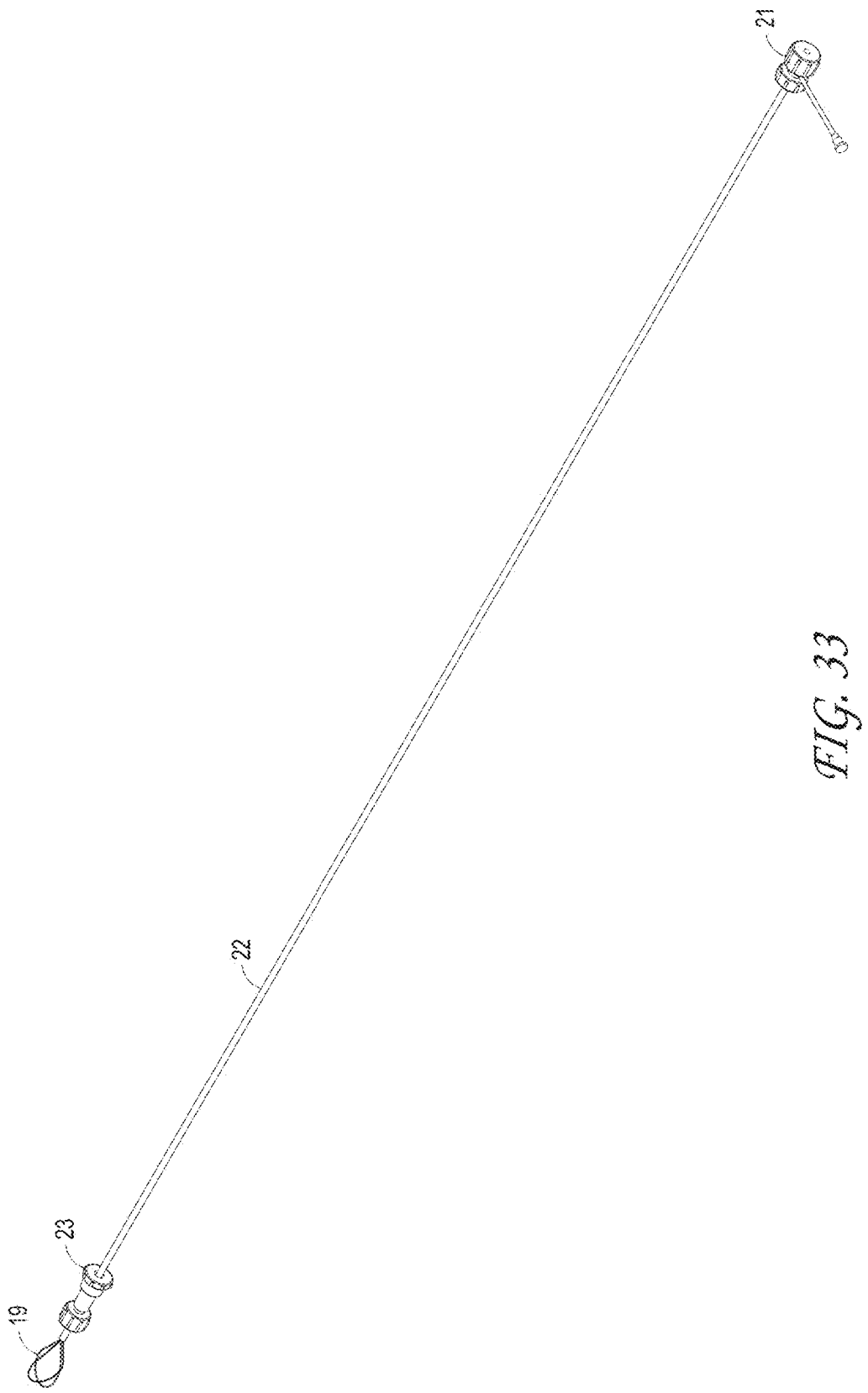
Figure 34:
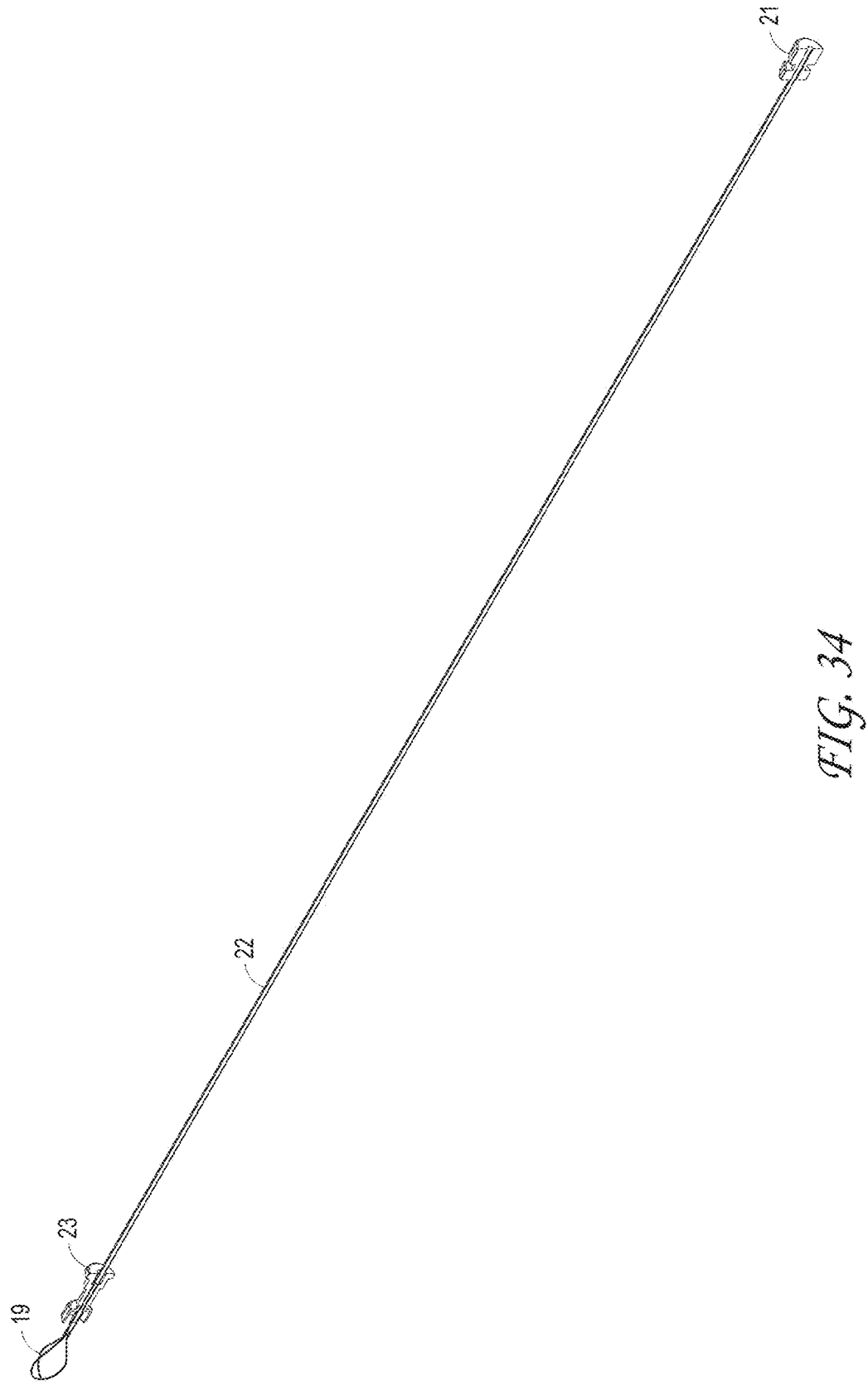
Figure 35:
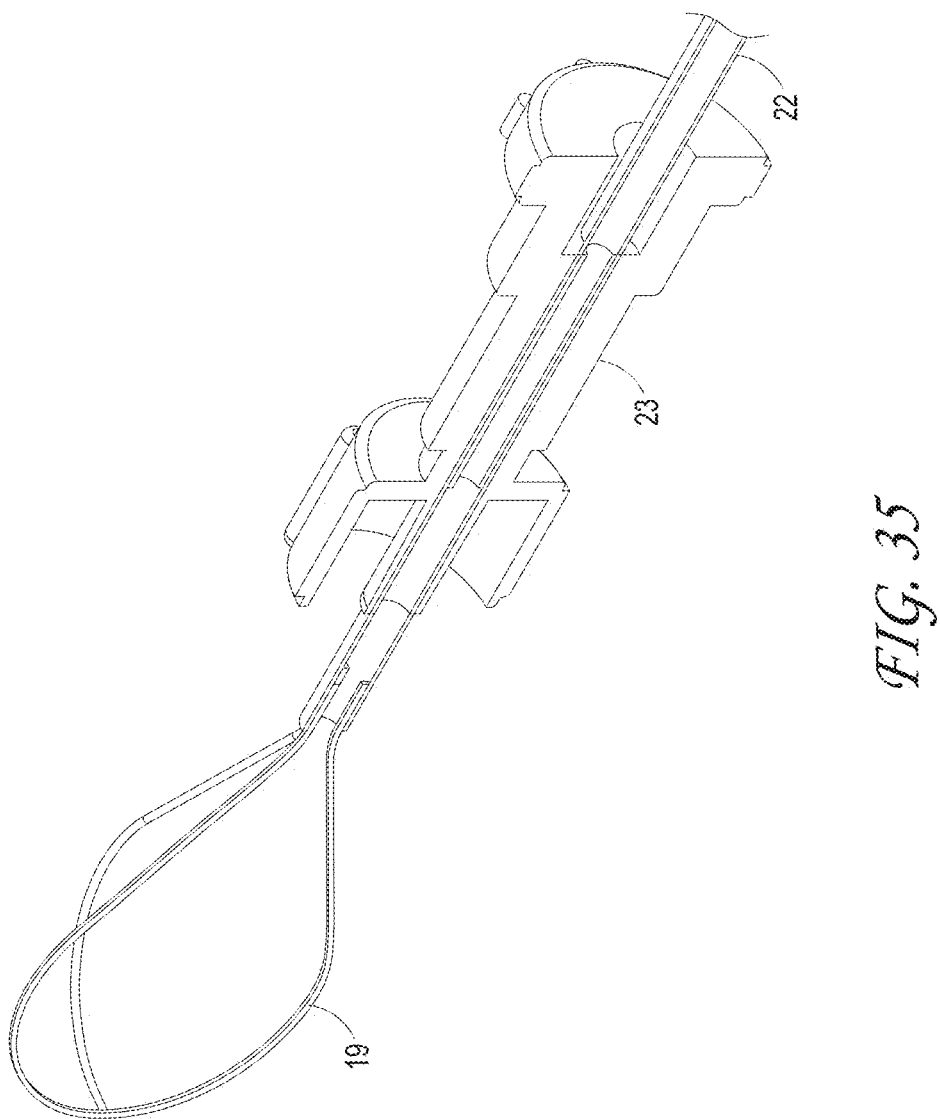
Figure 36:
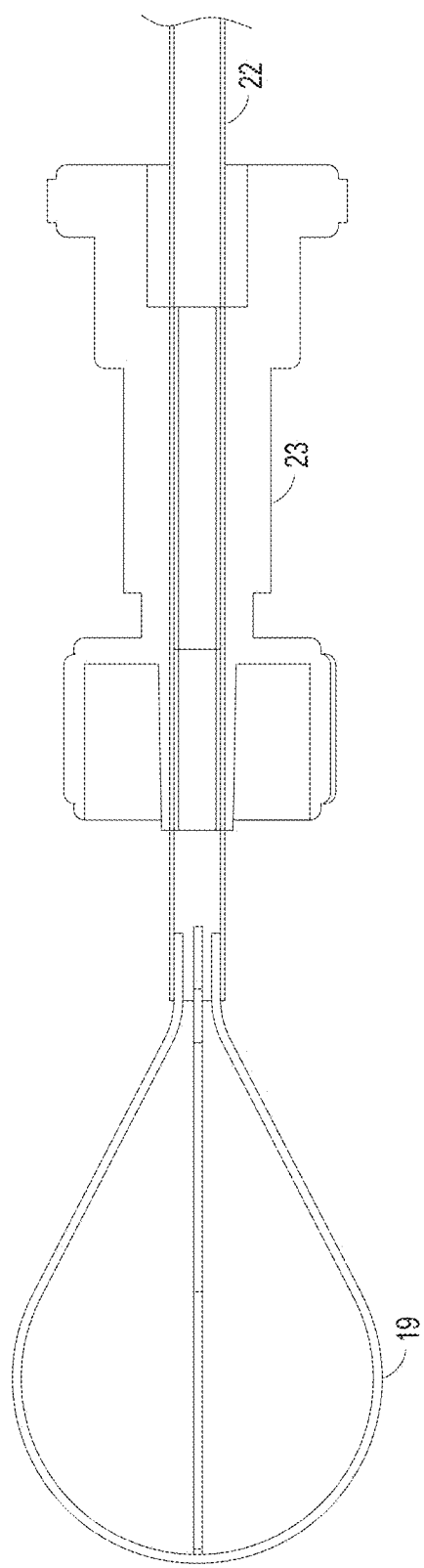
Figure 37:
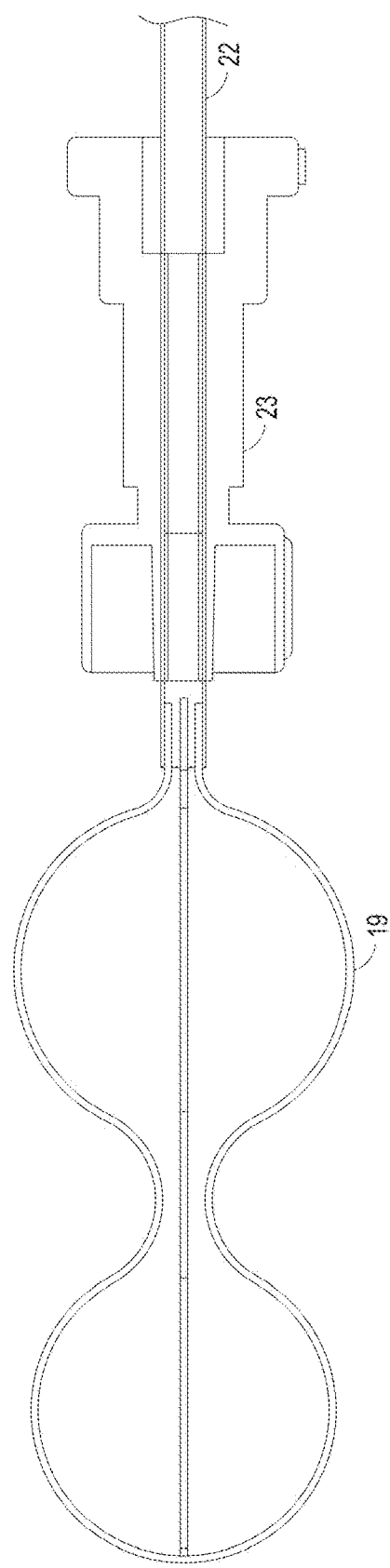
Figure 38:
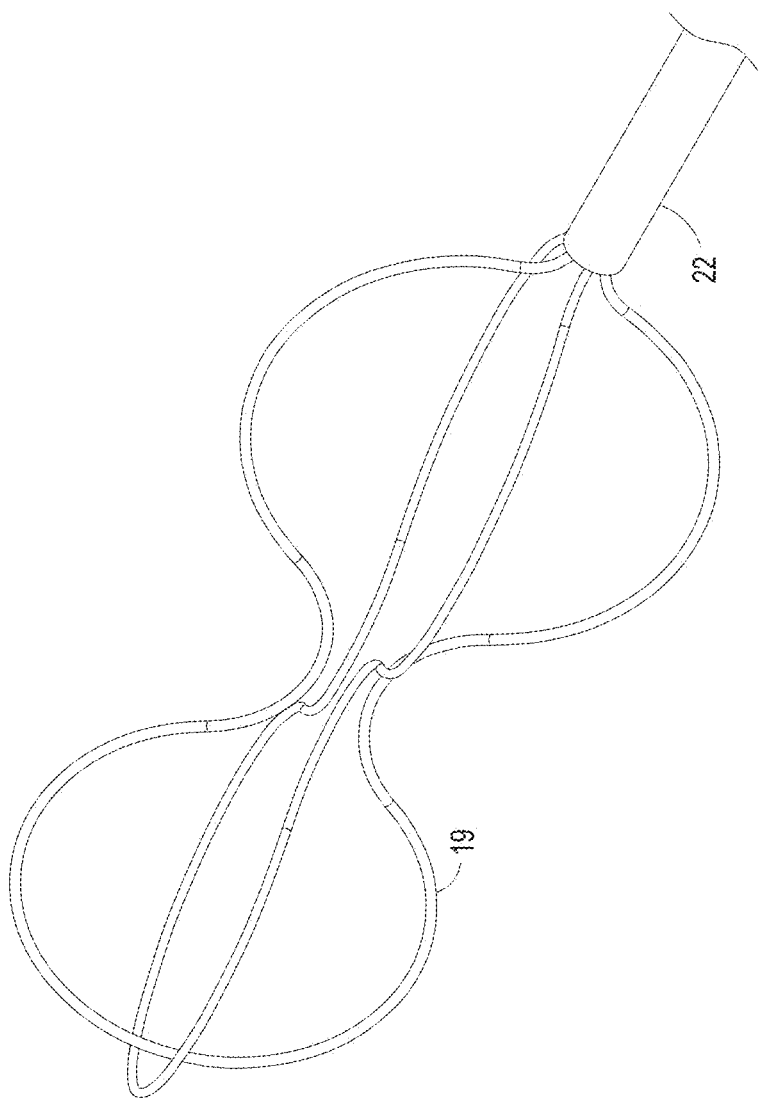
Figure 39:
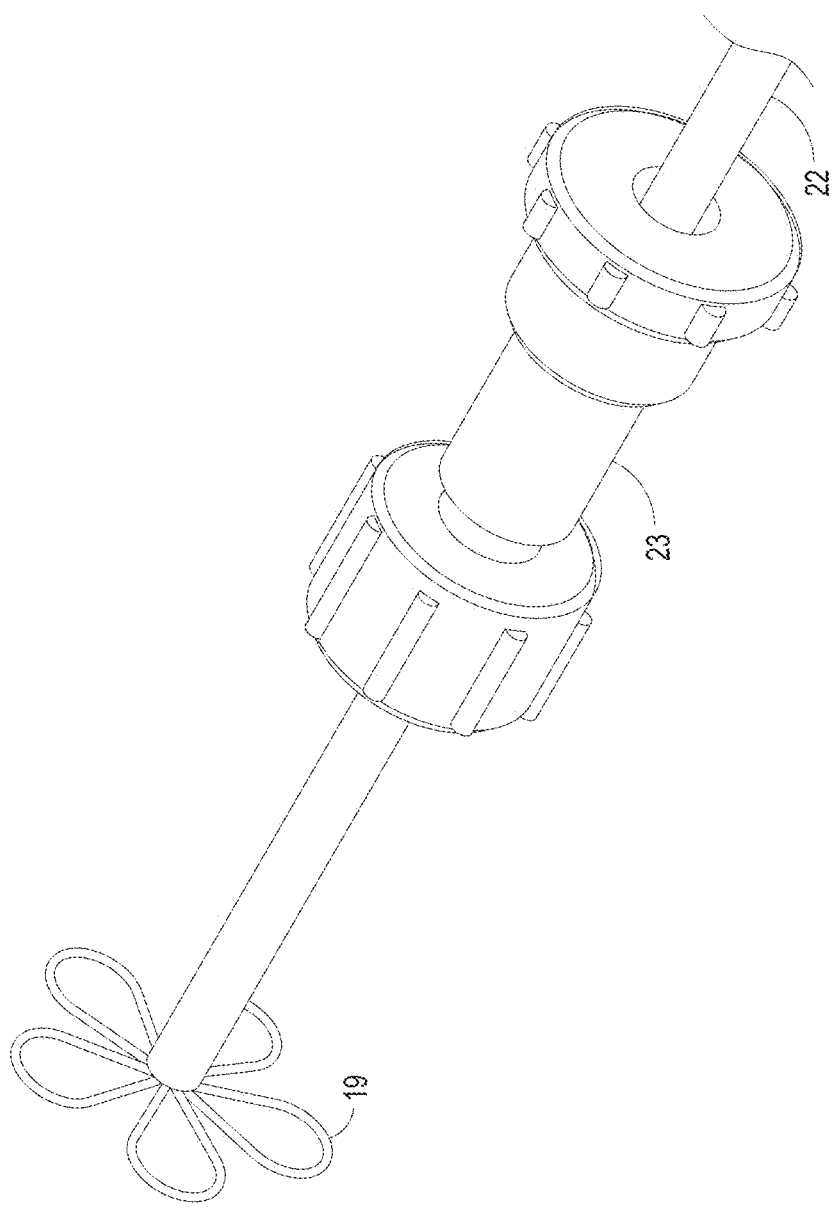
Figure 40:
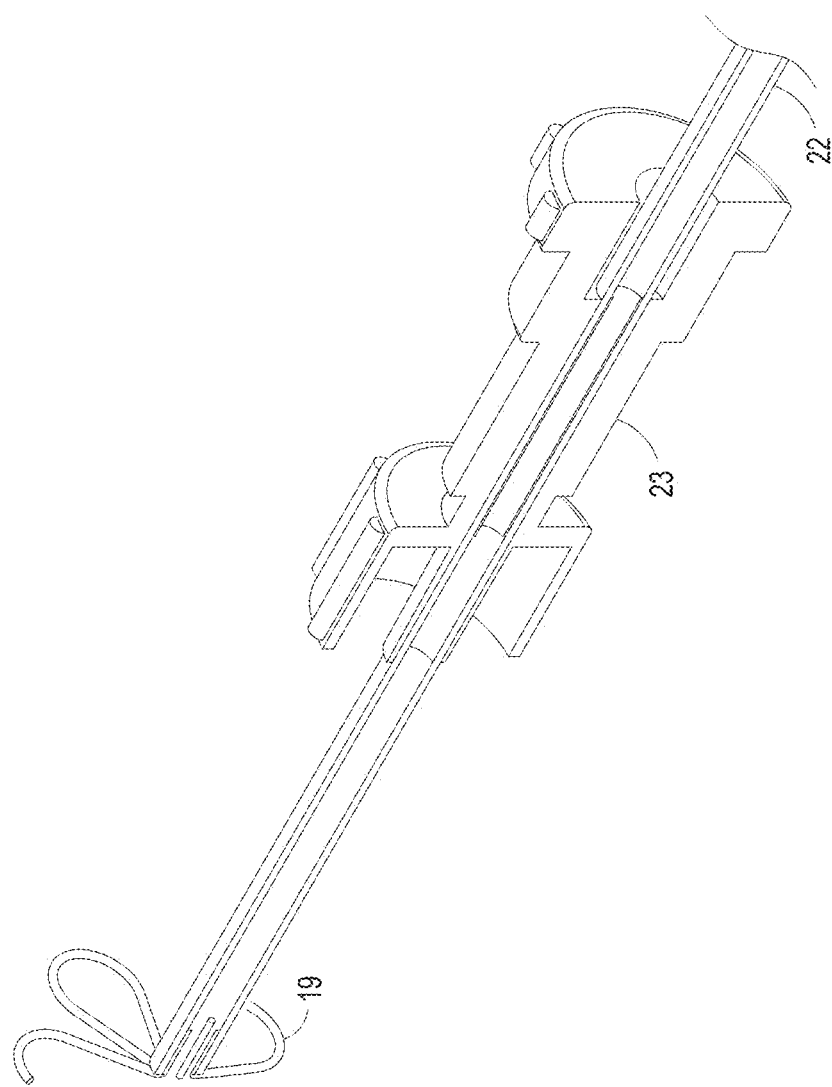

In some embodiments, as illustrated in FIGS. 28-29 for example, an optional suction catheter 2 can function to aspirate thrombus within the ALTC Device 8. The suction catheter 2 can include in some embodiments a distal funnel tip 9, elongate shaft body 16, and proximal connector with seal 3. FIG. 30 illustrates a close-up view of the funnel tip 9 which can be attached at the suction catheter shaft 16 distal end to aid in retrieving the thrombus and allow efficient suction. The funnel tip 9 can be made of, for example either polymeric and/or metallic materials. It can be tubular in shape, woven or braided, in some embodiments. Funnel tip 9 can be in various configurations to allow better retrieval and suction. In some embodiments, the funnel tip 9 has a funnel shape with a first, larger distal diameter, a transition section, and a second, smaller proximal diameter as illustrated. The suction catheter shaft 16 creates a pathway for the aspirated thrombus to travel proximally and exit the body and in some embodiments into the optional filter collection chamber. The shaft can be of various diameters, lengths and/or geometries to aid in the removal of materials such as blood clots. The suction catheter shaft can be made from suitable materials such as and not limited to Nylon, Polyurethane, Pebax, Polyethylene, PET, PTFE, ePTFE, PEEK, and polypropylene. In some embodiments, the suction catheter Shaft distal end is expandable so to accommodate large amount of blood clots. The suction catheter 2 can attach to the proximal end of filter collection chamber 5 to enable thrombus aspiration (or removal). In some embodiments, the suction catheter shaft 16 is deflectable at one, two, or more locations along the shaft length to accommodate various tortuous paths such as entry into the right atrium, right ventricle, main pulmonary artery, and left and right pulmonary artery. A proximal flush port 13 is also illustrated.

Figure 41:
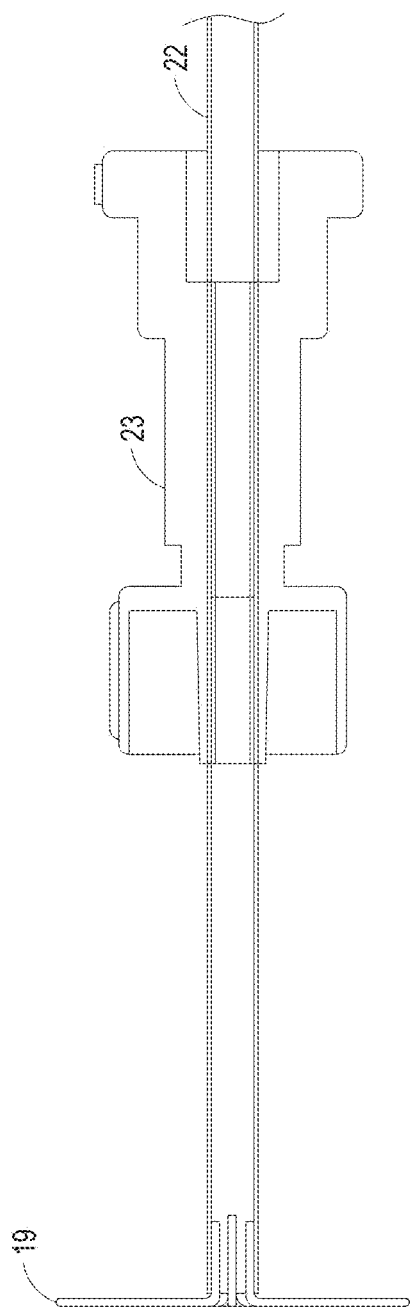

In some embodiments, a mechanical thrombectomy tool such as macerator 19 shown in FIGS. 32-41 for example, can function to disrupt and break up the thrombus within the ALTC Device 8. The macerator 20 can include a disruptor 19, shaft 22 and proximal connector with seal 21. Adjustable Touhy knob 23 distally is also shown just proximal to disruptor 19. The disruptor 19 can be attached to the distal end of the shaft 22. The macerator 20 can have various end effector tip configurations as illustrated in FIGS. 35-41 depending on the desired clinical result to break up the thrombus within the ALTC Device 8, including a bulbous shape (FIG. 36), proximal and distal bulbs with a narrow waist (FIG. 37), a plurality of proximal and distal bulbs with a narrow waist each offset by an angle, such as about 90 degrees (FIG. 38), a flower petal design with petals radiating radially outwardly from a central hub (FIG. 39), a hemipetal design (FIG. 40), or a substantially linear design orthogonal from the longitudinal axis of the shaft 22 (FIG. 41). The disruptor 19 collapses during insertion through the suction catheter 2 system and expands once exiting the catheter. The disruptor 19 can be made of, for example, metallic materials such as stainless steel, Nitinol, cobalt chrome, etc. The macerator can be activated either by manual rotation, manipulation and/or a motorized handle.

To macerate the thrombus, the macerator 19 is inserted through the suction catheter 2 and position within the ALTC Device 8. A manual technique applies to the luer connector 21 of the macerator 19 by rotating the luer connector 21 causing the disruptor 20 to rotate thereby breaking up the thrombus. Alternatively, the macerator 19 can be used with a motorized handle (not shown). Traversing the disruptor 20 axially through the entire length of the ALTC device 8 can aid in breaking up the thrombus.

The filter collection chamber 5 (FIG. 42) can function to suction and collect the blood clots. The filter collection chamber 5 can include, for example, a collection chamber 325, filter 324, plunger 323, inflow port 327 and outflow port 326. The filter collection chamber 5 can have an outflow port 326 attaching to the suction catheter 2 connector and an inflow port 327 where a syringe or a similar device can attach for aspiration. The collection chamber 325 has a filter system 324 residing inside the chamber 325 to allow filtering the blood and thrombus. The chamber 325 also has a plunger 323 for use in injecting fluid such as saline to fill the chamber 325 and push filtered blood back into the vasculature. The plunger 323 can serve as a seal on one side of the chamber.

Figure 42:
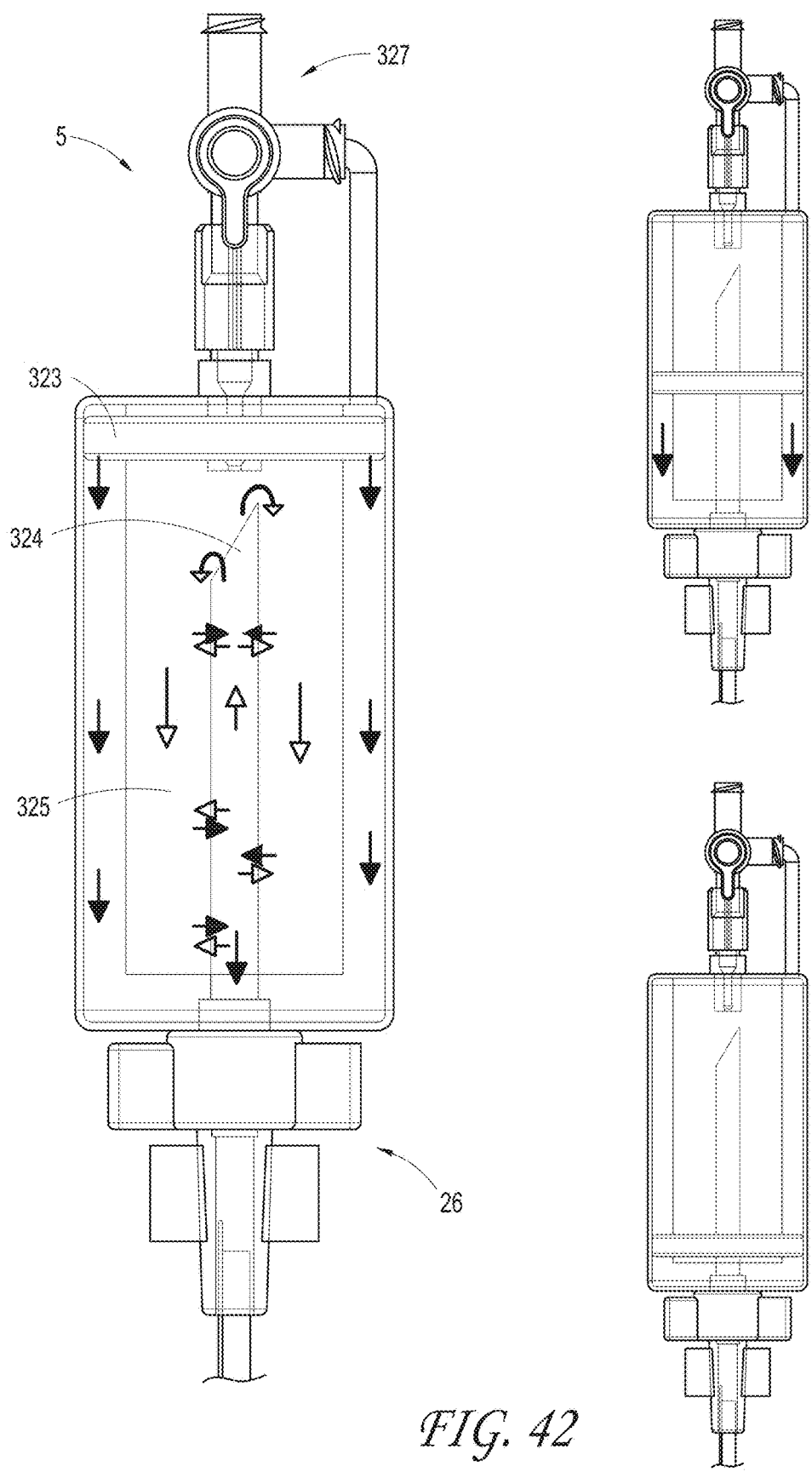
FIG. 42 illustrates a filter collection chamber that can include an inflow port to connect to a syringe, an outflow port to connect to the suction catheter, a plunger, a filter to filter blood clot or debris and retain in the chamber and a chamber to collect blood clot or debris, according to some embodiments of the invention.

To aspirate the thrombus from the system, the suction catheter 2 is attached to the filter collection chamber 5 (FIG. 42). A large syringe attaches to the proximal end of the filter collection chamber 5. Applying suction using the syringe causes the thrombus and blood clots to migrate into the filter collection chamber 5. Once all the thrombus is contained within the chamber 5, close stopcock, detach the syringe and fill with saline and reattach the syringe to the filter collection chamber 5. Alternatively, an extension tube and external saline filled syringe can be used to fill saline into the suction syringe. Injecting via the syringe will push saline into the chamber 325 causing the plunger 323 to push the blood back into the vasculature. The chamber 325 will return the blood and leave the thrombus inside the chamber 325. Alternatively, the filter collection chamber 5 can be detached without returning filtered blood to the system. Once the thrombus is removed, retract the suction catheter 2 inside the outer sheath 1. Retract the ALTC Device 8 into the outer sheath 1 and remove the entire system from the body.

Catheter systems as described herein can be utilized for a variety of indications depending on the desired clinical result. In some embodiments, the use is not limited to venous systems and can apply to other arterial, venous, or nonvascular areas such as neurovascular, peripheral vascular, cardiovascular, temporary embolic protection device for a cardiovascular procedure such as valve replacement, carotid protection, pulmonary protection during deep vein thrombectomy or embolectomy), or retrieval of an implant, medical device, or other material.

Figure 43:
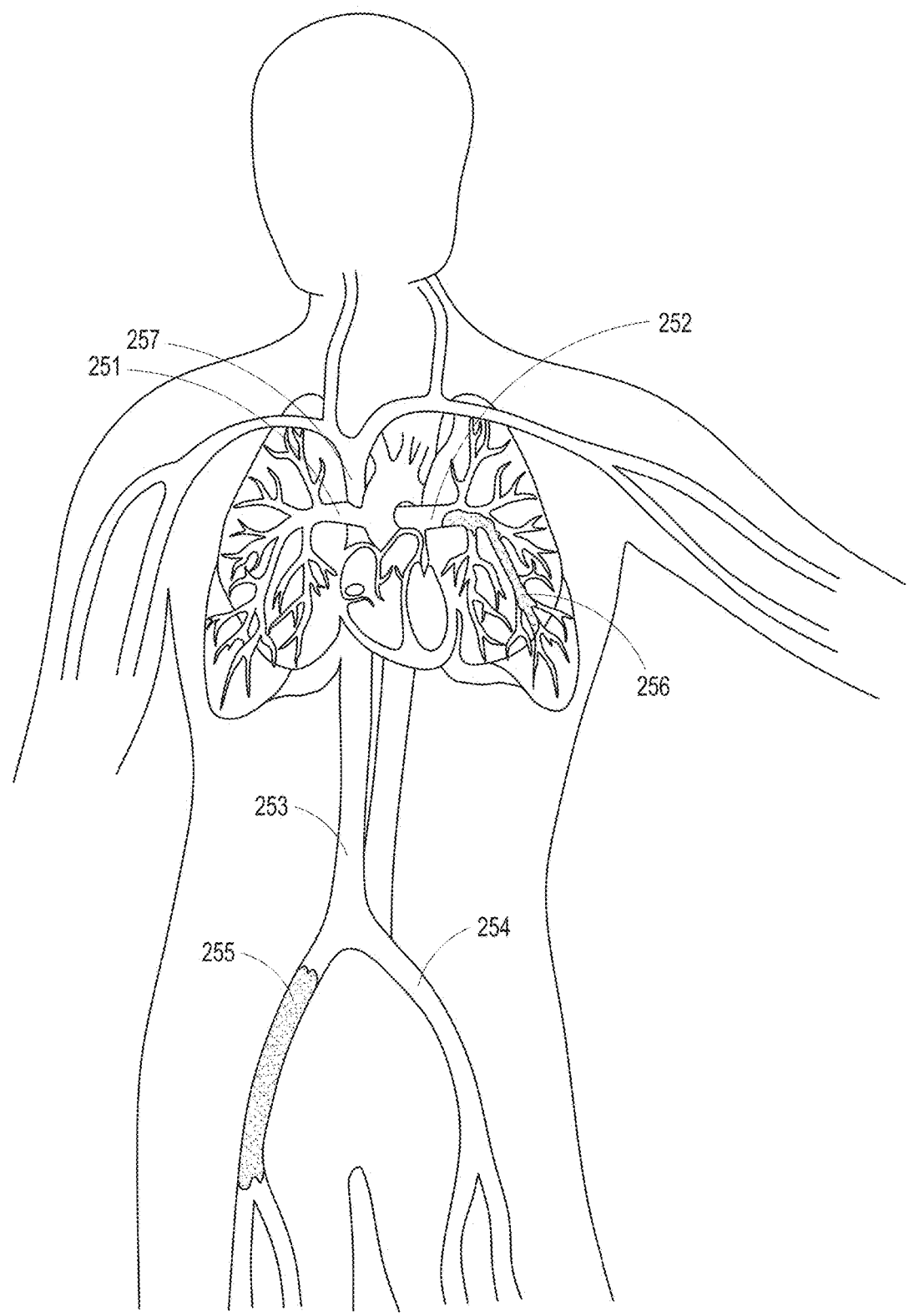
FIG. 43 illustrates a blood clot lodging in the left side of pulmonary system, according to some embodiments of the invention.

FIG. 43 illustrates a blood clot lodging in the left side of the pulmonary system. Shown is the right pulmonary artery 251, left pulmonary artery 252, inferior vena cava 253, left iliac artery 254, right iliac artery 255, a pulmonary embolus 256 in the left pulmonary artery 252 distally, and the superior vena cava 257.

Figure 44B:
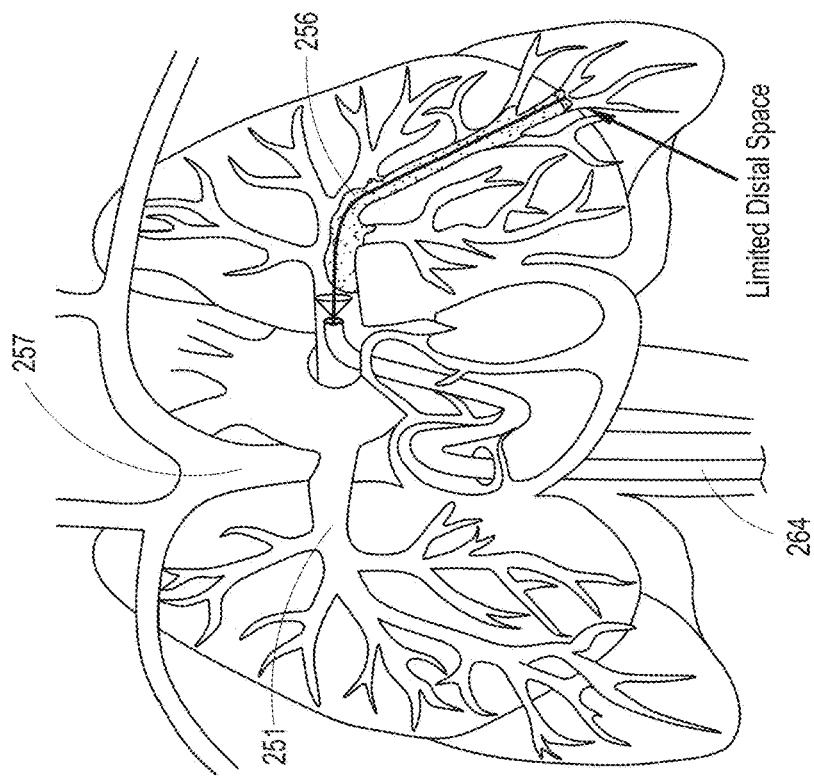
FIGS. 44A and 44B illustrate blood clots residing in the left side pulmonary system and the capture device respectively, according to some embodiments of the invention.
Figure 44A:
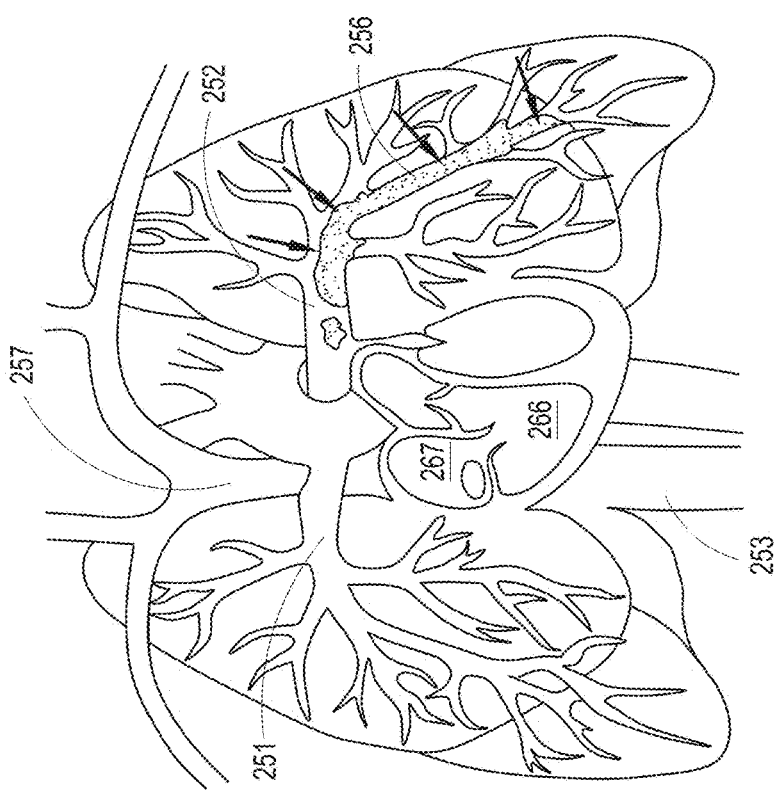

FIGS. 44A and 44B illustrate blood clots residing in the left side pulmonary system and the capture device respectively, according to some embodiments of the invention. In addition to the anatomical features illustrated in FIG. 43, also shown is the guide catheter 264, right ventricle 266, and right atrium 267. As shown in FIG. 44B, capture devices as described and illustrated herein can advantageously be utilized when there is very limited distal space, as the device is functional throughout a wide working axial range as discussed elsewhere herein.

Figure 45:
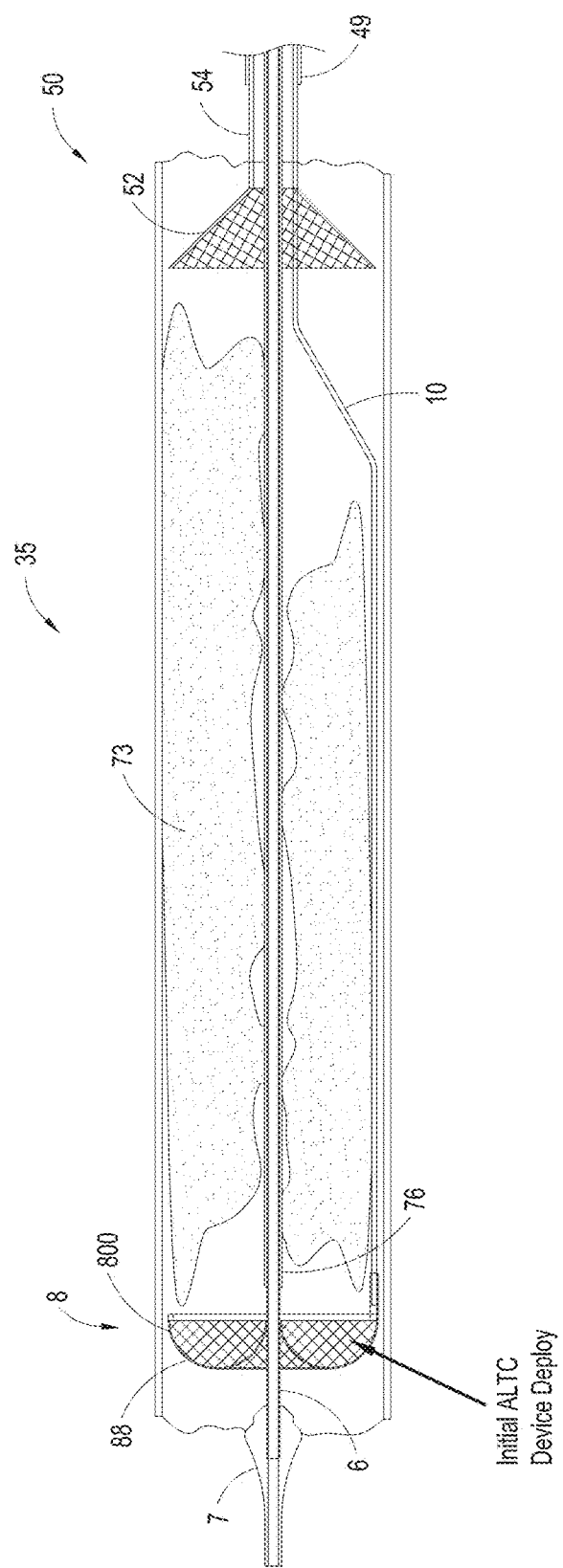
FIG. 45 illustrates the initial deployment configuration of the axial lengthening thrombus capture device positioned distal to the thrombus occluded area and a funnel tip positioned proximal to the thrombus occlusion, according to some embodiments of the invention.
Figure 46:
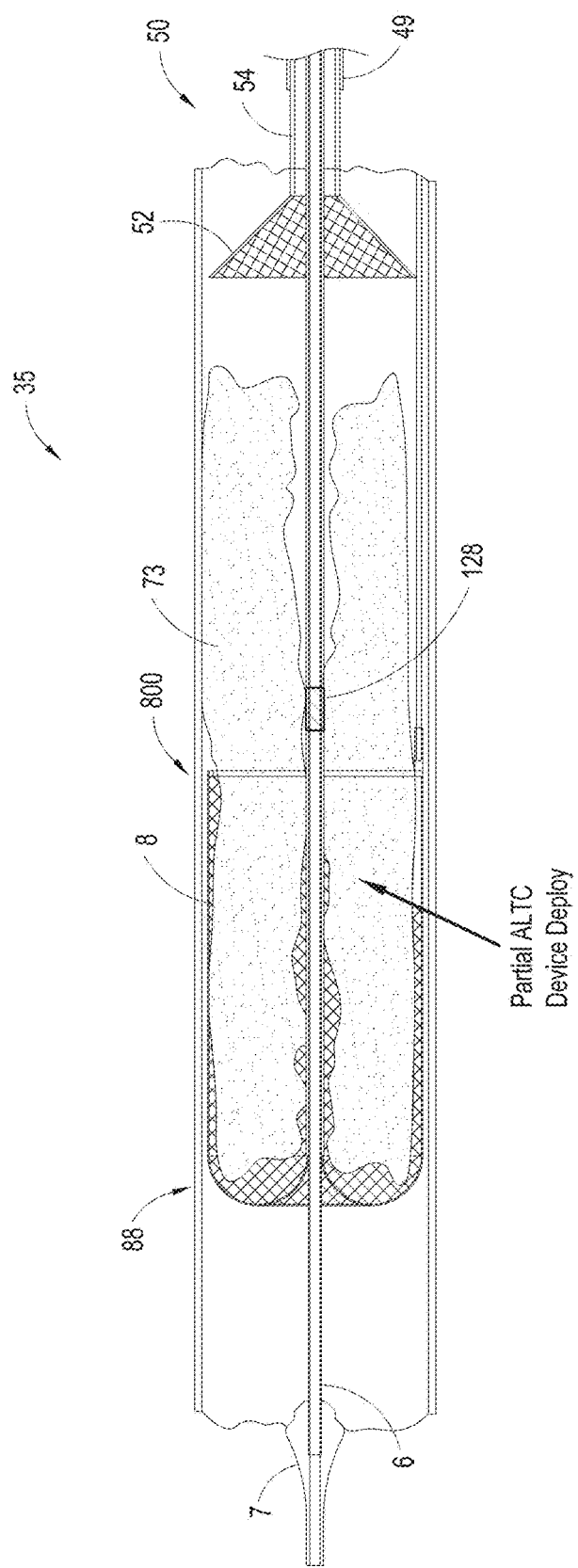
FIG. 46 illustrates the axial lengthening thrombus capture device lengthening proximally to capture the thrombus, according to some embodiments of the invention.
Figure 47:
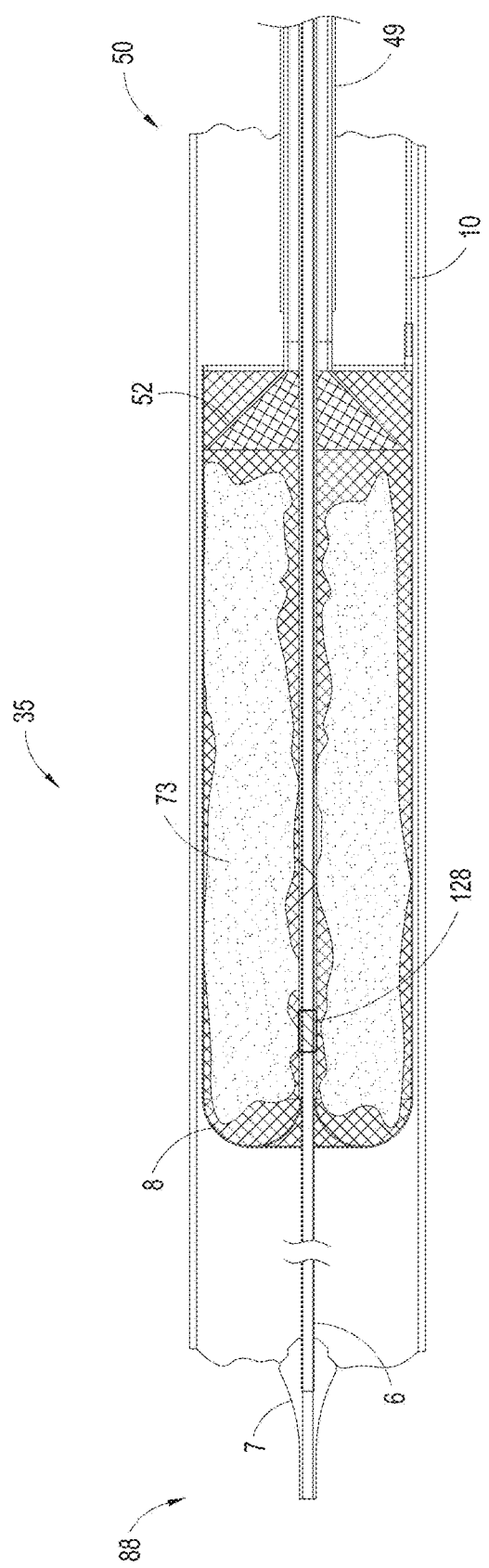
FIG. 47 illustrates the axial lengthening thrombus capture device completely capturing the thrombus, and a funnel tip is inside the axial lengthening thrombus capture device.

FIGS. 45-47 illustrate capture of a thrombus within a vessel, according to some embodiments. FIG. 45 illustrates the initial deployed configuration of the axial lengthening thrombus capture device (e.g., tubular mesh) 8 with end 800, dynamic fold point 88, and reserve radially compressed segment (not shown) terminating proximally at point 128 where the radially compressed segment is fixably attached to the outer sidewall of the guidewire lumen 6 is shown. The expanded segment of the tubular mesh 8 is positioned distal to the thrombus 73 occluded area and the expanding guide catheter 50 including distal funnel tip 52 with proximal expandable section, inner catheter 54 and outer catheter 49, or in some embodiments suction catheter funnel tip positioned proximal to the thrombus occlusion 73, according to some embodiments of the invention. In some embodiments, expanding guide catheter 50 as described elsewhere herein or a suction catheter can be utilized depending on if suction is desired. Also shown proximally is inner sheath 54 and outer sheath 49 of expanding guide catheter 50. Actuation of capture pullwire 10 alone or with capture catheter 12 such as axially in an appropriate direction (or capture catheter coupled to the outer sheath (not shown) in embodiments with a sleeve as previously described) can result in axial lengthening or shortening of the ALTC device 8 depending on the desired clinical result. FIG. 46 illustrates the axial lengthening tubular mesh 8 expandable segment lengthening proximally to capture the thrombus, according to some embodiments of the invention, with the associated radially compressed segment shortening reciprocally. FIG. 47 illustrates the axial lengthening thrombus capture device completely capturing the thrombus, and the expanding guide catheter funnel tip or alternatively the suction catheter funnel tip is inside the axial lengthening thrombus capture device. Subsequent suction via the suction catheter 2 in embodiments where suction is utilized can be performed to remove the blood clot or thrombus. The ALTC Device can lengthen to have a maximal length that covers the entire length of catheter system from, e.g., about 0.5 cm to about 125 cm. In some embodiments, the ALTC device may lengthen to about or at least about 2, 3, 4, 5, 6, 7, 8, 9, 10, 11, 12, 13, 14, 15, 20, or more centimeters. Depending on vessel diameter, the outer diameter of the ALTC device can range from, in some embodiments, about 1 millimeter up to about 80 millimeters. For example, large vessels such as the inferior vena cava, superior vena cava, descending, and ascending aorta, the diameter can range up to about 60, 70, 80, 90, 100 millimeters or more. Small vessels in the neurovascular system can be, for example, as small as about or less than about 5, 4.5, 4, 4.5, 3, 2.5, 2, 1.5, 1, 0.5, or less millimeters in diameter. The diameter of the ALTC device can achieve the similar effect of reducing or stretching the ALTC device diameter. In some embodiments, suction is not utilized or required, and the ALTC device envelops the clot, which can be mechanically pulled back into the capture catheter. In some embodiments, the ALTC device can be utilized to treat, for example, a clot in the carotid or cerebral arterial or venous circulation. The vessels to be treated could include, for example, the Circle of Willis, left or right common carotid or internal carotid arteries, anterior cerebral arteries, anterior communicating arteries, middle cerebral artery, posterior communicating arteries, carotid siphon, basilar arteries, vertebral arteries, or ophthalmic arteries for example, or any branches thereof. In some embodiments, the ALTC device can be utilized to treat, for example, a femoral vein, a brachial vein, a pulmonary vein, a breast vein, a cerebral vein, a brain sinus vein, a renal vein, a portal vein, a jugular vein, or another vein.

Figure 48A:
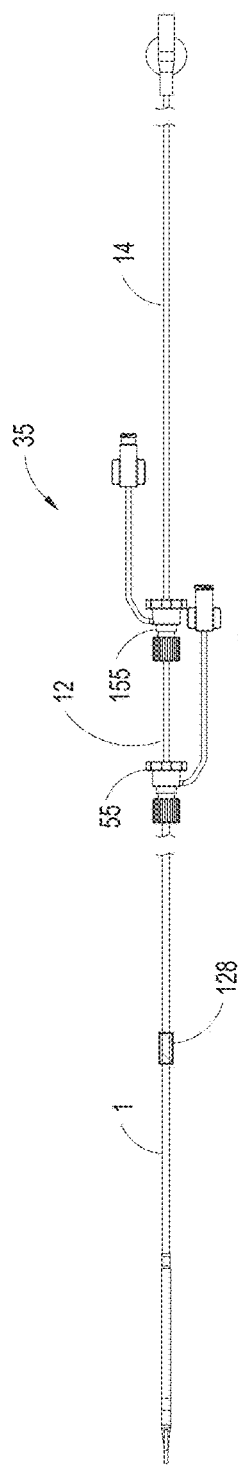
FIG. 48A illustrates the delivery configuration of the capture catheter device, according to some embodiments of the invention.
Figure 48B:
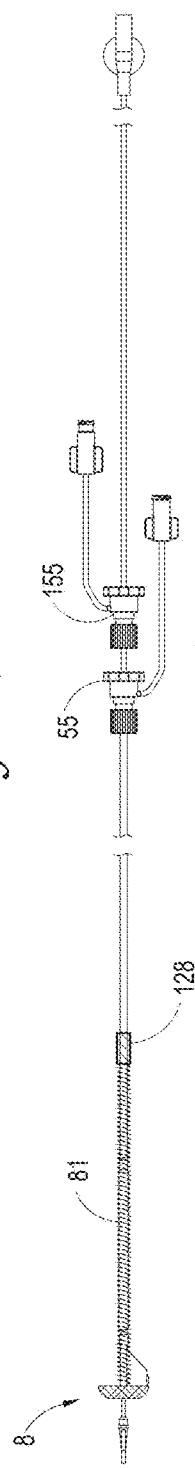
FIG. 48B illustrates the initial deployment position of the axial lengthening thrombus capture device, according to some embodiments of the invention.
Figure 48C:
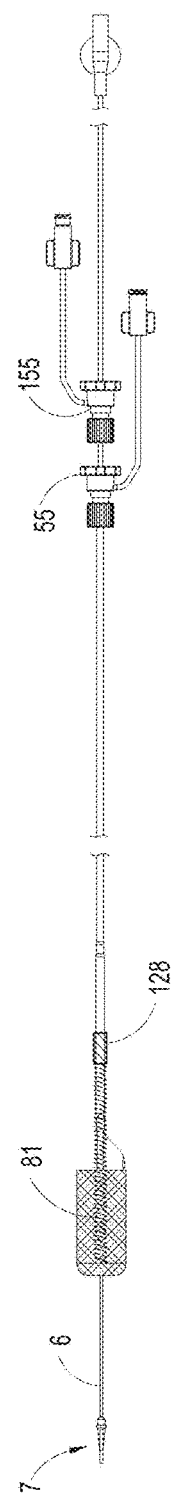
FIG. 48C illustrates the lengthening of the axial lengthening thrombus capture device, according to some embodiments of the invention.
Figure 48D:
FIG. 48D illustrate the final deployment of the axial lengthening thrombus capture device, according to some embodiments of the invention.

FIG. 48A illustrates another delivery configuration of the clot capture system 35 that can include features as previously described, according to some embodiments of the invention. FIG. 48B illustrates the initial deployment position of the axial lengthening thrombus capture device, according to some embodiments of the invention, and reversible coupling of the hub 55 of the capture catheter 155 to the hub 55 of the outer sheath. FIG. 48C illustrates the further lengthening of the expanded segment of the axial lengthening thrombus capture device, according to some embodiments of the invention, with reciprocal shortening of the reserve compressed segment 81. As illustrated, the guidewire tube 6 with nose tip 7 is maintained in position while the capture catheter reversibly coupled to the outer sheath can be withdrawn proximally. FIG. 48D illustrate the final deployment of the axial lengthening thrombus capture device at its maximal working length, according to some embodiments of the invention.

In some embodiments, systems and devices as disclosed herein can involve a general percutaneous technique, a cut-down procedure, or minimally invasive technique such as transapical, thoracoscopic, laparoscopic, or other techniques, for example, and not limited to transfemoral, transradial and/or internal jugular venous access. The technique can also apply to the arterial system, including neurovascular, cardiovascular, and peripheral vascular applications, as well as for use as an embolic protection device such as for a cardiovascular procedure such as valve replacement or repair for example. In some embodiments, a thrombectomy system can be delivered downstream of the aortic root, such as prior to the aortic arch, and a variable-length shape memory mesh structure such as an ALTC device with an open proximal end and closed distal end expanded prior to the index cardiovascular procedure, to capture downstream emboli, calcifications, or other debris. In some embodiments, the system can be deployed to prevent embolization during a deep vein thrombectomy or pulmonary embolectomy, for example. In another embodiment, the system can be deployed to prevent embolization or retrieval during acute ischemic stroke. Systems and methods as disclosed herein can also be utilized in non-vascular anatomy such as the biliary tree to capture gallstones, common bile duct stones, and pancreatic duct stones, for example, in the ureters or bladder to capture kidney stones, or in the fallopian tubes to capture ova or other materials, or in the gastrointestinal tract such as the esophagus, stomach, duodenum, jejunum, ileum, or colon to capture, for example, foreign bodies. Described herein are some embodiments of using the venous system to access the pulmonary artery to treat pulmonary embolism. The technique can also apply to other areas of the vasculature. Initial puncture to access the femoral vein. A short access guidewire is inserted into the femoral vein. Next, an appropriate 5 F or 6 F introducer sheath is inserted. The guidewire is exchanged for a 180 cm, 260 cm or 300 cm guidewire and advance pass the inferior vena cava, right atrium, right ventricle and the pulmonary artery to access the occluded treatment area. A longer length introducer/guiding catheter may be necessary to cross the tricuspid and pulmonary valve. Once the guidewire passes through the occluded treatment area, the 5 F or 6 F introducer sheath is exchanged for a long guiding catheter and position proximally near the occluded area. The catheter system 35 is inserted over the wire and through the guiding catheter and advance distally to the occluded area. The catheter system 35 can also utilize the outer sheath deflectable features to navigate through the vasculature without the use of a guiding catheter. Next, the catheter system's nose tip 7 passes through the occluded treatment area and positioned distal to the occluded treatment area. The Outer Sheath 1 is retracted to deploy the thrombus capture guide 11. The outer sheath 1 is retracted past the thrombus and positioned proximal to the thrombus (occluded area). The Suction Catheter 2 advances distally outside the Outer Sheath 1 and positions proximally to the occluded area, if suction is utilized.

To retrieve and capture materials such as blood clots or thrombus, the Thrombus Capture Guide 11 retracts by pulling the Capture Pullwire 10 proximally while push/pull Capture Catheter 12 to axially lengthen the ALTC Device 8 over the thrombus without substantially decreasing the device diameter. As needed, advancing the Capture Catheter shaft 12 distally while pulling the Capture Pullwire will allow the ALTC Device 8 to axially lengthen to capture the thrombus. Furthermore, the expandable Funnel Tip 9 of the Suction Catheter 2 (or the funnel tip of the expanding guide catheter) can be positioned at the proximal end of the occluded area to support and minimized thrombus movement. This maneuver continues until all thrombus is inside the ALTC Device 8. Once the thrombus is completely within the ALTC Device 8, pulling the ALTC Device 8 away from the occluded area can restore immediate blood flow while containing the thrombus inside the ALTC Device 8.

In some embodiments, the capture catheter shaft 12 and the guidewire tube 6 are configured to be positioned side-by-side adjacent (e.g., offset and not coaxial, and not passing within the opening 802 or other radially expanded portion of the tubular mesh 6) to the ALTC Device 8 and capture guide (shown, for example, in FIGS. 49A and 49B). Also illustrated is the dynamic fold point 88, reserve radially compressed segment 81 and compressed end at 128 fixed to the outer wall of the guidewire tube 6.

FIGS. 50A-50G illustrate the retrieval of thrombus into the expanding guide catheter wherein the ALTC device lengthens distally and creates additional space and the thrombus is redistributed and enable better retrieval into the expanding guide catheter. The funnel tip 52 and expanding section 53 of the expanding guide catheter also facilitate the ease of thrombus retrieval. For example, when the ALTC Device (e.g., tubular mesh 8) captures the blood clot inside, the ALTC Device 8 can advantageously stretch axially and compress radially beyond its working length (e.g., when the reserve radially compressed segment has been completely expanded, and/or by distal advance of the guidewire tube 6), effectively squeezing the blood clot radially to decrease its diameter/width. Fresh blood clots are typically soft and deformable. Applying axial stretching to the ALTC device can squeeze out the fluid that is within the blood clot, thereby reducing the size of blood clot and allowing blood clots to be removed from the vascular system more easily. The ability of the ALTC Device to lengthen dynamically also provides another clinically effective way to remove the large clot burden by redistributing the volume of blood clot or thrombus, as shown, for example, in FIG. 50A-50G. For example, with respect to current interventional devices such as filters and baskets, when blood clots or thrombus is collected and retrieved into a catheter such as a guiding catheter or sheath, the blood clot or thrombus can gather together or pooled at base of the filter or basket into a large "ball-like" shape and prevent the large "ball-like" thrombus to enter the lumen of the guiding catheter or sheath. A similar effect can occur when aspiration/suction is attempted using a smaller inner diameter guide catheter. However, the ALTC device can lengthen serially from the distal end to create additional length and space within the ALTC Device (as shown, for example, in FIGS. 50B, 50D, and 50F). By lengthening the ALTC Device's distal end, the blood clot or thrombus is redistributed within the ALTC device thereby reducing the ball-like size of the blood clot, thrombus, or other material for better retrievable inside the guiding catheter lumen (FIGS. 50C, 50E, 50G). These steps can be repeated for about or at least about 2, 3, 4, 5, or more cycles until all the blood clot and thrombus is retrieved in the catheter in a compacted form. Furthermore, the use of an expanding guide catheter with an expandable distal section in concert with the ALTC device can allow more efficient blood clot or thrombus removal, as illustrated, for example, in FIGS. 50A and 50C. The effectiveness of the ALTC Device 8 can be further demonstrated in an extreme vascular condition where there is minimal to no distal space available for conventional thrombectomy catheters to fully axially expand in order to be functional. The distal space beyond the distal end of the thrombectomy system can be in some cases less than about 3 cm, 2 cm, 1 cm, 5 mm, or less. In other words, the ALTC Device 8 can be delivered in a first, radially compressed configuration, and compressed by the outer sheath. Upon removal of the outer sheath, the ALTC Device 8 can transform into a radially expanded configuration and configured to capture thromboemboli even though the device may be in an axially compressed configuration. The ALTC Device 8 can then be axially expanded, such as, for example, at least about 1.25×, 1.5×, 2×, 2.5×, 3×, 3.5×, 4×, 4.5×, 5×, 5.5×, 6×, 6.5×, 7×, 8×, 9×, 10×, or more with respect to its fully functional axially compressed length while still maintaining a constant or substantially constant radially expanded diameter through a working range, such as between about 1 cm and about 50 cm, between about 1 cm and about 20 cm, between about 1 cm and about 10 cm, between about 1 cm and about 5 cm, or between about 1 cm and about 3 cm in some embodiments. In some embodiments, the ALTC device 8 has an open proximal end during delivery, and/or throughout its working axial length. The Thrombus Capture Guide 11 can advantageously deploy initially in the tight space while the ALTC device body remains inside the Capture Catheter shaft 12. Subsequently, the Thrombus Capture Guide retracts proximally to begin deploying the ALTC Device 8. The potential axially expanded length of the ALTC Device 8 is not necessarily limited and in some embodiments could extend to the entire length of the catheter system. The ALTC Device 8 can be collapsed and contained within the Capture Catheter shaft 12 and Outer Sheath 1 during introduction into the vasculature and expands when the Outer Sheath 1 retracts proximally to deploy the ALTC Device 8. The Capture Catheter shaft 12 can be made from suitable materials such as and not limit to Nylon, Polyurethane, Pebax, Polyethylene, PET, PTFE, ePTFE, PEEK, polypropylene. It is also advantageous and possible in some embodiments that the Capture Catheter shaft 12 is deflectable at various locations and multiple deflectable directions along the shaft length to accommodate various tortuous paths such as entry into the right atrium, right ventricle, main pulmonary artery, left and right pulmonary artery as previously described.

Figure 51:
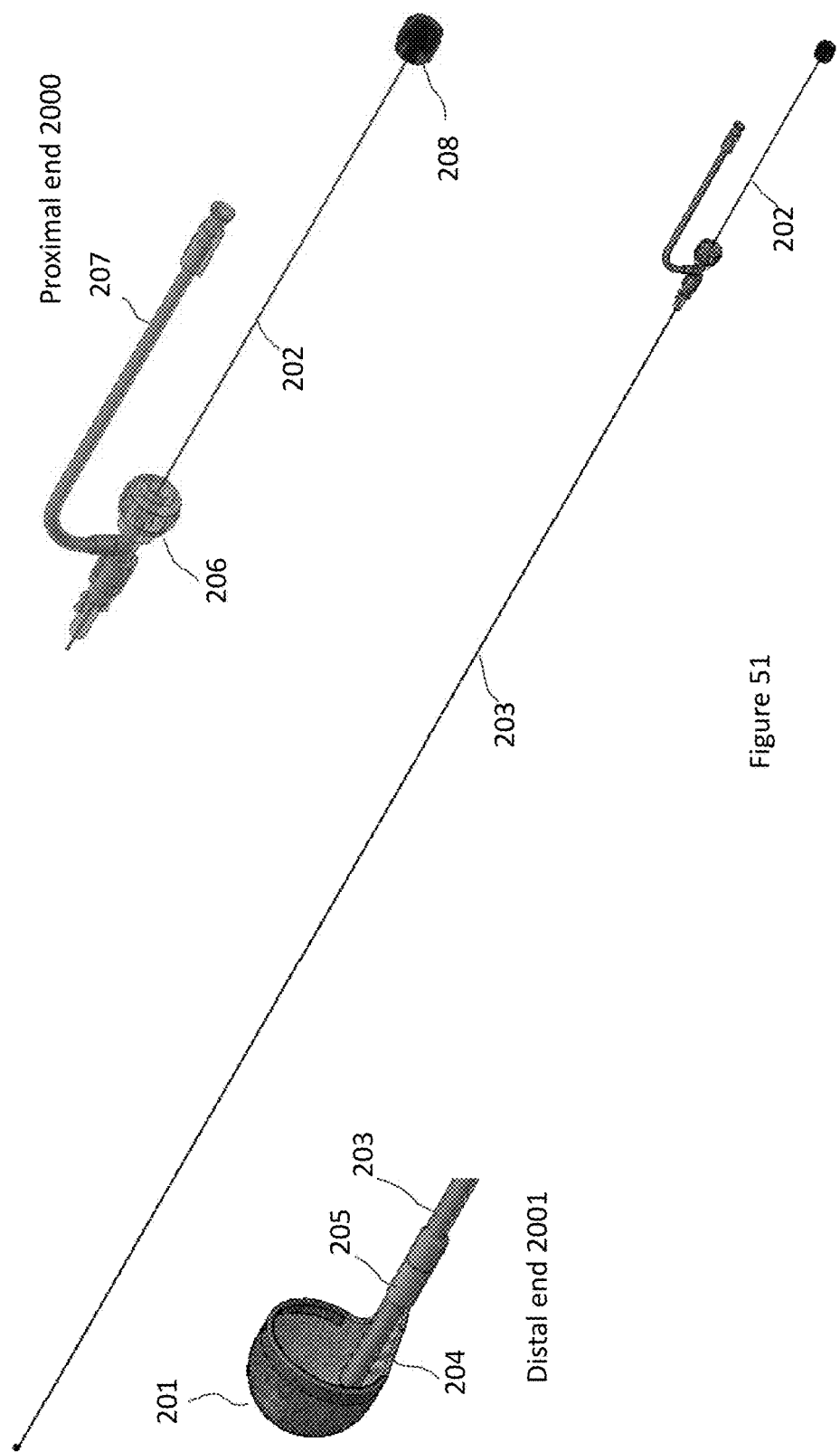
FIG. 51 illustrates an embodiment of a system for removing blood clots.

A perspective view of another embodiment of a capture system is shown in FIG. 51. FIG. 51 also illustrates non-limiting examples of various possible elements that can be included in a material capture system, according to some embodiments of the invention. As illustrated in FIG. 51, included in some embodiments are any number of, such as one, two, or more of the following components: a thrombus capturing device or ALTC device 201 having any of the features described herein, e.g., a pusher wire or inner pusher 202, a first tubular member such as an outer sheath 203, a loop or capture guide 204, and a coupler 205. The ALTC device 201 can attach to the capture guide 204. In some embodiments, the capture guide 204 comprises a metallic material, such as Nitinol. The capture guide 204 can be in the form of, for example, a loop, as shown, or any closed shape including an oval, ellipse, or polygon. The capture guide 204 can be in the form of an open shape such as any linear or non-linear segment. The ALTC device 201 and the capture guide 204 can be coupled such as being sutured together. The ALTC device 201 and the capture guide 204 can be encapsulated in a low durometer polymeric material. The capture guide 204 can be coupled to the outer sheath 203 via the coupler 205. The proximal end of the ALTC device 201 (not shown) can be coupled to the inner pusher 202.

The outer sheath 203 can, in some embodiments, be an elongate tubular member with a central lumen therethrough, and have a proximal end 2000 and a distal end 2001, both shown in FIG. 51. The distal end 2001 of the outer sheath 203 can be operably connected to a capture device (e.g., tubular mesh as described herein), which can be movably axially with respect to the outer sheath 203. The proximal end 2000 can include any number of, such as one, two, or more of the following components: a hemostasis assembly 206, a flush port 207, and a collapsed segment 208. The outer sheath 203 extends proximally and can be coupled to the hemostasis assembly 206. The inner pusher 202 extends proximally and can be coupled to a luer. In some embodiments, the inner pusher 202 can have a lumen to allow passage of a guidewire. In some embodiments, the inner pusher 202 is a solid shaft.

Figure 52:
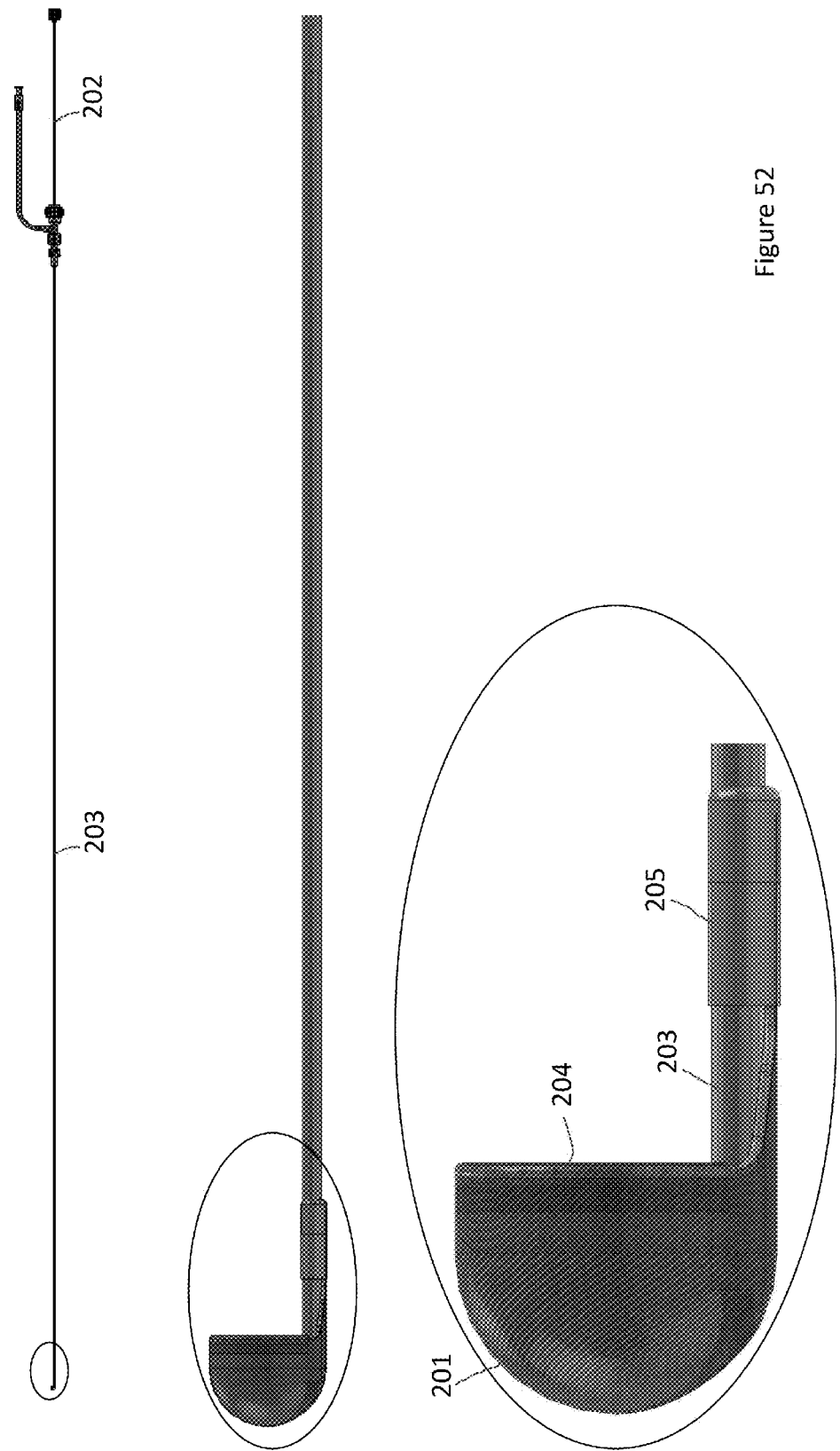
FIG. 52 illustrates the distal end of the capture device of the system of FIG. 51 in the deployed configuration.

FIG. 52 shows the distal end 2001 of the ALTC device 201 in a deployed configuration. In some embodiments, the ALTC device 201 in the initial deployed configuration has a low profile. A portion of the ALTC device 201 is extended while the remaining length of the ALTC device 201 is collapsed and contained within the outer sheath 203 as previously described. In some methods of use, the ALTC device 201 can be collapsed and tracked through a sheath or guide catheter (not shown) to the intended treatment area. In some embodiments, the guide catheter can be retracted proximally to initially deploy the ALTC device 201 and the capture guide 204. For instance, the retraction of the guide catheter can cause the capture guide 204 to expand. The capture guide 204 can include a compressed or constrained configuration while within the guide catheter. During the initial deployment, the capture guide 204 is released from a constrained position to a neutral position. In the neutral position, the capture guide 204 creates a perimeter for the ALTC device 201. In the case of a loop or other circular configuration, the capture guide 204 can create a constant diameter. In the case of other shapes or configurations, the capture guide 204 can create a constant cross-section. Alternatively or in combination, in other methods of use, the ALTC device 201 can be advanced distally from the guide catheter to deploy the ALTC device 201.

In some cases, only a small fractional portion of the ALTC device 201, such as less than about 50%, 45%, 40%, 35%, 30%, 25%, 20%, 15%, 10%, 5%, or less of the axial length of the device can be initially deployed and fully functional. The small portion can correspond to an amount of the ALTC device 201 which allows the capture guide 204 to assume the neutral position. During the deployment of the capture guide 204, a length of the ALTC device 201 can be retained within the outer sheath 203. The ALTC device 201 can follow a curve from the capture guide 204 to the outer sheath 203. Retracting the outer sheath 203 can lengthen the ALTC device 201 while maintaining a constant diameter or cross-section provided by the capture guide 204.

FIG. 53 illustrates an embodiment of an ALTC device 201 in the initially deployed configuration. As illustrated in FIG. 53, the ALTC device 201 can be in some embodiments a generally tubular structure, and in some cases a net-like mesh structure that is collapsible within the outer sheath 203. The ALTC device 201 is expandable to the diameter or cross-section provided by the capture guide 204. The ALTC device 201 can be axially lengthened or shortened, such as within a working range, by releasing the ALTC device 201 from the outer sheath 203. The ALTC device 201 can be axially lengthened or shortened while maintaining or substantially maintaining the diameter or cross-section provided by the capture guide 204. The ALTC device 201 can be deployed to form a generally tubular or cylindrical shape of varying axial lengths. The ALTC device 201 can be axially lengthened or shortened to retrieve and capture foreign or otherwise unwanted materials within the body, including the vascular system such as blood clots, thrombus and/or foreign materials. In some embodiments, an outer sheath is not present and a loader can be utilized to prepare the ALTC device 201 for delivery in a low crossing-profile configuration.

As shown, for example, in FIGS. 54 and 55, the ALTC device 201 can be axially lengthened. FIG. 54 illustrates the ALTC device 201 in a second configuration. The ALTC device 201 is in the second configuration wherein the deployed and expanded ALTC device 201 is longer than the initial deployed configuration in the axial direction. The remaining collapsed ALTC device 201 length resides inside the outer sheath 203 and is shorter than the initial deployed configuration. The outer sheath 203 can be retracted to axially lengthen the ALTC device 201. As the outer sheath 203 is retracted, the capture guide 204 is retracted since the capture guide 204 is coupled to the outer sheath 203 via the coupler 205. As the capture guide 204 is retracted, the ALTC device 201 is advance from the collapsed portion 208 to the expanded portion. The outer sheath 203 can be retracted proximally to axially lengthen the ALTC device 201. Alternatively or in combination, in other methods of use, the capture guide 204 can be retracted to axially lengthen the ALTC device 201, such as be retracting the outer sheath 203. The diameter or cross-section of the ALTC device 201 can remain constant or substantially constant between the initial deployed configuration and the second configuration.

Alternatively or in combination, in other methods of use, the inner pusher 202 is advanced distally to advance the proximal end of the ALTC device 201. As described herein, the proximal end of the ALTC device 201 is coupled to the inner pusher 202. In the second configuration, the inner pusher 202 is advanced distally to release a portion of ALTC device 201 from the outer sheath 203.

FIG. 55 illustrates an embodiment of an ALTC device 201 in a third configuration. The ALTC device 201 is in the third configuration wherein the deployed and expanded ALTC device 201 is longer than the second configuration in the axial direction. The remaining collapsed ALTC device 201 length resides inside the outer sheath 203 and is shorter than the second configuration. The outer sheath 203 can be retracted proximally to axially lengthen the ALTC device 201. The diameter or cross-section of the ALTC device 201 can remain constant or substantially constant between the second configuration and the third configuration. Alternatively or in combination, in other methods of use, in the third configuration, the inner pusher 202 is advanced distally to a greater extent. In the third configuration, the inner pusher 202 is advanced distally to release a longer portion of ALTC device 201 from the outer sheath 203.

Figure 56:
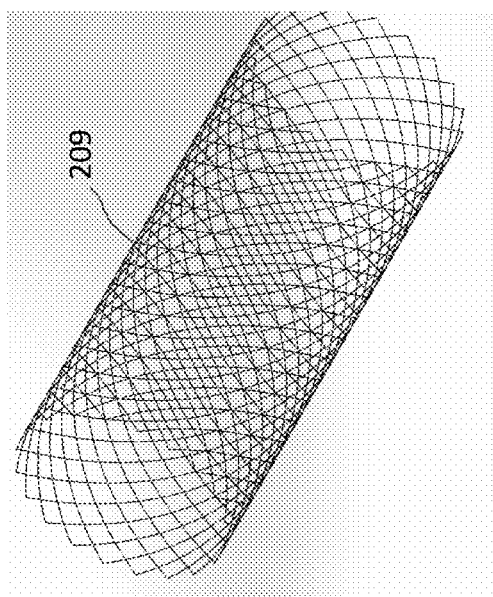
FIG. 56 illustrates an embodiment of the basket mesh element of the system of FIG. 51. The basket mesh element can made of metallic materials such as Nitinol. The mesh element can be braided or laser cut.

FIG. 56 illustrates an embodiment of the material capture, e.g., basket mesh element 209. The basket mesh element 209 can be a component of the ALTC device 201. The basket mesh element 209 can be a structural mesh that provides an appropriate shape as described herein. The basket mesh element 209 can comprise Nitinol or other materials. The basket element can be braided, weave, wireform or laser cut. The basket mesh element 209 can include a first end that couples to the capture guide 204. The basket mesh element 209 can be coupled to the capture guide 204 via a suture or other mechanical means including welding, clips, flanges, adhesive, lamination, etc. The basket mesh element 209 and the capture guide 204 can be encapsulated within a low durometer polymeric material. The second end of the basket mesh element 209 can be coupled to the inner pusher 202. The second end can be folded inward to couple to the inner pusher 202. The second end can be inverted to couple to the inner pusher 202. The second end 202 can form a tube within a tube configuration of the ALTC device 201.

Figure 57:
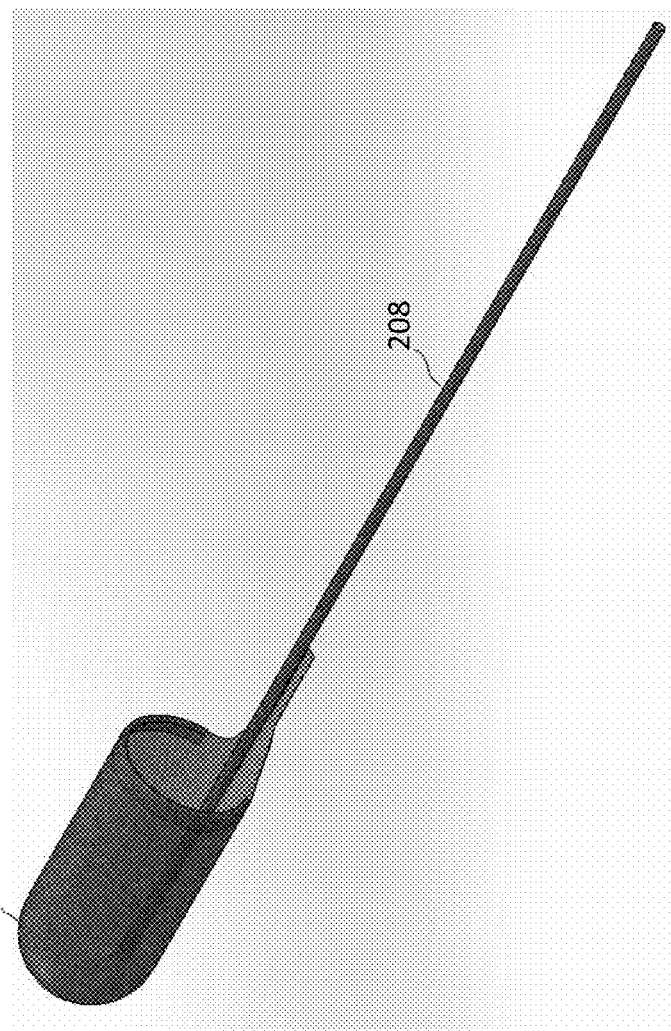
FIG. 57 illustrates an embodiment of a capture device element of the system of FIG. 51.

FIG. 57 illustrates an embodiment of the ALTC device 201. The ALTC device 201 has an expanded portion when the ALTC device 201 is deployed (e.g., initial deployed configuration, second configuration, third configuration, etc.). The expanded portion has a constant diameter or cross-section as described herein. The expanded portion, or a portion thereof, is coupled to the capture guide 204. The expanded portion is coupled to the outer sheath 203 via the capture guide 204 and the coupler 205. The ALTC device 201 has a collapsed portion 208. The collapsed portion 208 can reside within the lumen of the outer sheath 203. The collapsed portion 208 can be retained within the outer sheath 203 when the expanded portion is in the deployed configuration. The collapsed portion 208, or a portion thereof, can be coupled to the inner pusher 202. The collapsed portion 208 is everted as shown. During axial lengthening of the ALTC device 201, a portion of the collapsed portion 208 can roll-out at a distal region to transition between the collapsed portion 208 and the expanded portion.

Figure 58B:
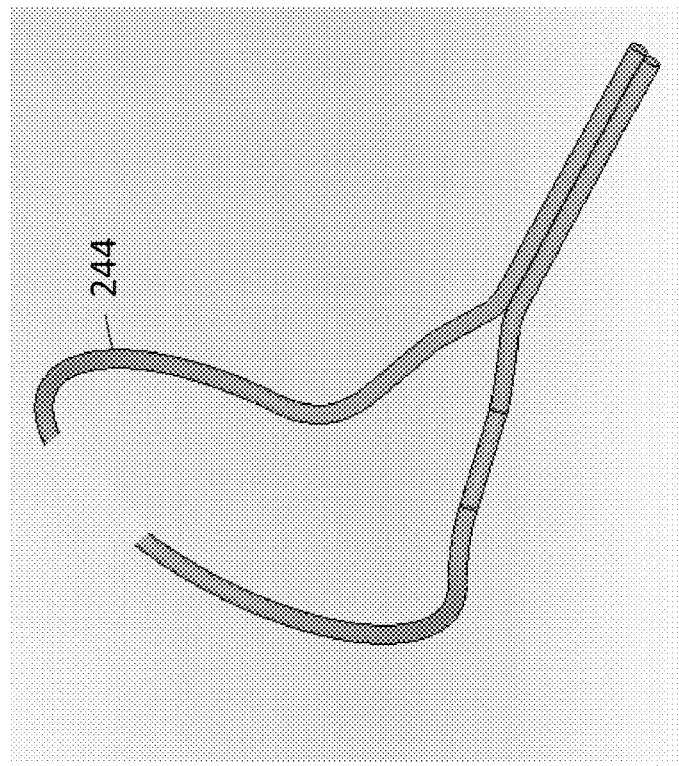
FIGS. 58A-58B illustrate embodiments of an expandable loop element of the system of FIG. 51.
Figure 58A:
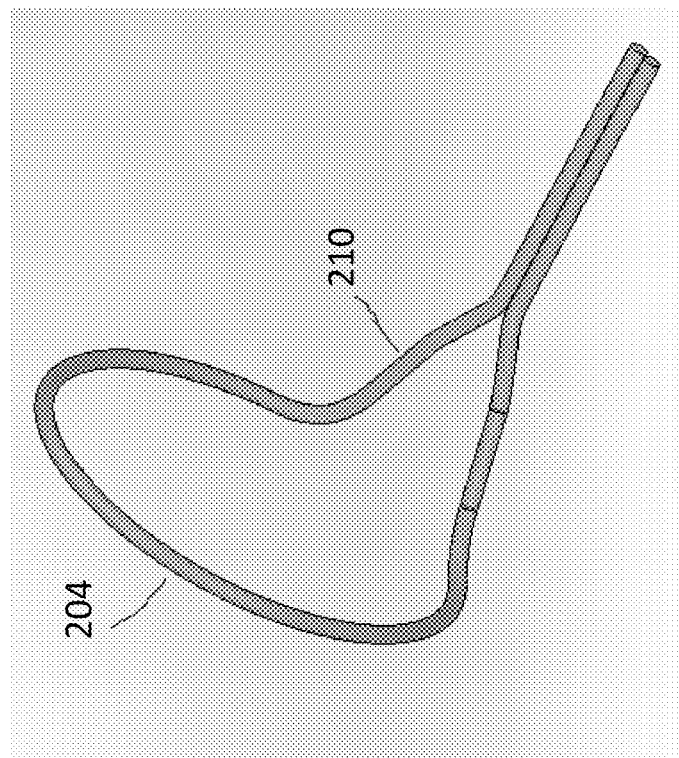

FIGS. 58A and 58B illustrate embodiments of the capture guide 204. FIG. 58A illustrates the capture guide 204. FIG. 58B illustrates the capture guide 244, which can include any of the features of capture guide 204. The capture guide 204 can form a continuous shape. The capture guide 204 can include leg elements 210. The leg elements 210 can transition the capture guide 204 from an axial direction to a perimeter shape. The perimeter shape can be circular as shown in FIG. 58A. The capture guide 204 can form a continuous loop. The capture guide 244 can include a non-continuous perimeter. As shown in FIG. 58B, the capture guide 244 can include a non-continuous loop. The capture guide 204, 244 can be made of a metallic material. In some embodiments, the capture guide 204, 244 is formed of a shape-memory material. In some embodiments, the capture guide 204, 244 is formed from Nitinol. The capture guide 204, 244 can be formed of a spring-like material such as a metal. The capture guide 204, 244 can be circular, elliptical, semi-circular, or any combination thereof. The capture guide 204, 244 can include a pre-shaped curve. The pre-shaped curve can be formed during the manufacturing of the capture guide 204, 244. The pre-shaped curve can be a neutral or expanded shape of the capture guide 204, 244. Upon release of a constraint, the capture guide 204, 244 will assume the pre-shaped curve. The capture guide 204, 244 can have any curved shape. The capture guide 204, 244 can have a single radius of curvature or multiple portions having different radii of curvature. The capture guide 204, 244 can be considered spring loaded based in part of the material and the shape of the capture guide 204, 244. In some embodiments, the anchors can include non-continuous shapes, such as hooks with sharp or atraumatic segments or tips in some cases.

The capture guide 204, 244 can have two or more leg elements 210. The leg elements 210 can be adjacent or adjoining within the guide catheter during delivery. The leg elements 210 can be relatively parallel or side-by-side during delivery in the collapsed configuration. The collapsed leg elements 210 can define a different diameter or cross-section as compared to the fully expanded or neutral configuration of the capture guide 204, 244. In some embodiments, the collapsed leg elements 210 enable the capture guide 204, 244 to have a smaller diameter or cross-section while collapsed within the guide catheter. For example, when the capture guide 204, 244 is fully expanded, the circular portion of the capture guide 204, 244 defines a diameter. For non-circular capture guide 204, 244, the capture guide 204, 244 can define a cross-section when fully expanded. Upon collapsing the leg elements 210, the circular portion of the capture guide 204, 244 defines a diameter that is smaller than the previous expanded configuration. The capture guide 204 can comprise one segment as shown in FIG. 58A with two ends that form a continuous loop configuration. The capture guide 244 can comprise multiple segments as shown in FIG. 58B and form a non-continuous loop.

During expansion, the leg elements 210 can bias the capture guide 204, 244 outward to assume the neutral configuration of the capture guide 204, 244. The leg elements 210 can be positioned at an angle relative to each other in the neutral configuration of the capture guide 204, 244. The leg elements 210 can include one or more bends to facilitate folding of the capture guide 204, 244. The one or more bends can enable the capture guide 204, 244 to fold in a low profile configuration along the longitudinal axis of the guide catheter.

Figure 59:
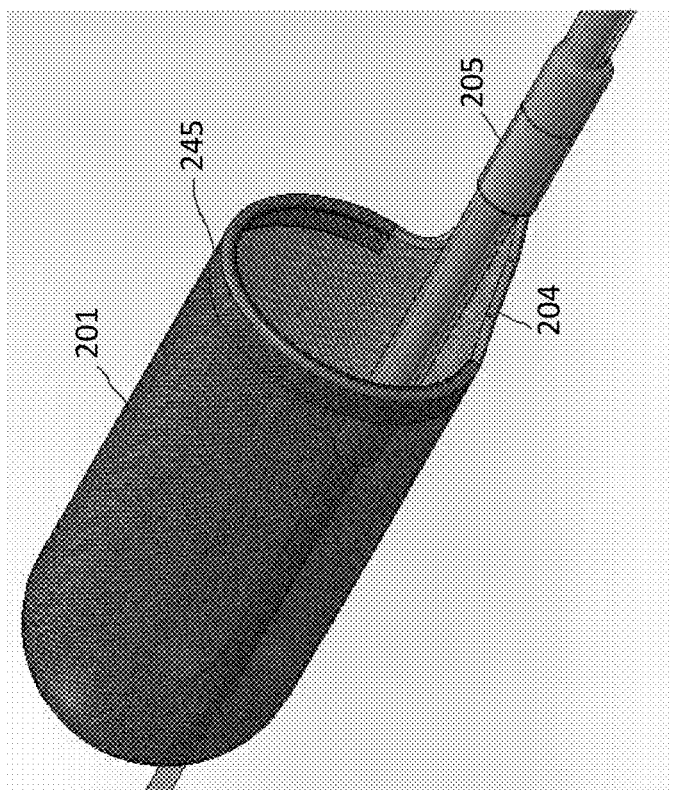
FIG. 59 illustrates a view of a capture device opening for a system for neuro thrombus.

FIG. 59 shows one aspect of the opening of the ALTC device 201. The end of the ALTC device 201, or a portion thereof, attaches to the capture guide 204. While the capture guide 204 is shown in FIG. 59, any capture guide or feature thereof can be coupled to the end of the ALTC device 201. The end of the ALTC device 201 and the capture guide 204 form an assembly. The assembly can be encapsulated within a low durometer polymeric material to form a polymeric coating or ring 245. The polymeric coating can encapsulate the assembly completely or a portion thereof. In the illustrated embodiment, the polymeric coating encapsulates a portion of the end of the ALTC device 201 and the capture guide 204. The polymeric coating can encapsulate the rounded portion of the capture guide 204 having a constant or substantially constant diameter. The polymeric coating can encapsulate the entire ALTC device 201, or any portion thereof. The area where the polymeric coating is void/not present can allow for easy movement. For instance, the area between the leg elements can be void. The void area can facilitate collapse of the capture guide 204. In some embodiments, the polymeric coating can be selectively applied. In some embodiments, the polymeric coating can form a ring or a portion of a ring. The polymeric coating can be applied to the outside of the material capture element, e.g., basket mesh element 208. The polymeric coating can be applied to the inside of the basket mesh element 208. The polymeric coating can be applied to the entire basket mesh element 208 to encapsulate the basket mesh element 208.

Figure 60:
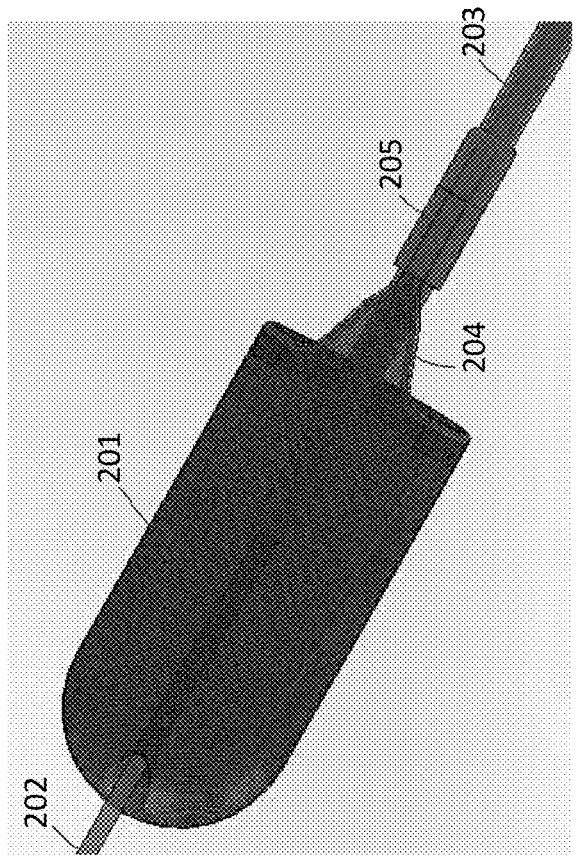
FIG. 60 illustrates another view of a capture device opening of FIG. 59.

FIG. 60 shows one aspect of the opening of the ALTC device 201. The ALTC device 201 can include a central, longitudinal axis. The outer sheath 203 can include a longitudinal axis. The inner pusher 202 can extend along the longitudinal axis of the outer sheath 203. The central, longitudinal axis of the ALTC device 201 can be offset from the longitudinal axis of the outer sheath 203. The central, longitudinal axis of the ALTC device 201 can be offset from the longitudinal axis of the inner pusher 202. The capture guide 204 can define the offset. For instance, the central, longitudinal axis of the ALTC device 201 can include the central point of the circle created by the capture guide 204. The central point of the capture guide 204 can be offset from the outer sheath 203. As described herein, the end of the ALTC device 201 is coupled to the inner pusher 202. The ALTC device 201 axially lengthens by releasing a portion of the ALTC device 201 from the outer sheath 203. The ALTC device 201 that is released follows a portion of the inner pusher 202 as shown in FIG. 59. The released portion of the ALTC device 201 curves outward and assumes the diameter of the capture guide 204. The ALTC device 201 can form an everted shape with a portion of the ALTC device 201 collapsed near the inner pusher 202 and a portion of the ALTC device 201 expanded to the diameter or cross-section of the capture guide 204. In some embodiments, the shape of the ALTC device 201 can resemble a tube within a tube. In some embodiments, the ALTC device 201 can be considered telescoping.

A perspective view of another system is shown in FIG. 61. FIG. 62 shows the proximal end of the system and FIG. 63 shows the distal end of the system. FIG. 64 shows a subassembly of the system. FIGS. 61-64 also illustrates non-limiting examples of various possible elements that can be included in a material capture system, according to some embodiments of the invention. As illustrated in FIG. 61, included in some embodiments are any number of, such as one, two, or more of the following components: an anchor assembly 221, a corewire and basket assembly 222, an anchor and pusher assembly 223, a proximal catheter assembly 224, and a distal catheter assembly 225. The anchor assembly 221 can include about or at least about one, two, three, four, five, or more anchors 241 configured to secure a clot. The anchor and pusher assembly 223 includes one or more anchors 241 and the anchor pusher 240. The anchors can be coupled to the pusher as described herein. The corewire and basket assembly 222 can include a corewire 242 and the ALTC device 201. The proximal catheter assembly 224 can include a shaft with one, two, or more lumens, e.g., the dual lumen shaft 243. FIG. 61 illustrates a dual lumen shaft 243 of the system. The dual lumen shaft 243 can be attached to the hemostasis housing 206 described herein. The dual lumen shaft 243 can be coupled to the capture guide 204 via the coupling 205. The illustrated embodiment shows a dual lumen shaft, but other configurations are contemplated. In some embodiments, the shaft has a single lumen. In some embodiments, the shaft is a multi-lumen shaft. The shaft can have about or more than about one lumen, two lumens, three lumens, four lumens, five lumens, six lumens, seven lumens, etc. In some embodiments, the anchor 241 is a single loop. In some embodiments, the anchor 241 is a continuous loop. In some embodiments, the anchor 241 has a closed perimeter. In some embodiments, the anchor 241 has an open perimeter. In some embodiments, the anchor 241 forms a circular shape. In some embodiments, the anchor 241 forms an oval. In some embodiments, the anchor 241 forms any round, closed shape.

FIG. 62 illustrates the proximal end of the system including the corewire and basket assembly 222, the anchor and pusher assembly 223, and the proximal catheter assembly 224. The corewire and basket assembly 222 and the anchor and pusher assembly 223 can reside in separate lumens of the dual lumen shaft 243. The system can include the corewire 242. The corewire 242 can include any of the features or function as the inner pusher 202. The corewire 242 can be coupled to a pusher lock 246. The anchor pusher 240 can extend through the pusher lock 246. The pusher lock 246 can be movable along the shaft of the anchor pusher 240. In some embodiments, the pusher lock 246 can limit the expansion of the anchors 241. In some embodiments, the pusher lock 246 can provide a tactile response when the anchors 241 are deployed by abutting the anchor and pusher assembly 223 with the pusher lock 246.

FIG. 63 illustrates the distal catheter assembly 225. The distal catheter assembly 225 can include any of the features described herein. The distal catheter assembly 225 can include the ALTC device 201. The distal catheter assembly 225 can include the coupler 205 between the outer shaft 203 and the capture guide 204.

FIG. 64 illustrates the anchor assembly 221. The anchor assembly 221 can comprise one or more anchors 241. The anchor assembly 221 can comprise about or at least about one anchor, two anchors, three anchors, four anchors, five anchors, six anchors, seven anchors, eight anchors, nine anchors, ten anchors, or more than ten anchors 241. The illustrated embodiment shows three anchors, but other configurations are contemplated. The anchor assembly 221 can include the anchor pusher 240. The anchor pusher 240 can include an elongate member comprising a shaft. The anchor pusher 240 can be extended proximally within the dual lumen shaft 243. The anchor pusher 240, or a portion thereof, can pass proximally through the proximal catheter assembly 224. The anchor pusher 240, or a portion thereof, can pass proximally through the pusher lock 246. The anchor pusher 240, or a portion thereof, can be connected to the luer hub. The anchor assembly 221 can be contained in the dual lumen shaft 243. The one or more anchors 241 can be coupled at a distal end of the anchor pusher 240. The one or more anchors 241 can be one anchor or a plurality of anchors 241. The anchors can be connected to the anchor pusher 240 in series, and regularly or irregularly spaced apart. In some embodiment, the diameter of the anchor 241 when expanded is smaller than the diameter of the capture guide 204 when expanded. In some embodiment, the diameter of the anchor 241 when expanded is smaller than the ALTC device 201 when expanded. The anchor 241 can be designed to fit within the ALTC device 201 when the ALTC device 201 is expanded. In some embodiments, the anchors can form symmetric or asymmetric loop shapes to circumscribe and stabilize a portion of the clot. In some embodiments, the anchors can be an mesh or braided element. In some embodiments, the anchor can be a balloon. In some embodiment, there can be a combination of braided mesh and balloon. In some embodiments, the anchors 241 can have a portion that extend radially outwardly from the elongate member in which they are attached.

Figure 65:
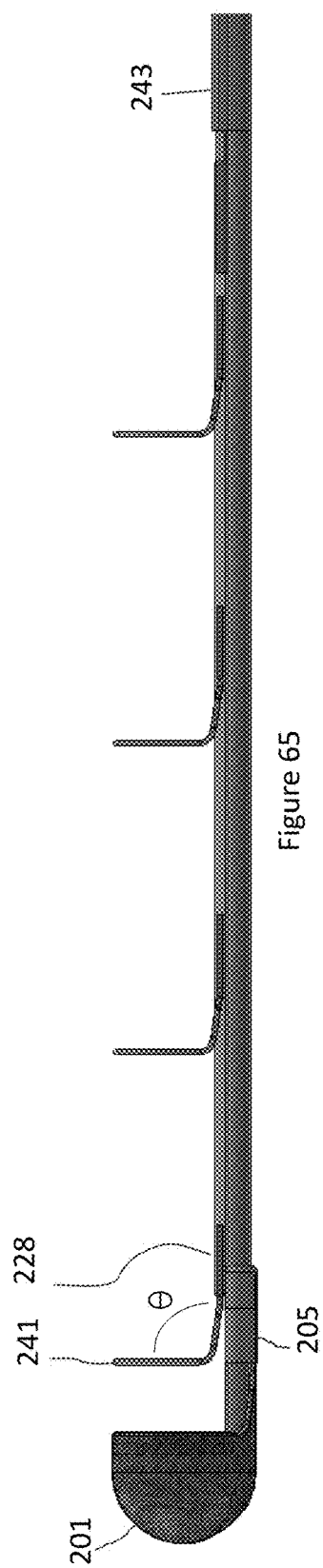
FIG. 65 illustrates a side view of a distal end of the capture device and anchors of the system of FIG. 61.

FIG. 65 illustrates a side view of the distal end of the ALTC device 201 and the anchors 241. The anchors 241 can include or be similar to any of the features of capture guide 204, 244 described herein. Each anchor 241 can form a continuous shape, or a discontinuous shape in other embodiments. Each anchor 241 can include leg elements 228. The leg elements 228 can transition the anchor 241 from an axial direction to a perimeter shape. The perimeter shape can be circular as shown in FIG. 64. The anchor 241 can form a continuous loop. The anchor 241 can include a non-continuous perimeter such as a non-continuous loop. The anchor 241 can be made of a metallic material. In some embodiments, the anchor 241 is formed of a shape-memory metal such as Nitinol. The anchor 241 can be circular, elliptical, semi-circular, or any combination thereof. Each anchor 241 can include a pre-shaped curve. Two or more anchors 241 can have the same pre-shaped curve. Two or more anchors 241 can have a different pre-shaped curve. The pre-shaped curve can be formed during the manufacturing of the anchors 241. The pre-shaped curve can be a neutral or expanded shape of the anchors 241. Upon release of a constraint, the anchors 241 can assume the pre-shaped curve. The pre-shaped curve of the anchors 241 can be similar to the pre-shaped curve of the capture guide 204. The anchors 241 can have a different radius of curvature from the capture guide 204. As described herein, the anchors 241 can have a smaller diameter than the capture guide 204. Alternatively, the anchors can have the same or larger diameter than the capture guide. In some embodiments, the anchors include barbed elements to attach to a clot. In some embodiments, the anchors are atraumatic and do not include any barbed or other sharp surfaces.

The anchor 241 can have two or more leg elements 228. The leg elements 228 can be adjacent or adjoining within the guide catheter during delivery, and relatively parallel to the. The leg elements 228 can be relatively parallel or side-by-side during delivery in the collapsed configuration. The collapsed leg elements 228 can define a different diameter or cross-section as compared to the fully expanded or neutral configuration of the anchor 241. In some embodiments, the collapsed leg elements 228 allow the anchor 241 to have a smaller diameter or cross-section while collapsed within the guide catheter. For example, when the anchor 241 is fully expanded, the circular portion of the anchor 241 defines a diameter. For non-circular anchors 241, the anchor 241 can define a cross-section when fully expanded. Upon collapsing the leg elements, the circular portion of the anchor 241 defines a diameter that is smaller than the previous expanded configuration. The anchor 241 can comprise one segment as shown in FIG. 64 that forms a continuous loop configuration. The anchor 241 can comprise multiple segments similar to capture guide 244 shown in FIG. 58B. The anchors 241 have a outwardly curving shape relative to the two or more leg elements 228.

The anchor 241 can include an expanded position as shown in FIG. 65. In the case of a shape memory material the expanded position can be a neutral position of the material. The anchor 241 can be configured to fold or bend during delivery. The anchor 241 can assume a low-profile configuration during delivery. The expanded anchor 241 can have any shape including round, circular, elliptical, etc. The anchors 241 expand to their preformed shape upon removal of a constraint, such as outer sheath 203, delivery catheter, or other constraining structure.

The expanded position of an anchor 241 can be defined by angle theta $\theta$. In some embodiments, the angle theta is measured from the leg element 228 to the circular portion of the anchor 241. In some embodiments, the angle theta is measured from the horizontal to the vertical extension of the anchor 241. In some embodiments, the angle theta is measured from the dual lumen shaft 243 to the expanded portion of the anchor 241. In some embodiments, the angle theta determines the vertical or substantially vertical orientation of the anchor 241. Each anchor 241 of a plurality of anchors 241 can have the same angle theta. If the anchors 241 are arranged in a series, the angle theta can be uniformly the same. Two or more anchors 241 can have the same angle theta, or angles that are within about 30, 25, 20, 15, 10, 5, 4, 3, 2, 1, or less degrees of each other.

Each anchor 241 of a plurality of anchors 241 can have a different angle theta. Two or more anchors 241 can have the different angle theta. If the anchors 241 are arranged in a series, the series of anchors 241 can also have different variations in the angle theta. For example, the first anchor 241 can have a first angle theta such as about or at least about 45 degrees, such as between about 0 and 90 degrees, between about 15 and 75 degrees, or between about 30 and 60 degrees in some cases. The next or immediately adjacent anchor 241 can have a second angle theta such as 135 degrees. The next or immediately adjacent anchor 241 can have a third angle theta such as 45 degrees. The series can continue to alternate between 45 degrees and 135 degrees or other desired angles. In some embodiments, the series of anchors can have different diameter.

In some embodiments, two or more anchors 241 can form a mirror image. In some embodiments, two or more anchors 241, 241 can extend from the dual lumen shaft 243 such that the circular portion of one anchor 241 substantially projects onto the circular portion of the other anchor 241. In some embodiments, two or more anchors 241 can be identical or substantially identical in orientation. In some embodiments, two or more anchors 241 can be coaxial. In some embodiments, two or more anchors 241 have different orientations relative to the dual lumen shaft 243. In some embodiments, two or more anchors 241 are not coaxial. In some embodiments, a first anchor 241 has a first axis extending through the circular portion of the first anchor 241 and the second anchor 241 has a second axis extending through the circular portion of the second anchor 241. In some embodiments, the first axis and the second axis can be skewed. In some embodiments, the first axis and the second axis are perpendicular. In some embodiments, the first axis and the second axis are parallel. In some embodiments, the first axis and the second axis are coaxial.

In some embodiments, the angle theta can range from 5 degrees to 175 degrees. Examples of the angle theta include 5 degrees, 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, 80 degrees, 85 degrees, 90 degrees, 95 degrees, 100 degrees, 105 degrees, 110 degrees, 115 degrees, 120 degrees, 125 degrees, 130 degrees, 135 degrees, 140 degrees, 145 degrees, 150 degrees, 155 degrees, 160 degrees, 165 degrees, 170 degrees, 175 degrees, etc., and ranges incorporating any two of the aforementioned values. Examples of the angle theta can be in the range of 0-20 degrees, 20-40 degrees, 40-60 degrees, 60-80 degrees, 80-100 degrees, 100-120 degrees, 120-140 degrees, 140-160 degrees, 160-180 degrees, etc. In some embodiments, the angle theta can be approximately 90 degrees. In such embodiment, the anchor 241 can be approximately vertical relative to the dual lumen shaft 243. In some embodiments, the angle theta can be approximately 45 degrees. In such embodiment, the anchor 241 can form an acute angle relative to the dual lumen shaft 243. In some embodiments, the angle theta can be approximately 135 degrees. In such embodiment, the anchor 241 can form an obtuse angle relative to the dual lumen shaft 243.

The anchor and pusher assembly 223, or a portion thereof, can be moved within the dual lumen shaft 243. In some embodiments, the anchor and pusher assembly 223 can be moved coaxially within a lumen of the dual lumen shaft 243. The anchor and pusher assembly 223 can be moved independently from the corewire and basket assembly 222. In some embodiments, the anchor and pusher assembly 223 can be moved simultaneously with the corewire and basket assembly 222. In some embodiments, the anchor and pusher assembly 223 can be advanced distally or proximally relative to the dual lumen shaft 243. In some embodiments, the anchor and pusher assembly 223 does not impact the movement of the ALTC device 201. The one or more anchors 241 can be moved independently of the ALTC device 201. As described herein, the one or more anchors 241 can be moved relative to a stationary ALTC device 201. As described herein, the ALTC device 201 can be moved relative to a stationary anchor 241.

Figure 66:
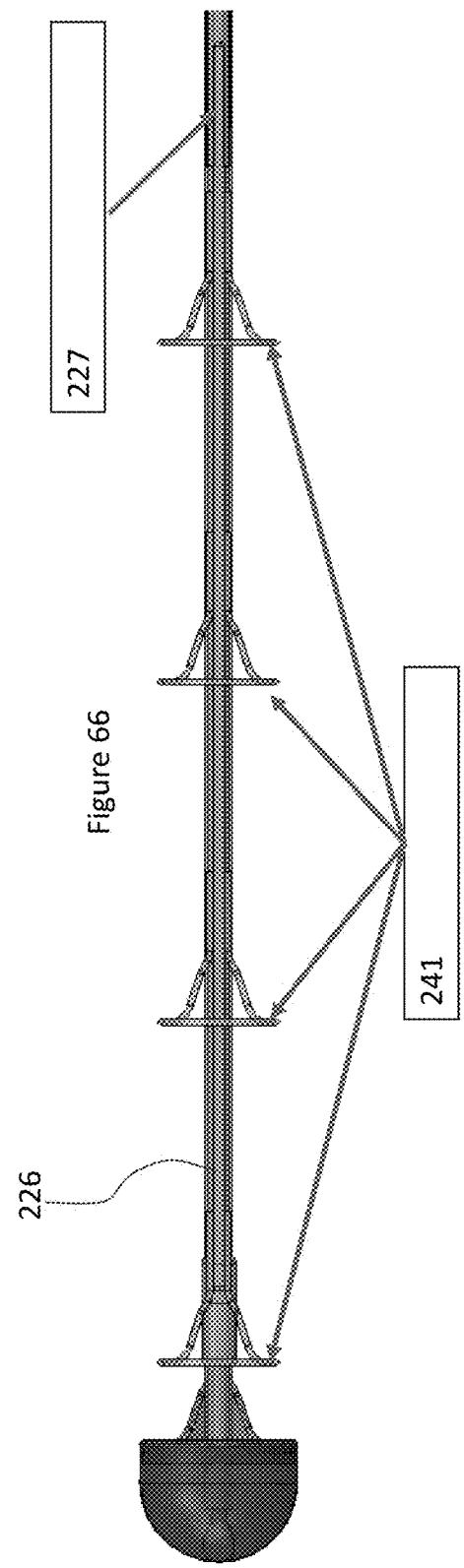
FIG. 66 illustrates a top view of a distal end of the capture device and anchors of the system of FIG. 61.

FIG. 66 illustrates a top view of the distal end of the ALTC device 201 and the anchors 241. The one or more anchors 241 can be coupled to a distal pusher 226. In some embodiments, the leg extensions 228 of the anchors 241 are coupled to the distal pusher 226. In some embodiments, the angle theta is measured from the distal pusher 226 to the expanded portion of the anchor 241. In the illustrated embodiment, each anchor 241 is coupled to the distal pusher 226. The movement of the distal pusher 226 causes simultaneous movement of all anchors 241 coupled thereto. In alternative embodiments, two or more distal pushers 226 are provided. Each of the two or more distal pushers 226 controls the movement of one or more anchors 241. The two or more distal pushers 226 can move independently such that two or more anchors 241 can move independently. Other configurations are contemplated. The distal pusher 226 can be coupled to a crescent pusher 227. In some embodiments, the crescent pusher 227 can provide rigidity to the distal pusher 226. The distal pusher 226 and the crescent pusher 227 can be affixed via welding, adhesive, mechanical interference, etc.

Figure 67:
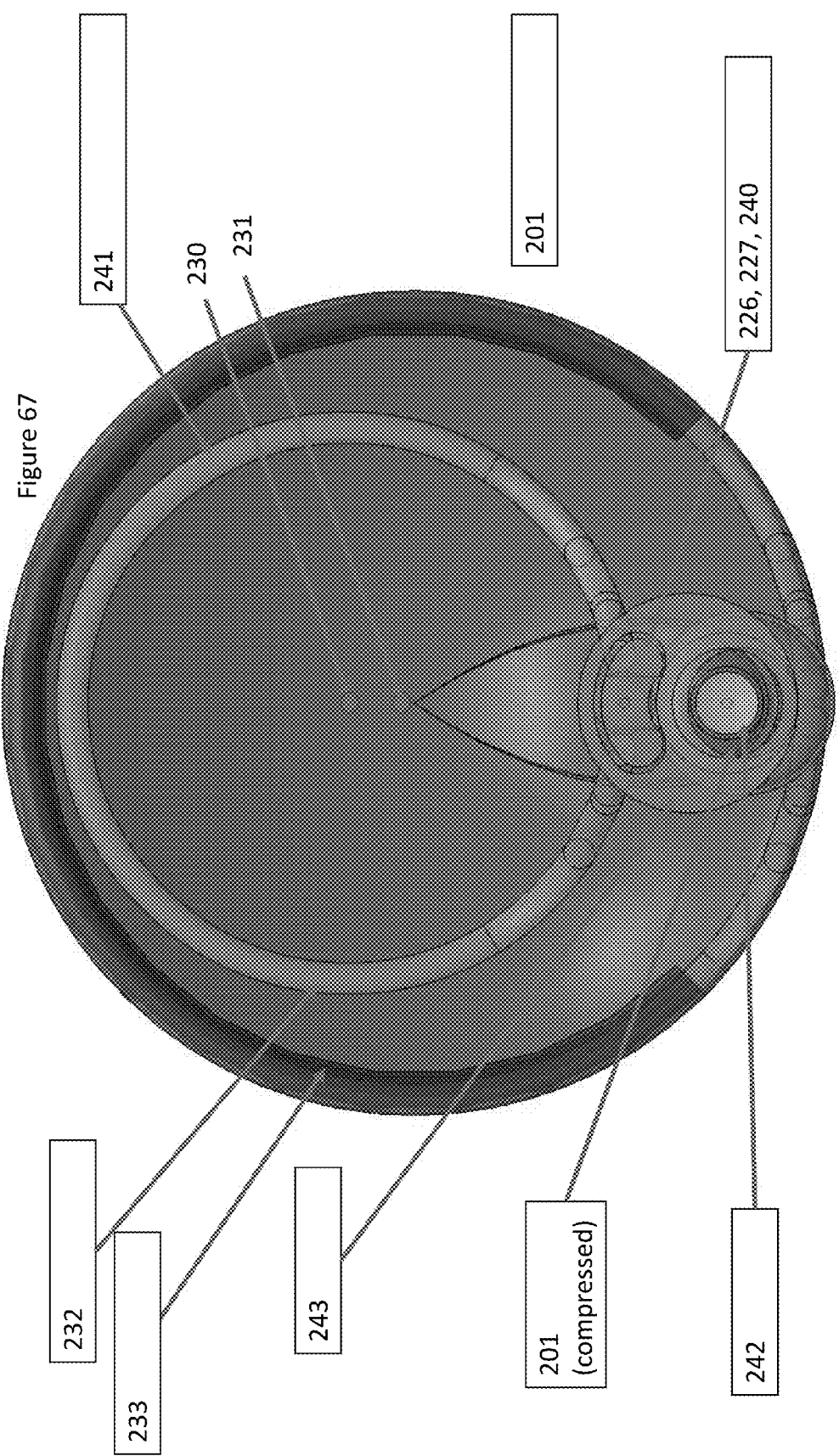
FIG. 67 illustrates a front view of a distal end of the capture device of the system of FIG. 61.
Figure 71D:
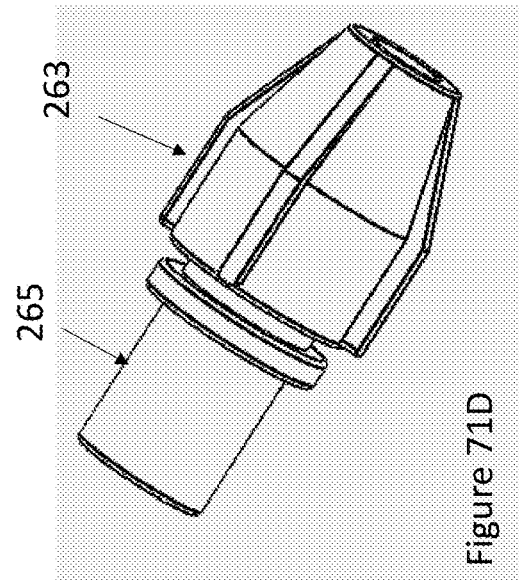
FIGS. 71A-71D illustrate views of a pusher lock of the pusher lock system of FIG. 70A.
Figure 71C:
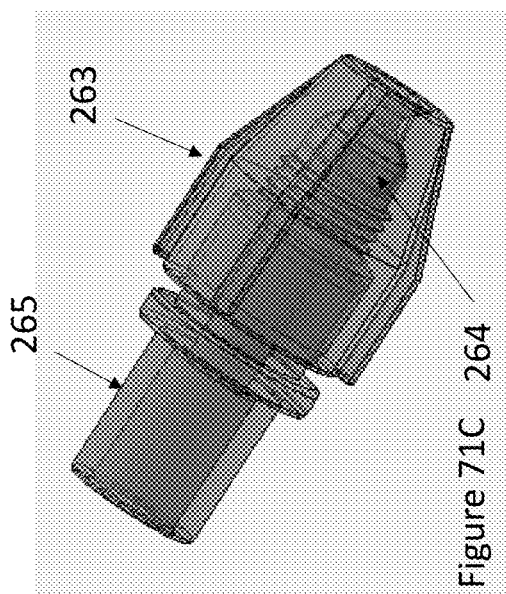
Figure 71A:
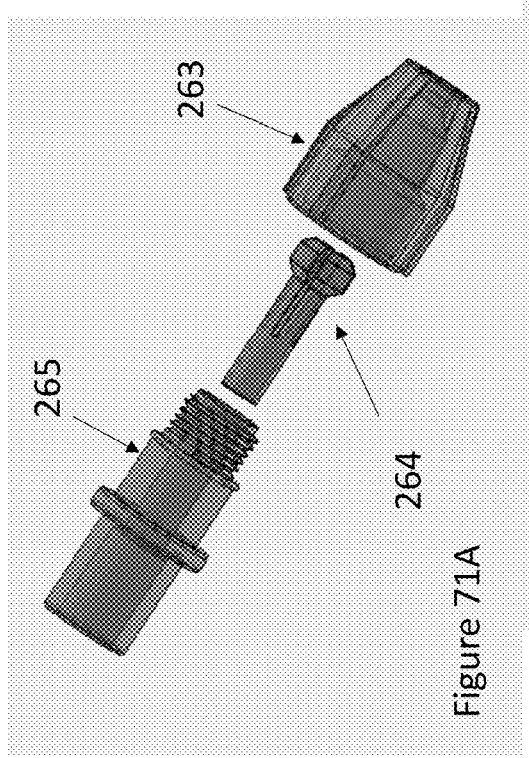
Figure 71B:
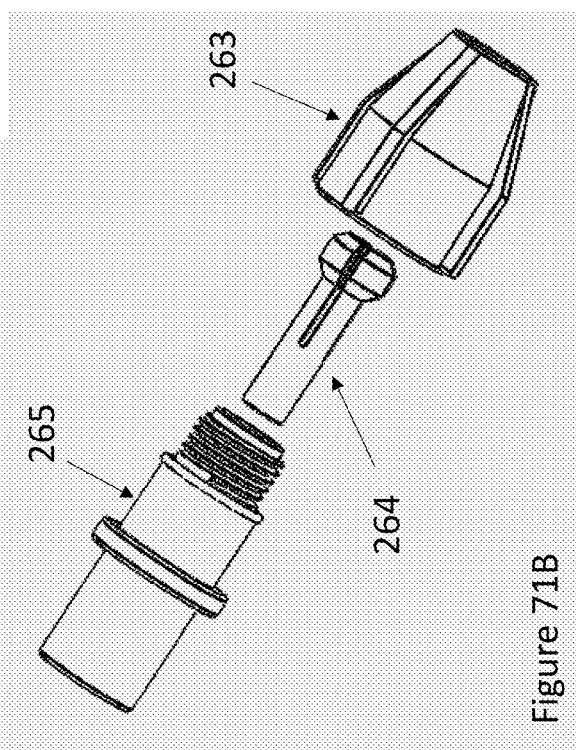

FIG. 67 illustrates a front view of the distal end of the ALTC device 201 and the anchors 241. The dual lumen shaft 243 is shown in cross section. In some embodiments, the dual lumen shaft 243 provides a lumen for the anchor and pusher assembly 223 and a lumen for the corewire and basket assembly 222. The two lumens can be separated such that movement of one assembly does not impact the movement of the other assembly. Other configurations are contemplated.

The corewire and basket assembly 222 includes the corewire 242. The corewire 242 is shown disposed in one lumen of the dual lumen shaft 243. The corewire 242 can include any of the feature or functions of the inner pusher 202 described herein. The compressed basket or compressed ALTC device 201 is disposed in the same lumen of the dual lumen shaft 243 as the corewire 242. The compressed ALTC device 201 can have any of the features or function as the collapsed segment 208 described herein. The outer shaft of the dual lumen shaft 243 is shown.

The anchor and pusher assembly 223 can include the distal pusher 226 and the crescent pusher 227 described herein. The crescent pusher 227 can be coupled to the anchor pusher 240, described herein. In some embodiments, the distal pusher 226, the crescent pusher 227, and the anchor pusher 240 are integrally or monolithically formed. In some embodiments, the distal pusher 226 is a portion of the anchor pusher 240. The crescent shape of the crescent pusher 227 may prevent rotation of the crescent pusher 227 within the dual lumen shaft 243. The crescent pusher 227 is shown a lumen of the dual lumen shaft 243.

The anchors 241 can be coupled to the anchor pusher 240, such that movement of the anchor pusher 240 causes movement of the one or more anchors 241. The anchors 241 can be coupled to the distal pusher 226, such that movement of the distal pusher 226 causes movement of the one or more anchors 241. In some embodiments, the anchors 241 can be welded to the distal pusher 226. The anchors 241 are arranged such that the anchors 241 are coaxial along central longitudinal axis 230. As shown in the illustrated embodiment, only one anchor is visible from the front view due to the coaxial nature of the anchors 241.

The ALTC device 201 is expanded as shown in FIG. 67. The outer diameter 232 of the anchor 241 can be smaller than the inner diameter 233 of the basket or ALTC device 201 in order for the ALTC device 201 to capture the anchors 241. The ALTC device 201 can capture one or more anchors depending on the axial length of the ALTC device 201. The axial length of the ALTC device 201 is adjustable based on the release of the ALTC device 201 from the dual lumen shaft 243. As a longer portion of the ALTC device 201 is released, the ALTC device 201 axially lengthens. As described herein, the ALTC device 201 remains at a constant diameter or cross-section as the ALTC device 201 lengthens. The capture guide 204 maintains the shape of the expanded ALTC device 201 as the ALTC device 201 axially lengthens. The capture guide 204 is smaller in diameter than the outer diameter 232 of the anchor 241.

The capture guide 204 can function as a centering device to center the system within the vessel. The capture guide 204 can be a similar diameter or cross-sectional shape as the vessel. In some methods of use, the capture guide 204 is smaller than the diameter of the blood vessel when the capture guide 204 is expanded. In some methods of use, the capture guide 204 is approximately equal to the diameter of the blood vessel when the capture guide 204 is expanded. In some methods of use, the ALTC device 201 is smaller than the diameter of the blood vessel when the ALTC device 201 is expanded. In some methods of use, the ALTC device 201 is approximately equal to the diameter of the blood vessel when the ALTC device 201 is expanded. In some methods of use, the ALTC device 201 contacts the vessel wall of the blood vessel. In some methods of use, the ALTC device 201 does not contact the vessel wall.

The capture guide 204 can include the central longitudinal axis 231. In some embodiments, the dual lumen shaft 243 can be offset from the central longitudinal axis 231. In some embodiments, the dual lumen shaft 243 can be coaxial with the central longitudinal axis 231 (not shown). The anchor 241 can include the central longitudinal axis 230. In some embodiments, the dual lumen shaft 243 can be offset from the central longitudinal axis 230. In some embodiments, the dual lumen shaft 243 can be coaxial with the central longitudinal axis 230 (not shown). In some embodiments, the central longitudinal axis 230 of the anchor 241 can be offset from the central longitudinal axis 231 of the capture guide 204. In some embodiments, the central longitudinal axis 230 of the anchor 241 can be coaxial with the central longitudinal axis 231 of the capture guide 204 (not shown). In some embodiments, the dual lumen shaft 243 can be positioned near an edge of the capture guide 203. Other configurations are contemplated.

FIGS. 68A-69C illustrate capture of a clot within a vessel, according to some embodiments. FIG. 68A illustrates the ALTC device 201 in the initially deployed configuration. As illustrated in FIG. 68A, the ALTC device 201 can be in some embodiments a generally semi-spherical mesh structure when initially deployed. The mesh structure is initially collapsible within a guide catheter or outer sheath 203. The guide catheter delivers the ALTC device 201 to the desired location within the body of the patient. The capture guide 204 is released from the constrained condition within the guide catheter or outer sheath 203. The capture guide 204 expands to have a cross-sectional shape. In some embodiments, the capture guide expands to a round or circular shape.

The ALTC device 201 is expandable to the diameter or cross-section provided by the capture guide 204. In some methods of use the ALTC device 201 is expanded by removal of a constraint. The ALTC device 201 can be released from a guide catheter. The guide catheter can be retracted to allow the capture guide 204 to expand. In some methods of use, the ALTC device 201 can be released from within the dual lumen shaft 243 by retraction of the dual lumen shaft. As described herein, one end portion of the ALTC device 201 is coupled to the capture guide 204. The ALTC device 201 can include a tubular mesh with a distal end. The ALTC device 201 can include a dynamic fold point as described herein such that the tubular mesh becomes everted upon release from the dual lumen shaft 243. The ALTC device 201 can include a reserve radially compressed segment within the dual lumen shaft terminating proximally at a point coupled to the inner pusher 202. In some methods of use, the expanded segment of the ALTC device 201 is positioned distal to the blood clot. The outer sheath 203 is positioned proximally, within, or adjacent to the blood clot.

FIG. 68B shows the ALTC device 201 in the initially deployed configuration. As described herein, the corewire and basket assembly and the anchor and pusher assembly can be independently actuated. The first anchor 241 can be released when the outer sheath 203 retracts proximally. The first anchor 241 can include a shape memory material such that the first anchor 241 assumes an expanded configuration. The first anchor 241 can expand such that the first anchor 241 is defined by the angle theta. The first anchor 241 expands from a low profile configuration to an expanded configuration. The low profile configuration can enable the anchor 241 to reside within the outer sheath 203 during delivery. In some additionally or alternative methods of use, the first anchor 241 can be released when the anchor pusher 240 advances distally.

The released anchor can be firmly secured to the clot. In some methods of use, the first anchor 241 can become entangled in the clot. In some methods of use, the first anchor 241 can reside against the clot. In some methods of use, the first anchor 241 can be designed to push the clot. In some methods of use, the first anchor 241 can be designed to perform a sweeping motion through the clot. The sweeping motion can be over an arc of the angle theta, or a portion thereof. The sweeping motion can break the clot, or a portion thereof.

FIG. 68C shows the ALTC device 201 in the initially deployed configuration. The second anchor 241 can be released when the outer sheath 203 retracts proximally. In some methods of use, the second anchor 241 can be released when the anchor pusher 240 advances distally. The second anchor 241 can include a shape memory material such that the second anchor 241 assumes an expanded configuration. The second anchor 241 can expand such that the second anchor 241 is defined by the angle theta. As described herein, the first anchor 241 and the second anchor 241 can have the same or different orientation for the angle theta.

FIG. 68D shows the ALTC device 201 in the initially deployed configuration. In some methods of use, the third anchor 241 can be released when the outer sheath 203 retracts proximally. In additional or alternative embodiments, the third anchor 241 can be released when the anchor pusher 240 is advanced distally. The third anchor 241 can include a shape memory material such that the third anchor 241 assumes an expanded configuration. The third anchor 241 can expand such that the third anchor 241 is defined by the angle theta. As described herein, the first anchor 241, the second anchor 241 and the third anchor 241 can have the same or different orientation for the angle theta.

The first anchor 241, the second anchor 241 and the third anchor 241 can be designed to be secured to the clot. The arrangement of the anchors 241 can be designed to facilitate engagement with the clot. For instance, the number of anchors, the spacing of the anchors, the cross-section dimension of the anchors, the shape of the anchors, the orientation of the anchors relative to the anchor pusher, the angle theta, the shape of the leg extension, the rapidness of the shape memory material to assume the neutral shape, the stiffness of the material, as well as other factors can be optimized to facilitate engagement of the anchors 241 with the clot.

The ALTC device 201 and the anchors 241 can retract proximally to remove the clot. In some methods of use, the ALTC device 201 can catch emboli or debris that dislodges during removal of the clot. In some methods of use, the ALTC device 201 is positioned downstream in a vessel to catch debris. The curved distal end of the ALTC device 201 can function as a net. In some methods of use, the anchors 241 can disrupt the clot to enable easier removal of the clot. In some methods of use, the sweeping motion of deploying the anchors 241 can break apart the clot.

FIGS. 69A-69C illustrates the axial lengthening sequence of the ALTC device 201, according to some embodiments. The dual lumen sheath 243 can be retracted to axially lengthen the ALTC device 201. As the dual lumen sheath 243 is retracted, the capture guide 204 is retracted since the capture guide 204 is coupled to the dual lumen sheath 243 via the coupler 205. As the capture guide 204 is retracted, the collapsed portion 208 becomes the expanded portion. The dual lumen sheath 243 can be retracted proximally to axially lengthen the ALTC device 201. Alternatively or in combination, in other methods of use, the capture guide 204 can be retracted to axially lengthen the ALTC device 201, such as be retracting the dual lumen sheath 243. The diameter or cross-section of the ALTC device 201 remains constant between the initial deployed configuration shown in FIG. 69A and the expanded configurations shown in 69B and 69C. In additional or alternative methods of use, the corewire 242 can be actuated to axially lengthen the ALTC device 201. The corewire 242 can be positioned within the dual lumen shaft 243. Actuation of the corewire 242 such as axially in the appropriate direction will release the constrained portion of the ALTC device 201. The movement of the corewire 242 can result in axial lengthening or shortening of the ALTC device 201.

FIG. 69A illustrates the system after deployment of the anchors 241. In some methods of use, the anchors 241 are deployed before axial lengthening of the ALTC device 201. In some methods of use, one or more steps of releasing an anchor and axially lengthening can occur in any order. In some methods of use, the first anchor is deployed and then the ALTC device 201 is axially lengthened to cover the first anchor. In some methods of use, the first and second anchors are deployed before the ALTC device 201 is axially lengthened to cover the first anchor or the second anchor. In some methods of use, the first, second, and third anchors are deployed before the ALTC device 201 is axially lengthened to cover the first anchor, the second anchor, or the third anchor. In some embodiments, two or more steps can occur simultaneously. In some methods of use, the first anchor is deployed and the ALTC device 201 is axially lengthened to cover the first anchor simultaneously. In some methods of use, the first and second anchor are deployed and the ALTC device 201 is axially lengthened to cover either the first anchor or the second anchor simultaneously. In some methods of use, the first, second, and third anchors are deployed and the ALTC device 201 is axially lengthened to cover the first anchor, the second anchor, or the third anchor simultaneously.

FIG. 69B illustrates the axial lengthening of the expanded portion of the ALTC device 201. The ALTC device 201 is lengthening proximally to capture the clot secured by the first anchor 241. The compressed or constrained segment of the ALTC device 201 is shortening within the dual lumen shaft 243 reciprocally. The dual lumen sheath 243 can be retracted to axially lengthen the ALTC device 201, as described herein. The ALTC device 201 can encapsulate the first anchor 241. The first anchor 241 can be sized to fit within the ALTC device 201 once the ALTC device 201 is axially lengthened.

FIG. 69C illustrates the axial lengthening of the expanded portion of the ALTC device 201. The ALTC device 201 is lengthening proximally to capture the clot secured by the first anchor 241, the second anchor 241, and the third anchor 241. The compressed or constrained segment of the ALTC device 201 is shortening within the dual lumen shaft 243 reciprocally. FIG. 69C illustrates the axial lengthening ALTC device 201 is sufficient to completely capture the clot. The ALTC device 201 and the anchors 241 can retract proximally to remove the clot.

The ALTC device 201 can be axially lengthened, such as within a working range, by releasing the ALTC device 201 from the sheath, which can have one, two, or more lumens in the sheath 243. The ALTC device 201 can be axially lengthened or shortened while maintaining or substantially maintaining the diameter or cross-section provided by the capture guide 204. The ALTC device 201 can be axially lengthened or shortened to retrieve and capture foreign or otherwise unwanted materials within the body, including the neurovascular system such as blood clots, thrombus and/or foreign materials.

The ALTC device 201 described herein can be sized to fit within a vessel of the neurovascular system, including any vessel noted elsewhere herein. As one example, the ALTC device 201 can be used to treat arteries, veins, and non-vascular lumens or regions. In some embodiments, the device can be configured to treat cerebral venous sinus thrombosis and cavernous sinus thrombosis. A thrombus, commonly called a clot, is the product of blood coagulation due to aggregated platelets and red blood cells connected by a fibrin protein to block a blood vessel. The thrombus can travel (embolize), such as propagating toward the heart, lungs or other organs. The removal of thrombus can reduce the risk of a stroke, myocardial infarction, and/or pulmonary embolisms. The ALTC device 201 can lengthen to have a maximal length that covers the entire length of anchors 241, e.g., from about 0.01 mm to about 100 mm. Depending on vessel diameter, the outer diameter of the ALTC device 201 can range from, in some embodiments, from about 0.01 millimeter up to about 10 millimeters. The diameter of the ALTC device can achieve the similar effect of reducing or stretching the ALTC device diameter. In some embodiments, suction is not utilized or required, and the ALTC device envelops the clot, which can be mechanically pulled back into the capture catheter. In some embodiments, the mechanical thrombectomy systems and methods as disclosed herein can be used in combination with, and/or coated with a therapeutic agent such as, for example, one or more anti-thrombotic or anti-platelet agents such as heparin, hirudin, warfarin, dabigatran, and/or enoxaparin; tPA, streptokinase, or urokinase, an anti-proliferative agent such as paclitaxel (Taxol), rapamycin (Sirolimus), zotarolimus, or tacrolimus; and the like depending on the desired clinical result.

FIGS. 70A and 70B illustrate views of an embodiment of a pusher lock system. The pusher lock system can be utilized with any of the system described herein. FIG. 70A also illustrates non-limiting examples of various possible elements that can be included in a material capture system, according to some embodiments of the invention. As illustrated in FIG. 70A, included in some embodiments are any number of, such as one, two, or more of the following components: a hemostasis seal 260, a pusher lock 261, and a pusher 262. The hemostasis seal 260 can include a plurality of seals at spaced apart locations in the pusher lock system. The hemostasis seal 260 can be similar to the seals shown in FIGS. 21E and 21F. The pusher lock 261 can include any of the features of pusher lock 246 described herein. The pusher 262 can include any of the features of the inner pusher 202. The pusher 262 can include any of the features of the corewire 242 described herein. The pusher 262 can include any of the features of the anchor pusher 240 described herein.

Referring first to the system shown in FIGS. 70A-B, the pusher 262 can include any of the features of the inner pusher 202 described herein. The pusher 262 can extend from the proximal end to the distal end. In some embodiments, the pusher extends from the nosetip of the catheter to the proximal end. In some embodiments, the pusher 262 is a single shaft. In some embodiments, the pusher 262 comprises one or more subcomponents. The pusher 262 can include an inner guidewire lumen shaft extending from the distal end toward the proximal end. The pusher 262 can include a pusher tube extending from the proximal end. The inner guidewire lumen shaft can be attached to a pusher tube to form a unitary structure. Other configurations are contemplated. The pusher 262 can comprise any material suitable to axially lengthen the ALTC device 201, as described herein. In some embodiments, the pusher 262 or a component thereof, comprises a metal such as stainless steel or titanium. In some embodiments, pusher tube can comprise stainless steel.

The pusher 262 can be positioned coaxially within a shaft. In some embodiments, the pusher 262 is placed within a middle shaft. The guidewire lumen shaft and the pusher tube assembly are positioned coaxially within the middle shaft. The pusher tube is extended beyond the middle shaft. The pusher tube can slide coaxially with respect to the middle shaft to either lengthen or shorten the ALTC device 201. During clinical use, if there is no locking mechanism for the pusher 262, the user can inadvertently actuate the pusher tube or the middle shaft prematurely, which will deploy the ALTC device 201. The pusher lock 261 helps to secure the pusher tube to the middle shaft during insertion of the catheter. The pusher lock 261 can be unlocked after unsheathing the ALTC device 201. The pusher lock 261 can be unlocked when the user is ready for lengthening the ALTC device 201.

In some alternative and additionally embodiments, the guidewire lumen shaft and the pusher tube assembly are positioned coaxially within the outer sheath 203. The pusher tube is extended beyond the outer sheath 203. The pusher tube can slide coaxially with respect to the outer sheath 203 to either lengthen or shorten the ALTC device 201. In some embodiments, the pusher tube extends beyond the outer sheath 203, as shown in FIG. 51. During clinical use, if there is no locking mechanism for the pusher 252, the user can inadvertently actuate the pusher tube or the outer sheath 203 prematurely, which will deploy the ALTC device 201. The pusher lock 251 helps to secure the pusher tube to the outer sheath 203 during insertion of the catheter. The pusher lock 261 can be unlocked after unsheathing the ALTC device 201. The pusher lock 261 can be unlocked when the user is ready for lengthening the ALTC device 201.

Referring now to the system shown in FIG. 62, the pusher 262 can include any of the features of the corewire 242 described herein. The pusher 262 can include any of the features of the anchor pusher 240 described herein. The pusher 262 can extend from the proximal end to the distal end. The pusher 262 can include an inner guidewire lumen shaft extending from the distal end toward the proximal end. The pusher 262 can include a pusher tube extending from the proximal end. Other configurations are contemplated.

The pusher 262 is positioned coaxially within a shaft. In some embodiments, the pusher 262 is placed within a middle shaft of the dual lumen shaft 243. The guidewire lumen shaft and the pusher tube assembly are positioned coaxially within the middle shaft. The pusher tube is extended beyond the middle shaft. The pusher tube can slide coaxially with respect to the middle shaft to either lengthen or shorten the ALTC device 201. During clinical use, if there is no locking mechanism for the pusher 262, the user can inadvertently actuate the pusher tube or the middle shaft of the dual lumen shaft 243 prematurely, which will deploy the ALTC device 201. The pusher lock 261 helps to secure the pusher tube to the middle shaft during insertion of the catheter. The pusher lock 261 can be unlocked after unsheathing the ALTC device 201. The pusher lock 261 can be unlocked when the user is ready for lengthening the ALTC device 201.

In some alternative or additional embodiments, the pusher 262 is placed within an upper shaft of the dual lumen shaft 243. The guidewire lumen shaft and the pusher tube assembly are positioned coaxially within the upper shaft. The pusher tube is extended beyond the upper shaft. The pusher tube can slide coaxially with respect to the upper shaft to deploy the anchors 241. During clinical use, if there is no locking mechanism for the pusher 262, the user can inadvertently actuate the pusher tube or the dual lumen shaft 243 prematurely, which will deploy the anchors 241. The pusher lock 261 helps to secure the pusher tube to the dual lumen shaft 243 after during insertion of the catheter. The pusher lock 261 can be unlocked after unsheathing the ALTC device 201. The pusher lock 261 can be unlocked after unsheathing the first anchor 241. The pusher lock 261 can be unlocked when the user is ready to deploy the anchors 241.

The method can include one or more of the following steps in any order. The delivery catheter can be prepared. The delivery catheter can be prepared at the bedside of a patient. The delivery catheter can be prepared according to one or more instructions. In some methods of use, the pusher lock 261 can be locked in position. The pusher lock 261 can be locked in position on the pusher 262. In some embodiments, the pusher lock 261 is locked in position by rotating the lock cap 263. In some embodiments, the pusher lock 261 can be locked by rotating clockwise. In some embodiments, the pusher lock 261 can be locked by rotating counterclockwise.

In some methods of use, a guidewire is positioned within a patient. In some methods of use, the inner guidewire lumen shaft of the pusher 262 can be guided over the guidewire. In some methods of use, the pusher tube of the pusher 262 can be guided over the guidewire. In some methods of use, the system is advanced over the guidewire. In some methods of use, the delivery catheter is advanced to the intended area for treatment. In some methods of use, the delivery catheter is retracted. In some methods of use, the outer sheath 203 is retracted to deploy the ALTC device 201.

In some methods of use, the pusher lock 251 is unlocked. In some methods of use, the pusher lock 261 is unlocked by rotating the lock cap 263 counterclockwise. In some methods of use, the pusher lock 261 is unlocked by rotating the lock cap 263 in an opposite direction. Upon unlocking the pusher lock 261, the ALTC device 201 can be lengthened. In some methods of use, the ALTC device is lengthened by axially actuating the middle shaft. In some methods of use, the ALTC device is lengthened by axially actuating the pusher tube. In some methods of use, the ALTC device is lengthened by axially actuating the outer sheath. In some methods of use, the ALTC device is lengthened by axially actuating the dual lumen shaft. The pusher lock 261 can be used to affix the pusher tube to the middle shaft as needed.

FIGS. 71A-71D illustrate views of a pusher lock 261 of the pusher lock system of FIG. 70A. As illustrated in FIG. 71A-71D, included in some embodiments are any number of, such as one, two, or more of the following components: the lock cap 263, a collet 264, and a lock body 265. The lock cap 263 and the lock body can include mating threads. In the illustrated embodiment, the lock cap 263 includes female threads and the lock body 265 includes male threads. The collet 264 is disposed between the lock cap 263 and the lock body 265. The pusher 252, or a portion thereof, is designed to be placed within the collet 264. The pusher 252 can extend through an opening in the lock cap 263, through the collet 264, and through an opening in the lock body 265. The lock cap 263 also includes a ramped surface designed to interact with the collet. As the lock cap 262 is rotated, the collet 264 can be brought into engagement with the ramped surface. Further rotation can cause the collet to collapse or tighten onto the pusher 252. Other configurations are contemplated.

Figure 72:
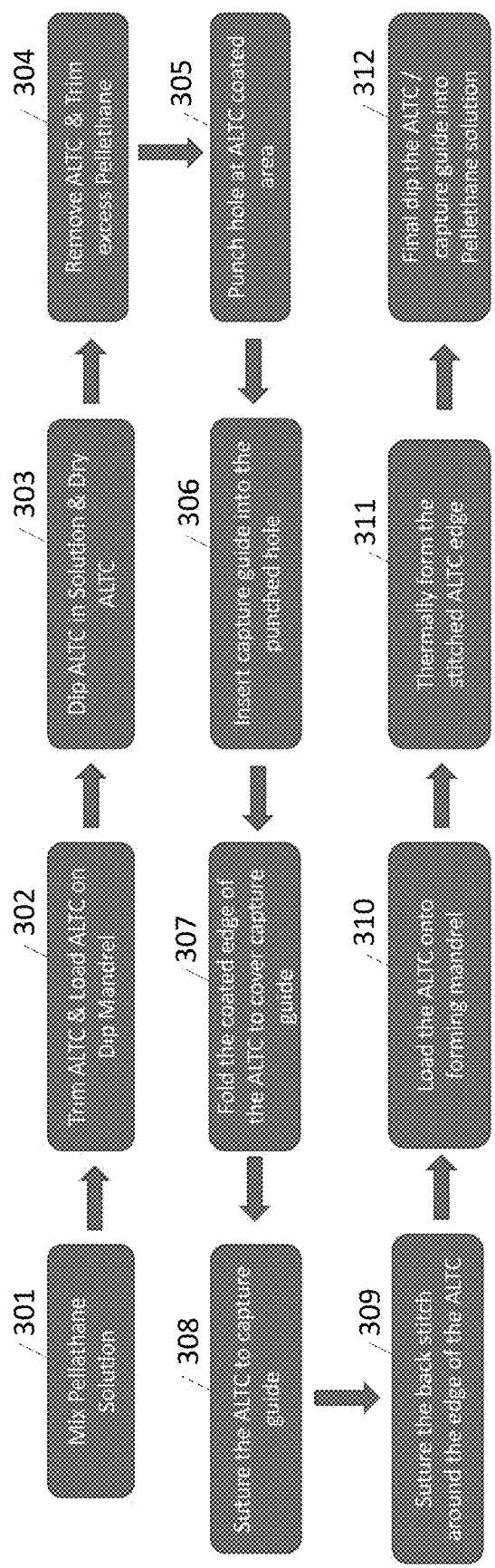
FIG. 72 illustrates a method of assembly an ALTC device to a capture guide.

FIG. 72 illustrates a flow chart of an embodiment of a method 300. In some embodiments, the method can assemble the end of the ALTC device 201 to the capture guide 204. The method can include one or more of the following steps, in any order. The step 301 can include mixing a thermoplastic and/or polyurethane, e.g., Pellethane solution. The solution is mixed using, e.g., a thermoplastic polyurethane, e.g., Pellethane and, e.g., a cyclic ester such as Tetrahydrofuran (THF). The mixture of Pellethane and Tetrahydrofuran (THF) ratio can range from, e.g., between about 1:1 and about 1:20 of Pellethane to THF. The ratio of Pellethane to Tetrahydrofuran can be, for example, about, at least about, or no more than about 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1.19; 1:20, or ranges including any two of the aforementioned values. The step 302 can include trimming the ALTC device 201. The end of the ALTC device 201 can be squared trim. The step 302 can include loading the ALTC device 201 on the dipping mandrel. The dipping mandrel can be made of polymeric and/or metallic materials such as HDPE, PTFE, stainless steel, etc. The mandrel can be non-coated or coated to allow ease of manufacturing. The step 303 can include dipping the ALTC device 201 in the solution. The ALTC device mounted on a dipping mandrel is slowly dipped into the Pellethane/THF solution. The step 303 can include drying the ALTC device 201. The ALTC device 201 can hang to allow to dry, or dried using other mechanisms. The step 304 can involve removing the ALTC device 201. The step 304 can involve trimming the excess Pellethane. The dipped end of the ALTC device 201 can encapsulate and fix the wire ends of the basket mesh element 209 from movement. The dipped end can prevent the wire ends of the basket mesh element 209 from being exposed. The ALTC device 201 is removed from the dipping mandrel. The excess Pellethane is trimmed close to the edge of the ALTC device 201.

The step 305 can include punching or otherwise creating one or more apertures in the Pellethane coating. The dipped area of ALTC device 201 can be punched to create holes at predetermine location to allow placement of the capture guide. Other methods of making holes in the coating are contemplated. The step 306 can include inserting the capture guide 204 into the punched hole. The capture guide 204 is inserted into the punched hole. The capture guide 204 can be woven through two or more holes. The capture guide can be threaded from one side of the ALTC device 201 to the other side of the ALTC device 201. The step 307 can include folding the edge of the ALTC device to cover the capture guide 204. The dipped coat edge of the ALTC device 201 is folded to cover the wire loop of the capture guide 204. The folding can protect and prevent the encapsulated wire ends of the basket mesh element 209 from protruding. The step 308 can include suturing the ALTC device 201 and the capture guide 204. The ALTC device 201 is sutured to the capture guide 204 using suture materials. Suture materials can include, for example, PET, PTFE, HMWPE, or other materials known in the art. The step 309 can include suturing around the edge of the ALTC device. The step 309 can include suture the back stitch around the edge.

The step 310 can include loading the ALTC device onto the forming mandrel. When the suturing is completed, the ALTC device 201 in then loaded onto the forming mandrel. The step 311 can include thermally forming the stitched ALTC edge. The step 311 can include thermally forming the stitched ALTC device edge using appropriate heating. The forming mandrel can be either polymeric or metallic materials such as PTFE, stainless steel, etc. The step 312 can include dipping the ALTC device and capture device. The ALTC device and capture device can be dipped in the Pellethane solution from step 301. The ALTC device and capture device can be dipped in another solution. The dipping process can include dipping the ALTC device 201 and capture guide 204 into the Pellethane/THF solution. The dipping can secure the assembly of the ALTC device 201 and capture device 204. The step 312 can include loading the assembly of the ALTC device 201 and capture device 204 onto the dipping mandrel. The dipping mandrel can be the same dipping mandrel of steps 302, 303. The dipping mandrel can be a different mandrel. The dipping mandrel for this step 312 can be made of polymeric and/or metallic materials such as HDPE, PTFE, stainless steel, etc. The mandrel for this step 312 can be non-coated or coated to allow ease of manufacturing. In some methods of use, a film or sheet of material can be used in addition or in place of one or more dipping steps. The film can be an extruded polymeric film. The sheet can be a sheet of low durometer polymer such as pellethane, polyurethane, tecothane, etc. The film or sheet can be used and place over the end of the ALTC device. In some methods of use, a film or sheet of material can be used in addition thermally forming the edge of the ALTC device 201. The film or sheet can be thermally fused. The film or sheet can be laminated together. Other manufacturing methods are contemplated.

FIGS. 73-94 illustrate embodiments of anchors. The anchors described herein can be used in conjunction with, or in place of, anchors 241. The one or more anchors described herein can form an anchor assembly 221 described herein. The anchor assembly 221 can include about or at least about one, two, three, four, five, or more anchors configured to secure a clot. In some embodiments, two or more anchors of the anchor assembly 221 can be the same. In some embodiments, two or more anchors of the anchor assembly 221 can be different. In some embodiments, two or more anchors of the anchor assembly 221 can be selected from anchors described herein. In some embodiment, the diameter of the anchor when expanded is smaller than the ALTC device 201 when expanded. In some embodiment, the anchor can be designed to fit within the ALTC device 201 when the ALTC device 201 is expanded. In some embodiments, the anchor can be designed to substantially the same or larger than the ALTC device 201. In some embodiments, the distal end of the ALTC device 201 has a flexible, atraumatic extension forming the distal end of the system. In some embodiments, the distal end of the ALTC device 201 has an anchor. In some embodiments, the anchor can have any shape to entangle a portion of the clot. In some embodiments, the anchor can have any shape to stabilize a portion of the clot. In some embodiments, the anchor can have any shape to provide radial support to the clot. In some embodiments, the anchor can have any shape to provide axial support to the clot. In some embodiments, the anchor can have any shape to move a portion of the clot, such as distally toward the ALTC device 201 or proximally away from the ALTC device 201. In some embodiments, the anchor can rotate. In some embodiments, the anchor can move axial to break up the clot.

The systems described herein can include the guidewire lumen 6, which can advance distally to lengthen the ALTC device 201. Referring to FIG. 5, the outer sheath 1 has an inner diameter configured to house the capture catheter 12 coaxially therein, and the capture catheter 12, which in turn has a lumen configured to house the guidewire tube 6 and the body of the ALTC device 8. The systems described herein can include the pusher 202 or corewire 242. Alternatively or in combination, in other methods of use, an end of the ALTC device 201 is coupled to the inner pusher 202. In the second configuration, the inner pusher 202 is advanced distally to release a portion of ALTC device 201 from a sheath. As the inner pusher 202 is advanced distally, a portion of the collapsed portion 208 becomes the expanded portion of the ALTC device 201. As the inner pusher 202 is advanced distally, the ALTC device 201 is axially lengthened. In additional or alternative methods of use, the corewire 242 can be actuated to axially lengthen the ALTC device 201. The corewire 242 can be positioned within the dual lumen shaft 243. Actuation of the corewire 242 such as axially in the appropriate direction will release the constrained portion of the ALTC device 201. The movement of the corewire 242 can result in axial lengthening or shortening of the ALTC device 201. In some embodiments, the systems described herein can include a fixed guidewire. In some embodiments, the systems described herein can be advanced along a guidewire. In some embodiments, the systems described herein can slide along a guidewire. In some embodiments, the systems described herein can include a lumen configured to slide along a guidewire. In some embodiments, the guidewire is a shaft. In some embodiments, the guidewire has a lumen. In some embodiments, the guidewire is a needle. In some embodiments, the guidewire is solid. In some embodiments, the guidewire is flexible. In some embodiments, the guidewire functions to guide the system within the body of the patient. In some embodiments, the guidewire functions to deploy one or more components of the device.

The system can include a dual axial lengthening basket and anchor capture device as described here. The anchors can be any configuration such as stent-like, balloon, coils, loops, wire forms into various geometric shapes (not shown), etc. such as the embodiments described herein. In some methods of use, the anchors can function to secure the emboli, thrombus or debris and allow for removal. In some methods of use, the anchors can function to break up the emboli, thrombus or debris. In some embodiments, the ALTC device 201 and the one or more anchors move or translate together. In some embodiments, the ALTC device 201 and the one or more anchors move or translate independently or separately. In some embodiments, one or more anchors can move as a unit with another anchor. In some embodiments, one or more anchors can move independently or separately from another anchor.

FIG. 73 illustrates an embodiment of an anchor 401. The anchor 401 can include any of the features of anchors described herein. In some embodiments, the anchor 401 can comprise symmetric loop shapes. In some embodiments, the anchor 401 can comprise asymmetric loop shapes. In some embodiments, the anchor 401 can comprise polygonal shapes or generally polygonal shapes. In some embodiments, the anchor 401 comprises generally hexagonal shapes. In some embodiments, the anchor 401 has a constant diameter. In some embodiments, the anchor 401 has two or more diameters. In the illustrated embodiments, the anchor 401 has an alternating larger diameter and smaller diameter. In some embodiments, the smaller diameter is more than 50% of the larger diameter, the smaller diameter is more than 60% of the larger diameter, the smaller diameter is more than 70% of the larger diameter, the smaller diameter is more than 80% of the larger diameter, the smaller diameter is more than 90% of the larger diameter, the smaller diameter is approximately equal to the larger diameter, etc. It is also understood the anchor can have various length. For example, the anchor can have sufficient length such that the anchor is partially deploy to accommodate the length of the clot. Furthermore, the remainder of the anchor is compressed with the delivery catheter and can be lengthen and expand to accommodate longer length clot as needed.

In some embodiments, the anchor 401 can be a mesh, braid or other network of wire or thread. In some embodiments, the anchor 401 can have an interlaced structure. In some embodiments, the anchor 401 can be formed from parallel or axial wires or threads 402. The parallel or axial wires or threads can be coupled or otherwise connected at junctions 403. The junctions 403 can couple two or more wires or threads 402 together. In some embodiments, the junctions 403 can be staggered to form the mesh structure. In some embodiments, the anchor 401 forms a helix. In some embodiments, the anchor 401 forms a double helix. In some embodiments, the anchor 401 forms a helical structure. In some embodiments, the anchor 401 forms an irregular mesh. In some embodiments, the anchor 401 forms a regular mesh. In some embodiments, the anchor 401 forms a fully connected structure. The anchor 401 can comprise a repeating or tessellating shape such as triangles, squares, or hexagons. The anchor can be laser-cut.

The anchor 401 can include an flexible tip 404. The flexible tip 404 can function as atraumatic soft tip. The opposite end of the anchor 401 is attached to the anchor pusher 240 and function in a similar manner described herein. The flexible tip 404 can be disposed within the outer sheath 203 described herein. The anchor pusher 240 can be disposed within the dual lumen shaft 243 described herein. The anchor pusher 240 can be disposed within any lumen of any device, shaft or catheter described herein. The anchor can be offset to the ALTC device. The anchor can be coaxial to the ALTC device. The anchor pusher 240 and the anchor 401 can be coupled together such that movement of the anchor pusher 240 causes movement of the anchor 401. In some embodiments, the flexible tip 404, anchor 401 and the anchor pusher 240 is cannulated for an "over the wire" configuration. The anchor pusher 240 can be guided over a guidewire for placement of the anchor 401.

FIG. 74 illustrates an embodiment of an anchor 405. The anchor 405 can include any of the features of anchors described herein, including anchor 401. In some embodiments, the anchor 405 can be a mesh, braid, laser cut or other network of wire or thread 406. In some embodiment, the anchor is made from one wire or thread. In some embodiments, the anchor 405 can be formed from parallel or axial wires or threads 406. The parallel or axial wires or threads can be coupled or otherwise connected at junctions 407. The junctions 407 can couple two or more wires or threads 406 together. In some embodiments, the junctions 407 can be staggered to form the mesh structure. In some embodiments, the junctions 407 can couple all of the wires or threads 406 together. In some embodiments, the junctions 407 can form a plurality of discrete subsections. In the illustrated embodiments, the anchor 405 can include three subsections formed from two junctions 407. Other configurations are contemplated (e.g., the anchor 405 includes two subsections formed from one junction 407, the anchor 405 can include four subsections formed from three junctions 407, the anchor 405 include five subsections formed from four junctions 407, etc.). In the illustrated embodiments, the anchor 405 has an alternating larger diameter and smaller diameter formed by the junctions 407. In some embodiments, the smaller diameter is less than 50% of the larger diameter, the smaller diameter is less than 40% of the larger diameter, the smaller diameter is less than 30% of the larger diameter, the smaller diameter is less than 20% of the larger diameter, the smaller diameter is less than 10% of the larger diameter, etc. It is also understood the anchor is not limited to metal only but other materials such as polymeric materials PTFE, PET, Nylon, Polyethylene, PEEK, Polypropylene, Polyimide.

FIG. 75 illustrates a distal end of a capture device system including the anchor 401. The system can be placed within a vessel 408. The vessel can be any target vessel within the body of a patient. In some embodiments, the vessel is in the central nervous system or a coronary or peripheral vessel as described elsewhere herein. The system is placed near an obstruction 409 or other source of debris or material. In some embodiments, the obstruction is a blood clot. In some embodiments, the obstruction is a neurological blood clot. In some embodiments, the obstruction is an emboli. In some embodiments, the obstruction is a foreign body.

FIG. 75 illustrates the system with the anchor 401 and the ALTC device 201 deployed. In some methods of use, one or more steps of releasing an anchor 401 and axially lengthening can occur in any order. In some methods of use, the anchor 401 is deployed before axial lengthening of the ALTC device 201. In some embodiments, the anchor forms only a single loop. In some embodiments, the single loop functions in a similar manner to the anchor 401. In some methods of use, the anchor 401 is deployed by axial movement of the anchor pusher 240. The anchor pusher 240 can release the anchor 401 from a sheath such as dual lumen sheath 243 described herein. In some methods of use, the anchor 401 is deployed and then the ALTC device 201 is axially lengthened to cover the anchor 401. In some methods of use, the anchor 401 is deployed before the ALTC device 201 is axially lengthened to cover the anchor 401. In some methods of use, the anchor 401 is partially deployed before the ALTC device 201 is axially lengthened to cover the anchor 401. In some methods of use, the anchor 401 is not deployed before the ALTC device 201 is axially lengthened. In some methods of use, the anchor 401 is deployed after the ALTC device 201 is axially lengthened. In some methods of use, the anchor 401 is partially deployed after the ALTC device 201 is partially axially lengthened. In some methods of use, the anchor 401 is deployed and the ALTC device 201 is axially lengthened simultaneously. In some methods of use, the anchor 401 is deployed and the ALTC device 201 is axially lengthened independently. In some methods of use, the anchor 401 is fixed and the ALTC device 201 is axially lengthened. In some methods of use, the ALTC device 201 is fixed and the anchor 401 is deployed or expanded. In some methods of use, the anchor 401 is only deployed if covered by the ALTC device 201. In some methods of use, the anchor 401 is only deployed the ALTC device 201 provides distal protection. The anchors described herein can function in any manner described herein.

In some methods of use, the ALTC device 201 is positioned distally to the anchor 401. In some methods of use, the ALTC device 201 is positioned downstream in the direction of blood flow. The direction of blood flow is shown in FIG. 75 by the red arrow. In some methods of use, the ALTC device 201 is positioned distal to the obstruction or clot. In some methods of use, the ALTC device 201 is positioned to capture fragments of the obstruction. In some methods of use, the ALTC device 201 provides distal protection during clot removal. In some methods of use, alternatively, the ALTC device 201 is positioned proximally to the anchor 401. In some methods of use, the ALTC device 201 is positioned upstream to the anchor 401. In some methods of use, alternatively, two or more ALTC device 201 are utilized. In some methods of use, one ALTC device 201 is positioned distally and one ALTC device 201 is positioned proximally. In some methods of use, the two ALTC device 201 can move toward each other. In some methods of use, the two ALTC device 201 can meet at an intermediate location. The systems described herein can include one or more ALTC devices 201. The systems described herein can include one or more ALTC devices 201 positioned as described herein. In some embodiment, the anchor 401 can position distal to the ALTC device 201 (not shown).

In some methods of use, the anchor 401 is positioned distally to the ALTC device 201. In some methods of use, the anchor can function to block emboli. In some methods of use, the anchor 401 is positioned downstream in the direction of blood flow, or upstream in other embodiments. The direction of blood flow is shown in FIG. 75 by the arrow. In some methods of use, the anchor 401 is positioned distal to the obstruction or clot. In some methods of use, the anchor 401 is positioned to capture fragments of the obstruction. In some methods of use, the ALTC device 201 is lengthened for clot removal. In some methods of use, alternatively, two or more the anchors 401 are utilized. In some methods of use, one, two, or more anchors 401 are positioned distally and one, two, or more anchors 401 are positioned proximally of the ALTC device 201. In some methods of use, the two anchors 401 can move toward each other. In some methods of use, the two anchors 401 can meet at an intermediate location. The systems described herein can include one, two, or more anchors 401. The systems described herein can include one, two, or more anchors 401 positioned as described herein.

In some embodiments, the anchor is deployed adjacent to the clot. In some embodiments, the anchor is deployed within the clot. In some embodiments, the anchor is deployed distal to the clot. In some embodiments, the anchor is deployed proximal to the clot. In some methods of use, the anchor 401 deploys within the obstruction or clot. In some methods of use, the anchor 401 is positioned to entangle the obstruction. In some methods of use, the anchor 401 is positioned distally to the obstruction or downstream in the direction of blood flow. In some methods of use, the anchor 401 can move proximally through the obstruction. In some methods of use, the anchor 401 is positioned proximally to the obstruction or upstream in the direction of blood flow. In some methods of use, the anchor 401 can move distally through the obstruction. In the illustrated embodiment, the obstruction or clot can pass through the anchor 401. In the illustrated embodiment, the obstruction or clot can be caught in the anchor 401. In some methods of use, the anchor 401 moves after deployment. For instance, the anchor 401 can move distally therefore moving the obstruction distally. The anchor 401 can move proximally therefore moving the obstruction proximally. In some embodiments, the anchor 401 can rotate. After deployment of the anchor 401, the obstruction and the anchor 401 can move together as a unit. After deployment of the anchor 401, the obstruction, the anchor 401, and the ALTC device 201 can move together as a unit. In some methods of use, the anchor 401 moves after axially lengthening of the ALTC device 201. In some methods of use, the anchor 401 moves before axially lengthening of the ALTC device 201.

FIGS. 76A-76C illustrates the axial lengthening sequence of the ALTC device 201, according to some embodiments. The ALTC device 201 can be lengthened in any manner described herein. In some methods of use, the ALTC device 201 can be lengthened by retraction of a constraining member such as a sheath. As the sheath is retracted, the capture guide 204 is expanded. After the capture guide 204 is expanded, a portion of the ALTC device 201 is expanded. In some methods of use, the sheath dual lumen sheath 243 can be retracted to axially lengthen the ALTC device 201. In some embodiments, for the dual lumen sheath 243 in some cases, there may be no outer sheath required to constrain the device. In some embodiments, the dual lumen sheath 243 constrains the ALTC device 201. In some embodiments, the dual lumen sheath 243 constrains the anchors. In some embodiments, the dual lumen sheath 243 is loaded with the ALTC device 201. In some embodiments, the dual lumen sheath 243 is loaded with the one or more anchor. In some embodiments, the ALTC device 201 and the one or more anchor are loaded in a single lumen of a single lumen sheath. In some embodiments, the ALTC device 201 and the one or more anchor are loaded in a single lumen of a dual lumen sheath. In some embodiments, the ALTC device 201 and the one or more anchor are loaded in separate lumens of a sheath. In some embodiments, the ALTC device 201 and the one or more anchor are advanced from a single lumen of a single lumen sheath. In some embodiments, the ALTC device 201 and the one or more anchors are advanced from a single lumen of a dual lumen sheath. In some embodiments, the ALTC device 201 and the one or more anchors are advanced from separate lumens of a sheath. In some embodiments, the device would be loaded in a sheath/guide/microcatheter in advance. Effectively, in some cases the guide/microcatheter can be used as a sheath.

In some embodiments, the ALTC device 201 maintains the diameter of the capture guide 204. In some methods of use, the ALTC device 201 can be lengthened by extension of a member such as a pusher 202 or corewire 242. Alternatively or in combination, in other methods of use, the inner pusher 202 is advanced distally to advance an end of the ALTC device 201. As described herein, an end of the ALTC device 201 is coupled to the inner pusher 202. In the second configuration, the inner pusher 202 is advanced distally to release a portion of ALTC device 201 from a sheath. As the inner pusher 202 is advanced distally, a portion of the collapsed portion 208 becomes the expanded portion of the ALTC device 201. As the inner pusher 202 is advanced distally, the ALTC device 201 is axially lengthened.

FIG. 76A illustrates the system after deployment of the anchor 401. In some methods of use, the anchor 401 is deployed before axial lengthening of the ALTC device 201. The capture guide 204 is expanded and a portion of the ALTC device 201 is expanded. FIG. 76A illustrates the axial lengthen device or ALTC device 201 with an expandable anchor 401 positioned near the opening end of the ALTC device 201. In some embodiments, the expandable anchor 401 can be independently movable such that expandable anchor 401 can retract proximally or distally while the ALTC device 201 is stationary. In some embodiments, alternatively, the anchor 401 and the ALTC device 201 can move together as one unit. In some embodiments, the ALTC device 201 and the expandable anchor 401 are collapsed in the delivery configuration. In some embodiments, the ALTC device 201 and the expandable anchor 401 are expanded when deployed within the target vessel.

FIG. 76B illustrates the axial lengthening of the expanded portion of the ALTC device 201. In some methods of use, the ALTC device 201 is lengthening proximally to encapsulate the anchor 401. In some methods of use, the anchor 401 has captured an obstruction or clot. In some methods of use, the ALTC device 201 is lengthening proximally to encapsulate the obstruction or clot. In some methods of use, the ALTC device 201 is lengthening proximally to encapsulate only a portion of the anchor 401. The collapsed portion 208 of the ALTC device 201 is shortened as the ALTC device 201 is axially lengthened. In some methods of use, the ALTC device 201 is not lengthened proximally to encapsulate a portion of the anchor 401. In some methods of use, the ALTC device 201 and the anchor 401 remain in the position shown in FIG. 76A during clot removal.

FIG. 76C illustrates the axial lengthening of the expanded portion of the ALTC device 201. The ALTC device 201 is lengthening proximally to capture the clot secured by the anchor 401. In some methods of use, the ALTC device 201 is lengthening proximally to circumscribe the entire anchor 401. The collapsed portion 208 of the ALTC device 201 is shortened as the ALTC device 201 is lengthened. For instance, collapsed portion 208 has a smaller axial length in FIG. 76C than in FIG. 76B. FIG. 76C illustrates the axial lengthening ALTC device 201 is sufficient to completely capture the clot. In some methods of use, the ALTC device 201 and the anchor 401 can retract proximally to remove the clot. In some methods of use, the ALTC device 201 and the anchor 401 can retract proximally while the configuration shown in FIG. 76A. In some methods of use, the ALTC device 201 and the anchors 401 can retract proximally while the ALTC device 201 does not circumscribe the entire anchor 401.

In FIG. 76C, the deployed and expanded ALTC device 201 is longer, e.g., in length, than the deployed and expanded ALTC device 201 in FIG. 76B. The collapsed portion 208 resides inside the outer sheath 203 or dual lumen shaft 243 and is shorter in FIG. 76C than in FIG. 76B. The diameter or cross-section of the ALTC device 201 can remain constant or substantially constant during axially lengthening. The diameter or cross-section of the ALTC device 201 can in some cases remain constant between the initial deployed configuration shown in FIG. 76A and the expanded configurations shown in 76B and 76C. In some embodiments, two or more steps can occur simultaneously. In some methods of use, the anchor 401 is partially deployed and the ALTC device 201 is axially lengthened to cover the anchor 401 simultaneously.

FIGS. 77A-77C illustrate additional views of the system. The anchor 405, or any of the anchors described herein, can be deployed in a similar manner as anchor 401. In some embodiments, the ALTC device 201 is axially lengthened with the expandable anchor 401 positioned near the opening end of the ALTC device 201. In some embodiments, the ALTC device 201 is extended over the expandable anchor 401. In some embodiments, the ALTC device 201 is positioned distal to the obstruction, clot, emboli, and/or foreign body for distal protection. In some embodiments, the ALTC device 201 is positioned distally or downstream in the direction of blood flow. In some embodiments, the expandable anchor 401 is deployed within the obstruction. In some embodiments, the ALTC device 201 retracts proximally over the expandable anchor 401 and the obstruction. In some embodiments, the obstruction is removed. In some embodiments, the ALTC device 201 is positioned distal to the obstruction for distal protection. In some embodiments, the expandable anchor 401 deploys within the obstruction and retracts to remove the obstruction while the ALTC device 201 remains in position. In some embodiments, the ALTC device 201 retracts subsequently to remove emboli. In some embodiments, the expandable anchor 401 and the ALTC device 201 retract as one unit to remove the obstruction. In some embodiments, the ALTC device 201 is retracted over the expandable anchor and obstruction and the entire device is removed.

Figure 78:
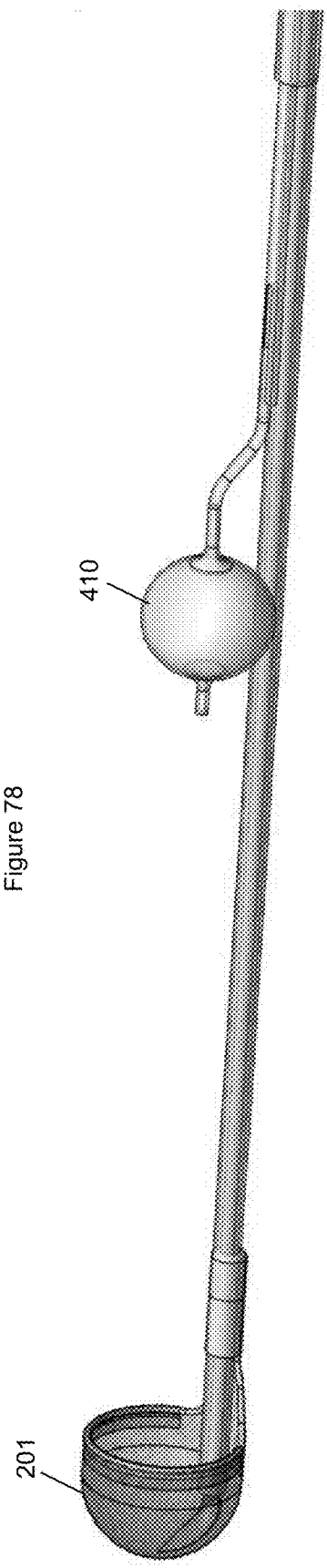
FIG. 78 illustrates a distal end of a capture device system including an embodiment of an anchor.
Figure 79:
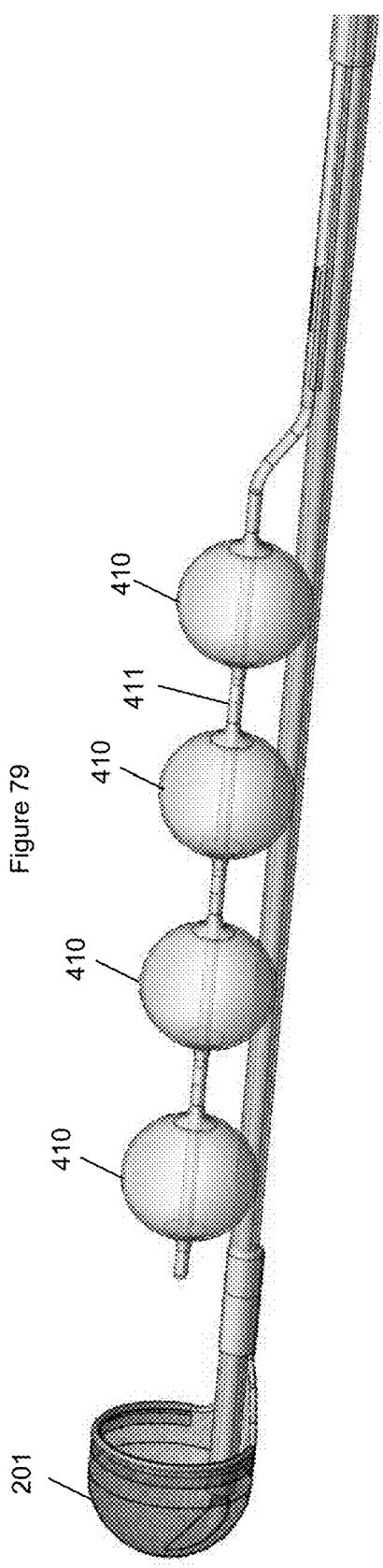
FIG. 79 illustrates a distal end of a capture device system including an embodiment of an anchor.

FIG. 78 illustrates another embodiment of an anchor 410. The anchor 410 can include any of the features of anchors described herein. In some embodiments, the anchor 410 can include a balloon. Balloon materials can be compliant, semi-compliant, or non-compliant. In some embodiments, the anchor 410 can comprise a spherical balloon. In some embodiments, the anchor 410 can comprise an oblong balloon. In some embodiments, the anchor 410 can include one or more shaped ends, including conical, square, spherical, tapered, etc. In some embodiments, the anchor 410 can includes a dog bone shaped with proximal and distal areas of increased diameter balloon or stepped balloon having two or more different diameters. In some embodiments, the anchor 410 can include an axially or radially offset balloon. In some embodiments, the anchor 410 can comprise any shape including a conical balloon, tapered balloon, stepped balloon, square balloon, polygonal balloon, etc. In some embodiment, the balloons can be in series or in parallel or circumferentially or radially. Additional balloon shapes are disclosed in U.S. patent application Ser. No. 11/851,848, filed Sep. 7, 2007 and published Jul. 23, 2013 as U.S. Pat. No. 8,491,623 ("Vogel"), which is incorporated by reference in its entirety. In some embodiments, the anchor 410 has a diameter. In some embodiments, the anchor 410 has two or more diameters. In some embodiments, the smaller diameter is more than 50% of the larger diameter, the smaller diameter is more than 60% of the larger diameter, the smaller diameter is more than 70% of the larger diameter, the smaller diameter is more than 80% of the larger diameter, the smaller diameter is more than 90% of the larger diameter, the smaller diameter is approximately equal to the larger diameter, etc. In some embodiments, two or more anchors 410 have the same shape. For instance, two or more anchors 410 can be spherical. In some embodiments, two or more anchors 410 can be identical. In some embodiments, two or more anchors 410 have a different shape. For instance, the first anchor 410 can be spherical and the second anchor 410 can be oblong. In some embodiments, two or more anchors 410 have a different diameter or cross-section. FIG. 78 illustrates the ALTC device 201 with a single balloon. In some embodiments, the balloon is independently movable relative to the ALTC device 201. In some embodiments, the balloon and ALTC device 201 can also retracted as one unit. FIG. 79 for example illustrates balloons 410 are positioned in series. In some embodiment, the balloons can position side-by-side, in parallel, circumferentially, and/or radially. Further in some embodiments, the balloons' shape and diameter can be configured so that there are gaps between the balloons to allow potential blood flow.

In some embodiments, the anchor 410 can be inflated. In some embodiments, an inflation medium such as gas or liquid is supplied to the anchor 410. In some embodiments, the anchor 410 can be inflated to form a rigid body. In some embodiments, the anchor 410 can be inflated to transmit a force to the obstruction, such as force to compress or move the obstruction. In some embodiments, the anchor 410 can be deflated. The inflation medium can be removed from the anchor 410. In some embodiments, the anchor 410 has a rough or textured outer surface. In some methods of use, the anchor 410 becomes entangled with the obstruction or clot described herein. In some embodiments, the anchor 410 has a smooth outer surface. In some embodiments, the anchor 410 can compress the obstruction or clot thereby opening the blood vessel. The anchor 410 can apply a compressive force on the obstruction during inflation of the anchor 410. In some embodiments, the anchor 410 can be self-deployed. In some embodiments, the anchor 410 can include a shape memory material to deploy the anchor 410.

FIG. 79 illustrates an embodiment including a plurality of anchors, such as a first anchor 410, a second anchor 410, a third anchor 410, and a fourth anchor 410. The system can include one or more of the anchors 410. In the illustrated embodiment, the system includes four anchors 410 but other configurations are contemplated (e.g., two anchors, three anchors, five anchors, six anchors, seven anchors, eight anchors, nine anchors, ten anchors, etc.). In some embodiments, two or more anchors 410 are inflated simultaneously. For instance, the anchors 410 can be coupled such that fluid can flow between the anchors 410. In some embodiments, two or more anchors 410 are inflated independently. For instance, each anchor can be separately supplied fluid for inflation, or include a common inflation lumen. In some embodiments, two or more anchors 410 are inflated in series. In some embodiments, two or more anchors 410 are inflated in parallel. In some embodiments, two or more anchors 410 are deflated simultaneously. In some embodiments, two or more anchors 410 are deflated independently. In some embodiments, two or more anchors 410 are deflated in series. In some embodiments, two or more anchors 410 are deflated in parallel. The two or more anchors 410 can be coupled via an inflation lumen 411. The inflation lumen 411 can allow delivery of the fluid to inflate the anchors.

FIG. 79 illustrates the ALTC device 201 with a series of balloons positioned near the opening end of the ALTC device 201. In some embodiments, the balloons are independently movable relative to the ALTC device 201. In some embodiments, the balloons and the ALTC device 201 can also retracted as one unit. In some embodiments, the balloons function as anchors as described herein to entangle the clot. In some embodiments, the balloons function to compress the clot to open the target vessel. Other functions for the balloons are contemplated. In some embodiments, the balloons have a uniform size and shape, but can be positioned adjacent each other in order of increasing or decreasing diameter, or have different shapes in some embodiments.

Figure 80:
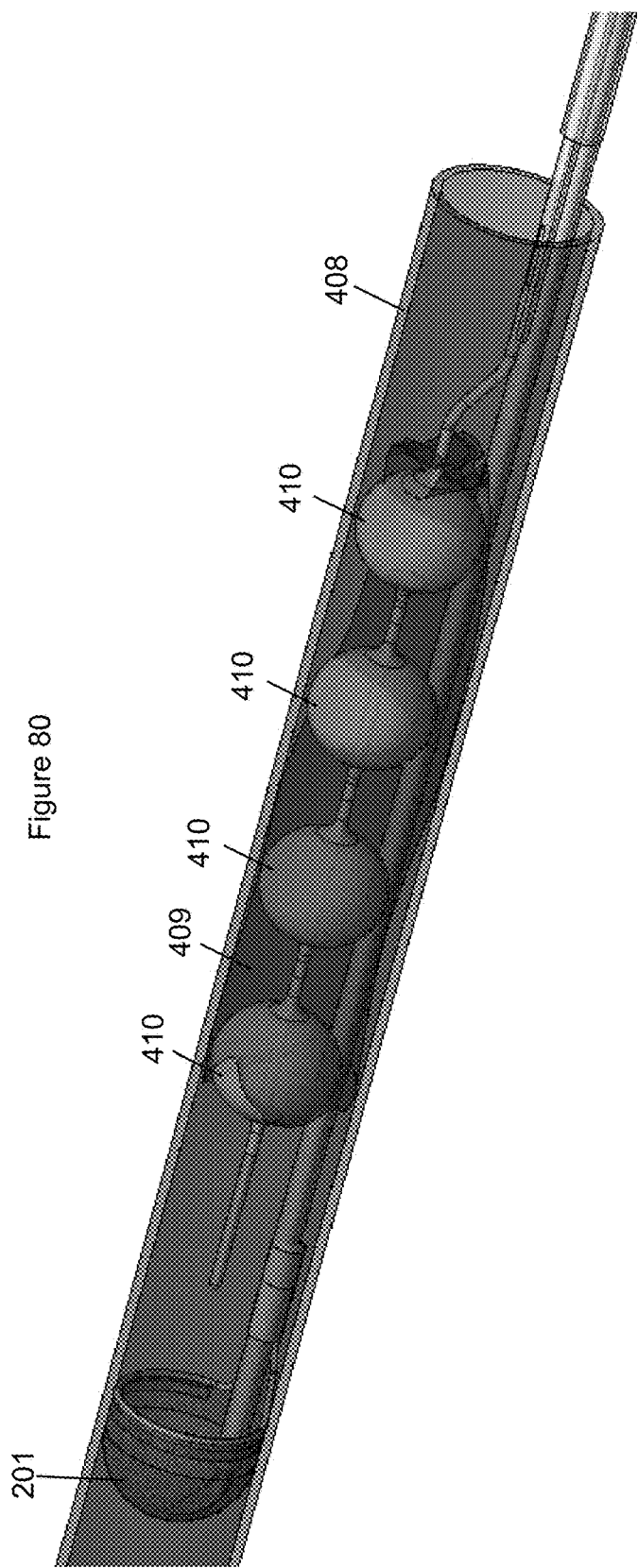
FIG. 80 illustrates the capture device system in a vessel of FIG. 79.

FIG. 80 illustrates the system within the vessel 408 with the obstruction 408 after deployment of the anchors 410. In some methods of use, the anchors 410 are inflated before axial lengthening of the ALTC device 201. In some methods of use, one or more steps of deploying or inflating anchors 410 and axially lengthening can occur in any order. In some methods of use, the anchors 410 are inflated and then the ALTC device 201 is axially lengthened to cover the anchors 410. In some methods of use, two or more anchors 410 can be inflated before the ALTC device 201 is axially lengthened. In some methods of use, the anchors 410 are fixed such that the anchors 410 need not be inflated. In some methods of use, one or more anchors 410 are deflated before the ALTC device 201 is axially lengthened. In some methods of use, one or more anchors 410 are inflated after the ALTC device 201 is axially lengthened. In some methods of use, the anchors 410 are inflated and the ALTC device 201 is axially lengthened simultaneously. In some methods of use, the anchors 410 are inflated and the ALTC device 201 is axially lengthened independently. In some methods of use, the anchors 410 are only inflated if covered by the ALTC device 201.

FIG. 80 illustrates the ALTC device 201 positioned distal to the obstruction. FIG. 80 illustrates the balloons expanding within the obstruction. In some embodiments, one or more anchors 410 are positioned distally to the obstruction before inflation. After inflation, the one or more distal anchors 410 can push the obstruction proximally. In some embodiments, one or more anchors 410 are positioned proximally to the obstruction before inflation. After inflation, the one or more distal anchors 410 can push the obstruction distally toward the ALTC device 201.

In some methods of use, the ALTC device 201 is positioned distally to the anchors 410. In some methods of use, the ALTC device 201 provides distal protection during clot removal, akin to a filter in some cases. In some methods of use, the anchors 410 inflate within the obstruction. In some methods of use, the anchors 410 are positioned to entangle the obstruction. In some methods of use, the anchors 410 move after deployment. In some methods of use, the anchors 410 move simultaneously. In some methods of use, the anchors 410 move independently, or all in concert in some cases. In some methods of use, the anchors 410 move distally therefore moving the obstruction distally. In some methods of use, the anchors 410 move toward the ALTC device 201. After deployment of the anchors 410, the obstruction and the anchors 410 can move together as a unit. In some methods of use, the anchors 410 move after axially lengthening of the ALTC device 201. In some methods of use, the anchors 410 move before axially lengthening of the ALTC device 201.

FIG. 81 illustrates an embodiment of an anchor 415. The anchor 415 can include any of the features of anchors described herein. In some embodiments, the anchor 415 can comprise a disk. In some embodiments, the anchor 415 can be arcuate shaped such as round or circular, or ovoid. In some embodiments, the anchor 415 can have a constant or variable diameter. In some embodiments, the anchor 415 can be any shape, including a polygon, elliptical, etc. In some embodiments, the anchor 415 can be entirely flat or have flat surfaces. In some embodiments, the anchor 415 can be concave, convex, or another curved shaped. For instance, a first surface 416 of the anchor 415 can be concave and a second surface 417, opposite the first surface can be concave. For instance, a first surface 416 of the anchor 415 can be convex and a second surface 417, opposite the first surface can be convex. In some embodiments, the anchor 415 can have a smooth outer surface. In some embodiments, the anchor 415 can include a roughened or porous outer surface. The anchor can conform when contacting a surface such as a vessel wall.

In some embodiments, the anchor 415 can be deployed similar to anchor 241. In some embodiments, the anchor 415 can self-deploy. In some embodiments, the anchor 415 can include a shape memory material to deploy the anchor 415. In some embodiments, the anchor 415 can be inflated. In some embodiments, an inflation medium such as gas or liquid is supplied to the anchor 415. In some embodiments, the anchor 415 can be deflated. FIG. 81 illustrates the ALTC device 201 with a single disk positioned proximal to the ALTC device 201. In some embodiments, the expandable disk is independently movable relative to the ALTC device 201. In some embodiments, the expandable disk and ALTC device 201 can also be retracted as one unit. In some embodiment, the anchor 415 is adjacent, side-by-side or offset to the ALTC device 201. In some embodiment, the anchor 415 is coaxial or in-line to the ALTC device.

FIG. 82 illustrates an embodiment including a first anchor 415, a second anchor 415, a third anchor 415, a fourth anchor 415, a fifth anchor 415, and a sixth anchor 415. The system can include one, two, or more of the anchors 415. In the illustrated embodiment, the system includes six anchors 415 but other configurations are contemplated (e.g., about, at least about, or no more than about two anchors, three anchors, four anchors, five anchors, seven anchors, eight anchors, nine anchors, ten anchors, etc.). In some embodiments, the anchor 415 comprises a helix or helical structure. For instance, the first anchor 415 can be joined with the second anchor 415 to form a helix. A helical anchor is disclosed, for example, in FIG. 6A of PCT/IB2014/066389, filed Nov. 27, 2014 and published Jun. 4, 2015 as WO 2015/079401 ("Yachia"), which is incorporated by reference in its entirety.

In some embodiments, two or more anchors 415 are deployed simultaneously. In some embodiments, two or more anchors 415 are deployed independently. For instance, the first anchor 415 and the second anchor 415 can be deployed independently. In some embodiments, two or more anchors 415 are deployed in series. For instance, the first anchor 415 can be deployed before the second anchor 415. In some embodiments, two or more anchors 415 are deployed in parallel. FIG. 82 illustrates the ALTC device 201 with a series of expandable disks positioned proximal to the ALTC device 201. In some embodiments, the expandable disks are independently movable relative to the ALTC device 201. In some embodiments, the expandable disks and ALTC device 201 can also be retracted as one unit.

Figure 83:
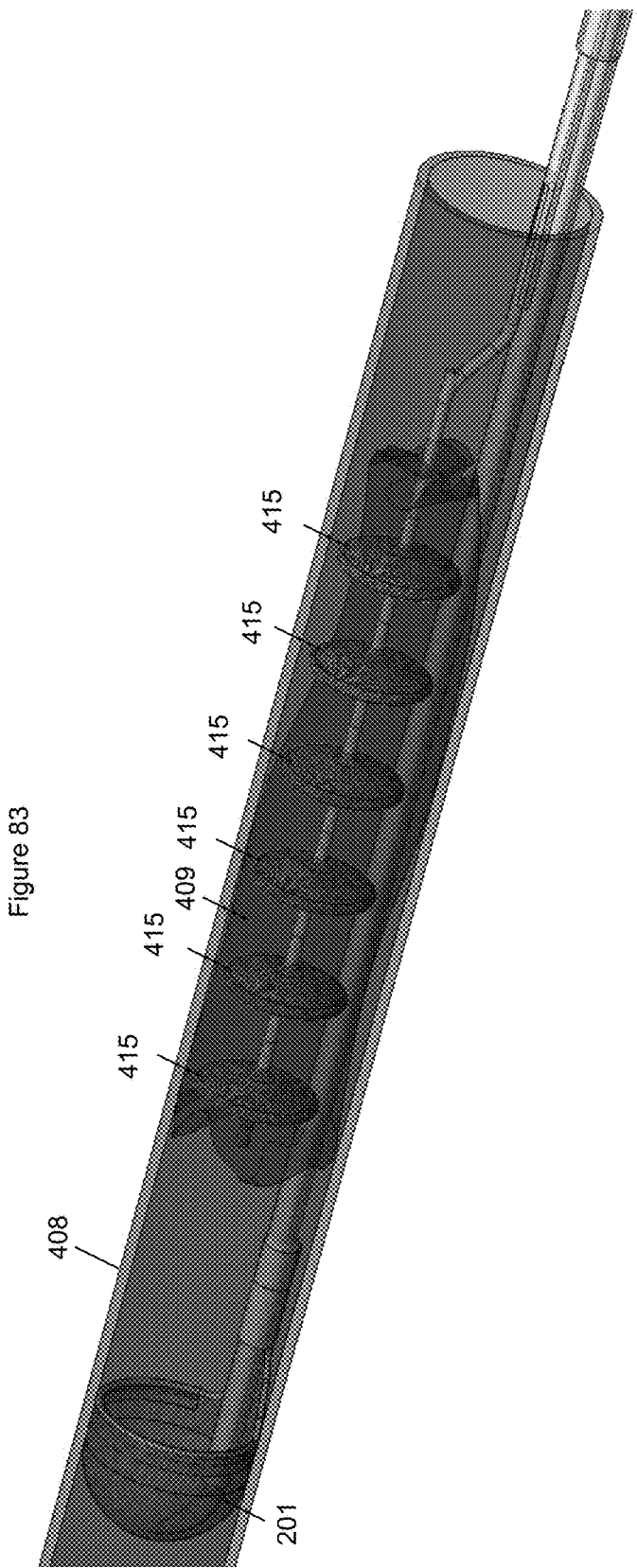
FIG. 83 illustrates the capture device system in a vessel of FIG. 82.

FIG. 83 illustrates the system within the vessel 408 with the obstruction 409. In some methods of use, one or more steps of deploying or inflating anchors 415 and axially lengthening can occur in any order. In some methods of use, the anchors 415 are deployed before axial lengthening of the ALTC device 201. In some methods of use, one or more anchors 415 are deployed before the ALTC device 201 is axially lengthened to cover the anchors 410. In some methods of use, one or more anchors 415 are deployed after the ALTC device 201 is axially lengthened. In some methods of use, the anchors 415 are deployed and the ALTC device 201 is axially lengthened simultaneously. In some methods of use, the anchors 415 are only deployed if covered by the ALTC device 201. FIG. 83 illustrates the ALTC device 201 positioned distal to the obstruction and the expandable disks deployed within the obstruction. The single disk embodiment shown in FIG. 81 can be deployed within the obstruction in a similar manner. In some methods of use, the ALTC device 201 is positioned distally to the anchors 415. In some methods of use, the ALTC device 201 provides distal protection during clot removal. In some methods of use, the anchors 415 deploy within the obstruction or clot. In some methods of use, the anchors 415 move after deployment.

Figure 84:
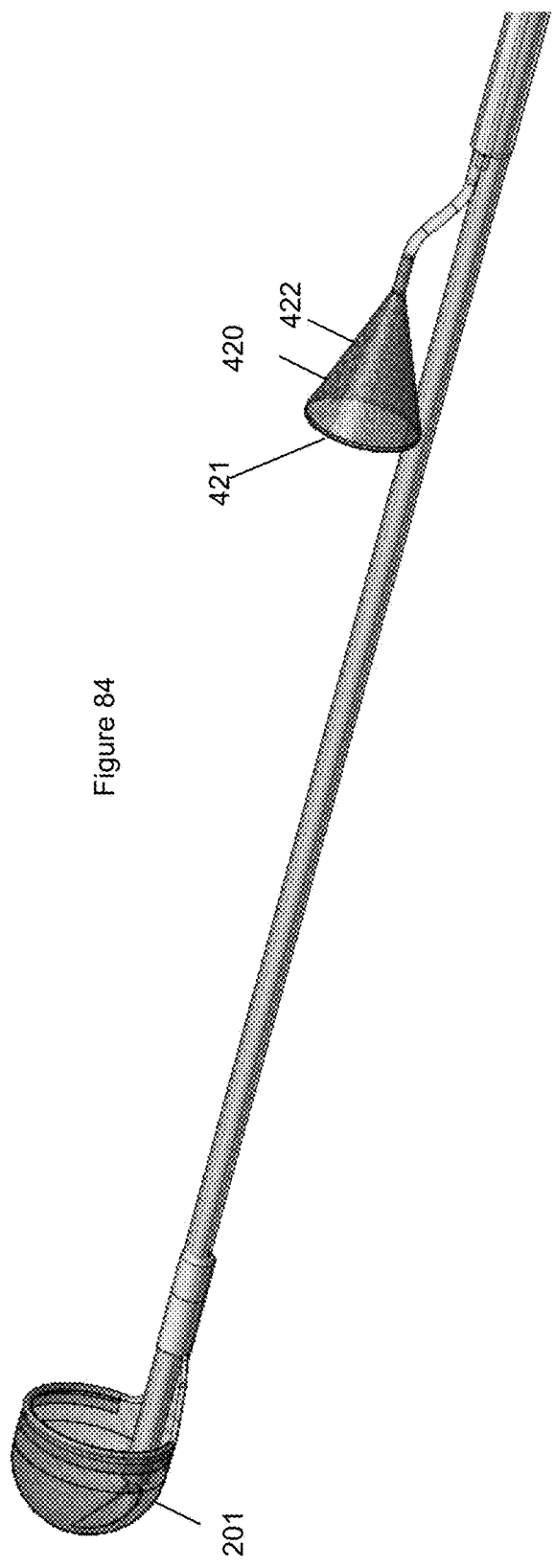
FIG. 84 illustrates a distal end of a capture device system including an embodiment of an anchor.

FIG. 84 illustrates an embodiment of an anchor 420. The anchor 420 can include any of the features of anchors described herein. In some embodiments, the anchor 420 can comprise a funnel. In some embodiments, the anchor 420 can include a round or circular opening. In some embodiments, the anchor 420 can taper from a larger diameter or cross-section to a smaller diameter or cross-section. In some embodiments, the anchor 420 can taper along the length of the anchor 420. In some embodiments, the anchor 420 can be any generally conical shape. In some embodiments, the anchor 420 can include an inflection point. In some embodiments, the anchor 420 can include a radially outward flare. In some embodiments, the anchor 420, or a surface thereof, is concave. In some embodiments, the anchor 420, or a surface thereof, is convex. In some embodiments, the anchor 420 can have a smooth outer surface. In some embodiments, the anchor 420 can include a roughened or porous outer surface. In some embodiment, the anchor 420 is adjacent, side-by-side or offset to the ALTC device 201. In some embodiment, the anchor 420 is coaxial or in-line to the ALTC device.

In some embodiments, the anchor 420 is formed as a mesh or braid, laser cut or stent structure. The funnel shape of the anchor 420 can in some cases assist in retrieving and containing the obstruction or clot. In some embodiments, the anchor 420 comprises structural features to assist in the deployment of the funnel shape, such as to hold the rim 421 of the funnel shape open. In some embodiments, the anchor 420 can include struts comprising a shape memory or self-expanding material such as nitinol, or other stent structure, mesh, and/or webbing. In some embodiments, the anchor 420 can be deployed similar to anchor 241. In some embodiments, the anchor 420 can be self-deployed. In some embodiments, the anchor 420 can include a shape memory material to deploy the anchor 420. The anchor 420 can include a rim 421. The rim 421 can include any of the features of the capture guides described herein.

In some embodiments, the proximal end opening of the anchor 420 includes the rim 421 that takes the form of, in some embodiments, a radially expandable shape memory partial or full ring-like annular structure. The rim 421 expands once freed or released from a constraining member such as any sheath or tube described herein. In some embodiments, the rim 421 is coupled with a portion of a mesh, interlaced structure, or covering 422. In some other embodiments, the rim 421 and the proximal end of the covering 422 can be sutured in place using silk or polymeric filaments such as Ultra-High Molecular Weight polyethylene, Nylon, PET, PTFE. In some embodiments, the covering 422 comprises with a low durometer polymeric material.

The rim 421 and/or the covering 422 can be formed, for example, from metallic, shape memory, or other appropriate materials. In some embodiment, the rim 421 can include a loop configuration and be formed from nitinol shape memory wire of various geometries such as round, oval, elliptical, flat, and the like. The rim 421 can be formed of different shapes such as a circular loop, oval loop, z-shape, etc. In some embodiment, the rim 421 can be shaped set either into coils, multiple full circles, full circle or partial circles where the ends of the wire formed into two legs. The partial circle can be from, for example, 180 degrees to 359 degrees or 220 degrees to 359 degrees. The legs can be configured to be off-axis to the loop such that it can be right angle, acute or obtuse angle relative to the loop. It can be arcuate and form a partial or full ring as illustrated, and can circumscribe or otherwise form an outer diameter, and define the proximal-most end of the anchor 420. The anchor 420 can in some embodiments include a single loop or multiple loops positioned along the length of the covering 422. The anchor 420 can be configured to be compressed and positioned within a lumen of a shaft during introduction into the vascular system where the anchor 420 is configured to be positioned coaxially within the obstruction or clot. In some methods of use, the anchor 420 is configured to be deployed to entangle with the obstruction or clot.

FIG. 84 illustrates the ALTC device 201 with an expandable funnel like anchor. In some embodiments, the funnel shaped anchor is positioned proximal to the ALTC device 201. In some embodiments, the funnel shaped anchor is independently movable relative to the ALTC device 201. In some embodiments, alternatively, the anchor and ALTC device 201 can move as one unit.

Figure 85:
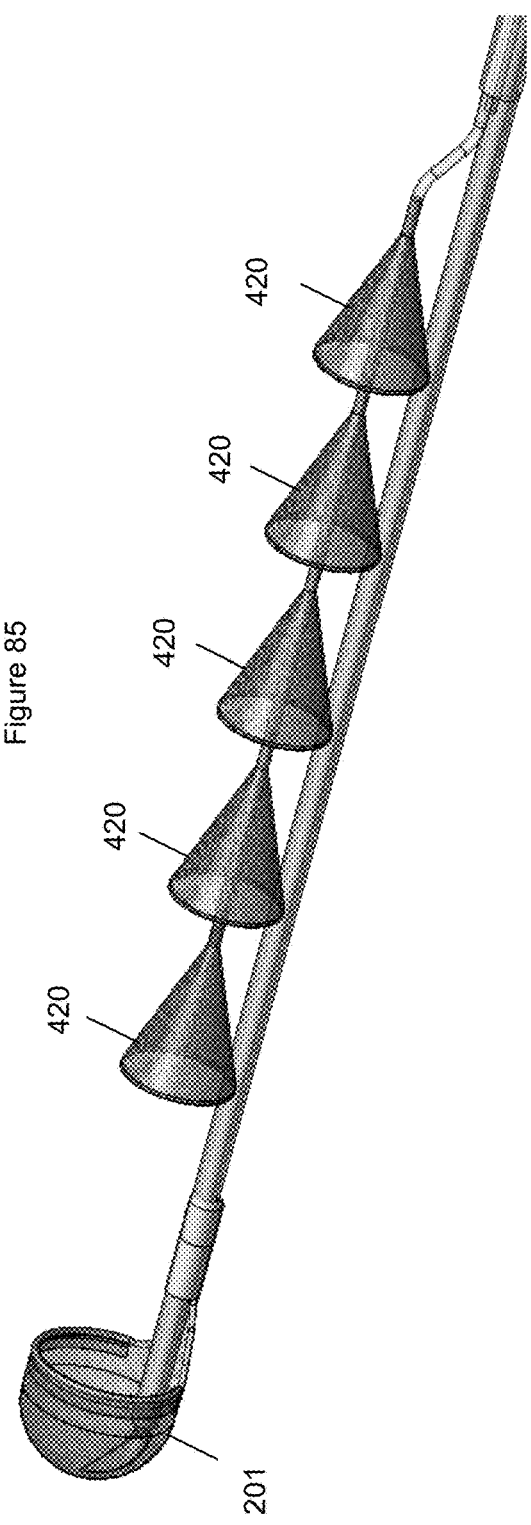
FIG. 85 illustrates a distal end of a capture device system including an embodiment of an anchor.

FIG. 85 illustrates an embodiment including a plurality of anchors, such as a first anchor 420, a second anchor 420, a third anchor 420, a fourth anchor 420, and a fifth anchor 420. The system can include one or more of the anchors 420. In the illustrated embodiment, the system includes five anchors 420 but other configurations are contemplated (e.g., two anchors, three anchors, four anchors, six anchors, seven anchors, eight anchors, nine anchors, ten anchors, etc.). In some embodiments, two or more anchors 420 are deployed simultaneously. In some embodiments, two or more anchors 420 are deployed independently. For instance, the first anchor 420 and the second anchor 420 can be deployed independently. In some embodiments, two or more anchors 420 are deployed in series. For instance, the first anchor 420 can be deployed before the second anchor 420. In some embodiments, two or more anchors 420 are deployed in parallel. FIG. 85 illustrates the ALTC device 201 with expandable funnel like anchors. In some embodiments, the funnel shaped anchors are positioned proximal to the ALTC device 201. In some embodiments, the funnel shaped anchors are independently movable relative to the ALTC device 201. In some embodiments, alternatively, the anchors and ALTC device 201 can move as one unit.

FIG. 86 illustrates the system within the blood vessel 408 and the obstruction 409. In some methods of use, one or more steps of deploying one or more anchors 420 and axially lengthening can occur in any order. In some methods of use, one or more anchors 420 are deployed before axial lengthening of the ALTC device 201. In some methods of use, the anchors 420 are deployed before the ALTC device 201 is axially lengthened to cover the anchors 420. In some methods of use, one or more anchors 420 are deployed after the ALTC device 201 is axially lengthened. In some methods of use, the anchors 420 are deployed and the ALTC device 201 is axially lengthened simultaneously. In some methods of use, the anchors 420 are deployed and the ALTC device 201 is axially lengthened independently. In some methods of use, the anchors 420 are only deployed if covered by the ALTC device 201. In some methods of use, the ALTC device 201 is positioned distally to the anchors 420. In some methods of use, the ALTC device 201 provides distal protection during clot removal. In some methods of use, the anchors 420 deploy within the obstruction or clot. In some methods of use, the anchors 420 move after deployment.

FIG. 86 illustrates an embodiment in which the anchors 420 face forward. The anchors 420 can taper inward from a distal end 423 to a proximal end 424. The rim 421 of each anchor 420 can be located at the distal end 423 of each anchor 420. FIG. 87 illustrates a system with anchors 420 deployed within a vessel 408 comprising an obstruction 409. FIG. 87 illustrates an embodiment in which the anchors 420 face backward. The anchors 420 can taper inward from the proximal end 424 to a distal end 423. The rim 421 of each anchor 420 can be located at the proximal end 424 of each anchor 420. In some embodiments, the anchors 420 have a single configuration, e.g., all anchors 420 face forward as shown in FIG. 86, all anchors 420 face backward as shown in FIG. 87. In some embodiments, two or more anchors 420 have a different configuration, e.g., the first anchor 420 faces forward and the second anchor 420 faces backward. In some embodiments, the anchor 420 can switch between facing forward and facing backward. In some embodiments, the anchors 420 can be configured to roll out, invert, evert, and/or variably lengthen proximally or distally between facing forward and facing backward. In some embodiments, one or more anchors 420 can be configured to switch between facing forward and facing backward. In some embodiments, one or more anchors 420 can be fixed as either facing forward or facing backward. FIGS. 86 and 87 illustrate the ALTC device 201 positioned distal to the obstruction. FIGS. 86 and 87 illustrate the expandable funnel shape anchors deployed within the obstruction.

The anchors described herein can have any shape. Other expandable shapes and/or geometric anchors are contemplated. In some embodiments, the anchor can be shaped as a coil. In some embodiments, the anchor can be shaped as a loop. In some embodiments, the anchor can be shaped as a clover. In some embodiments, one or more anchors are offset to the ALTC device 201. In some embodiments, the anchor can be coaxial to the ALTC device 201 wherein the anchors can be attached to the shaft of the ALTC device 201. In some embodiments, this configuration allows the anchor and the axial lengthen device move as one unit.

U.S. patent application Ser. No. 14/602,014, filed Jan. 21, 2015 and published Aug. 9, 2016 as U.S. Pat. No. 9,408,620 ("Rosenbluth"); U.S. patent application Ser. No. 08/723,619, filed Oct. 20, 1996 and published Apr. 20, 1999 as U.S. Pat. No. 5,895,398 ("Wensel"); U.S. patent application Ser. No. 08/968,146, filed Nov. 12, 1997 and published Sep. 7, 1999 as U.S. Pat. No. 5,947,985 ("Imran"); U.S. patent application Ser. No. 09/756,476, filed Jan. 8, 2001 and published Dec. 16, 2003 as U.S. Pat. No. 6,663,650 ("Sepetka"); U.S. patent application Ser. No. 09/789,332, filed Feb. 20, 2001 and published Jan. 11, 2005 as U.S. Pat. No. 6,840,950 ("Sanford"); U.S. patent application Ser. No. 12/581,960, filed Oct. 20, 2009 and published Jan. 10, 2012 as U.S. Pat. No. 8,092,486 ("Berrada"); U.S. patent application Ser. No. 11/580,546, filed Oct. 13, 2006 and published Aug. 28, 2012 as U.S. Pat. No. 8,252,017 ("Paul"); U.S. patent application Ser. No. 12/564,892, filed Sep. 22, 2009 and published Oct. 30, 2012 as U.S. Pat. No. 8,298,252 ("Krolik") are all incorporated by reference herein in their entireties.

Figure 88A:
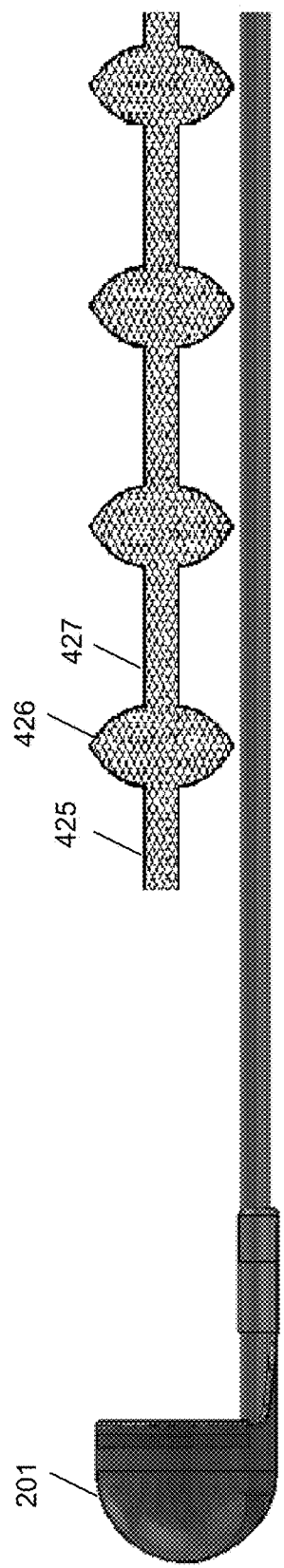
FIGS. 88A-88R illustrate embodiments of an anchor.
Figure 88B:
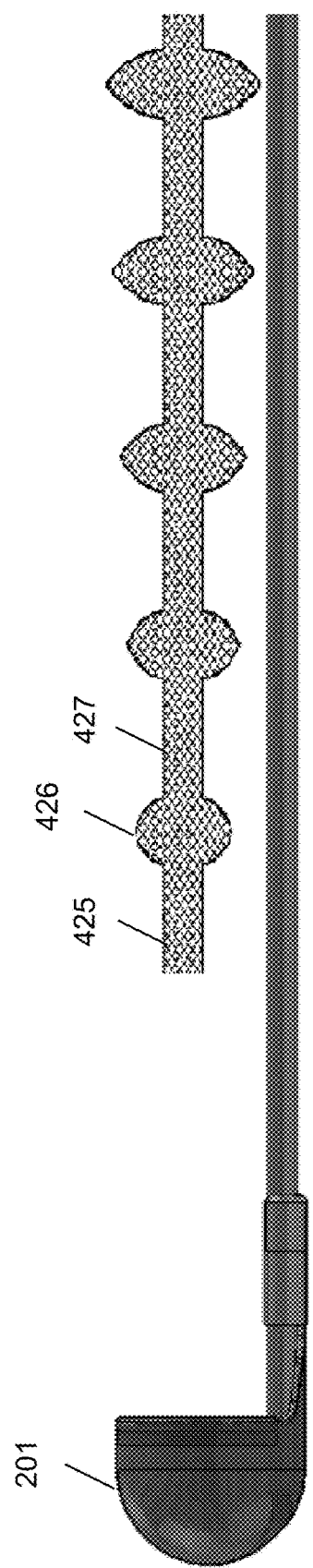
Figure 88C:
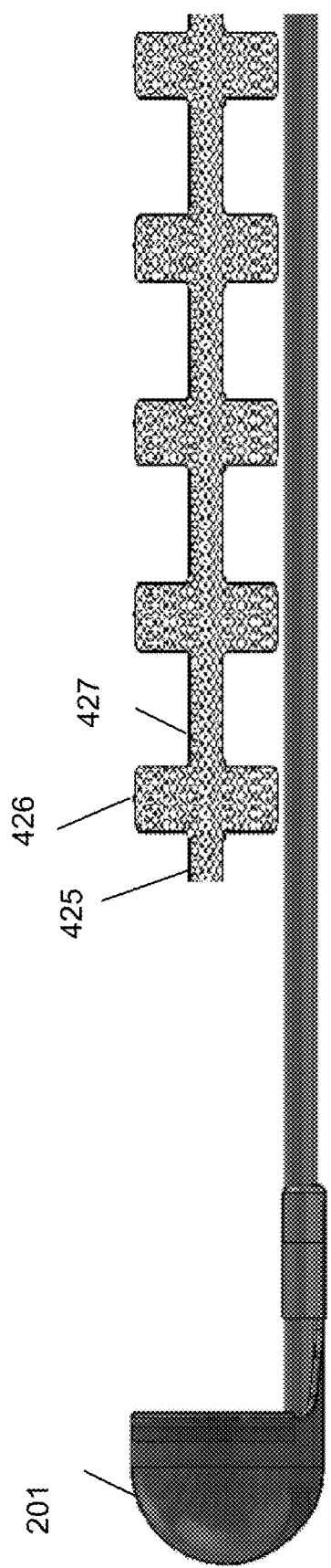
Figure 88D:
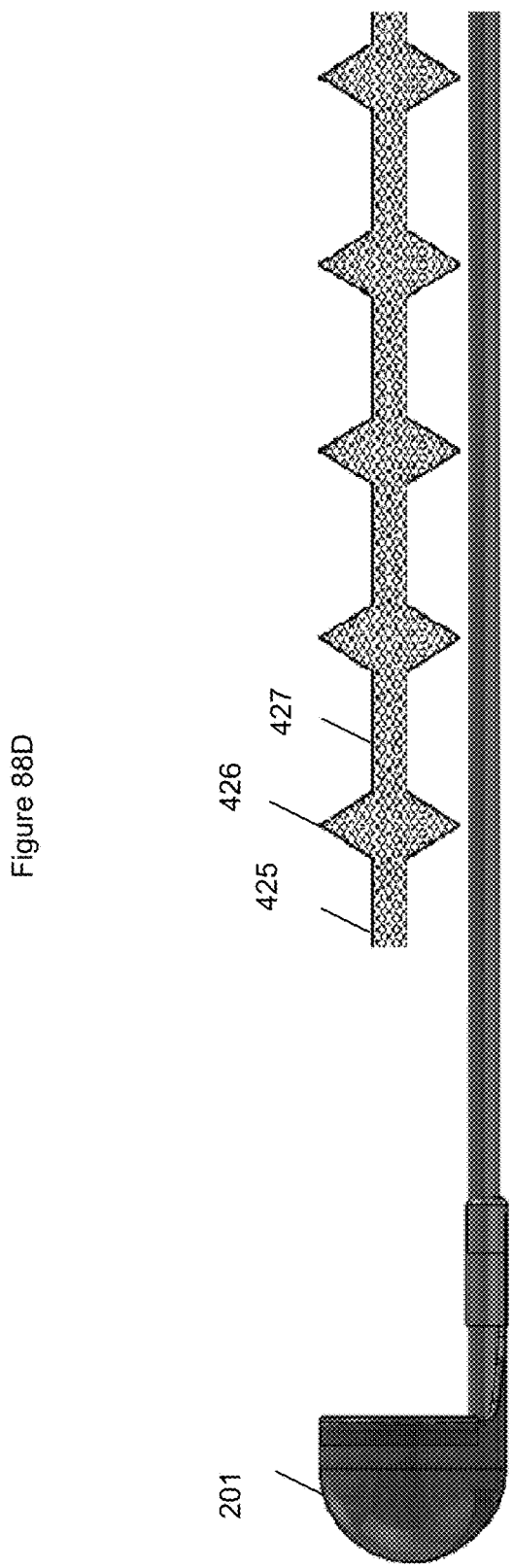
Figure 88F:
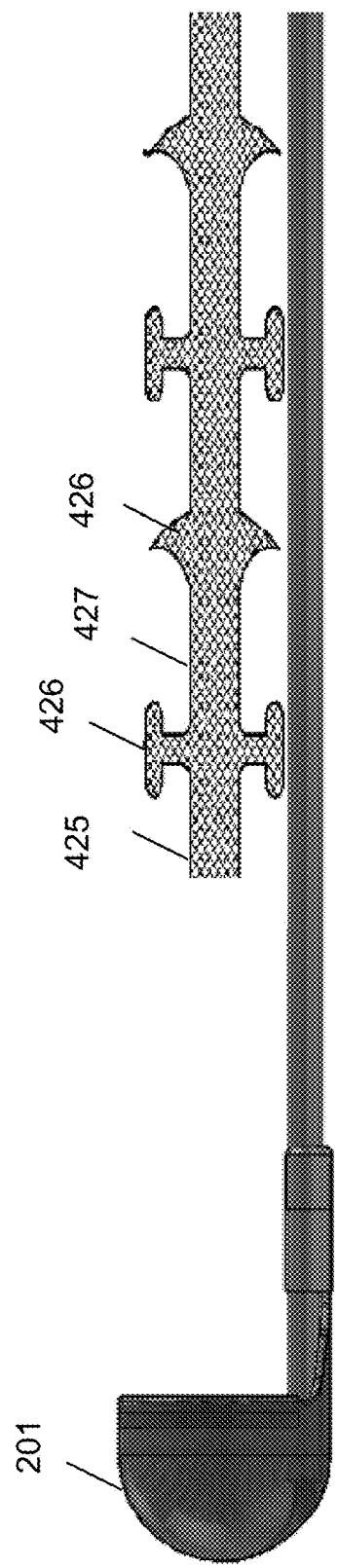
Figure 88G:
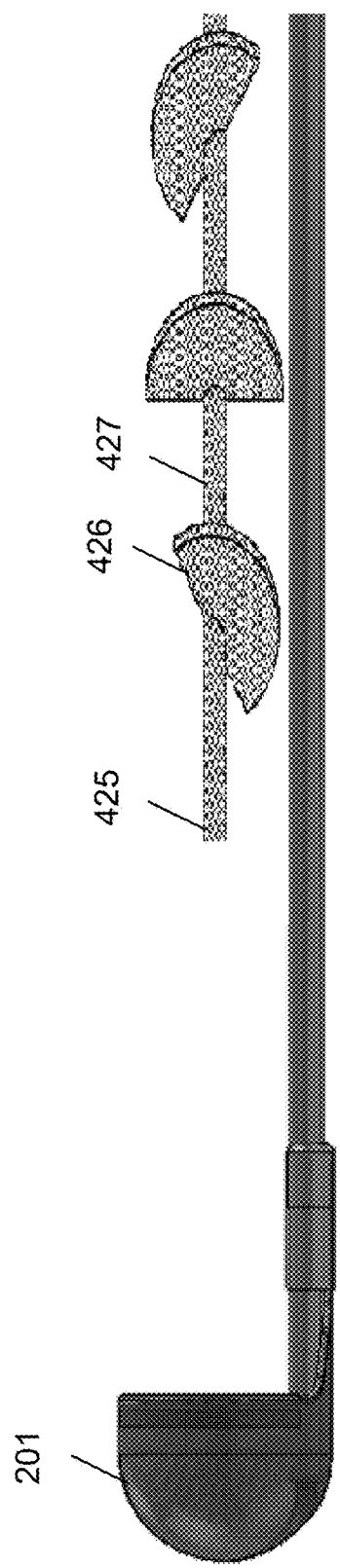
Figure 88H:
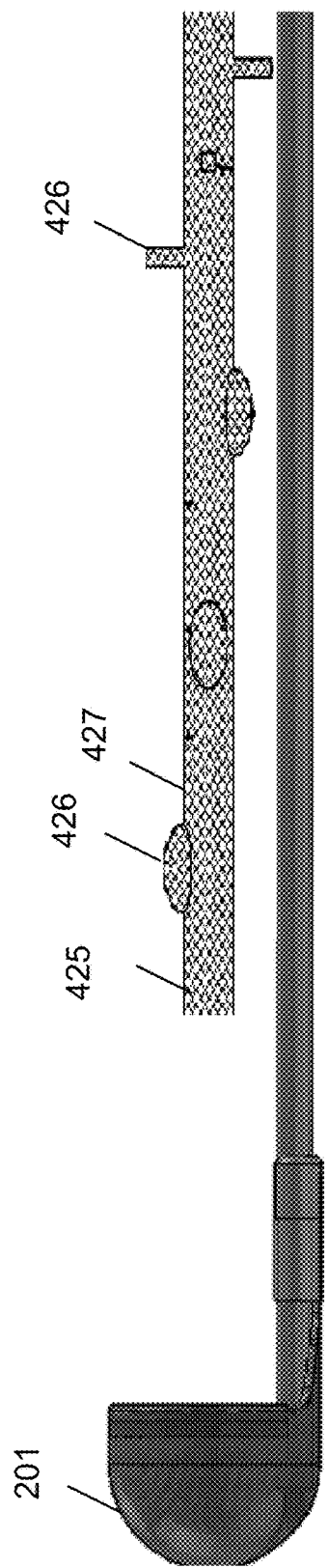

In some embodiments, the clot treatment device described by Rosenbluth et al. can be used in place of, or in combination with, the anchors described herein. Referring now to FIGS. 88A-88H, embodiments of an anchor 425 are disclosed. Referring to FIG. 88A, the radially extending portions 426 between the generally cylindrical sections 427 of the anchor 425 are defined by a cylindrical disk shape with a rounded triangular cross-section. Referring to FIG. 88B, the radially extending portions 426 between the generally cylindrical sections 427 of the anchor 425 are defined by a cylindrical disk shape with a rounded triangular cross-section wherein the diameter of the disk increases along the length of the anchor 425 thus forming a conical exterior extent. Referring to FIG. 88C, the radially extending portions 426 between the generally cylindrical sections 427 of the anchor 425 are defined by a cylindrical disk shape with a rectangular cross-section. Referring to FIG. 88D, the radially extending portions 426 between the generally cylindrical sections 427 of the anchor 425 are defined by a cylindrical disk shape with a linear (non-rounded) triangular cross-section. Referring to FIG. 88E, some of the radially extending portions 426 between the generally cylindrical sections 427 of the anchor 425 are defined by a cylindrical disk shape with a rounded cross-section and others have a rectangular cross section. Referring to FIG. 88F, the radially extending portions 426 between the generally cylindrical sections 427 of the anchor 425 alternate between cylindrical disk shape with a T-shaped cross-section and a flare-shaped cross-section. Referring to FIG. 88G, the radially extending portions 426 between the generally cylindrical sections 427 of the anchor 425 are defined by a partial cylindrical disk shapes. Referring to FIG. 88H, the radially extending portions 426 between the generally cylindrical sections 427 of the anchor 425 are defined by tabs and bumps or protuberances arising from the cylindrical surface of the anchor 425. In some embodiments, the anchors described herein provide greater surface area along the anchor than an anchor that is uniformly cylindrical. In some methods of use, the increased surface area facilitates the treatment and/or retrieval of the obstruction or clot.

In some embodiments, the anchor 425 can have a generally cylindrical shape that, during use, provides a flow lumen for blood across a clot. The anchor 425 is not, however, limited to a generally cylindrical shape. For example, the shape can be generally conical, generally concave or generally convex along its axis, so long as such shapes provide the aforesaid lumen for blood flow. In some embodiments, the anchor 425 also has a series of radially extending portions 426 which are separated by generally cylindrical portions 427. In some embodiments, the clot treatment device 425 can be porous so as to allow the flow of blood therethrough. In some embodiments, the anchor 425 is made from a mesh or braided material. The material can be a superelastic material such as nitinol or an alternative material such as cobalt chrome alloy. In some embodiments, the anchor 425 can be made from a wire lattice, wire braid or stent. In some embodiments, the anchor 425 can be self expanding.

In some embodiments, the anchor radially expands into the clot. In some methods of use, at least a portion of the anchor expands distal of the clot. As shown in some figures herein, at least one of the anchors of a plurality of anchors can be located distal to the clot upon expansion of the anchors. In some methods of use, upon expansion of the anchor, blood flowthrough the clot is restored. More specifically, the blood is now free to move through the mesh of the anchor and exit the anchor distal to the clot. As a result, the acute condition of blockage is corrected thus immediately improving the circulation of oxygenated blood in the patient. The expansion, inflation, or deployment of the anchors described herein can impinge or cut into the clot material. This entanglement can enhance the subsequent removal of the clot since portions of the clot collect between the radially extending portions 426; through the pores of the mesh forming the radially extending portions 426; along the longitudinal cylindrical sections 427 between the radially extending portions 426 of the anchor 425; and/or within the anchor 425 itself.

In some methods of use, the deployment of the anchor 425 results in an outwardly expanding generally cylindrical force being urged against an inner surface of the clot. In some methods of use, this force pushes the clot material outwardly and creates a lumen through which blood flow is restored. In some methods of use, the outwardly expanding generally cylindrical force can vary in magnitude along the axis of the anchor, due in part to the shape of the anchor. In some embodiments, the deployment of the anchor changes the angular orientation of the anchor with respect to the axis of the system. In some methods of use, this angular change or twisting can improve or enhances adherence of clot material to the anchor 425.

The clot treatment devices disclosed in Rosenbluth may be included in a system with the ALTC device 201 described herein. The ALTC device 201 can surround the clot treatment devices similar to the anchors described herein. After the clot treatment device has been expanded, the ALTC device 201 can be axially lengthened to capture the clot. In one embodiment, the clot treatment device and the ALTC device 201 are pulled back simultaneously in a proximal direction. This is followed by the entire system being withdrawn.

Figure 88I:
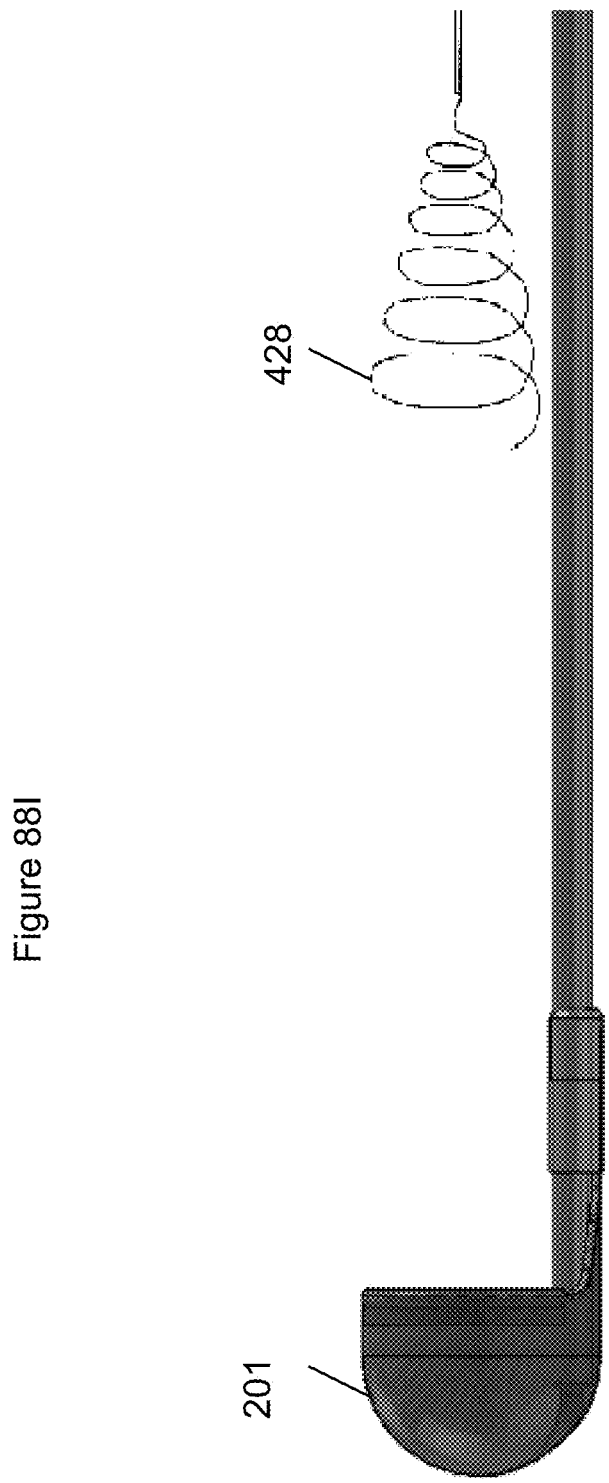
Figure 88J:
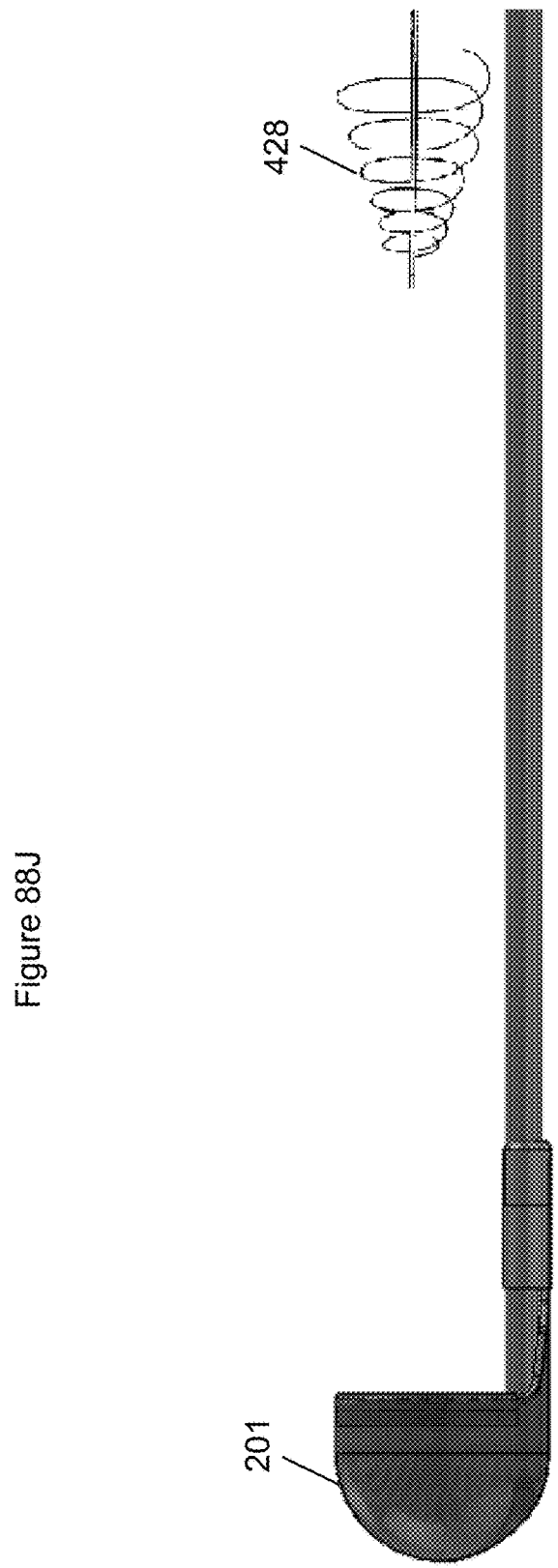

The clot and foreign body removal device of Wensel can be used in place of, or in combination with, the anchors described herein. Referring now to FIGS. 88I-88J, embodiments of the anchor 428 are disclosed. The anchor 428 can be a clot capture coil. In some embodiments, the coil is made from a flexible solid elastic or superelastic material which has shape memory, e.g., it can deform to a straight position and then return to a resting coil configuration. In some embodiments, the coil is made out of a solid nitinol wire with a diameter of, e.g., about 0.0005 inches to about 0.038 inches. Nitinol is preferred in some cases because of its superelasticity and its shape memory. However, other solid materials that are also elastic or superelastic and have shape memory could also be used such as some synthetic plastics, metallic alloys, and the like. The diameter of the coils can vary depending on the size of the vessel occluded. The diameter can range from about 1 mm for small vessels to about 30 mm for large vessels such as the pulmonary arteries or inferior vena cava. The length of the coil can also vary but typically ranges from about 3 to about 300 mm in the proximal to distal direction. Because the nitinol coil is superelastic, the coil can be extended to a completely straight configuration with the use of minimal force and then reform to its natural resting configuration when the force is removed. In some embodiments, the coil is made out of a solid biphasic material which changes shape upon heating or the passage of electric current. In some embodiments, the coil is cone-shaped.

In some embodiments, the anchors described herein can comprise a shape memory body. The anchor can comprise a single wire or multiple wires. The anchor can comprise one or more loops. The anchor can comprise one or more helices. In some embodiments, the loops and/or helices can have an increasing diameter from proximal to distal end of the anchor. In some embodiments, the loops and/or helices can have a decreasing diameter from proximal to distal end of the anchor. In some embodiments, the loops and/or helices can have a variable diameter from proximal to distal end of the anchor.

Figure 88K:
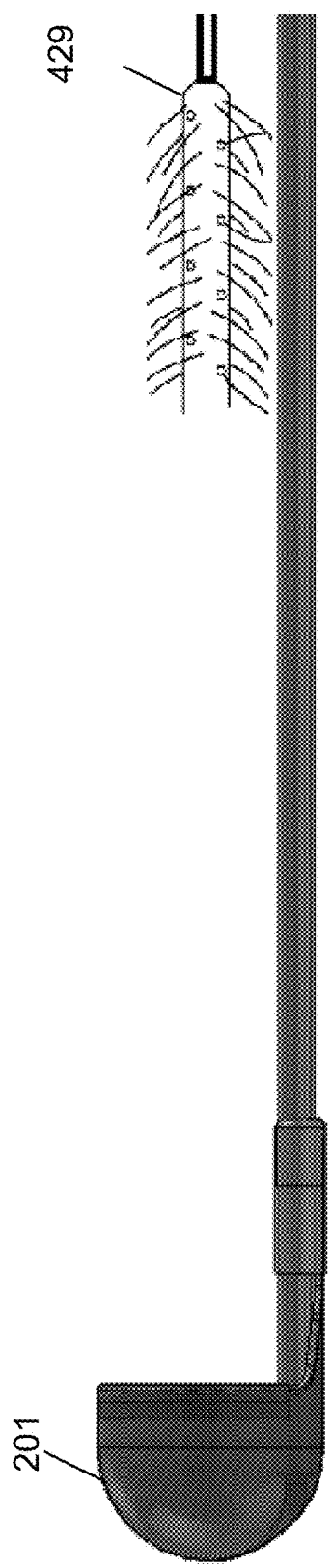

The apparatus of Imran can be used in place of, or in combination with, the anchors described herein. Referring now to FIG. 88K, an embodiment of the anchor 429 is disclosed. The anchor 429 can include a brush. The brush is formed on the distal extremity of the flexible elongate tubular member. The brush is comprised of a plurality of radially extending bristles formed of a suitable soft material such as Nylon with the brush having an outer diameter corresponding generally to the inner diameter of the lumen defined by the wall. The distal extremity is provided with a plurality of randomly disposed ports interposed between the bristles for supplying irrigation liquid to the brush. With irrigation liquid being supplied through the ports and aspiration taking place through the aspiration port, the brush can be rotated by rotating the proximal extremity of the therapeutic catheter. By moving the catheter back and forth, the bristles can come into engagement with the wall throughout the entire length of the chamber to remove the plaque in small particles. As the small particles are removed they can be aspirated from the chamber through the aspiration port.

Figure 88L:
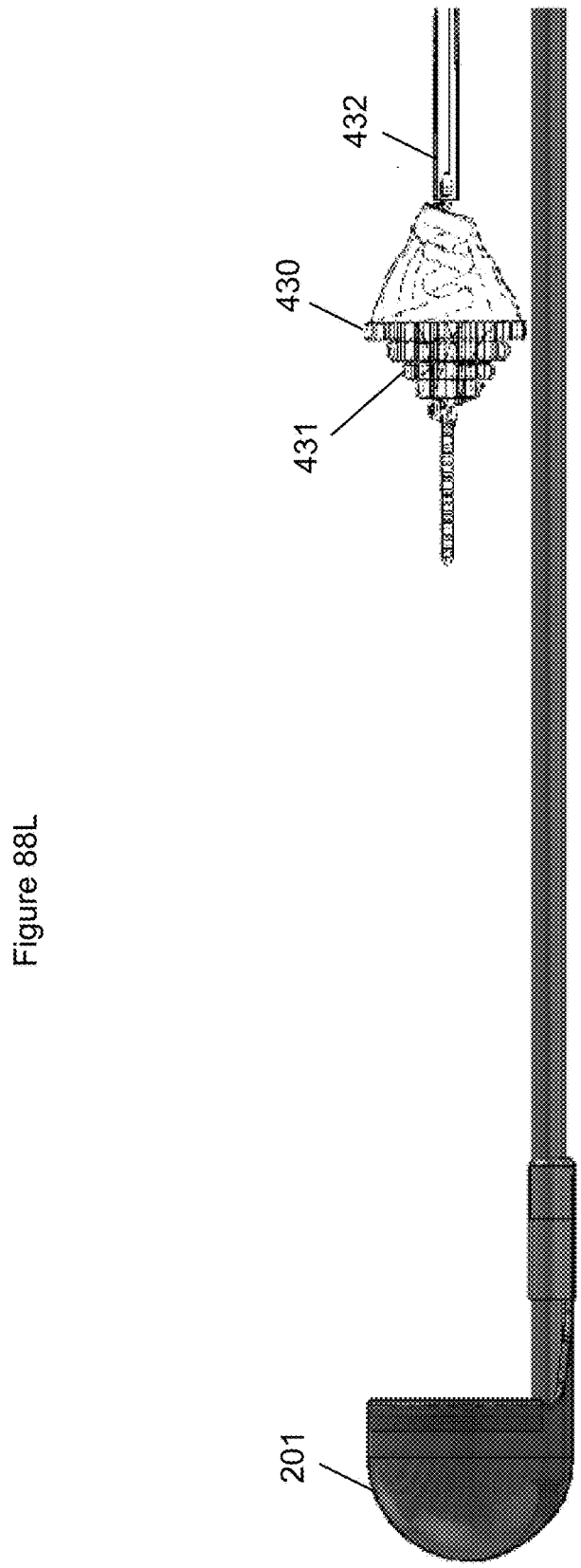
Figure 88M:
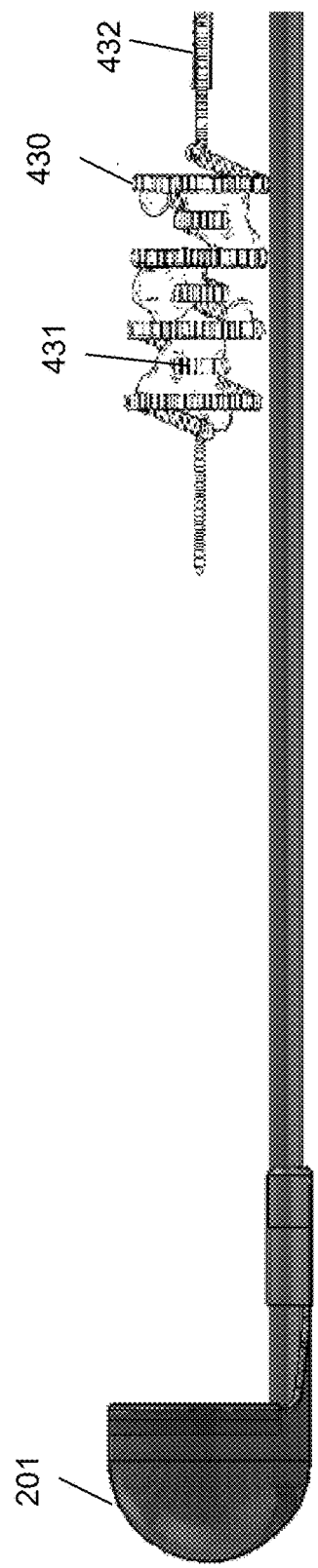

The obstruction removal device of Sepetka can be used in place of, or in combination with, the anchors described herein. Referring now to FIGS. 88L-88M, the obstruction removing device 430 has an engaging element 431 extending from an insertion element 432. The engaging element 431 is movable from a collapsed position to an expanded position. When the engaging element 431 is contained within a sheath or other member, the engaging element 431 is in a relatively straight configuration. The engaging element 431 has a distal portion, which forms a relatively closed structure, which can catch or trap the obstruction, or any part thereof, to prevent migration of the obstruction or part thereof. The engaging element has a proximal portion which is formed with smaller coils than the distal portion. The proximal portion engages the obstruction as described below. The engaging element 431 preferably has a number of markers which provide an indication as to how much of the engaging element extends from the sheath. For example, markers may indicate when the engaging element 431 is ½, ¾ or fully exposed. In this manner, the user may quickly advance the engaging element 431 through the sheath without inadvertently exposing and advancing the engaging element 431 out of the sheath. The markers can also be used to provide a controlled diameter of the engaging element 431 since the diameter of the engaging element is known for the various positions corresponding to the markers. The markers may also be used to size the vessel in which the engaging element 431 is positioned by observing when the engaging element 431 engages the vessel walls and determining the size of the engaging element 431 using the markers.

The engaging element 431 is preferably made of a superelastic material, such as nitinol, and has a diameter of, in some cases, about 0.005-0.018 inch, about 0.005-0.010 inch or about 0.008 inch. The engaging element 431 can have a rounded, atraumatic tip to prevent damage to the vessel and facilitate advancement through the vessel and/or sheath. A radiopaque wire, such as platinum ribbon having a width of 0.004 inch and a thickness of 0.002 inch, is preferably wrapped around the engaging element 431 to improve radiopacity. The device is preferably self-expanding but may also be expanded with an actuator. The actuator is preferably a thin filament which is tensioned to move the device to the expanded position. An advantage is that the filament extends through the same lumen as the device thereby minimizing the overall size of the device. It is understood that throughout discussion of the devices and methods herein that any of the anchors described herein may be expanded using the actuator rather than being self-expanding. The obstruction removal device shown in FIG. 88M has a first section with larger diameter coils than a second section. A third section also has larger coils than the second section with the second section positioned between the first and third sections. The obstruction removal device may have a number of alternating small and large sections which can enhance the ability of the obstruction removal device to engage various obstructions. The obstruction removal device can have four large sections with relatively large coils and three sections having smaller coils, but other configurations are contemplated with different numbers of sections.

Figure 88N:
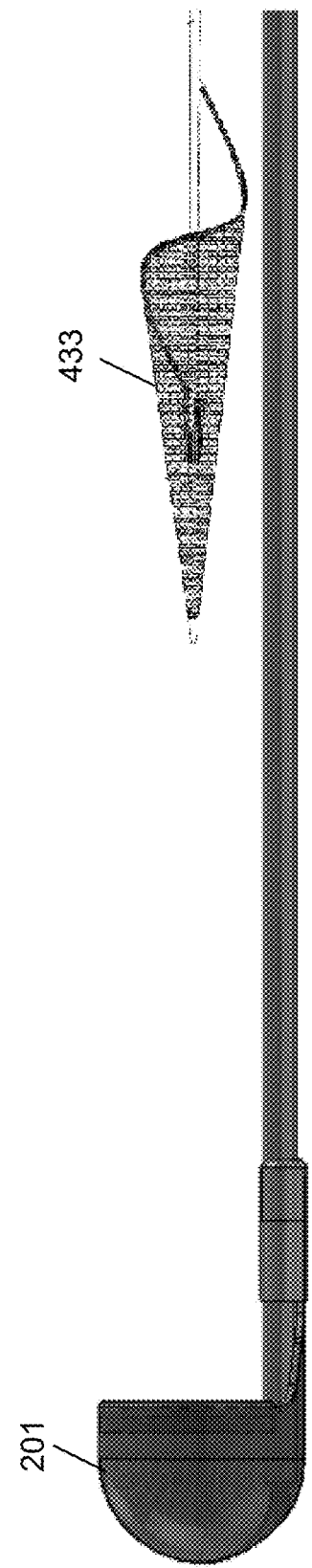

The expansion elements of Sanford can be used in place of, or in combination with, the anchors described herein. Referring now to FIG. 88N, an anchor 433 is shown. The anchor 433 can include a helical expansion ring connected to the inlet of the anchor. Expansion ring has a proximal end and a distal end. The distal end can be fixed to guidewire. Alternately, the anchor could have resilient, expansion material embedded in its inlet. The anchor can include inclined "sail" at its inlet. The sail acts as an expansion mechanism to expand the anchor when exposed to blood flow. In some embodiments, the anchor has its inlet coated with a hydrogel coating which swells upon contact with blood and acting to expand the inlet of filter.

Figure 88O:
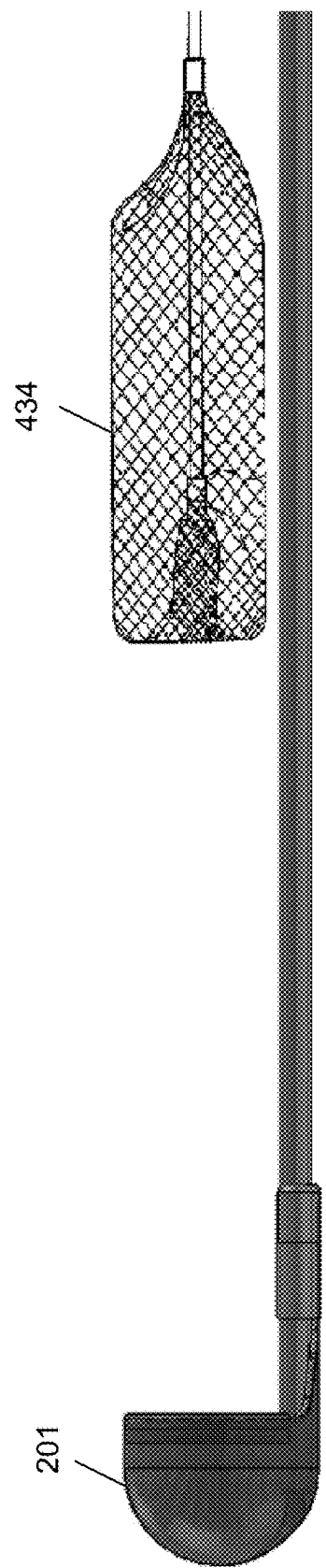

The filter devices of Berrada can be used in place of, or in combination with, the anchors described herein. Referring now to FIG. 88O, the anchor 434 can be an everting filter. Everting filter includes a flexible, mesh, filter body. The filter body may be formed of a plurality of wires or strands which can be used to form the mesh filter body through a variety of methods, for example, braiding, knitting, weaving, helically winding, and counterwinding. The mesh can be fused at some or all of the fiber or strand intersection points. The mesh can also be electrospun, and formed of sheet or film having holes formed by laser drilling, punching, dissolving components selectively, and the like. The strands can be formed of material such as wire, which can be metallic wire or polymeric wire. The wire may be substantially circular in cross section or may have any number of square, rectangular or irregular cross sectional profiles. The mesh is preferably self-expanding. The self-expanding mesh can be formed totally or in part from self-expanding Nitinol, Elgiloy, titanium, or stainless steel wires and the like, and combinations thereof. The self-expanding mesh can also be formed of engineering polymers, for example, liquid crystal polymer, PEEK, polyimide, polyester, and the like. A preferred mesh is formed of Nitinol wires, which can be heat set to the desired expanded shape. The mesh can preferably be heat set to a desired bias shape. Another mesh is highly elastic, and preformed by mechanical overstress to the desired expanded shape. The mesh is preferably made radiopaque by means of plating, core wires, tracer wires, or fillers that have good X-ray absorption characteristics compared to the human body. The mesh may be either partly or totally radiopaque.

The filter body may be seen to have a plurality of pores or openings between the filter body strands or wires. The pores have an average pore size over the filter body, where the individual pore sizes may vary depending upon the location over the filter body. The filter body also has a proximal opening formed in filter body proximal region. The filter body may also be considered to have an interior within the filter body and an exterior defined outside of the filter body. The everted shape of filter defines an everted cavity or concave region bounded by filter body everted surface region or cavity side walls and the filter body distal-most extent. It may be seen from inspection of FIG. 88O that axially translating proximal ring relative to distal ring while holding the filter body diameter consistent may change the degree of eversion of filter body. The filter material occupying distal-most region may therefore change with the degree of eversion of filter, with different locations of filter body being distal-most varying as a function of the degree of eversion. The length of a distal cavity will increase with increasing eversion.

Figure 88Q:
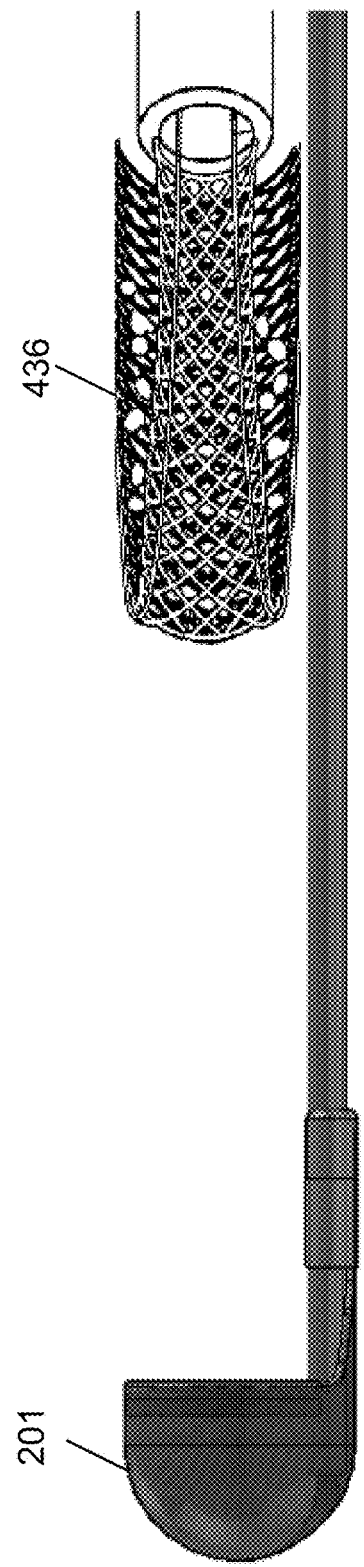

The filter devices of Paul can be used in place of, or in combination with, the anchors described herein. Referring now to FIGS. 88P-88Q, the anchor 435 and anchor 436 are everted. The anchor 435 is everted to form a proximally facing concave geometry. The filter portion may be everted by moving the control wires proximally, thereby pulling the first end of the filter portion back over the rest of the filter portion. Further, the filter portion may also be made of a shape memory material such that the filter portion has two defined geometries. For example, the mesh material may be made of a shape memory alloy so that the mesh material is biased into a straight tubular geometry in a non-everting state at a first temperature. The first temperature being controlled, for example, by fluid flowing through the guiding member across the medical device. At a second temperature, such as the ambient temperature inside the vessel, the filter portion is biased into a proximally facing concave geometry. When the filter portion is biased into the proximally facing concave geometry, the filter portion everts causing the filter portion 1 to expand against the inner wall of the vessel. While the medical device is expanded against the inner wall of the vessel, the filter portion serves to collect emboli that may break free from the stenosed area preventing such emboli from blocking smaller vessels downstream of the medical device. When everted, the first end of the filter portion is biased against the inner wall of the vessel forcing the fluid to flow through the proximally facing concave geometry formed by the filter portion. Therefore, emboli are trapped in the distal region of the proximally facing concave geometry. The medical device remains in this expanded state during the interventional procedure to capture any emboli that break free from the stenosis. After the interventional procedure is completed, the medical device may be removed. To trap the emboli in the filter portion, the control wires may be pulled further proximally drawing the filter portion against the guiding member.

For anchor 436, the control wires extend through the tubular geometry of the filter portion. Accordingly, the control wires form a frame structure along the length of the filter portion. The control wires may be made of a synthetic material, a stainless steel, or a shape memory alloy, such as Nitinol. The shape memory characteristics of the control wire may be used to support the first end of the filter portion against the inner wall of the vessel. Supporting the filter portion against the wall of the vessel ensures that the fluid will flow through the proximally facing concave geometry formed by the everted filter portion, thereby causing emboli to be trapped by the medical device.

Figure 88R:
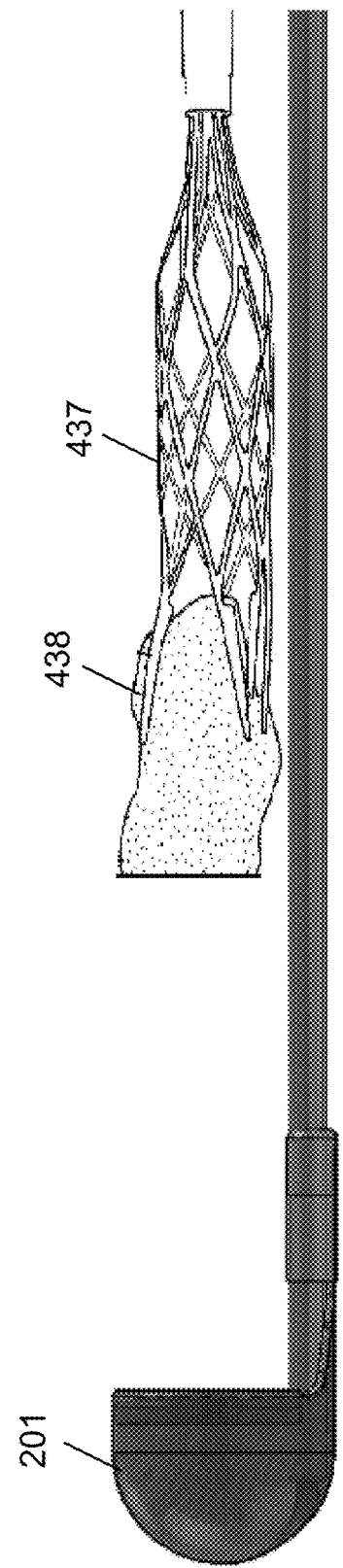

The cages of Krolik can be used in place of, or in combination with, the anchors described herein. Referring now to FIG. 88R, the anchor 437 can include a macerator cage. Generally, the macerator cage includes a closed proximal or first end and an open distal or second end. The cage may include a plurality of struts extending between the first and second ends and/or around a periphery of the cage, thereby defining a cylindrical or other tubular outer wall including a plurality of apertures.

The open distal end of the cage may include a plurality of distally protruding elements or distal tips 438. The cage includes at least two different types of struts. For example, the cage may include a plurality of relatively thick struts that extend substantially continuously along a length of the cage e.g., in a first helical configuration between the first and second ends. In addition, the cage may include a plurality of relatively thin struts, which may connect adjacent thick struts together. As shown, the thin struts are not substantially continuous as are the thick struts, but may extend in a discontinuous pattern helically and/or circumferentially around the cage. Optionally, the thin struts may also have bends or other features, e.g., relatively thinned or perforated portions, that allow the struts to bend relatively easily compared to the thick struts. The apertures may be defined by the spaces between the thick struts and the thin struts, thereby defining a desired pore size for the cage.

The distal tips 438 on the open end may provide a substantially atraumatic distal end for the cage, e.g., to prevent puncture or other damage to a wall of a body lumen within which the cage is deployed. In addition or alternatively, the distal tips 438 may be sufficiently flexible to allow the distal tips to twist helically and/or interlock with one another during use. The distal tips 438 may facilitate engaging and/or removing obstructive material within a body lumen. Alternatively, the distal tip 438 can include a series of slots or indentations spaced apart along a length of the distal tip e.g., that may allow the distal tips to entangle with each other and/or with the obstructive material captured or otherwise engaged by the distal tips to facilitate removal. For example, when the cage is rotated, the distal tips 438 and obstructive material may be wound together, e.g., such that portions of other distal tips and/or obstructive material may enter the slots and the distal tips 438 become interlocked with one another.

During distal advancement, the cage may be concurrently advanced and rotated, e.g., manually or using a driveshaft. This may cause the distal tips 438 of the cage to track along the inside wall of the body lumen, e.g., in a helical manner as the cage is advanced. When thrombus or other obstructive material is encountered, the distal tips 438 may pass between the material and the wall of the body lumen, thereby positioning the material inside the cage. In some methods of use, the anchors described herein are rotated. In some methods of use, the anchors described herein are translated.

The distal tips 438 of the cage may facilitate separation and/or capture of material within the cage. For example, the edges of the distal tips may provide distal leading edges of the cage that are not a substantially smooth cylinder but define an undulating surface. Consequently, the distal tips 438 of the cage may act as a saw by repeatedly making contact with the material as the cage is rotated, which may increase the chance of material being dislodged from the wall of the body lumen and/or captured within the cage. To further ensure that the leading edge of the cage passes between the unwanted material and the wall of the body lumen, the distal tips 438 and/or edges of the struts may also act as blades shearing along the wall of the body lumen to draw adherent material into the cage. Thus, the struts may cut or otherwise separate the interface between the body lumen and the obstructive material.

The distal tips 438 may be formed such that they conform substantially to the cylindrical shape of the cage, e.g., defining a diameter similar to the rest of the expanded cage, although alternatively the distal tips 438 may be biased radially outwardly, e.g., to ensure that the distal tips 438 pass between the wall of the body lumen and the obstructive material and/or enhance engagement of the distal tips against the wall of the body lumen. Alternatively, the distal tips 438 may by biased to extend radially inwardly, e.g., laterally inwardly, relative to a central longitudinal axis of the apparatus, e.g., to prevent substantial risk of damage to the wall of the body lumen.

The systems described herein are intended for use in any size vessel. The systems can be deployed in vessels with a diameter about 10 µm, 20 µm, 30 µm, 40 µm, 50 µm, 60 µm, 70 µm, 80 µm, 90 µm, 100 µm, 200 µm, 300 µm, 400 µm, 500 µm, 600 µm, 700 µm, 800 µm, 900 µm, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, between 1 mm and 8 mm, between 10 µm, and 1 mm, between 100 µm and 1 mm, between 100 µm and 10 mm etc. The anchors can have a diameter or cross-section about 10 µm, 20 µm, 30 µm, 40 µm, 50 µm, 60 µm, 70 µm, 80 µm, 90 µm, 100 µm, 200 µm, 300 µm, 400 µm, 500 µm, 600 µm, 700 µm, 800 µm, 900 µm, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, less than 10 mm, less than 1 mm, less than 100 µm, less than 10 µm, etc. The ALTC device 201 can have a diameter or cross-section about 10 µm, 20 µm, 30 µm, 40 µm, 50 µm, 60 µm, 70 µm, 80 µm, 90 µm, 100 µm, 200 µm, 300 µm, 400 µm, 500 µm, 600 µm, 700 µm, 800 µm, 900 µm, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, less than 10 mm, less than 1 mm, less than 100 µm, less than 10 µm, etc., or ranges incorporating any two of the aforementioned values. It is contemplated that different sizes of the systems will be available for selection by the user based on the obstruction and the target vessel.

Figure 89:
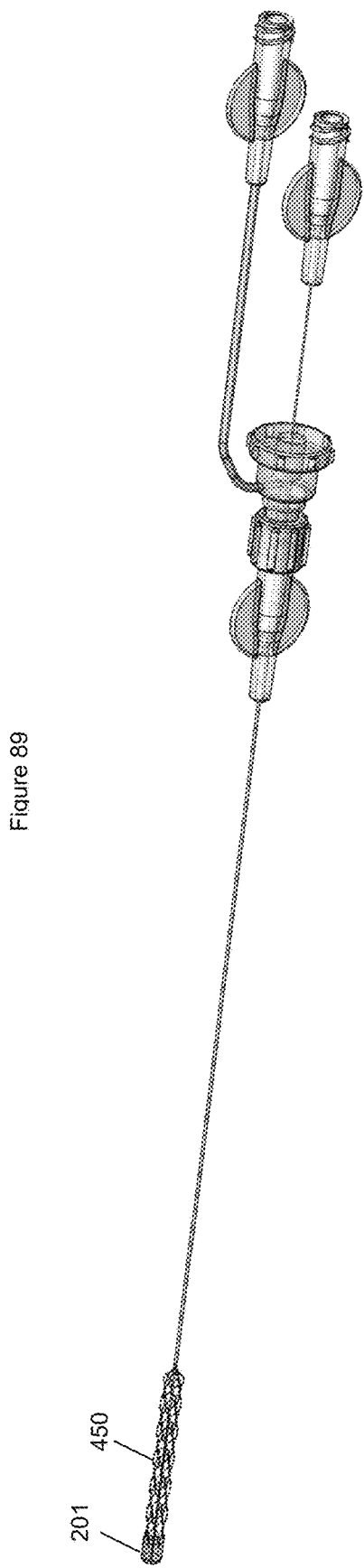
FIG. 89 illustrates an embodiment of a system designed for removing a blood clot.

A perspective view of another embodiment of a capture system is shown in FIG. 89. FIG. 89 also illustrates non-limiting examples of various possible elements that can be included in a material capture system, according to some embodiments described herein. As illustrated in FIG. 89, included in some embodiments are any number of, such as one, two, or more of the following components: a thrombus capturing device or ALTC device 201 having any of the features described herein, e.g., a pusher wire or inner pusher 202, a first tubular member such as an outer sheath (not shown), and an anchor such as any of the anchors described herein. FIG. 89 illustrates an anchor 450. In some embodiments, the ALTC device 201 can attach to the anchor 450. In some embodiments, the anchor 450 functions as the capture guide 204 described herein. In some embodiments, the anchor 450 comprises a metallic material, such as Nitinol. The anchor 450 can be in the form of, for example, a loop, as shown, or any closed shape including an oval, ellipse, or polygon. The anchor 450 can be in the form of an open shape such as any linear or non-linear segment. The ALTC device 201 and the anchor 450 can be coupled such as being sutured together. The ALTC device 201 and the anchor 450 can be encapsulated in a low durometer polymeric material. The anchor 450 can be coupled to the outer sheath 203. The proximal end of the ALTC device 201 can be coupled to an inner pusher 202 as described herein. The anchor 450 can have any of the features of anchors described herein, including anchor 401.

The anchor 450 can be connected to an anchor pusher 451. The anchor pusher 451 can, in some embodiments, be an elongate tubular member with a central lumen therethrough, and have a proximal end and a distal end, both shown in FIG. 89. The distal end of the anchor pusher 451 can be operably connected to the anchor 450 (e.g., tubular mesh as described herein). In some embodiments, anchor 450 can be fixed or stationary with respect to the anchor pusher 451. In some embodiments, anchor 450 can be move axially with respect to the anchor pusher 451. The proximal end can include any number of, such as one, two, or more of the following components: a hemostasis assembly 206, a flush port 207, and a collapsed segment 208. The anchor pusher 451 extends proximally and can be coupled to the hemostasis assembly 206. The anchor pusher 451 extends proximally and can be coupled to a luer. In some embodiments, the anchor pusher 451 can have a lumen to allow passage of a guidewire. In some embodiments, the anchor pusher 451 is a solid shaft.

FIG. 89 also shows the distal end of the ALTC device 201 in a deployed configuration. In some methods of use, a portion of the ALTC device 201 is axially extended while the remaining length of the ALTC device 201 is collapsed and contained within a sheath as previously described. In some methods of use, the ALTC device 201 can be collapsed and tracked through a sheath or guide catheter (not shown) to the intended treatment area. In some embodiments, the guide catheter can be retracted proximally to initially deploy the ALTC device 201 and the self expandable anchor 450. For instance, the retraction of the guide catheter can cause the anchor 450 to expand. The anchor 450 can include a compressed or constrained configuration while within the guide catheter. During the initial deployment, the anchor 450 is released from a constrained position to a neutral position. In the neutral position, the anchor 450 creates a perimeter for the ALTC device 201. In the case of a loop or other circular configuration, the anchor 450 can create a constant diameter. In the case of other shapes or configurations, the anchor 450 can create a constant cross-section. Alternatively or in combination, in other methods of use, the ALTC device 201 can be advanced distally from the guide catheter to deploy the ALTC device 201.

In some cases, only a small fractional portion of the ALTC device 201, such as less than about 50%, 45%, 40%, 35%, 30%, 25%, 20%, 15%, 10%, 5%, or less of the axial length of the device can be initially deployed. The small portion can correspond to an amount of the ALTC device 201 which allows the anchor 450 to assume the neutral position. During the deployment of the anchor 450, a length of the ALTC device 201 can be retained within the outer sheath 203. The ALTC device 201 can follow a curve from the anchor 450 to the outer sheath 203. Retracting the outer sheath 203 can lengthen the ALTC device 201 while maintaining a constant diameter or cross-section provided by the anchor 450. In some embodiments, the proximal end of the ALTC device 201 is fixed relative to the anchor 450. In some embodiments, the ALTC device 201 can axially lengthen by releasing the compressed portion 208 as described herein. In some methods of use, the ALTC device 201 is axially lengthened. In some methods of use, the ALTC device 201 is not axially lengthened. The ALTC device 201 can serve as distal protection without further axially lengthening. In some embodiments, the ALTC device 201 is deployed before the anchor 450. In some embodiments, the ALTC device 201 is deployed after the anchor 450.

FIG. 89 illustrates a system including a dual ALTC device 201 and anchor 450. The anchor functions to replace the nitinol. In some methods of use, the ALTC device 201 and the anchor 450 retract together. In some methods of use, the ALTC device 201 and the anchor 450 move as a unit. In some embodiments, the distal end consists of axial lengthen device wherein the opening end attaches to an expandable anchor. The ALTC device 201 comprises a proximal opening. In some embodiments, the capture guide 204 is replaced with an anchor, such as anchor 450. The proximal opening of the ALTC device 201 is coupled to the anchor 450 such that the ALTC device 201 and the anchor move together. In some embodiments, the distal end of the axial lengthen device is fixed to the pusher 202 that extends proximally. The ALTC device 201 can be coupled to the pusher 202. The pusher 202 can push the compressed portion 208 from the sheath 451 to cause axially lengthening of the ALTC device 201. The pusher 202 can extend to the proximal end of the system to be controlled by the user. In some embodiments, the proximal end of the expandable anchor attaches a pusher tube 451 extending proximally and attaches to a hemostasis housing. In some embodiments, the proximal end of the anchor 450 is coupled to the anchor pusher 451. The anchor pusher 451 can extend proximally and attach to the hemostasis housing as described herein. The system can be designed for thrombectomy. The system can include a distal basket or ALTC device 201 and anchor 450. The anchor 450 can be made of wireform, laser cut or stent-like structure. The materials can be such as shape memory, stainless steel, Cobalt Chromium.

Figure 90:
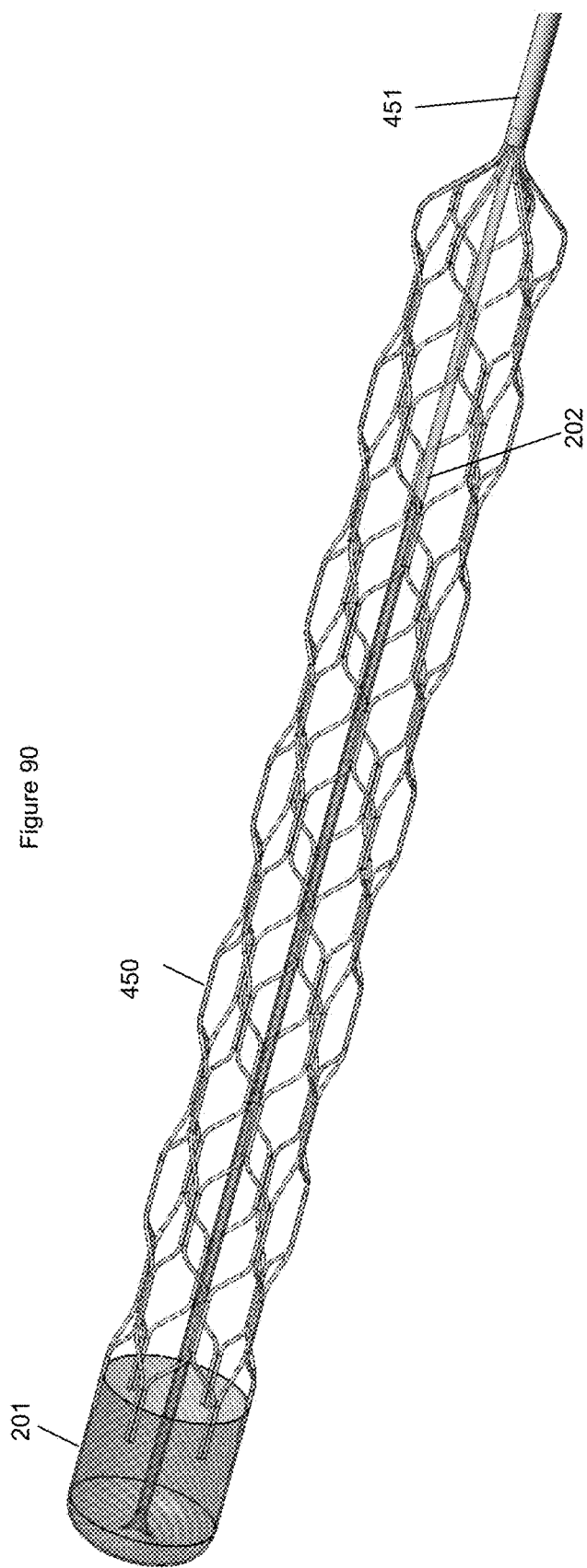
FIG. 90 illustrates a distal end of the system of FIG. 89.

FIG. 90 illustrates the distal end of the system of FIG. 89. The system includes the ALTC device 201 and the expandable anchor 450. In some embodiments, the ALTC device 201 and the anchor 450 are fixed and move as one unit. In some embodiments, the distal end of the expandable anchor 450 attaches to the opening end of the ALTC device 201. In some embodiments, the proximal end of the anchor 450 attaches to the catheter shaft 451. In some embodiments, the distal end of the ALTC device 201 extends through the anchor 450. In some embodiments, the distal end of the ALTC device 201 extends through the anchor 450 centrally or along a longitudinal axis. In some embodiments, the distal end of the ALTC device 201 extends through the anchor 450 along an axis offset from the longitudinal axis of the anchor 450. The distal end of the ALTC device 201 can be the compressed portion 208 as described herein. In some embodiments, the distal end of the ALTC device 201 is coupled to a pusher wire 202. In some embodiments, the distal end of the ALTC device 201 is coupled to the pusher wire 202 or other device described herein.

In some embodiments, alternatively, the distal end of the expandable anchor 450 is separated from the opening end of the ALTC device 201. In some embodiments, the proximal end of the expandable anchor 450 attaches to distal end of catheter shaft. In some embodiments, the body of the ALTC device 201 extends through the anchor 450 centrally and attaches to the pusher 202. The pusher 202 can be contained within the pusher tube 451, sheath 203, dual lumen sheath 243 or other constraining member described herein. The anchor 450 can be designed to collapse within the pusher tube 451. The ALTC device 201 can be designed to collapse within the pusher tube 451. In some methods of use, the ALTC device 201 can be released from the pusher tube 451 by proximal movement of the pusher tube 451. In some methods of use, the anchor 450 can be released by proximal movement of the pusher tube 451. In some methods of use, the ALTC device 201 can be released from the pusher tube 451 by distal movement of the pusher 202. In some methods of use, the anchor 450 can be released by distal movement of the pusher 202.

Figure 91:
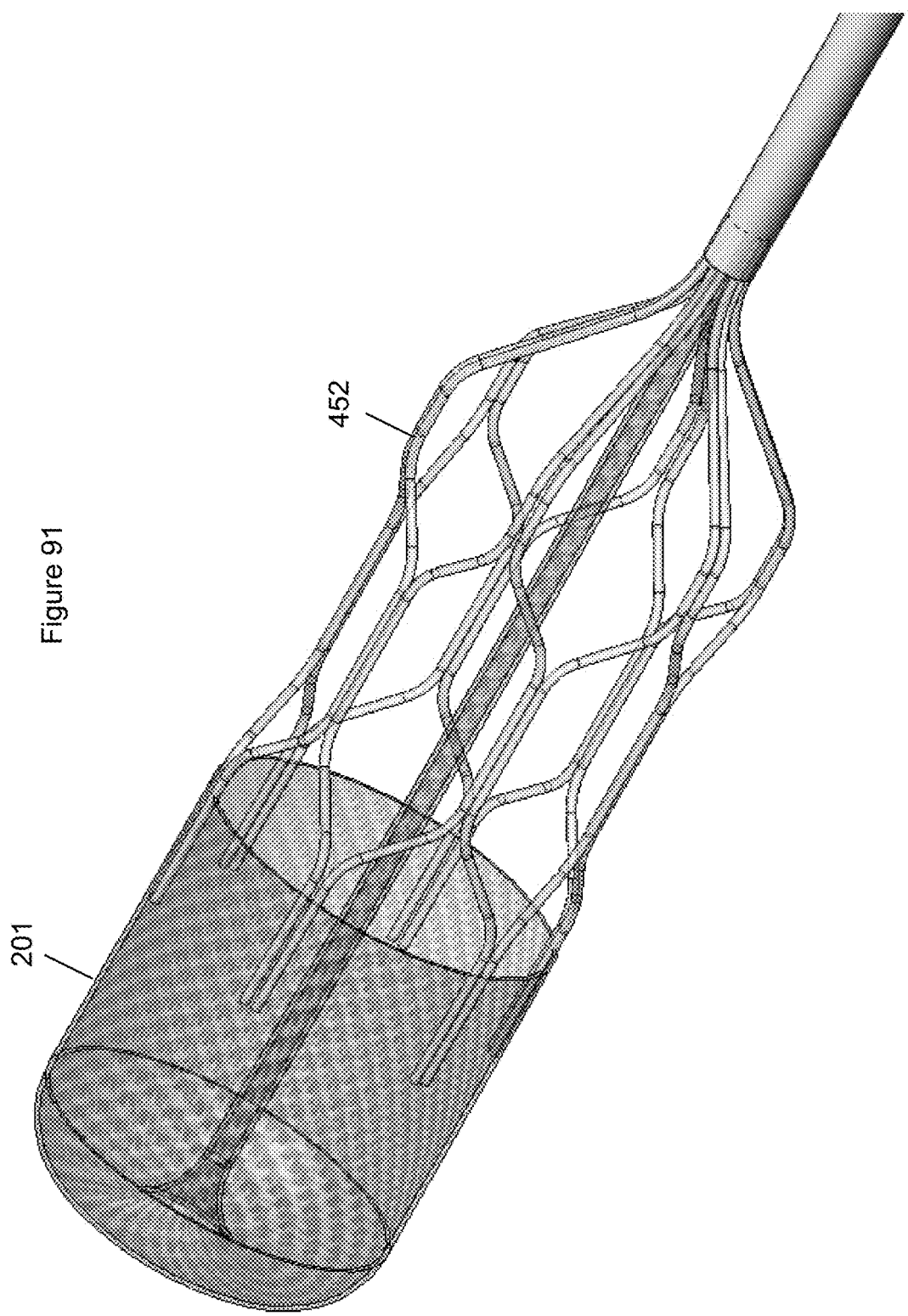
FIG. 91 illustrates a distal end of a system including an embodiment of an anchor.

FIG. 91 illustrates another embodiment of a capture system, which can have any of the features described herein. The capture system includes an anchor 452. The anchor 452 can have any of the features of anchors described herein, including anchor 405. A portion of the anchor 452 can be contained within the pusher tube 451. In some embodiments, the ALTC device 201 can attach to the anchor 452 as described herein.

FIG. 92 illustrates another embodiment of a capture system, which can have any of the features described herein. The capture system includes an anchor 453. In some embodiments, the ALTC device 201 can attach to the anchor 453 as described herein. In some embodiments, the anchor 453 is formed as a stent structure. The anchor 453 can includes a plurality of struts. Each strut can be connected to the ALTC device 201 at one or more locations. In the illustrated embodiment, each strut is connected to the ALTC device 201 at two locations but other configurations are contemplated (e.g., one location, three locations, four locations, five locations, a plurality of locations, etc.). In some embodiments, the struts can be equally spaced. In some embodiments, the struts are not equally spaced. In some embodiments, the struts can include a zig-zag pattern or bends 454. In some embodiments, the bends 454 can improve flexibility of the capture system. In some embodiments, the bends 454 can allow the capture system to turn. In some embodiments, the bends 454 can be located near a proximal end of the anchor 453. In some embodiments, the bends 454 can be located near a distal end of the anchor 453. In some embodiments, the struts of the anchor 453 assist in retrieving and containing the obstruction or clot. In some embodiments, the struts comprise a shape memory or self-expanding material such as nitinol. In some embodiments, the anchor 453 can be self-expanded.

FIGS. 93-94 illustrate another embodiment of a capture system, which can have any of the features described herein. The capture system includes anchor 455. In some embodiments, the struts 456 of the anchor 455 can be straight. In some embodiments, the struts 456 can include a straight portion. In some embodiments, the straight portion in near a proximal end of the anchor. FIGS. 93-94 illustrates the axial lengthening of the expanded portion of the ALTC device 201. The ALTC device 201 is lengthening proximally. The compressed or constrained segment of the ALTC device 201 is shortened within the pusher tube 241. In some embodiments, the pusher tube 241 can be retracted to axially lengthen the ALTC device 201, as described herein. The ALTC device 201 and the anchor 455 can be retracted as a unit. FIG. 93 illustrates the axial lengthening device and the expandable anchor in the initial configuration. FIG. 94 illustrates the axial lengthening device and the expandable anchor wherein the axial lengthening device is lengthened.

Figure 95:
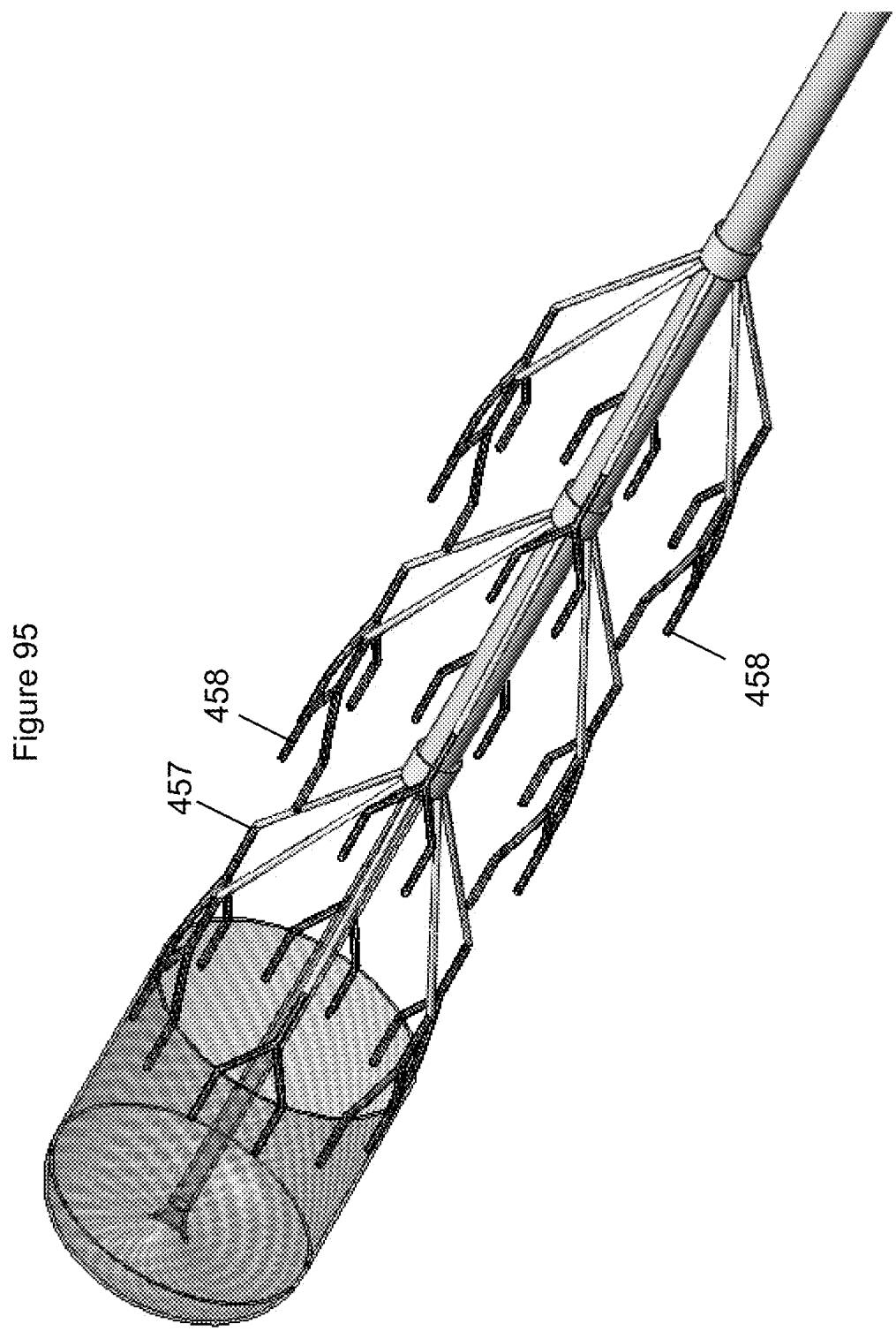
FIG. 95 illustrates a distal end of a system including an embodiment of an anchor.

FIG. 95 illustrates another embodiment of a capture system, which can have any of the features described herein. The capture system includes an anchor 457. In some embodiments, a portion of the anchor 457 is connected to the ALTC device 201. The anchor 457 can include one or more distal tips 458. In some embodiments, one or more distal tips 458 are not connected to the ALTC device 201. The distal tips 458 can function as distal tips described herein.

The distal tips 458 may provide a substantially atraumatic distal end, e.g., to prevent puncture or other damage to a wall of a body lumen within which the anchor 457 is deployed. The distal tips 458 may facilitate engaging and/or removing obstructive material within a body lumen. Alternatively, the distal tips 458 can entangle with each other and/or with the obstructive material captured or otherwise engaged by the distal tips 458 to facilitate removal. The distal tips 458 may facilitate separation and/or capture of material. The distal tips 458 of the anchor 457 may act as a saw by repeatedly making contact with the material, which may increase the chance of material being dislodged from the wall of the body lumen and/or captured within the anchor 457. To further ensure that the leading edge of the anchor 457 passes between the unwanted material and the wall of the body lumen, the distal tips 458 and/or edges may also act as blades shearing along the wall of the body lumen to draw adherent material into the anchor 457. Thus, the distal tips 458 may cut or otherwise separate the interface between the body lumen and the obstructive material. The distal tips 458 may be formed such that they conform substantially to the cylindrical shape of the ALTC device 201, e.g., defining a diameter similar to the rest of the ALTC device 201. In some embodiments, the distal tips 458 may be biased radially outwardly or biased to extend radially inwardly. Other configurations of the distal tips 458 are contemplated.

In some embodiments, the systems described herein comprise a fixed ALTC device 201. In some embodiments, the ALTC device 201 is inserted into the patient in the initial configuration. For instance, the capture guide 204 described herein can be fixed such that the ALTC device 201 assumes the initial configuration. In some embodiments, the ALTC device 201 does not lengthen. In some embodiments, the axial length of the ALTC device 201 is fixed. In some embodiments, the anchor is fixed. In some embodiments, the anchor is inserted into the patient in the expanded or inflated configuration. In some embodiments, the anchor does not expand or inflate within the body of the patient. In some embodiments, the anchor has a fixed shape or configuration. In some embodiments, the system includes a clot buster or debulking at the front end. In some embodiments, the clot buster moves distally to break apart the clot. In some embodiments, the clot buster is a portion of the anchor. In some embodiments, the clot buster is separate device.

FIGS. 96A-96B illustrate an expandable guide catheter 460. The guide catheter 460 includes an expandable distal end, configured to be positioned away from a user, within a body of a patient. The guide catheter 460, or at least the distal end, can feature at least a dual braid layer including an outer layer and an inner layer. In some embodiments, the expandable guide catheter 460 can include a dual layer structure. In some embodiments, the expandable guide catheter 460 can include an outer braid layer 461. In some embodiments, the outer braid layer 461 is coated with a material such as one or more polymeric materials. In some embodiments, the expandable guide catheter 460 can include an inner braid layer 462. In some embodiments, the inner braid layer 462 is not coated with a polymeric material. In some embodiments, a portion of the inner braid layer 462 is not coated. In some embodiments, a distal portion of the inner braid layer 462 is not coated. In some embodiments, a length of the inner braid layer 462 is not coated. In some embodiments, the entire length of the inner braid layer 462 is not coated. In some embodiments, a portion of the outer braid layer 461 is coated. In some embodiments, a distal portion of the outer braid layer 461 is coated. In some embodiments, a length of the outer braid layer 461 is coated. In some embodiments, the entire length of the outer braid layer 461 is coated. In some embodiments, the outer braid layer 461 remains coated or encased with the polymer during the procedure.

In some embodiments, the outer braid layer 461 is coated with a polymer. The polymer can be any material including Pellethane, Silicone, Tecoflex, Tecothane, Latex, Pebax. The polymer can function akin to a slip layer. The polymer can facilitate the sliding of the catheter against a target vessel. In some embodiments, the inner braid layer 462 is not coated with a polymer, instead, retains the mesh-like structure as shown. The inner braid layer 462 advantageously provides decreased surface area, decreased surface contact, and/or decreased friction relative to an object within the lumen of the catheter. For instance, the mesh-like structure of the inner braid layer 462 has less surface area to contact the object within the lumen than a solid, inner wall. The inner braid layer 462 allows for a retrieval catheter, one or more anchors, the obstruction, or the ALTC device 201 to more easily slide axially when withdrawn proximally through the lumen. In some methods of use described herein, the ALTC device 201 can be axially lengthened over one or more anchors before retraction into the guide catheter 406. In some methods of use described herein, the ALTC device 201 can be axially lengthened over an obstruction such as a clot before retraction into the guide catheter 406. In some methods of use described herein, the ALTC device 201 can provide distal protection as the ALTC device 201 is retracted into the guide catheter 460.

In some embodiments, the guide catheter 460 has a funnel shape at the distal end. In some embodiments, distal refers to the portion of the guide catheter 460, or component thereof, which is furthest from the user during use, while proximal refers to the portion of the guide catheter 460 or component thereof which is closest to the user. In some embodiments, the distal end of the guide catheter 460 is positioned within the body of the patient and the proximal end is outside the body of the patient.

In some embodiments, the expandable guide catheter 460 can include any of the features of the ALTC device 201 described herein. In some embodiments, the mesh can be made from metallic materials such as individual non-elastic wires. In some embodiments, the mesh can be made from elastic elements. In some embodiments, the mesh can be made from a combination of elastic and non-elastic wires. In some embodiments, the dual braid can be made of either polymeric or metallic materials. In some embodiments, the metallic materials can be Nitinol, stainless steel, steel, shape memory alloy, elastic alloy, Nickel Titanium alloy, etc. In some embodiments, the braid wire diameter can range from 0.0005" to 0.030", e.g., 0.0005", 0.001", 0.0015", 0.002", 0.0025", or 0.003", between 0.0005"-0.0015", between 0.001"-0.002", between 0.0015"-0.0025", between 0.002"-0.003" etc. Other configurations of braid wire diameter are contemplated. The braid wire can be woven in any pattern. In some embodiments, the guide catheter 460 can include at least one polymer layer. The at least one polymer layer can applied to any surface of the braid wire. The braid wire can include one or more woven patterns, for instance a first wave pattern in a first portion of the guide catheter 460 and a second wave pattern in a second portion of the guide catheter 460. The woven pattern can be a typical over under pattern, e.g., two over, two under; one over, one under, etc. The woven paten can from a tubular braid. In some embodiments, the guide catheter 460 can include multiple layers of braid wire.

The braid wire can form a mesh. In some embodiments, the cross-section of the wire can be any shape including round, polygonal, elliptical, etc. The shape of the wire can be flat, square, ribbon, round, etc. In some embodiments, the total braid angle can range from 10 degrees to 170 degrees. In some embodiments, the total braid angle is 0 degrees, 10 degrees, 20 degrees, 30 degrees, 40 degrees, 50 degrees, 60 degrees, 70 degrees, 80 degrees, 90 degrees, 100 degrees, 110 degrees, 120 degrees, 130 degrees, 140 degrees, 150 degrees, 160 degrees, 170 degrees, 180 degrees, between 0-45 degrees, between 45-90 degrees, between 90-135 degrees, between 135-180 degrees, etc. In some embodiments, the braid density can range from 5 PPI to 60 PPI. In some embodiments, the braid density is less than 5 PPI, 5 PPI, 10 PPI, 15 PPI, 20 PPI, 25 PPI, 30 PPI, 35 PPI, 40 PPI, 45 PPI, 50 PPI, 55 PPI, 60 PPI, 65 PPI, 70 PPI, 75 PPI, 80 PPI, between 0-20 PPI, between 20-40 PPI, between 40-60 PPI, between 60-80 PPI, etc. In some embodiments, the inner diameter can range from 1 F to 30 F. In some embodiments, the inner diameter is less than 1 F, 1 F, 2 F, 3

F, 4 F, 5 F, 6 F, 7 F, 8 F, 9 F, 10 F, 11 F, 12 F, 13 F, 14 F, 15 F, 16 F, 17 F, 18 F, 19 F, 20 F, 21 F, 22 F, 23 F, 24 F, 25 F, 26 F, 27 F, 28 F, 29 F, 30 F, 31 F, 32 F, 33 F, 34 F, 35 F, between 0 F-5 F, between 5 F-10 F, between 15 F-20 F, between 20 F-25 F, between 25 F-30 F, between 30 F-35 F, etc. In some embodiments, the outer diameter can range from 2 F up to 33 F. In some embodiments, the outer diameter is less than 1 F, 1 F, 2 F, 3 F, 4 F, 5 F, 6 F, 7 F, 8 F, 9 F, 10 F, 11 F, 12 F, 13 F, 14 F, 15 F, 16 F, 17 F, 18 F, 19 F, 20 F, 21 F, 22 F, 23 F, 24 F, 25 F, 26 F, 27 F, 28 F, 29 F, 30 F, 31 F, 32 F, 33 F, 34 F, 35 F, between 0 F-5 F, between 5 F-10 F, between 15 F-20 F, between 20 F-25 F, between 25 F-30 F, between 30 F-35 F, etc.

In some embodiments, the expandable guide catheter 460 can include a shaft. In some embodiments, the expandable guide catheter 460 can include a shaft that expands under compression. In some embodiments, the expandable guide catheter 460 can include a shaft that lengthens under compression. In some embodiments, the expandable guide catheter 460 can include a shaft that expands upon release of a constraint. In some embodiments, the expandable guide catheter 460 can include a shaft that expands due to temperature. In some embodiments, the expandable guide catheter 460 can include a shaft that expands to assume a neutral configuration.

In some embodiments, the expandable guide catheter 460 can include an inverted structure. In some embodiments, one end of the braid begins at the proximal end and extends to the distal end where it folds inward and extends back to the proximal end. In some embodiments, the dual braid extends from the proximal end to the distal end. In some embodiments, the braid at the distal end can be continuous. In some embodiments, the braid at the distal end can be discontinuous. In some embodiments, one end of the braid begins at the proximal end and extends to the distal end wherein it folds inward and extends back to the proximal region. In some embodiments, one end of the braid begins at the proximal end and extends to the distal end wherein it folds outward and extends back to the proximal region. The outer braid layer 461 and the inner braid layer 462 are concentric.

In some embodiments, the outer layer braid 461 is encapsulated with polymeric materials. In some embodiments, the polymer layer can have uniform wall thickness. In some embodiments, the polymer layer can have uniform density. In some embodiments, the polymer layer can have uniform wall thickness throughout the entire catheter length. In some embodiments, the polymer layer can have non-uniform wall thickness. In some embodiments, the proximal end of the catheter wall thickness is thicker than the wall thickness at the distal end. In some embodiments, the polymeric material can have the same softness (durometer) through the catheter length. In some embodiments, the polymeric material can have different or a variety of softness (durometer) through the catheter length. In some embodiments, the polymeric material is expandable. In some embodiments, the polymeric material is flexible. In some embodiments, the outer layer composite is expandable. In some embodiments, polymeric materials can be any elastomer materials such as Polyurethane, Pellethane, Silicone, Tecoflex, Tecothane, Latex, Pebax and/or combination thereof. In some embodiments, the polymer can be coupled to the braid material through any methods known in the art. In some embodiments, the polymer can be coated, molded, dipped or thermally fused onto the braid.

In some embodiments, the guide catheter 460 has a funnel shape at distal end. In some embodiments, the guide catheter outer braid is encapsulated from the proximal end to the distal end near the funnel. In some embodiments, the funnel outer and inner braid layer is not encapsulated with polymer. In some embodiments, the funnel outer braid is encapsulated with polymer. In some embodiments, the inner braid layer can be encapsulated with polymer and the outer layer is not.

The guide catheter 460 can function as an access system. In some embodiments, the guide catheter 460 is introduced in a compressed diameter configuration. In some embodiments, after introduction, the guide catheter 460 may be radially expanded to accommodate passage of larger diameter surgical instruments therethrough such as ALTC device 201 and/or the anchors described herein.

The guide catheter 460 can be useful for forming and enlarging access area in target locations within a patient's body. In some embodiments, the guide catheter 460 is delivered in a small diameter configuration and expanded. In some embodiments, only a distal end or a funnel end is expanded. In some embodiments, the guide catheter 460 can change the size of the lumen that the guide catheter 460 is inserted into, such as enlarging a vessel by pressing against the vessel wall. The guide catheter 460 can include a polymeric coating that facilitates sliding contact with the vessel wall.

In some embodiments, passage of the ALTC device 201 through the guide catheter 460 can cause expansion of the guide catheter 460. In some embodiments, the collapsed ALTC device 201 can be sized to fit within the guide catheter 460. In some embodiments, the expanded ALTC device 201 can be sized to fit within the guide catheter 460. In some embodiments, the expanded ALTC device 201 can be retracted through the guide catheter 460. In some embodiments, the one or more expanded anchors can be retracted through the guide catheter 460. In some embodiments, the one or more expanded anchors can be sized to fit within the guide catheter 460. The uncoated inner braid layer 462 reduces sliding contact between the guide catheter 460 and any components passed therethrough.

In some embodiments, the guide catheter 460 can function as a variable sized cannula. In some embodiments, the guide catheter 460 can function as a tissue dilator. In some embodiments, the guide catheter 460 can change shape during axial compression of the braid. In some embodiments, axial shortening can cause radial expansion of the guide catheter 460. In some embodiments, the guide catheter 460 can be variably expanded based on the amount of compressive force. In some embodiments, the guide catheter 460 is self-expanding. In some embodiments, the guide catheter 460 is expanded by a mechanism e.g., pull strings, release from a constraint, application of compressive force, application of tension, etc. In some embodiments, the guide catheter 460 is a shape memory material.

In some embodiments, the guide catheter 460 can facilitate the removal of a blockage within the vasculature of a patient. In some embodiments, the guide catheter 460 can surround the one or more anchors that are entangled in the clot. In some embodiments, the surface of the clot can slide easily within the guide catheter, due in part, to the inner surface of the guide catheter 460. In some embodiments, the guide catheter 460 can slide easily within the target vessel, due in part, to the outer surface of the guide catheter 460. In some embodiments, the guide catheter 460 can be collapsed after receiving the one or more anchors. In some embodiments, the guide catheter 460 can surround the ALTC device 201 which itself encapsulates the obstruction. In some embodiments, the outer surface of the ALTC device 201 can slide easily within the guide catheter, due in part, to the inner surface of the guide catheter 460. In some embodiments, the guide catheter 460 can be collapsed after receiving the ALTC device 201.

Systems and methods can be utilized or modified for use in connection with those described herein can be found, for example, in U.S. patent application Ser. No. 11/101,224, filed Apr. 7, 2005 and published Jul. 2, 2013 as U.S. Pat. No. 8,475,487 ("Bonnette"); U.S. patent application Ser. No. 12/738,702, filed Oct. 27, 2008 and published Oct. 21, 2010 as U.S. Patent Pub. No. 20100268264 ("Bonnette '264") are all incorporated by reference herein in their entireties.

In some methods of use, the ALTC device 201 is used in combination with a thrombectomy catheter, such as an AngioJet® thrombectomy device or potentially an aspiration catheter may be used to remove the embolic debris. In some methods of use, one or more anchors described herein is used in combination with a thrombectomy catheter or an aspiration catheter, such as an AngioJet® thrombectomy device. The use of the AngioJet®, a rheolytic cross stream thrombectomy catheter, can include an inherent ability to remove thrombus of larger diameter than the catheter's diameter. However, the disruptive strength of the device falls off with the radial distance from the catheter. Hence, at some radial distance the clot can be stronger than the disruptive force generated by the AngioJet® cross stream flow patterns. In the case of organized thrombus, this radial distance from the catheter can be smaller than for softer thrombus.

Water jet thrombectomy procedures in general can be limited in ability in some cases. However, adding mechanical disruption such as by use of the anchors described herein can unexpectedly and synergistically improve water jet ablation. By combining mechanical agitation, e.g., abrasive intimate contact of thrombus by a flexible and expandable anchor component and an ALTC device 201, with a rheolytic thrombectomy catheter (AngioJet®), a variety of thrombus can be cleared than can be cleared by mechanical agitators or rheolytic cross stream thrombectomy catheters individually.

Another aspect and feature of some embodiments of the devices of the present disclosure is a device having the ability to capture large and small embolic debris. Another aspect and feature of the devices of the present disclosure is a device having the ability to temporarily capture debris which may later be removed by manual aspiration or by the use of an AngioJet® thrombectomy device and catheter or which may be treated by thrombolytics. Another aspect and feature of the devices of the present disclosure is a device having the ability to macerate debris to a clinically insignificant size (depending on the area of the body) or to a size which can be pharmacologically treated or removed by another device, such as an AngioJet® thrombectomy device and catheter. Another aspect and feature of the devices of the present disclosure is a device having the ability to macerate non-embolic debris, such as a stationary thrombus, by pulling the device through such an obstruction.

Systems and methods can be utilized or modified for use in connection with those described herein can be found, for example, in U.S. patent application Ser. No. 14/774,735, filed Mar. 17, 2014 and published Jan. 28, 2016 as U.S. Pub No. 20160022290 ("Johnson"); U.S. patent application Ser. No. 13/741,845, filed Jan. 15, 2013 and published Jan. 2, 2014 as U.S. Patent Pub. No. 20140005712 ("Martin") are all incorporated by reference herein in their entireties.

An intravascular ultrasound (IVUS) transducer disclosed in Johnson can be incorporated into the systems described herein. In some embodiments, an intravascular ultrasound (IVUS) transducer can be added to or incorporated into the delivery system and method. A pressure sensor can be used to measure the pressure at various positions within the vasculature, which can be used to determine blood flow, while the intravascular ultrasound (IVUS) transducer can be used to measure fluid flow and/or provide imaging within the vessel. In some embodiments, the pressure sensor and/or IVUS transducer can be incorporated into the guidewire at one or more locations, such as the distal end or distal portion of a guidewire, as well as being incorporated into intermediate and proximal portions of the guidewire. The guidewire with the pressure sensor and/or the IVUS transducer can be used much like a normal guidewire to help navigate the delivery device through the vasculature, with the added benefit of providing pressure measurements and ultrasound imaging to help in the navigation, to visualize the device placement site, and to monitor and ensure proper device deployment. In some embodiments, the IVUS transducer generates image slices as it is advanced and retracted which can then be assembled together to form a three dimensional reconstruction of the vasculature and/or the device within the vasculature. In some embodiments, the guidewire with the pressure sensor and/or IVUS transducer can be fastened to a catheter in a similar manner to that described below for a catheter having a pressure sensor and/or IVUS transducer that is fastened to another catheter.

Use of the ultrasound imaging system can allow the operator to deliver the device without fluoroscopy or using less fluoroscopy, thereby reducing the radiation exposure to the patient, while allowing more accurate evaluation of the vasculature, aiding placement of the device and allowing confirmation that device placement was proper. The imaging can be used to aid in the deployment of the filters or other devices. The imaging can also be used to aid in the retrieval of the deployed devices by providing visualization of, for example, the retrieval features on the deployed device and of the retrieval features, such as loops on a snare, of the retrieval device. The vasculature and implant location can be imaged prior to deployment, after deployment and/or during deployment. The imaging can be used during the retrieval process. The imaging can be used to aid in positioning of the filter or device within the vasculature. The imaging can be used to image the deployment location and determine the appropriate sizing of the filter or other device. The imaging can be used to help estimate treatment duration.

Although imaging systems described above have been primarily described as ultrasound based, other imaging systems can be used instead or in addition. For example, the imaging system can be based on intravascular ultrasound (IVUS), Forward-Looking IVUS (FLIVUS), optical coherence tomography (OCT), piezoelectric micro-machined ultrasound traducer (PMUT), and/or FACT.

Other components described by Martin can also be incorporated into the systems described herein. All or some of the device can be designed to increase their ability to adhere to the obstruction. For example, the wires may be coupled to an energy source (e.g., RF, ultrasonic, or thermal energy) to "weld" to the obstruction. Application of energy to the device can allow the surrounding portion to deform into the obstruction and "embed" within the obstruction. Alternatively, the device can impart a positive charge to the obstruction to partially liquefy the obstruction sufficiently to allow for easier removal. In another variation, a negative charge could be applied to further build thrombus and nest the device for better pulling force. The wires can be made stickier by use of a hydrophilic substance(s), or by chemicals that would generate a chemical bond to the surface of the obstruction. Alternatively, the filaments may reduce the temperature of the obstruction to congeal or adhere to the obstruction.

Another aspect applicable to variations of the devices can be to configure the devices (whether the traversing filament or the surrounding portion) for better adherence to the obstruction. One such mode includes the use of coatings that bond to certain clots (or other materials causing the obstruction.) For example, the wires may be coated with a hydrogel or adhesive that bonds to a thrombus. Accordingly, as the device secures about a clot, the combination of the additive and the mechanical structure of the device may improve the effectiveness of the device in removing the obstruction. Coatings may also be combined with the capturing portions or catheter to improve the ability of the device to encapsulate and remove the obstruction (e.g., a hydrophilic coating).

Such improvements may also be mechanical or structural. Any portion of the capturing portion can have hooks, fibers, or barbs that grip into the obstruction as the device surrounds the obstruction. The hooks, fibers, or barbs can be incorporated into any portion of the device. However, it will be important in some embodiments that such features do not hinder the ability of the practitioner to remove the device from the body.

In addition to additives, the device can be coupled to an RF, microwave, magnetic, thermal, cryo, or other power source, to allow electrical, current, ultrasound or RF energy to transmit through the device and induce clotting or cause additional coagulation of a clot or other obstruction.

The methods described herein may also include treating the obstruction prior to attempting to remove the obstruction. Such a treatment can include applying a chemical or pharmaceutical agent with the goal of making the occlusion shrink or to make it more rigid for easier removal. Such agents include, but are not limited to chemotherapy drugs, or solutions, lytic agents such as tPA, urokinase, or streptokinase for example, an anticoagulant, a mild formalin, or aldehyde solution.

Various other modifications, adaptations, and alternative designs are of course possible in light of the above teachings. Therefore, it should be understood at this time that the inventions may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the inventions are susceptible to various modifications, and alternative forms, specific examples thereof have been shown in the drawings and are herein described in detail. It should be understood, however, that the inventions are not to be limited to the particular forms or methods disclosed, but to the contrary, the inventions are to cover all modifications, equivalents, and alternatives falling within the spirit and scope of the various embodiments described. Any methods disclosed herein need not be performed in the order recited. The methods disclosed herein include certain actions taken by a practitioner; however, they can also include any third-party instruction of those actions, either expressly or by implication. For example, actions such as "inserting a catheter transfemorally" includes "instructing the insertion of a catheter transfemorally." The ranges disclosed herein also encompass any and all overlap, subranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A clot capture system, comprising:
   an expandable guide catheter;
   a tubular body comprising a first end, a second end, and an axial length therebetween, the first end having an opening,
   wherein the tubular body is compressed in a first configuration,
   wherein the tubular body is transformable to a second configuration in which at least the first end of the tubular body is expanded but the second end of the tubular body and a portion of the tubular body remains compressed, and wherein the tubular body has a first expanded axial length, wherein the tubular body is inverted such that a portion of the compressed tubular body is within a portion of the expanded tubular body,
   wherein the tubular body is transformable to a third configuration in which the tubular body has a second expanded axial length greater than the first expanded axial length, and
   wherein the tubular body in the third configuration is configured to be retracted through the expandable guide catheter.

2. The clot capture system of claim 1, wherein the tubular body is configured to slide relative to an inner layer of the expandable guide catheter.

3. The clot capture system of claim 1, wherein the expandable guide catheter is configured to reduce sliding contact between the expandable guide catheter and any components pass therethrough.

4. The clot capture system of claim 1, wherein the expandable guide catheter is configured to function as a variably sized cannula.

5. The clot capture system of claim 1, wherein the expandable guide catheter is self-expanding.

6. The clot capture system of claim 1, wherein the expandable guide catheter comprises a dual layer structure.

7. The clot capture system of claim 1, wherein the expandable guide catheter comprises an inner braid layer and an outer braid layer.

8. The clot capture system of claim 1, wherein the expandable guide catheter comprises at least one coated layer.

9. The clot capture system of claim 1, further comprising an anchor.

10. The clot capture system of claim 1, further comprising two or more anchors, wherein the two or more anchors are spaced axially apart along a longitudinal axis.

11. The clot capture system of claim 1, further comprising an anchor configured to entangle a clot.

12. The clot capture system of claim 1, further comprising an anchor coupled to the tubular body.

13. A method of using a clot capture system, comprising:
positioning a clot capture system near an obstruction, the clot capture system comprising:
an expandable guide catheter;
a tubular body comprising a first end, a second end, and an axial length therebetween, the first end having an opening, wherein the tubular body is compressed in a first configuration,
transforming the tubular body to a second configuration in which at least the first end of the tubular body is expanded but the second end of the tubular body and a portion of the tubular body remains compressed, and wherein the tubular body has a first expanded axial length, wherein the tubular body is inverted such that a portion of the compressed tubular body is within a portion of the expanded tubular body;
transforming the tubular body to a third configuration in which the tubular body has a second expanded axial length greater than the first expanded axial length to encapsulate the obstruction; and
retracting the tubular body through the expandable guide catheter.

14. A clot capture system, comprising:
a guide catheter;
a shape memory tubular body comprising a first end, a second end, and an axial length therebetween, the first end having an opening,
wherein the shape memory tubular body is configured to be compressed during delivery,
wherein the shape memory tubular body is transformable to a configuration in which the opening is expanded and a first segment of the shape memory tubular body extending axially from the opening is expanded to a fold point, the first segment having a first expanded axial length, and a second segment of the shape memory tubular body extending axially from the fold point to the second end of the shape memory tubular body such that the second segment of the shape memory tubular body extends at least partially within the first segment of the shape memory tubular body, wherein the second segment is relatively compressed with respect to the first segment,
wherein the shape memory tubular body is configured to be axially lengthened,
wherein shape memory tubular body is configured to be retracted through the guide catheter.

15. The clot capture system of claim 14, wherein the guide catheter comprises an expandable distal end.

16. The clot capture system of claim 14, wherein the guide catheter comprises a dual braid layer.

17. The clot capture system of claim 14, wherein at least a portion of the guide catheter comprises a polymeric coating.

18. The clot capture system of claim 14, wherein at least an outer portion of the guide catheter comprises a coating.

19. The clot capture system of claim 14, wherein at least a portion of the guide catheter comprises a mesh.

20. The clot capture system of claim 14, wherein at least an inner portion of the guide catheter provides decreased surface area, decreased surface contact, and/or decreased friction relative to an object within a lumen of the guide catheter.

* * * * *

UNITED STATES PATENT AND TRADEMARK OFFICE
CERTIFICATE OF CORRECTION

PATENT NO. : 10,238,482 B2
APPLICATION NO. : 16/011251
DATED : March 26, 2019
INVENTOR(S) : Thanh Van Nguyen et al.

Page 1 of 1

It is certified that error appears in the above-identified patent and that said Letters Patent is hereby corrected as shown below:

Page 2, (Item (63)), Related U.S. Application Data, Line 2, change "continuation" to --continuation-in-part--.

Page 2, (Item (63)), Related U.S. Application Data, Line 4, change "continuation" to --continuation-in-part--.

Signed and Sealed this
Third Day of September, 2019

Andrei Iancu
*Director of the United States Patent and Trademark Office*